United States Patent
Liao et al.

(10) Patent No.: US 10,431,751 B2
(45) Date of Patent: Oct. 1, 2019

(54) COMPOUND AND ORGANIC ELECTRONIC DEVICE COMPRISING THE SAME

(71) Applicant: Nichem Fine Technology Co., Ltd., Jhubei, Hsinchu County (TW)

(72) Inventors: Liang-Di Liao, Jhubei (TW); Shwu-Ju Shieh, Jhubei (TW); Chi-Chung Chen, Jhubei (TW)

(73) Assignee: SHANGHAI NICHEM FINE CHEMICAL CO., LTD., Shanghai (CN)

( * ) Notice: Subject to any disclaimer, the term of this patent is extended or adjusted under 35 U.S.C. 154(b) by 217 days.

(21) Appl. No.: 15/416,507

(22) Filed: Jan. 26, 2017

(65) Prior Publication Data

US 2017/0213970 A1 Jul. 27, 2017

Related U.S. Application Data

(60) Provisional application No. 62/287,724, filed on Jan. 27, 2016.

(51) Int. Cl.
*H01L 51/50* (2006.01)
*H01L 51/00* (2006.01)
(Continued)

(52) U.S. Cl.
CPC ........ *H01L 51/0085* (2013.01); *C07C 211/61* (2013.01); *C07C 255/51* (2013.01);
(Continued)

(58) Field of Classification Search
None
See application file for complete search history.

(56) References Cited

U.S. PATENT DOCUMENTS

2017/0317283 A1* 11/2017 Mujica-Fernaud ........................ H01L 51/006

FOREIGN PATENT DOCUMENTS

| CN | 103833507 | 6/2014 |
| CN | 106432107 A † | 2/2017 |

(Continued)

OTHER PUBLICATIONS

Evidence-1: Organic Chemistry (eighth edition), Paula Yurkanis Bruice, Global Edition, pp. 660, 661, 668, 678, Publication Date: Jan. 15, 2016, Pearson Education, Inc., NJ, USA; Pages/Lines Cited: pp. 660, 661, 668, 678.†

(Continued)

*Primary Examiner* — Gregory D Clark

(74) *Attorney, Agent, or Firm* — Muncy, Geissler, Olds & Lowe, P.C.

(57) ABSTRACT

A novel compound is disclosed, which is represented by the following Formula (I):

(I)

(Continued)

wherein Ar₁, Ar₂, Ar₃, Ar₄, L, Q, G, n1, n2, m1, m2 and q represent the same as defined in the specification. In addition, an organic electronic device is also disclosed, and an organic layer therein comprises the novel compound of the present invention.

13 Claims, 19 Drawing Sheets

(51) Int. Cl.

| | |
|---|---|
| C07F 15/00 | (2006.01) |
| C09K 11/06 | (2006.01) |
| C07C 255/51 | (2006.01) |
| C07D 213/06 | (2006.01) |
| C07D 213/22 | (2006.01) |
| C07D 213/57 | (2006.01) |
| C07D 235/18 | (2006.01) |
| C07D 239/26 | (2006.01) |
| C07D 239/74 | (2006.01) |
| C07D 251/24 | (2006.01) |
| C07C 211/61 | (2006.01) |
| C07D 223/14 | (2006.01) |
| C07D 307/91 | (2006.01) |
| C07D 313/06 | (2006.01) |
| C07D 213/38 | (2006.01) |
| H01L 51/42 | (2006.01) |

(52) U.S. Cl.
CPC .......... *C07D 213/06* (2013.01); *C07D 213/22* (2013.01); *C07D 213/38* (2013.01); *C07D 213/57* (2013.01); *C07D 223/14* (2013.01); *C07D 235/18* (2013.01); *C07D 239/26* (2013.01); *C07D 239/74* (2013.01); *C07D 251/24* (2013.01); *C07D 307/91* (2013.01); *C07D 313/06* (2013.01); *C07F 15/0033* (2013.01); *C09K 11/06* (2013.01); *H01L 51/006* (2013.01); *H01L 51/0056* (2013.01); *H01L 51/0057* (2013.01); *H01L 51/0061* (2013.01); *H01L 51/0067* (2013.01); *H01L 51/0072* (2013.01); *H01L 51/5016* (2013.01); *C07C 2603/18* (2017.05); *C07C 2603/98* (2017.05); *C07C 2603/99* (2017.05); *C09K 2211/1007* (2013.01); *C09K 2211/1029* (2013.01); *C09K 2211/1033* (2013.01); *C09K 2211/185* (2013.01); *H01L 51/0058* (2013.01); *H01L 51/0073* (2013.01); *H01L 51/42* (2013.01); *H01L 51/5056* (2013.01); *H01L 51/5072* (2013.01); *H01L 51/5088* (2013.01); *H01L 51/5096* (2013.01); *Y02E 10/549* (2013.01)

(56) References Cited

FOREIGN PATENT DOCUMENTS

| | | |
|---|---|---|
| JP | 2017-203026 | 11/2017 |
| KR | 10-2011-0041730 | 4/2011 |
| KR | 10-2012-0047038 | 5/2012 |
| KR | 10-2012-0048125 | 5/2012 |
| KR | 10-2012-0093076 | 8/2012 |
| KR | 10-2013-0140303 | 12/2013 |
| WO | WO-2016/087017 | 6/2016 |

OTHER PUBLICATIONS

Evidence-2: Integration of 1H NMR spectra (proton) from NMR theory of Spectroscopy of Organic Chemistry Lecture Website at University of Colorado Boulder, which was built by Dr. Patty Feist et al. (from < http://www.orgchemboulder.com:80/Spectroscopy/nmrtheory/NMRtutorial.shtml> 1 page, Dec. 14, 2016, retrieved from Internet Wayback Machine < http://web.archive.org/web/20161214110543/http://www.orgchemboulder.com:80/Spectroscopy/nmrtheory/NMRtutorial.shtml> on Feb. 7, 2018); Pages/Lines Cited: lines 2-3 & 4-5.†

Evidence-3: Real-Time Enzyme Kinetics by Quantitative NMR Spectroscopy and Determination of the Michaelis−Menten Constant Using the Lambert‑W Function, pp. 1943-1948, by Cheenou Her et al., J. Chem. Educ., 2015; Pages/Lines Cited: p. 1946 printed on bottom, right col., lines 13-17.†

Evidence-4: Proton Nuclear Magnetic Resonance Spectroscopy, Lecture of Structure Determination Using Spectroscopic Methods at University of Wisconsin, pp. 1-38, by Dr. Hans J. Reich, 2017 (from https://www.chem.wisc.edu/areas/reich/nmr/Notes-05-HMR-v26-part1.pdf); Pages/Lines Cited: p. 8, lines 3-4, Proton Nuclear Magnetic Resonance Spectroscopy.†

Evidence-5: hint of step 4 "Check that the integration of the peak matches the number of hydrogens in the molecule", webpage of Golden Rules to Nuclear Magnetic Resonance Spectroscopy (NMR) Analysis, 1 page, by Dr. Madalee Gassaway, Publication Date: Oct. 23, 2017 (from http://blog.cambridgecoaching.com/golden-rules-to-nuclear-magnetic-resonance-spectroscopy-nmr-analysis-part-1-0); Pages/Lines Cited : hint of step 4, webpage of Golden Rules to Nuclear Magnetic Resonance Spectroscopy (NMR) Analysis.†

Evidence-6: Doubly Ortho-Linked Quinoxaline/Diphenylfluorene Hybrids as Bipolar, Fluorescent Chameleons for Optoelectronic Applications, pp. 10992-10993, Chien-Tien Chen et al., J. Am. Chem. Soc., Publication Date: Aug. 8, 2006. Pages/Lines Cited: p. 10992 printed on bottom left corner, right col.†

Evidence-7: Doubly Ortho-linked Quinoxaline/Diphenylfluorene Hybrids as Bipolar, Fluorescent Chameleons for Optoelectronic Applications, pp. S1-S23, by Chien-Tien Chen et al., Publication Date: 2006, which is 1H NMR spectrum (p. S20) in Supporting Information from Evidence-6. Pages/Lines Cited: S20 printed on top right corner.†

Evidence-8: Doubly Ortho-Linked cis-4,4'-Bis(diarylamino)stilbene/Fluorene Hybrids as Efficient Nondoped, Sky-Blue Fluorescent Materials for Optoelectronic Applications, pp. 7478-7479, by Yi Wei et al., J. Am. Chem. Soc., Publication Date: May 25, 2007. Pages/Lines Cited: p. 7478 printed on bottom left corner, right col.†

Evidence-9: Doubly Ortho-linked cis-4,4'-Bis(diarylamino)stilbene/Fluorene Hybrids as Efficient Non-doped, Sky-blue Fluorescent Materials for Optoelectronic Applications, pp. S1-S22, by Yi Wei et al., 2007, which is 1H NMR spectrum (p. S16) in Supporting Information from Evidence-8. Pages/Lines Cited: S16 printed on top right corner.†

Evidence-10: Switching of non-helical overcrowded tetrabenzoheptafulvalene derivatives, pp. 2029-2034, by Jiye Luo et al., Chemical Science, Publication Date: Jul. 21, 2011. Pages/Lines Cited: p. 2031 printed on bottom right corner, left col.†

Evidence-16: Doubly Ortho-linked Quinoxaline/Triarylamine Hybrid as a Bifunctional, Dipolar Electroluminescent Template for Optoelectronic Applications, pp. 1-12, by Chien-Tien Chen et al., Publication Date: 2005, which is 1H NMR spectroscopic data (pp. 5 and 6) in Supporting Information from Evidence-15. Pages/Lines Cited: p. 5 and 6.†

Evidence-15: Doubly ortho-linked quinoxaline/triarylamine hybrid as a bifunctional, dipolar electroluminescent template for optoelectronic applications, pp. 3980-3982, Chien-Tien Chen et al., Chem. Commun, Publication Date: Jul. 8, 2005. Pages/Lines Cited: p. 3980 printed on bottom left corner.†

Evidence-14: Supplementary Information—Polycationic ligands in gold catalysis: Synthesis and applications of extremely π-acidic catalysts, pp. S1-S231, by Javier Carreras et al., Publication Date: 2013, which is 1H NMR spectrum (p. S200) in Supporting Information from Evidence-13. Pages/Lines Cited: 5200 printed on bottom right corner.†

Evidence-13: Polycationic Ligands in Gold Catalysis: Synthesis and Applications of Extremely π‑Acidic Catalysts, pp.

(56) References Cited

OTHER PUBLICATIONS 18815-18823, by Javier Carreras et al., Journal of the American Chemical Society, Publication Date: Dec. 5, 2013. Pages/Lines Cited: p. 18817 printed on bottom.†

Evidence-12: The Synthesis of Novel p-Quinone Methides: O-Dealkylation of 5-(p-Alkyloxyaryl)-10,11-dihydrodibenzo[a,d]cyclohepten-5-ols and Related Compounds, pp. 2607-2619, by Benjamin Taljaard et al., Eur. J. Org. Chem., Publication Date: Dec. 31, 2005. Pages/Lines Cited: p. 2612 printed on bottom left corner, right col.†

Evidence-11: Supporting Information for: Switching of Non-Helical Overcrowded Heptafulvalene Derivatives, pp. 1-59, by Jiye Luo et al., Publication Date: 2011, which is 1H NMR spectrum (p. 30) in Supporting Information from Evidence-10. Pages/Lines Cited: p. 30.†

\* cited by examiner
† cited by third party

COMPOUND AND ORGANIC ELECTRONIC DEVICE COMPRISING THE SAME

CROSS REFERENCE TO RELATED APPLICATION

This application claims the benefit of filing date of U.S. Provisional Application Ser. No. 62/287,724, entitled "Novel Compound and Organic Electronic Device Using the Same" filed Jan. 27, 2016 under 35 USC § 119(e)(1).

BACKGROUND

1. Field

The present invention relates to a novel compound and an organic electronic device using the same.

2. Description of Related Art

It is well known that organic light emitting device (OLED device) was initially invented and proposed by Eastman Kodak Company through a vacuum evaporation method. Tang and VanSlyke of Kodak Company deposited an electron transport material such as $Alq_3$ on a transparent indium tin oxide (abbreviated as ITO) glass formed with an organic layer of aromatic diamine thereon, and subsequently completed the fabrication of an organic electroluminescent (EL) device after a metal electrode is vapor-deposited onto the $Alq_3$ layer. The organic EL device currently becomes a new generation lighting device or display because of high brightness, fast response speed, light weight, compactness, true color, no difference in viewing angles, without using any LCD backlight plates, and low power consumption.

Recently, some interlayers such as electron transport layer and hole transport layer are added between the cathode and the anode for increasing the current efficiency and power efficiency of the OLEDs. For example, an organic light emitting diode (OLED) 1' shown as FIG. 1 is designed to consist of: a cathode 11', an electron injection layer 13', a light emitting layer 14', a hole transport layer 16', and an anode 18'.

Recently, for effectively increasing the lighting performance of OLEDs, OLED manufactures and researchers have made great efforts to develop different compounds used as the materials for the OLEDs. However, in spite of various compounds have been developed, the current phosphorescence OLEDs still cannot perform outstanding luminous efficiency and device lifetime. Accordingly, in view of the conventional or commercial materials for OLEDs still including drawbacks, the inventor of the present application has made great efforts to make inventive research thereon and eventually provided novel compounds for OLED.

SUMMARY

The object of the present disclosure is to provide a novel compound and an organic electronic device comprising the same.

According to one or more embodiments, a compound is represented by Formula (I) below:

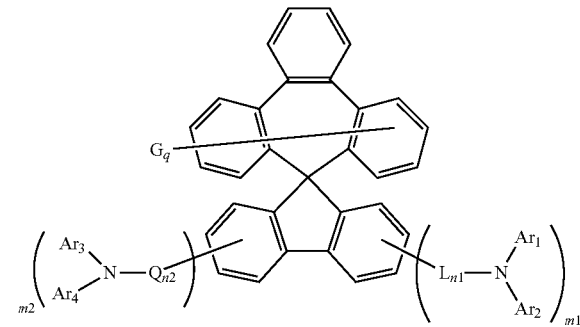

wherein, $Ar_1$, $Ar_2$, $Ar_3$, and $Ar_4$ are each independently hydrogen, deuterium, a substituted or unsubstituted $C_1$-$C_{20}$ alkyl group, a substituted or unsubstituted $C_6$-$C_{40}$ aryl group, a substituted or unsubstituted $C_1$-$C_{40}$ heterocyclic group, or a substituted or unsubstituted amine group; or $Ar_1$ and $Ar_2$ together with the nitrogen atom to which they are bonded is a substituted or unsubstituted $C_1$-$C_{40}$ heterocyclic group; or $Ar_3$ and $Ar_4$ together with the nitrogen atom to which they are bonded is a substituted or unsubstituted $C_1$-$C_{40}$ heterocyclic group;

L and Q are each independently a substituted or unsubstituted $C_6$-$C_{40}$ arylene group;

G is deuterium, a substituted or unsubstituted $C_1$-$C_{20}$ alkyl group, a substituted or unsubstituted $C_6$-$C_{40}$ aryl group, a substituted or unsubstituted $C_1$-$C_{40}$ heterocyclic group, or —$NR_1R_2$;

$R_1$ and $R_2$ are each independently hydrogen, deuterium, a substituted or unsubstituted $C_1$-$C_{20}$ alkyl group, a substituted or unsubstituted $C_6$-$C_{40}$ aryl group, or a substituted or unsubstituted $C_1$-$C_{40}$ heterocyclic group;

n1 and n2 are each independently 0 or 1;

m1 and m2 are each independently 0, 1 or 2, and with the proviso that m1 and m2 are not 0 at the same time; and q is 0, 1, or 2.

According to one or more embodiments, an organic electronic device comprises: a first electrode; a second electrode; and an organic layer disposed between the first electrode and the second electrode, wherein the organic layer comprises the compound of the aforesaid Formula (I).

The present disclosure provides a novel compound. When the compound of the present disclosure is used in an organic electronic device, the efficiency of the organic electronic device can be improved. Especially, when the novel compound of the present disclosure is used as one material of an organic light emitting device, the luminous efficiency of the organic light emitting device can further be improved.

DETAILED DESCRIPTION

Figure 1:
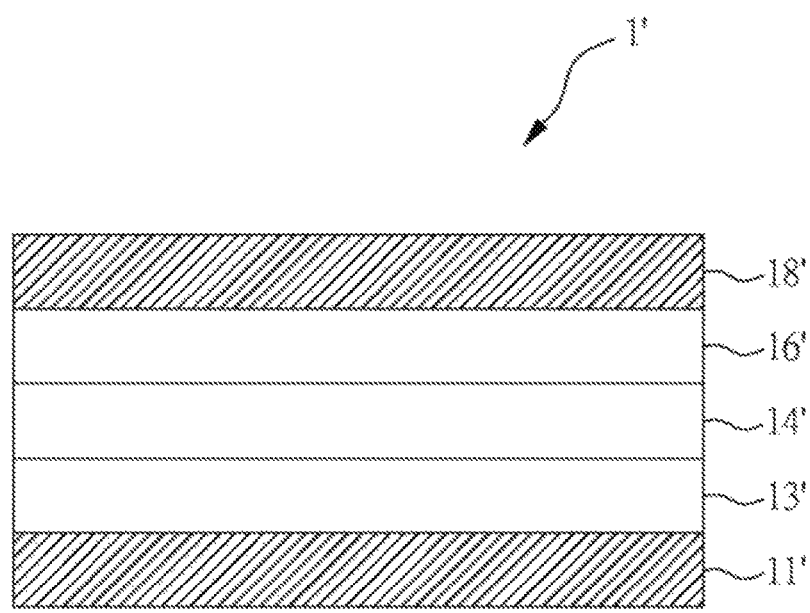
FIG. 1 is a perspective view showing an OLED device of the prior art.

Hereinafter, the present disclosure is described in detail. The present disclosure has been described in an illustrative manner, and it is to be understood that the terminology used is intended to be in the nature of description rather than of limitation. Many modifications and variations of the present disclosure are possible in light of the teachings. Therefore, it is to be understood that within the scope of the appended claims, the invention may be practiced otherwise than as specifically described.

Compound

A compound according to one exemplary embodiment may be represented by the following Formula (I).

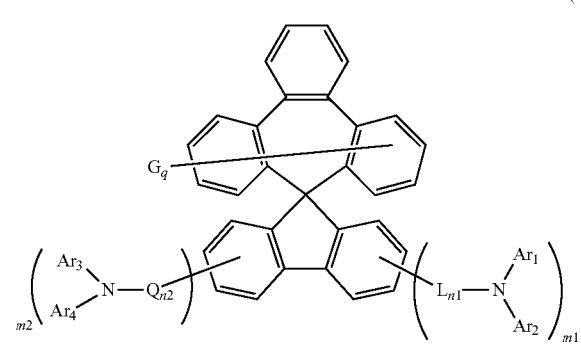

(I)

In formula (I), $Ar_1$, $Ar_2$, $Ar_3$, and $Ar_4$ may be each independently hydrogen, deuterium, a substituted or unsubstituted $C_1$-$C_{20}$ alkyl group, a substituted or unsubstituted $C_6$-$C_{40}$ aryl group, a substituted or unsubstituted $C_1$-$C_{40}$ heterocyclic group, or a substituted or unsubstituted amine group; or $Ar_1$ and $Ar_2$ together with the nitrogen atom to which they are bonded may be a substituted or unsubstituted $C_1$-$C_{40}$ heterocyclic group; or $Ar_3$ and $Ar_4$ together with the nitrogen atom to which they are bonded may be a substituted or unsubstituted $C_1$-$C_{40}$ heterocyclic group;

L and Q may be each independently a substituted or unsubstituted $C_6$-$C_{40}$ arylene group;

G may be deuterium, a substituted or unsubstituted $C_1$-$C_{20}$ alkyl group, a substituted or unsubstituted $C_6$-$C_{40}$ aryl group, a substituted or unsubstituted $C_1$-$C_{40}$ heterocyclic group, or —$NR_1R_2$;

$R_1$ and $R_2$ may be each independently hydrogen, deuterium, a substituted or unsubstituted $C_1$-$C_{20}$ alkyl group, a substituted or unsubstituted $C_6$-$C_{40}$ aryl group, or a substituted or unsubstituted $C_1$-$C_{40}$ heterocyclic group;

n1 and n2 may be each independently 0 or 1;

m1 and m2 may be each independently 0, 1 or 2, and with the proviso that m1 and m2 are not 0 at the same time; and q may be 0, 1, or 2.

According to one embodiment, $Ar_1$, $Ar_2$, $Ar_3$, and $Ar_4$ can be each independently a substituted or unsubstituted $C_6$-$C_{40}$ aryl group, or a substituted or unsubstituted $C_1$-$C_{40}$ heterocyclic group; or $Ar_1$ and $Ar_2$ together with the nitrogen atom to which they are bonded can be a substituted or unsubstituted $C_1$-$C_{40}$ heterocyclic group; or $Ar_3$ and $Ar_4$ together with the nitrogen atom to which they are bonded can be a substituted or unsubstituted $C_1$-$C_{40}$ heterocyclic group. Preferably, $Ar_1$, $Ar_2$, $Ar_3$, and $Ar_4$ are each independently a substituted or unsubstituted $C_6$-$C_{40}$ aryl group, or a substituted or unsubstituted $C_1$-$C_{40}$ heteroaryl group; or $Ar_1$ and $Ar_2$ together with the nitrogen atom to which they are bonded is a substituted or unsubstituted $C_1$-$C_{40}$ heteroaryl group; or $Ar_3$ and $Ar_4$ together with the nitrogen atom to which they are bonded is a substituted or unsubstituted $C_1$-$C_{40}$ heteroaryl group.

According to one embodiment, $Ar_1$, $Ar_2$, $Ar_3$, and $Ar_4$ may be each independently substituted or unsubstituted phenyl, substituted or unsubstituted biphenyl, substituted or unsubstituted terphenyl, substituted or unsubstituted fluorenyl, substituted or unsubstituted tribenzyloxepinyl, substituted or unsubstituted dibenzofuranyl, substituted or unsubstituted dibenzothiofuranyl, substituted or unsubstituted naphthyl, or substituted or unsubstituted tribenzyl-azepinyl group. Preferably, $Ar_1$, $Ar_2$, $Ar_3$, and $Ar_4$ are each independently unsubstituted phenyl, phenyl substituted with alkyl, unsubstituted biphenyl, unsubstituted terphenyl, unsubstituted fluorenyl, fluorenyl substituted with alkyl, unsubstituted tribenzyloxepinyl, unsubstituted dibenzofuranyl, or unsubstituted naphthyl.

According to one embodiment, m1 may be 1; and m2 may be 0 or 1. According to another embodiment, m1 may be 1 and m2 may be 0. According to further another embodiment, m1 may be 1 and m2 may be 1.

According to one embodiment, m1 may be 1; m2 may be 0; and $Ar_1$ and $Ar_2$ together with the nitrogen atom to which they are bonded may be a substituted or unsubstituted $C_1$-$C_{40}$ heteroaryl group. Preferably, $Ar_1$ and $Ar_2$ together with the nitrogen atom to which they are bonded is unsubstituted tribenzyl-azepinyl group.

According to one embodiment, when m1 and m2 are not 0 at the same time, -$L_{n1}$-$NAr_1Ar_2$ and -$Q_{n2}$-$NAr_3Ar_4$ can be the same.

According to one embodiment, m1 and m2 are 1, and -$L_{n1}$-$NAr_1Ar_2$ and -$Q_{n2}$-$NAr_3Ar_4$ can be the same.

According to one embodiment, L and Q may be each independently substituted or unsubstituted phenylene, biphenylene, or naphthylene. Preferably, L and Q are each independently unsubstituted phenylene.

According to one embodiment, q may 0 or 1.

When q is 1, G may be a substituted or unsubstituted $C_6$-$C_{40}$ aryl group, a substituted or unsubstituted $C_1$-$C_{40}$ heterocyclic group, or —$NR_1R_2$, in which $R_1$ and $R_2$ are each independently a substituted or unsubstituted $C_6$-$C_{40}$ aryl group. Preferably, G is a substituted or unsubstituted $C_1$-$C_{40}$ heteroaryl group containing a nitrogen atom, or —$NR_1R_2$, in which $R_1$ and $R_2$ are the same and are a substituted or unsubstituted phenyl, biphenyl or naphthylene. More preferably, G is unsubstituted pyridyl, or —$NR_1R_2$, in which $R_1$ and $R_2$ are unsubstituted phenyl.

According to one embodiment, G, -$L_{n1}$-$NAr_1Ar_2$ and -$Q_{n2}$-$NAr_3Ar_4$ can be the same. For example, when m1 is 1 and m2 is 0, G and -$L_{n1}$-$NAr_1Ar_2$ can be the same.

According to another embodiment G, -$L_{n1}$-$NAr_1Ar_2$ and -$Q_{n2}$-$NAr_3Ar_4$ can be different. For example, when m1 is 1 and m2 is 0, G and -$L_{n1}$-$NAr_1Ar_2$ can be different.

According to one embodiment, the compound of Formula (I) can be represented by any one of Formulas (I-1) to (I-18) below.

(I-1)
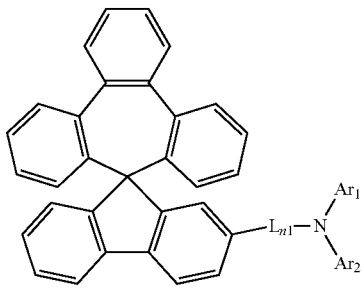

(I-2)
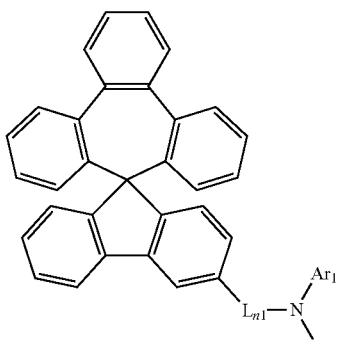

(I-3)
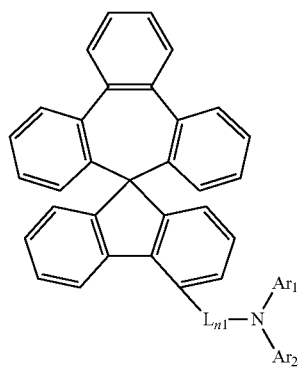

(I-4)
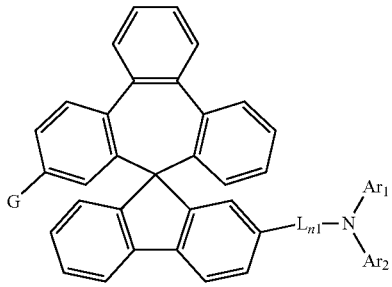

(I-5)
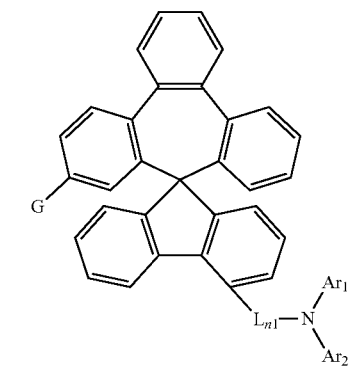

(I-6)
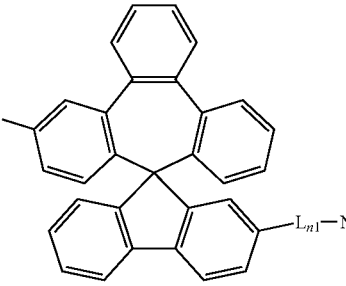

(I-7)
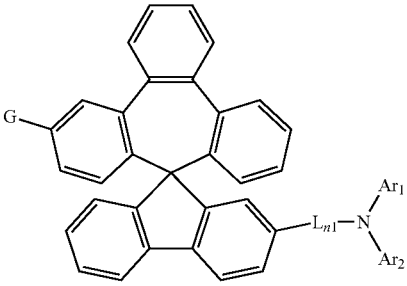

-continued
(I-8)
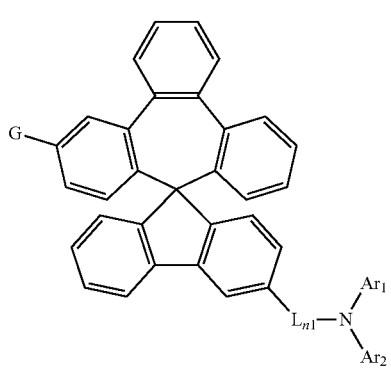
(I-9)
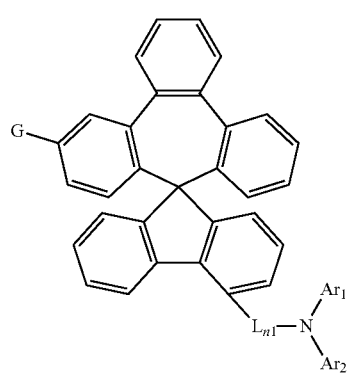
(I-10)
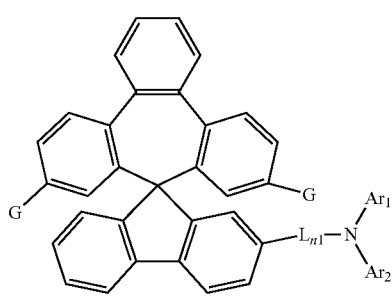
(I-11)
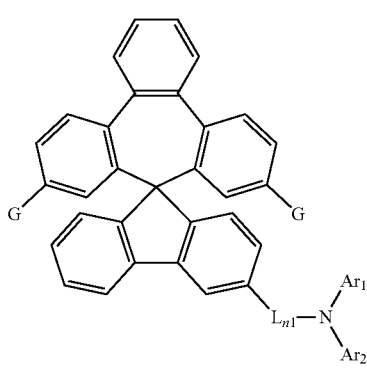
(I-12)
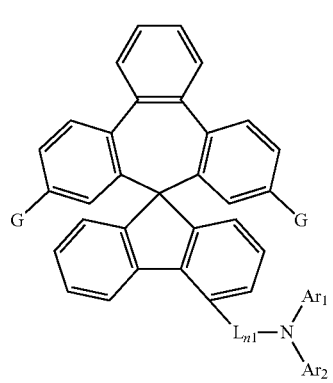
(I-13)
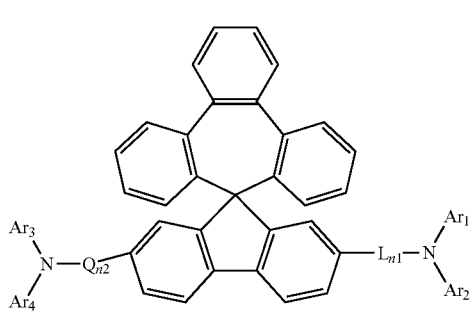
(I-14)
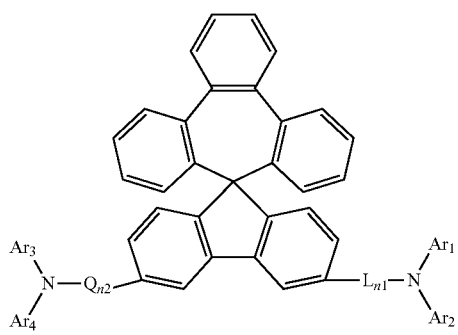
(I-15)
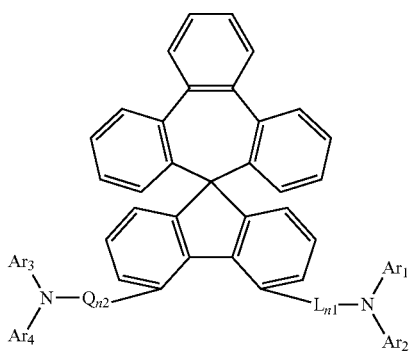

(I-16)
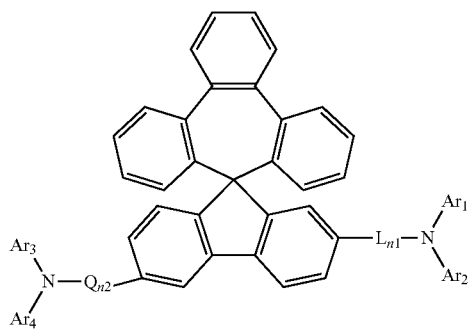
(I-17)
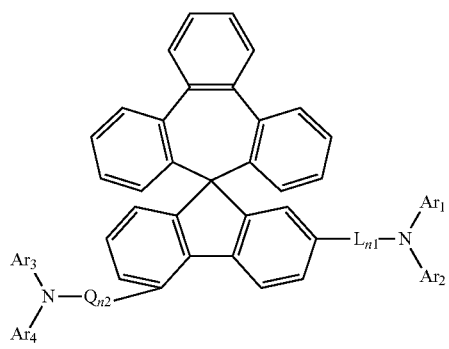
(I-18)
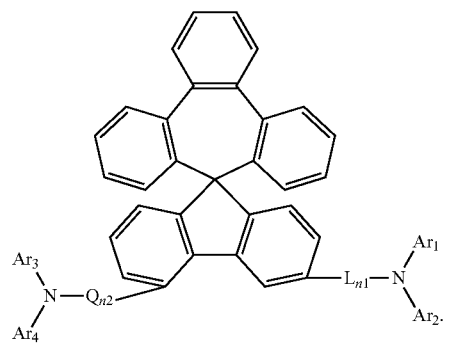
$Ar_1$, $Ar_2$, $Ar_3$, $Ar_4$, L, Q, G, n1, and n2 in Formulas (I-1) to (I-18) represent the same as those described above.
According to one embodiment, $-L_{n1}-NAr_1Ar_2$ and $-Q_{n2}-NAr_3Ar_4$ can be each independently selected from the group consisting of:
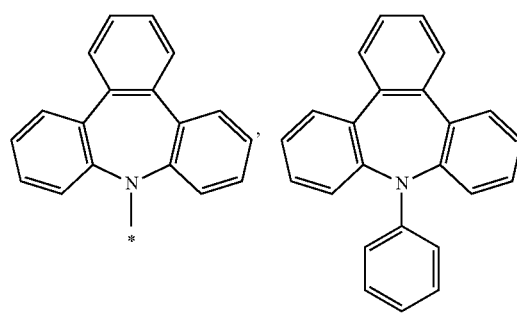
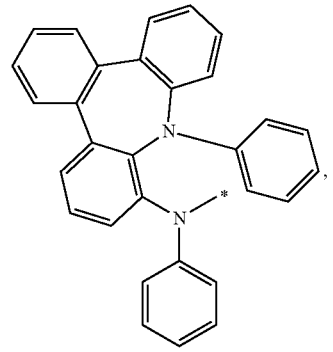
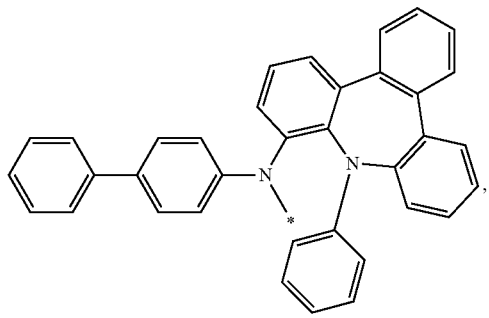
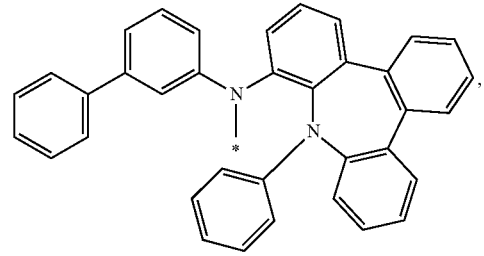
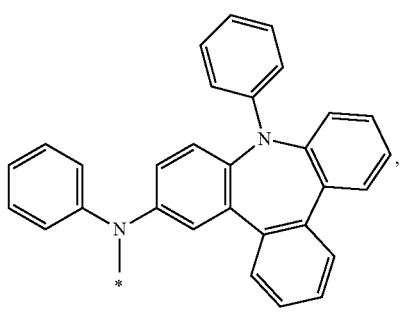
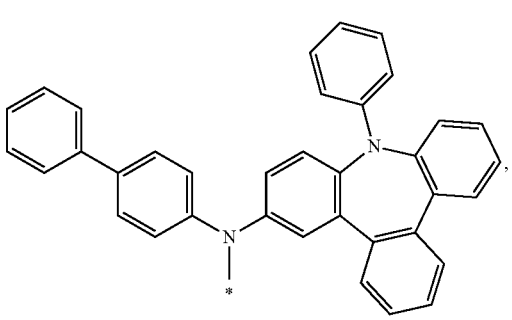

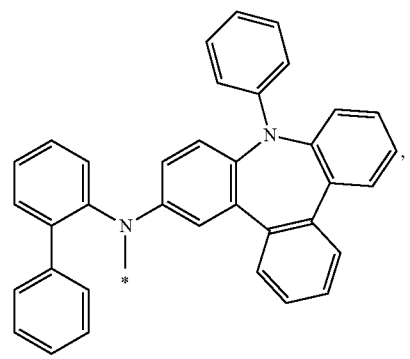
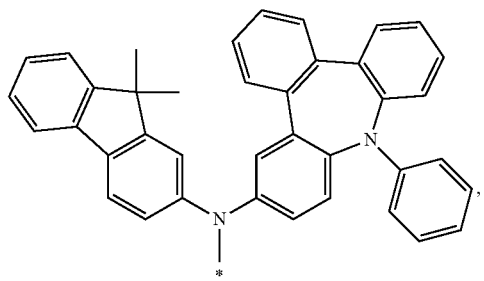
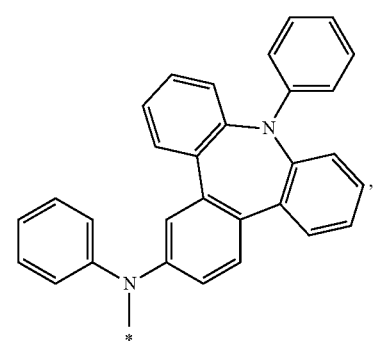
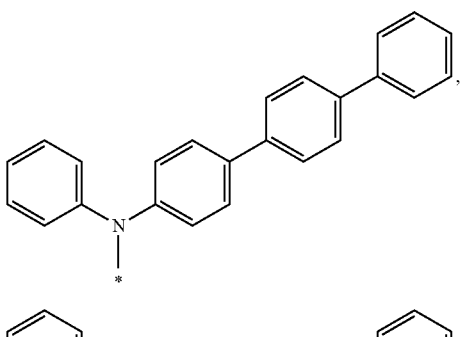
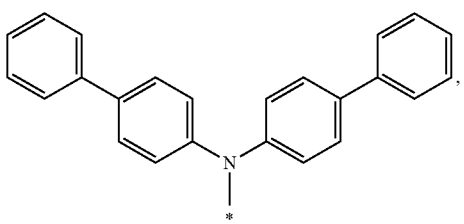
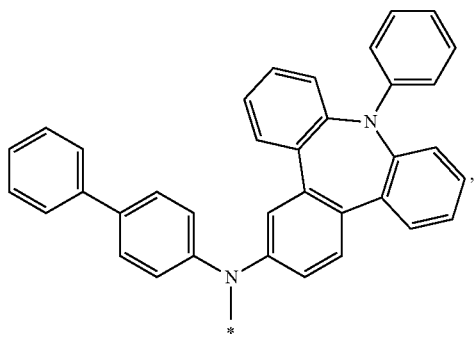
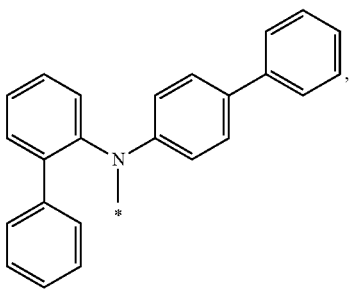
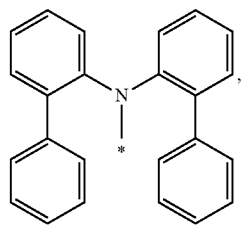
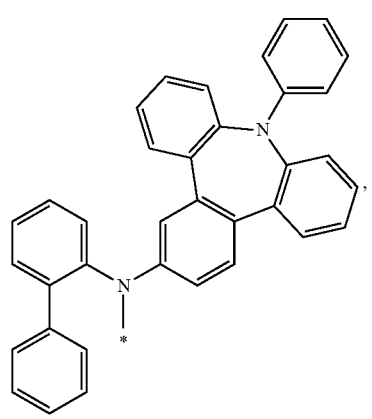
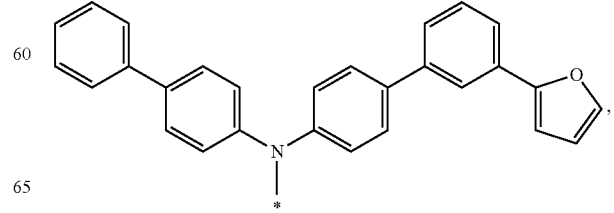

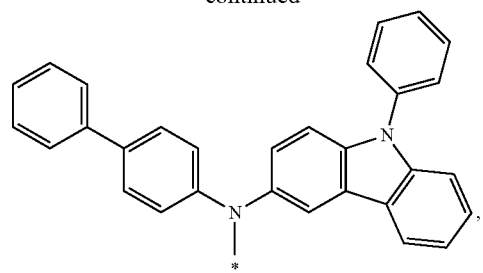
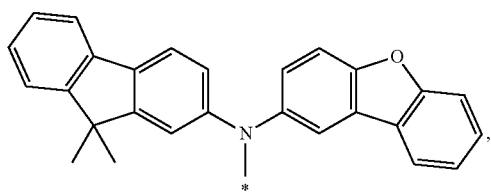
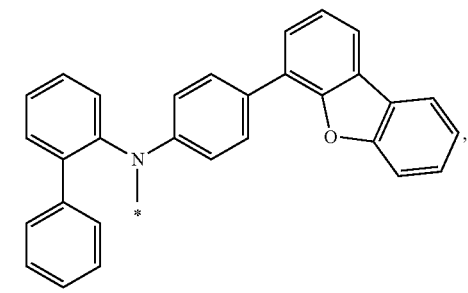
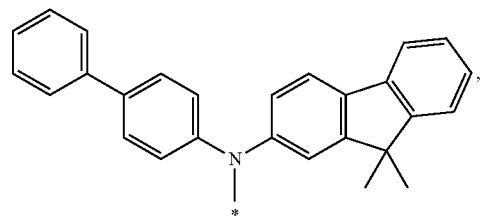
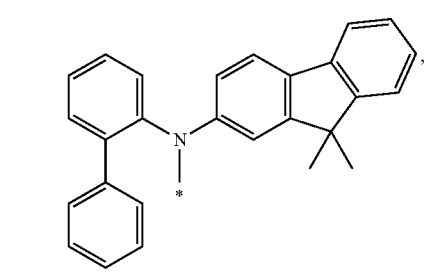
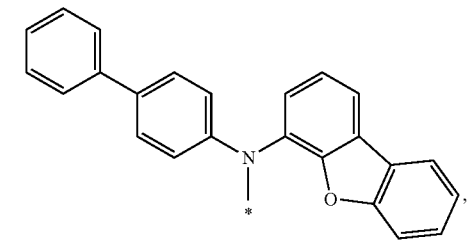
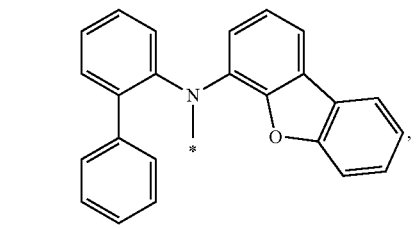
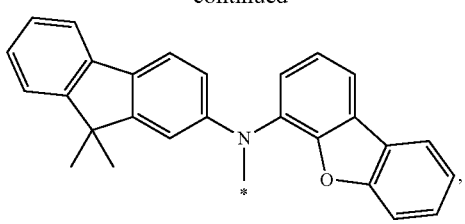
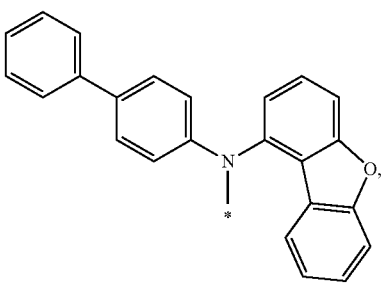
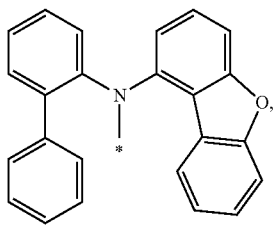
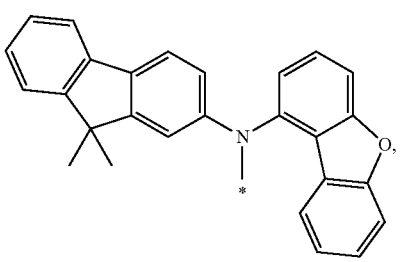
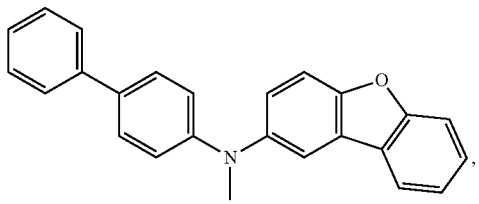
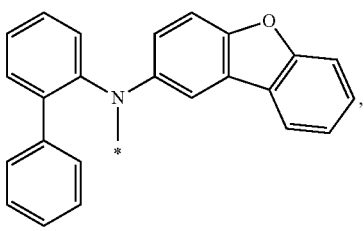
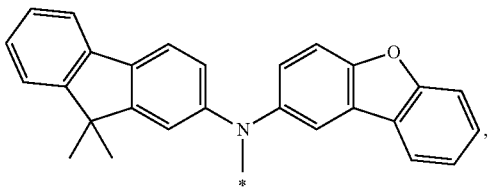

15
-continued
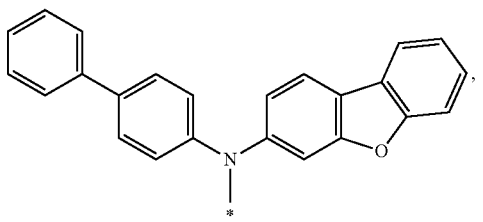
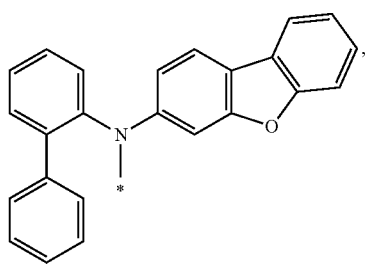
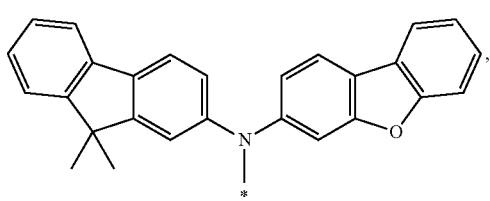
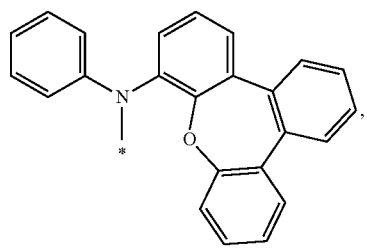
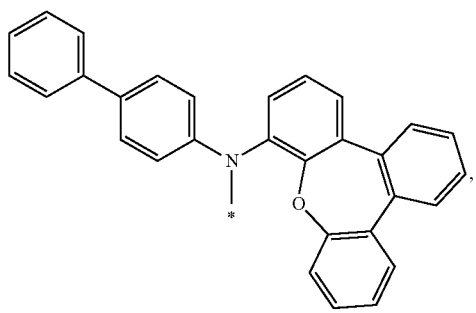
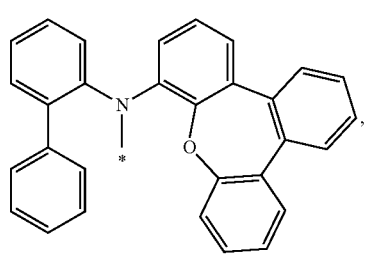
16
-continued
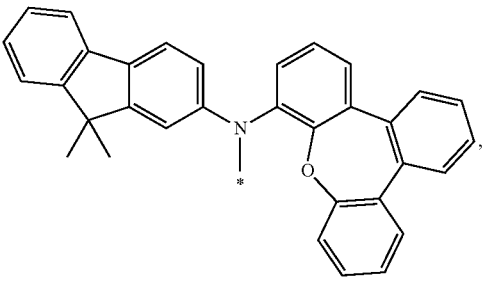
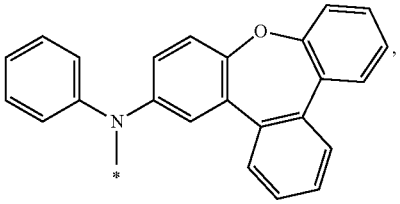
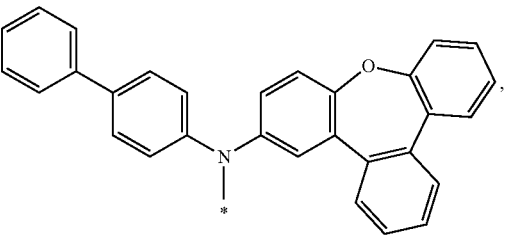
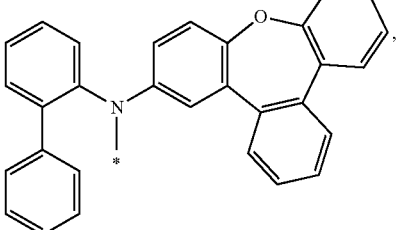
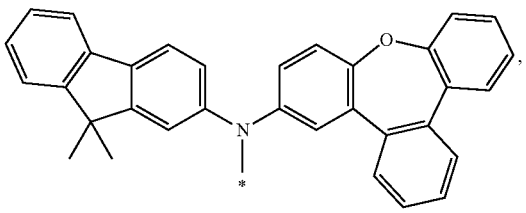
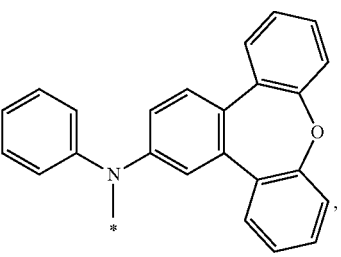
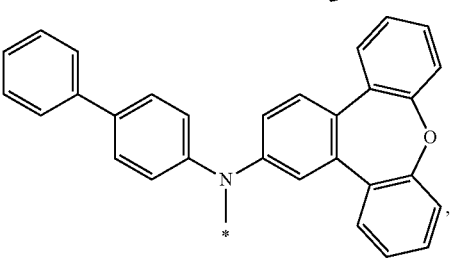

-continued

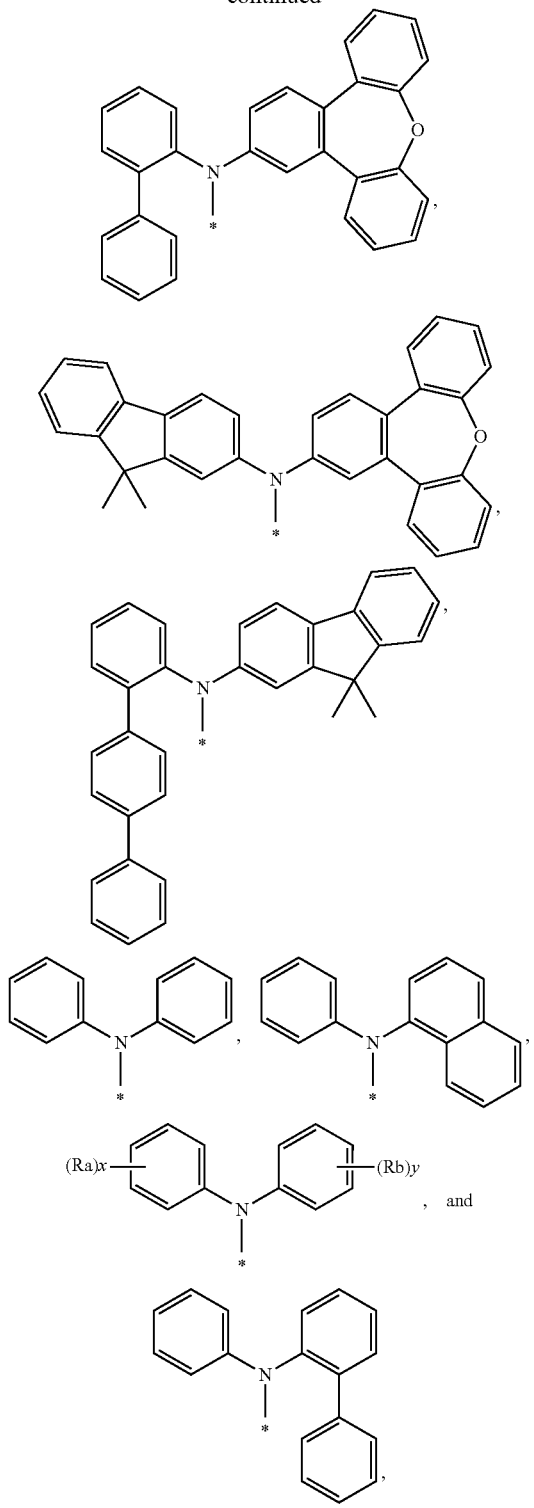

wherein * represents bonding positions, Ra and Rb are each independently $C_{1-20}$ alkyl, and x and y are each independently 1 or 2. Herein, Ra and Rb can be the same. X and y can be the same. Examples of Ra and Rb can be methyl, ethyl or propyl. In addition, n1 or n2 can be 0.

According to one embodiment, n1 is 0 and n2 is 1. According to another embodiment, n1 is 1 and n2 is 1. In these two embodiments, $L_{n1}$-NAr$_1$Ar$_2$ and -Q$_{n2}$-NAr$_3$Ar$_4$ can be each independently selected from the group consisting of:

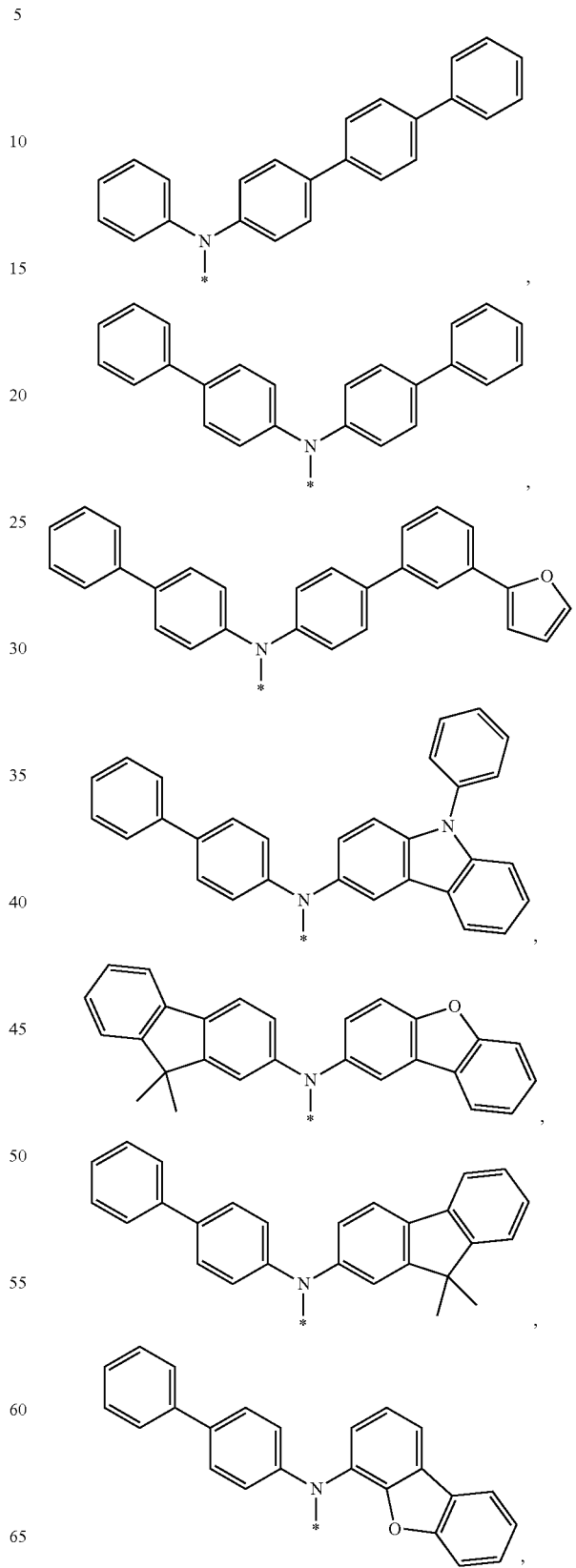

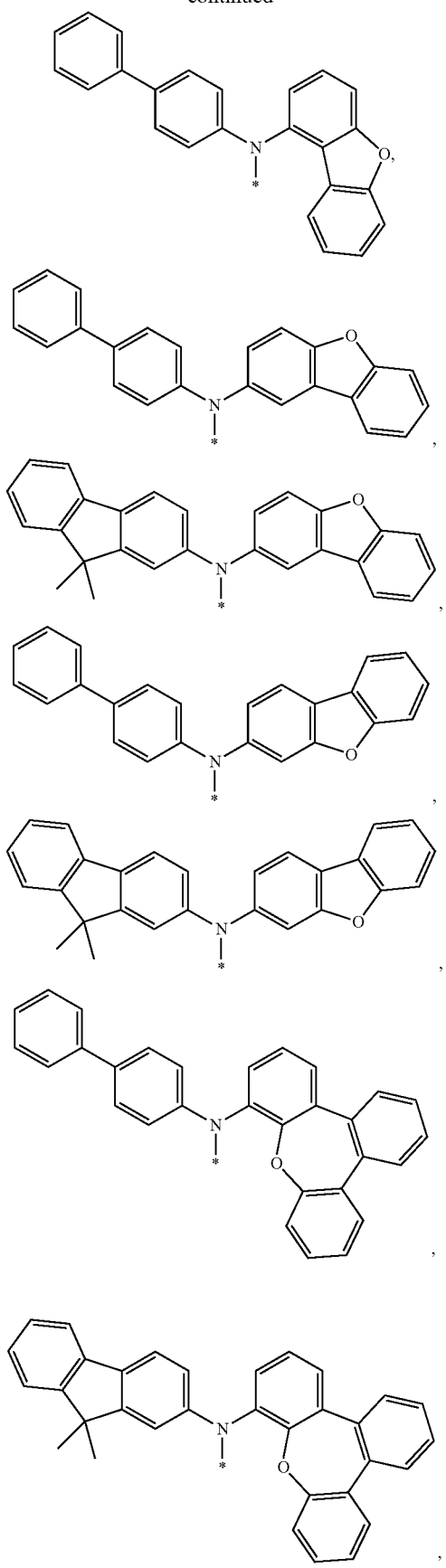
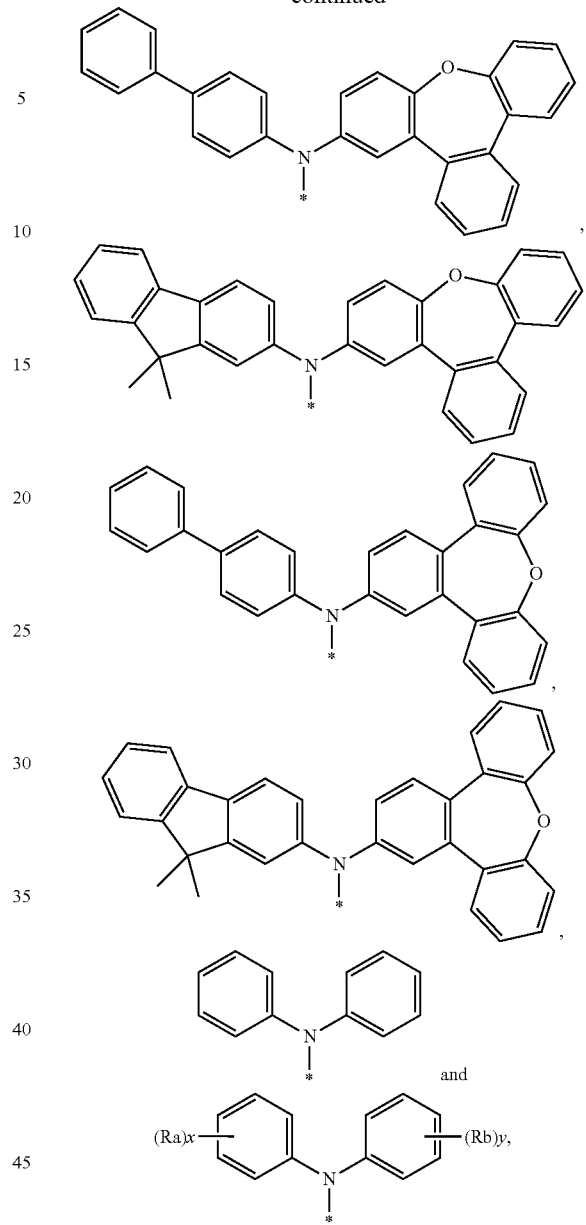

wherein * represents bonding positions. The definitions of Ra, Rb, x and y are the same as those illustrated above. In these two embodiments, L and Q can be each independently a substituted or unsubstituted $C_6$-$C_{40}$ arylene group such as phenylene.

Hereinafter, substitutes of Formula (I) is described in detail. Substitutes that are not defined in the present disclosure are defined as known in the art.

In the present disclosure, the unsubstituted alkyl group can be linear or branched. Examples of the alkyl group include $C_1$-$C_{20}$ alkyl, $C_{1-10}$ alkyl, or $C_{1-6}$ alkyl. Specific examples of the unsubstituted alkyl group include, but are not limited to, methyl, ethyl, n-propyl, iso-propyl, n-butyl, sec-butyl, iso-butyl, tert-butyl, pentyl, neo-pentyl, or hexyl. Herein, at least one hydrogen atom of the unsubstituted alkyl group may be substituted with a halogen group, an alkyl group, an alkenyl group, an alkoxy group, a cycloalkyl group, an aryl group, an arylalkyl group, an arylalkenyl group, a heterocyclic group, a nitrile group, or an acetylene group.

In the present disclosure, the unsubstituted aryl group refers to aromatic hydrocarbon group. Examples of the aryl group can be $C_6$-$C_{40}$ aryl, or $C_6$-$C_{20}$ aryl. In addition, examples of the aryl group can a monocyclic, bicyclic, tricyclic, or polycyclic aromatic hydrocarbon group; wherein two or more rings may be fused to each other or linked to each other via a single bond. Specific examples of the unsubstituted aryl group include, but are not limited to phenyl, biphenylyl, terphenyl, quarterphenyl, naphthyl, anthryl, benzanthryl, phenanthryl, naphthacenyl, pyrenyl, chrysenyl, benzo[c]phenanthryl, benzo[g]chrysenyl, triphenylenyl, fluorenyl, spirobifluorenyl, benzofluorenyl, or dibenzofluorenyl. Herein, at least one hydrogen atom of the unsubstituted aryl group may be substituted with the same substituents described above related to the alkyl group. In addition, the definition of the arylene group is similar to those stated above, and the detail description of the arylene group is not repeated herein.

In the present disclosure, the unsubstituted heterocyclic group refers to non-aromatic or aromatic hydrocarbon group. Examples of the heterocyclic group can be a $C_1$-$C_{40}$ heterocyclic group, $C_2$-$C_{20}$ heterocyclic group or a $C_4$-$C_{20}$ heterocyclic group. In addition, examples of the heterocyclic group can be a monocyclic, bicyclic, tricyclic, or polycyclic heteroaryl or heterocycloalkyl having at least one heteroatom which is selected from the group consisting of O, S and N; wherein two or more rings may be fused to each other or linked to each other via a single bond. Specific examples of the unsubstituted heterocyclic group include, but are not limited to, pyroryl, pyrazinyl, pyridinyl, piperidinyl, indolyl, isoindolyl, imidazolyl, benzoimidazolyl, furyl, ozazolyl, thiazolyl, triazolyl, thiadiazolyl, benzothiazolyl, tetrazolyl, oxadiazolyl, triazinyl, carbazolyl, benzofuranyl, isobenzofuranyl, dibenzofuranyl, dibenzothiofuranyl, dibenzothiophenyl, quinolyl, isoquinolyl, quinoxalinyl, phenantridinyl, acridinyl, phenanthrolinyl, phenazinyl, phenothiazinyl, phenoxazinyl, oxazolyl, oxadiazoyl, furazanyl, thienyl, benzothiophenyl, tribenzyloxepinyl, thiophenyl, or benzooxazolyl. Herein, at least one hydrogen atom of the unsubstituted heterocyclic group may be substituted with the same substituents described above related to the alkyl group.

In one embodiment, two or more aryl or hetero rings may be directly linked to each other to form a spiro structure. For example, fluorenyl and tribenzo-cycloheptatrienyl may be linked to each other to form a Spiro structure.

In the present disclosure, halogen includes F, Cl, Br and I; and preferably is F or Br.

In the present disclosure, the unsubstituted alkoxy group refers to a moiety that the alkyl defined above coupled with an oxygen atom. Examples of the alkoxy group can include linear or branched $C_{1-10}$ alkoxy, or linear or branched $C_{1-6}$ alkoxy. Specific examples of alkoxy include, but are not limited to, methoxy, ethoxy, n-propoxy, iso-propoxy, n-butoxy, iso-butoxy, sec-butoxy, tert-butoxy, pentyloxy, neopentyloxy or hexyloxy. Herein, at least one hydrogen atom of the unsubstituted alkoxy group may be substituted with the same substituents described above related to the alkyl group.

In the present disclosure, the unsubstituted cycloalkyl group refers to a monovalent saturated hydrocarbon ring system having 3 to 20 carbon atoms, or 3 to 12 carbon atoms. Specific examples of the unsubstituted cycloalkyl group include, but are not limited to, cyclopropyl, cyclobutyl, cyclopentyl, cyclohexyl, cycloheptyl, and cyclooctyl. Herein, at least one hydrogen atom of the unsubstituted cycloalkyl group may be substituted with the same substituents described above related to the alkyl group.

In the present disclosure, the unsubstituted alkenyl group can be linear or branched, and have at least one carbon-carbon double bond. Examples of the alkenyl group include $C_1$-$C_{20}$ alkenyl, $C_{1-10}$ alkenyl, or $C_{1-6}$ alkenyl. Specific examples of the unsubstituted alkenyl group include, but are not limited to ethenyl, propenyl, propenylene, allyl, or 1,4-butadienyl. Herein, at least one hydrogen atom of the unsubstituted alkenyl group may be substituted with the same substituents described above related to the alkyl group.

Examples of the compound of Formula (I) may include any one of the following compounds (1) to (224).

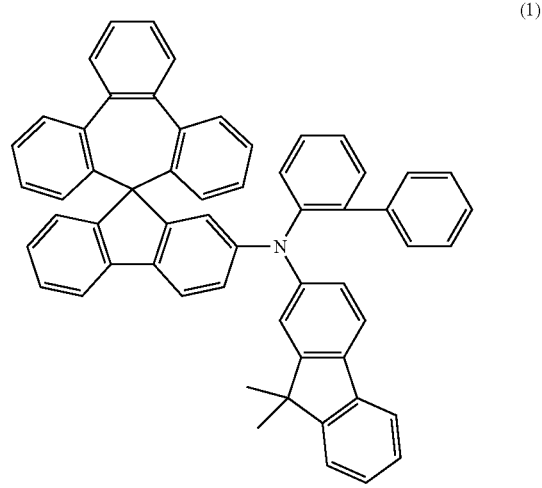

(1)

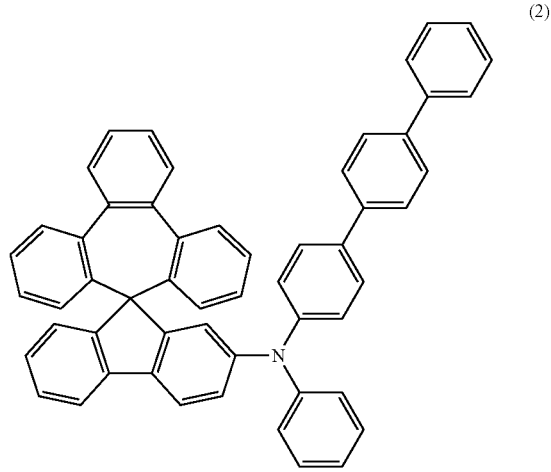

(2)

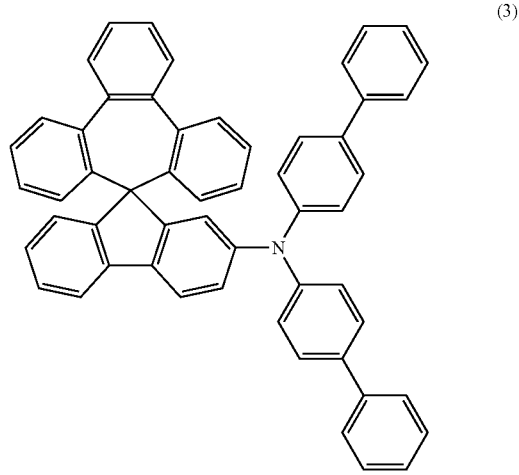

(3)

(4)
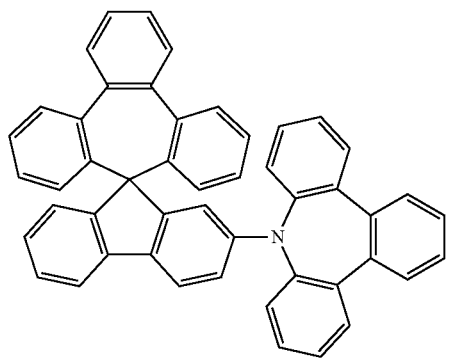
(5)
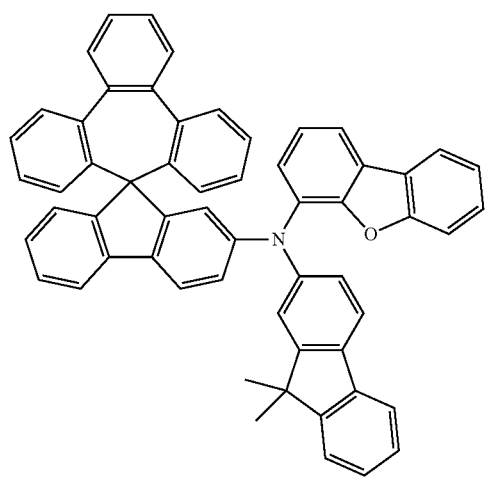
(6)
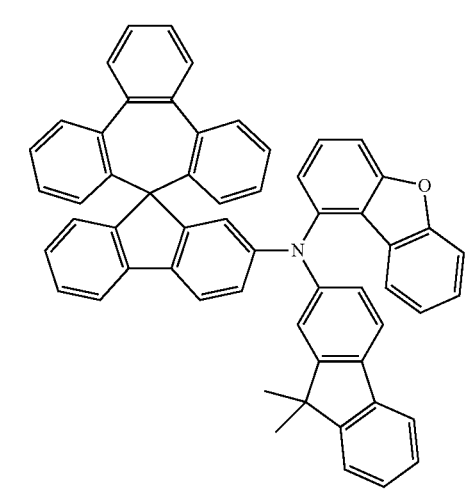
(7)
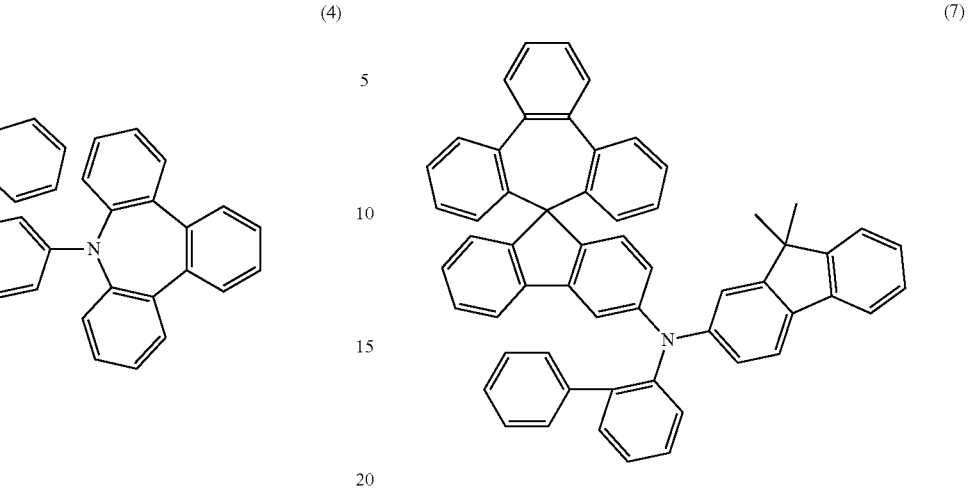
(8)
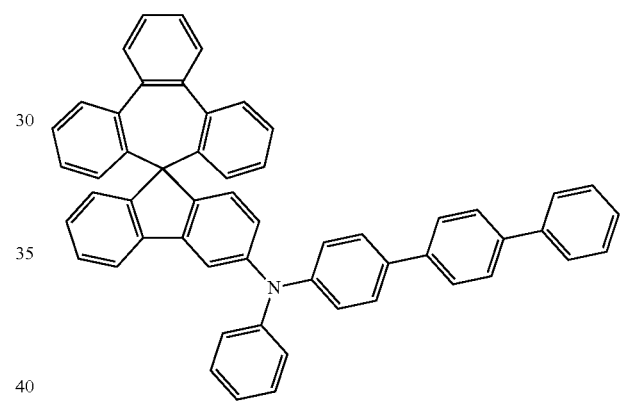
(9)
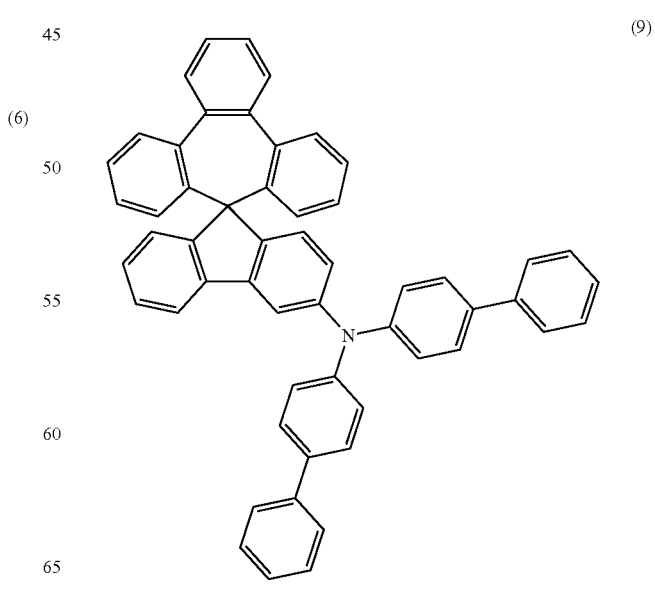

(10)
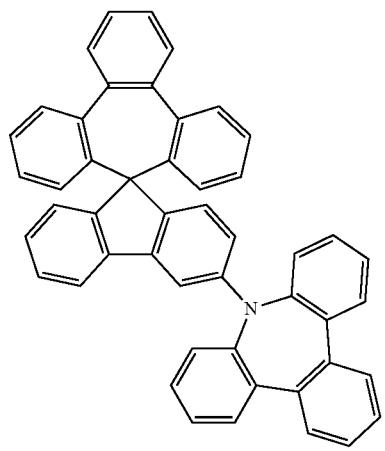
(11)
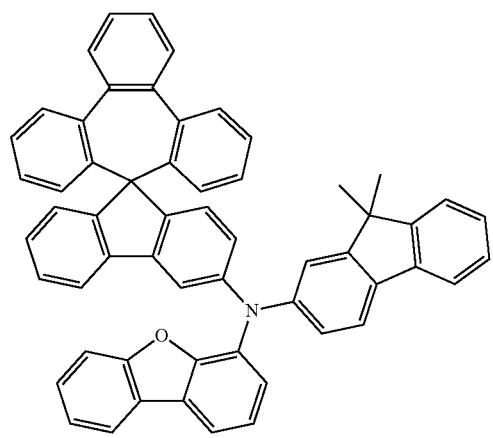
(12)
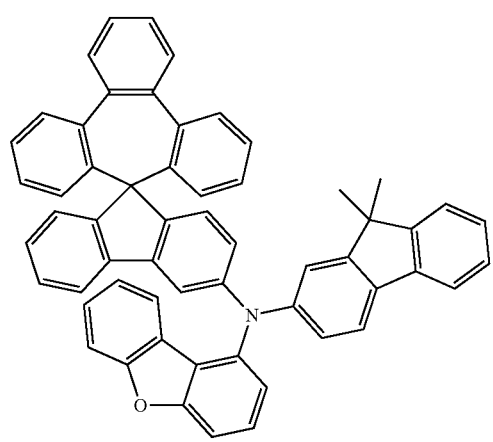
(13)
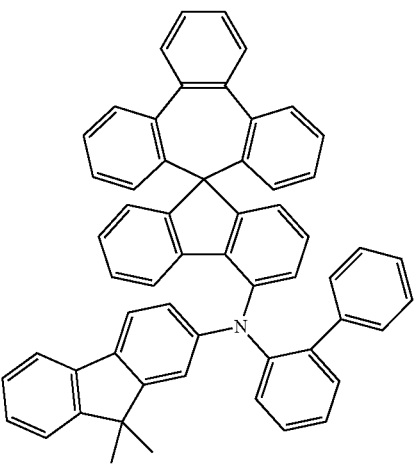
(14)
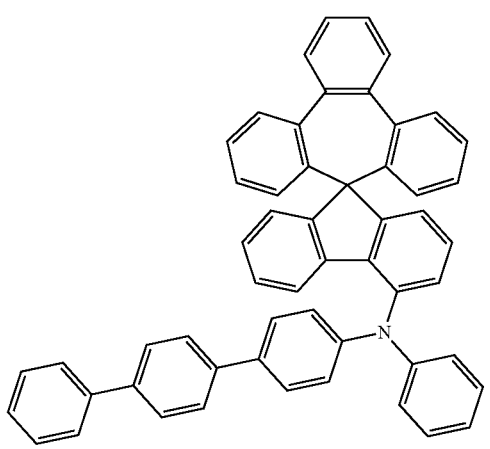
(15)
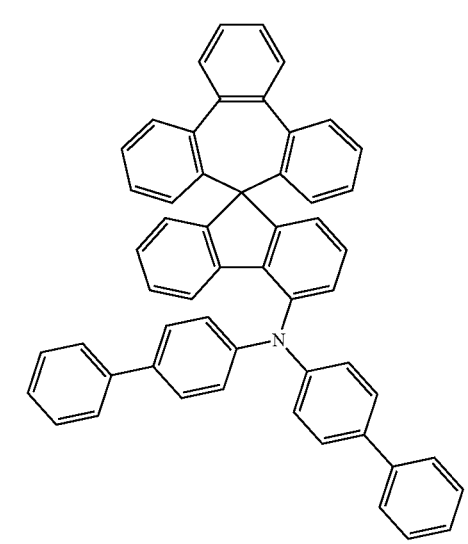

(16) 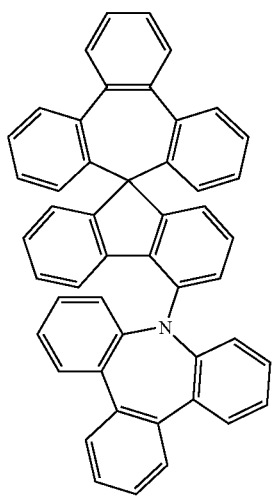
(17) 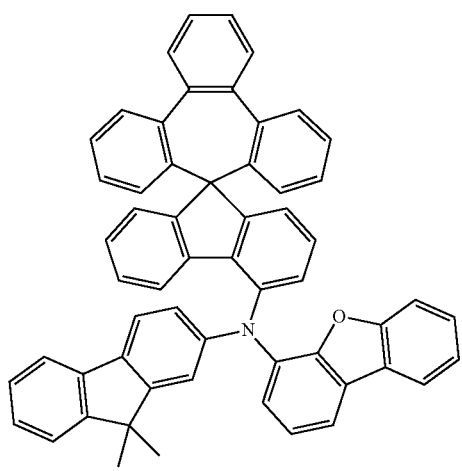
(18) 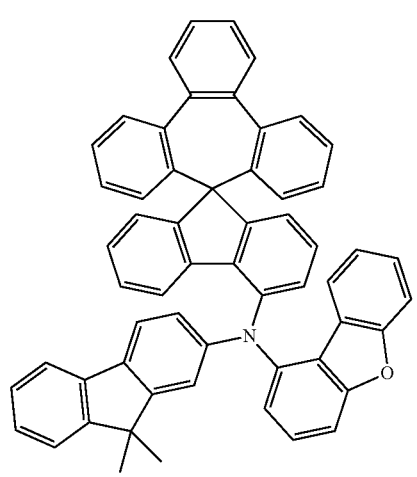
(19) 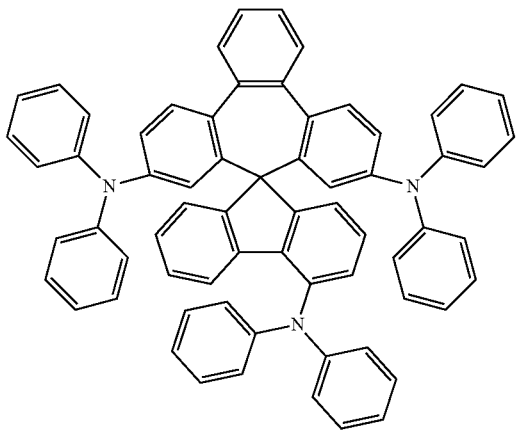
(20) 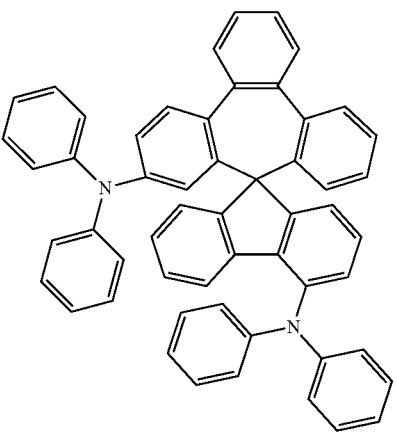
(21) 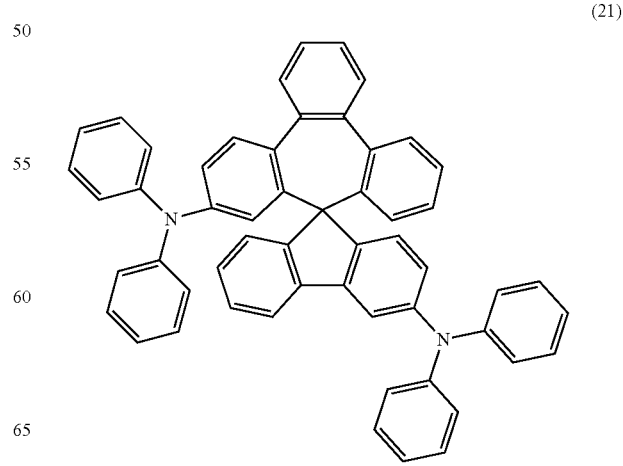

(22)
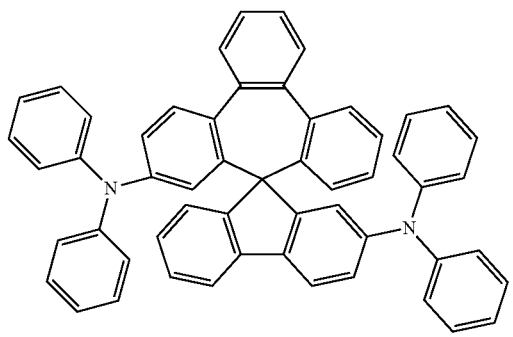
(23)
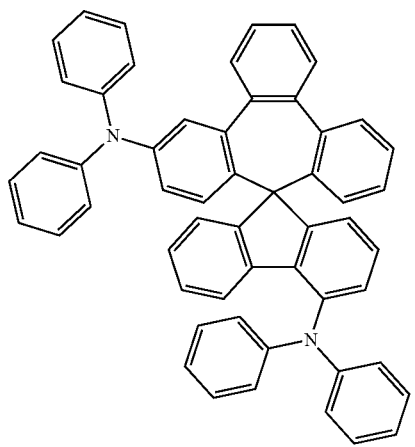
(24)
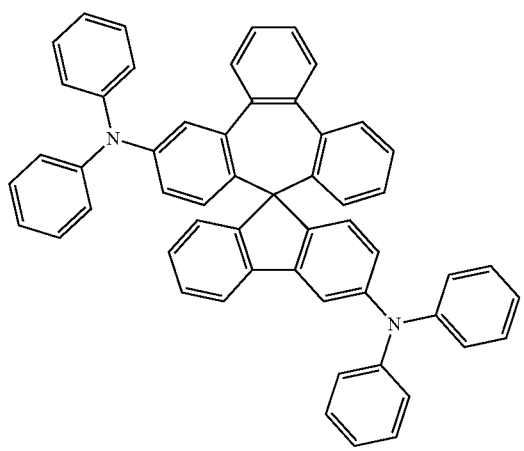
(25)
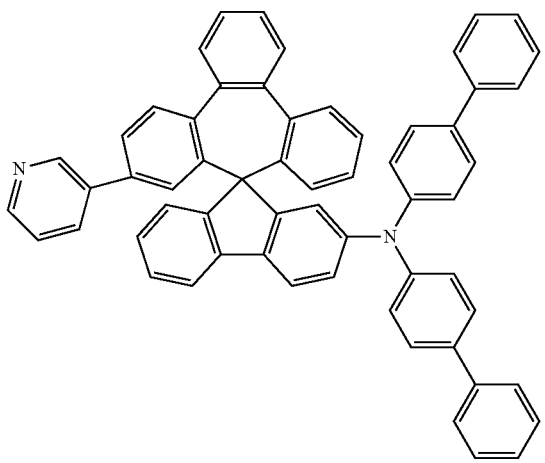
(26)
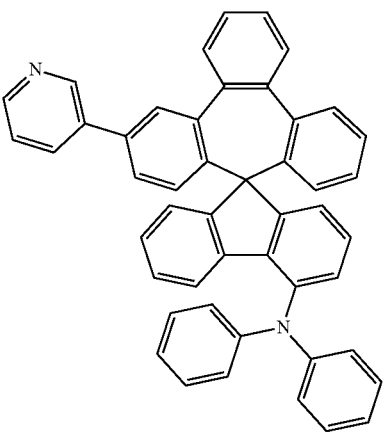
(27)
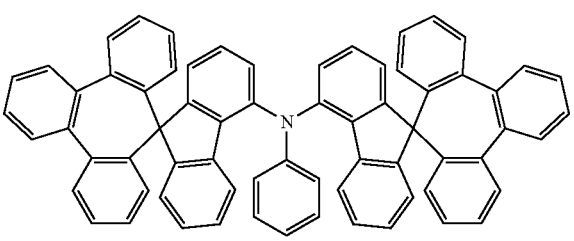
(28)

(29)
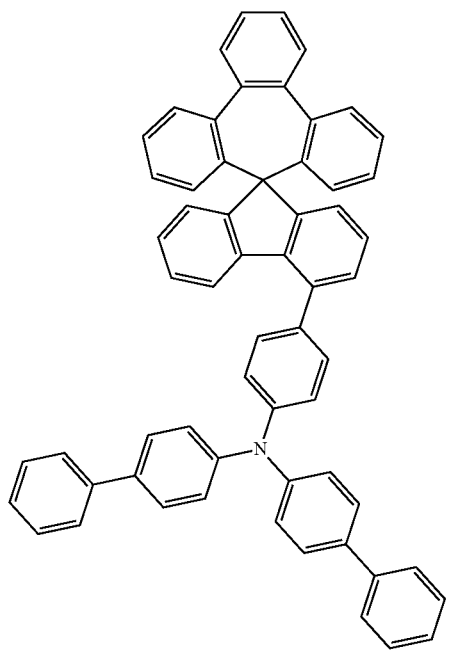
(32)
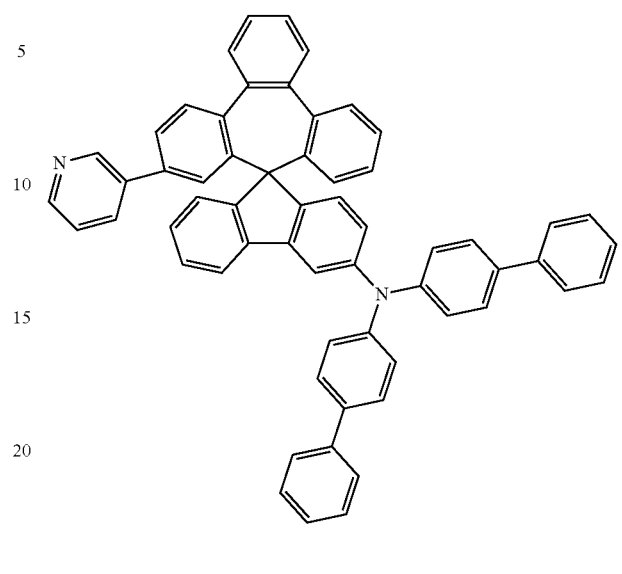
(30)
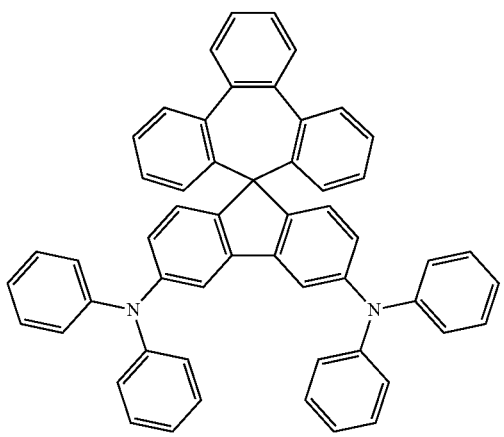
(33)
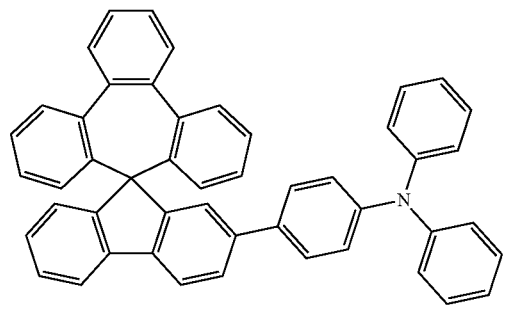
(31)
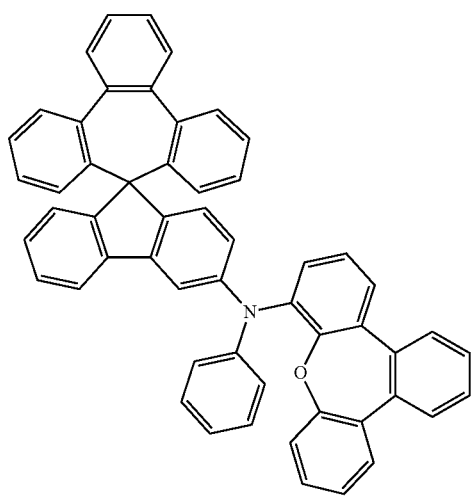
(34)
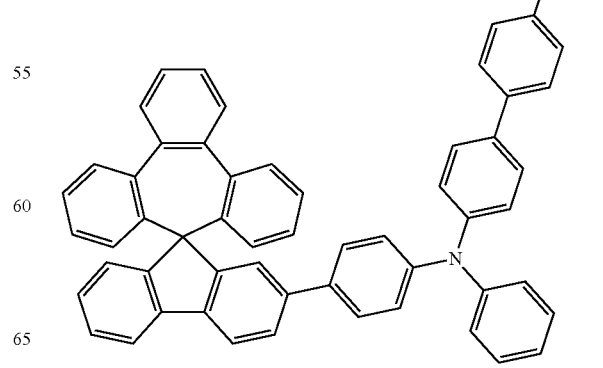

(35)
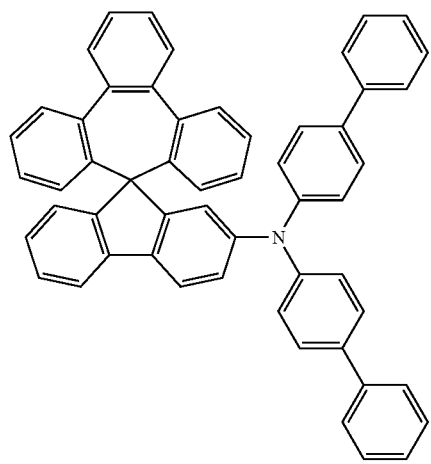
(38)
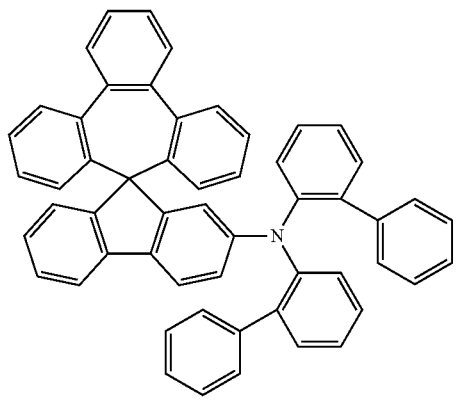
(36)
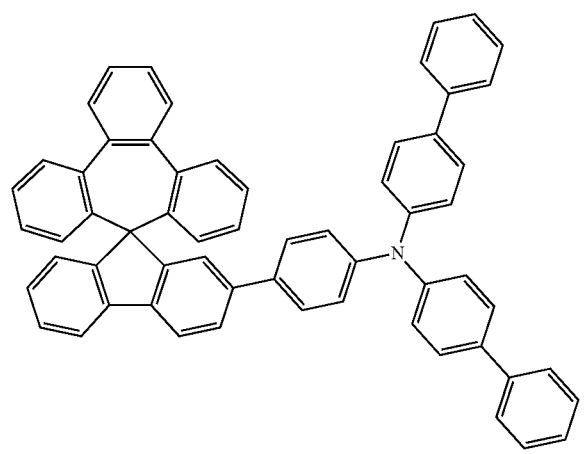
(39)
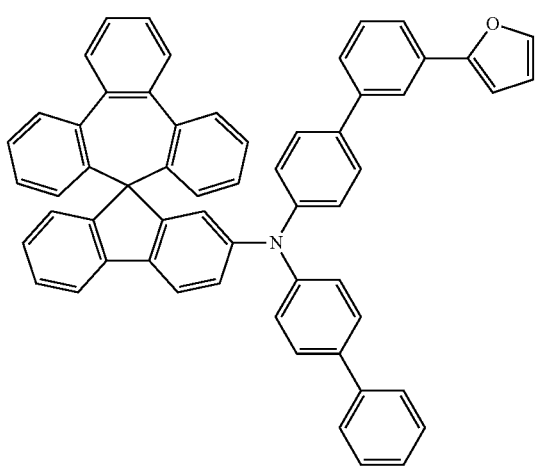
(37)
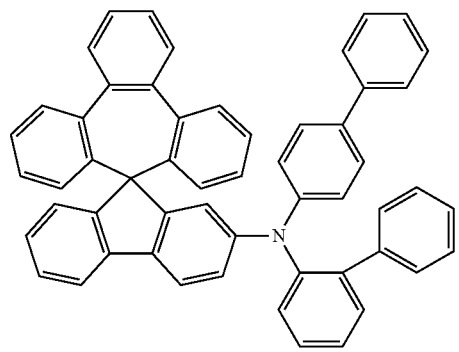
(40)
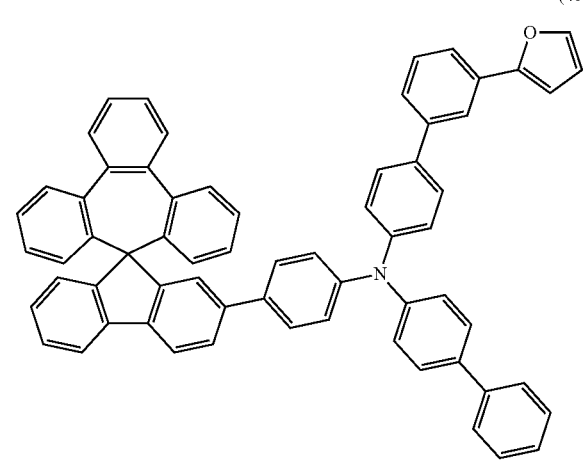

(41)
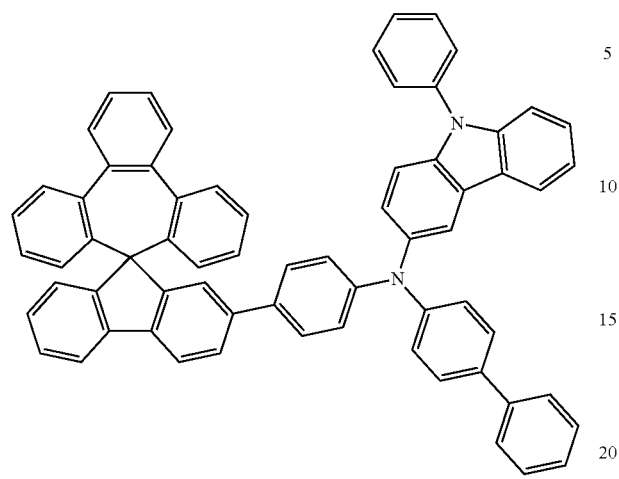
(42)
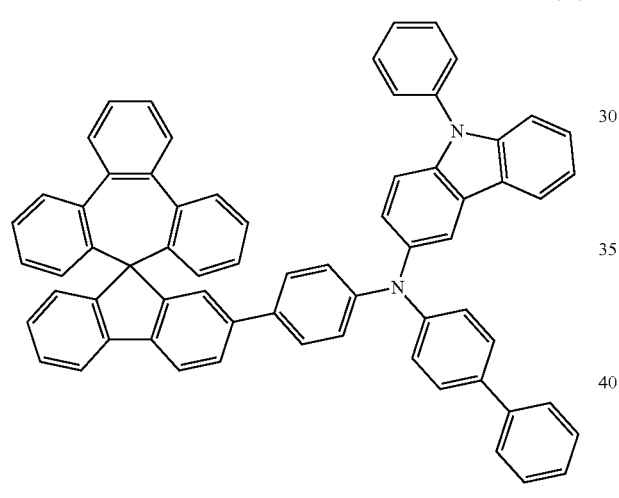
(43)
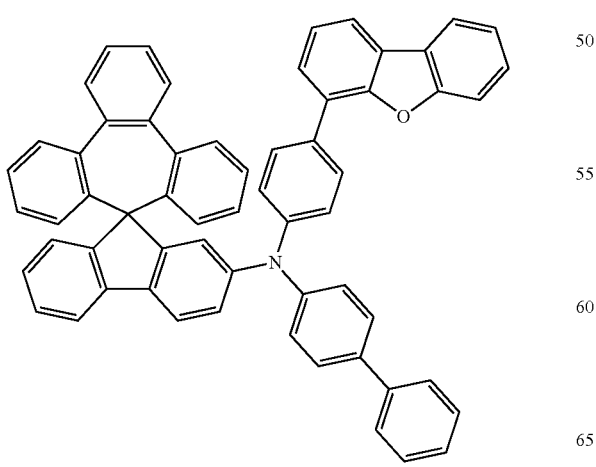
(44)
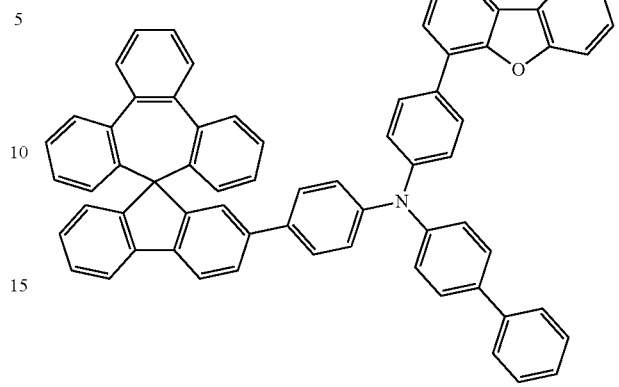
(45)
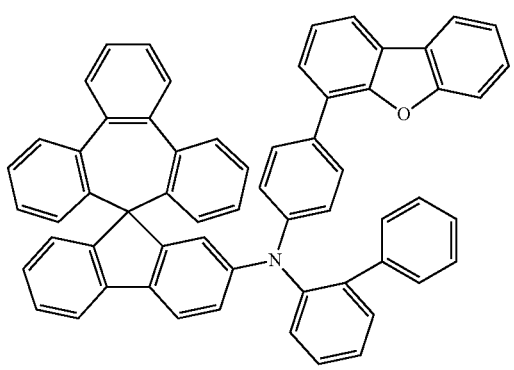
(46)
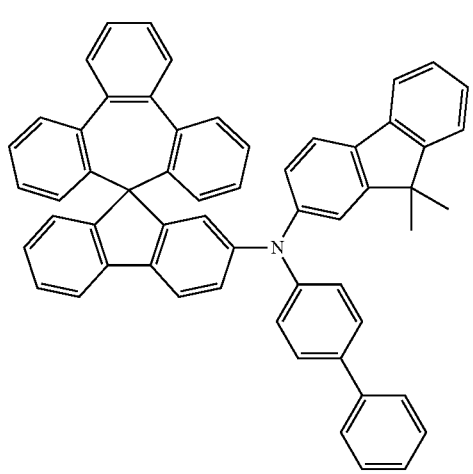

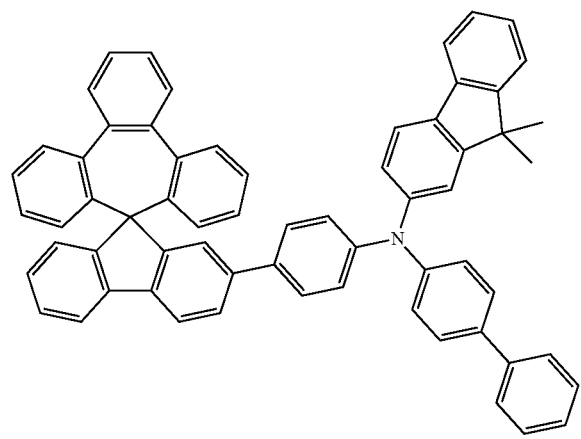
(47)
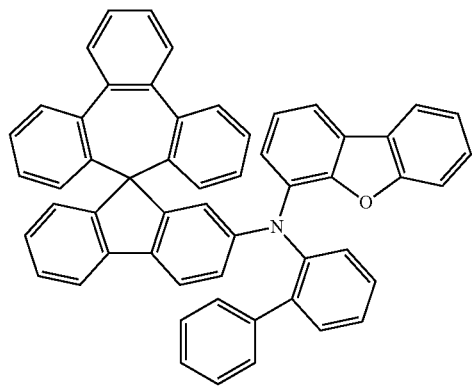
(50)
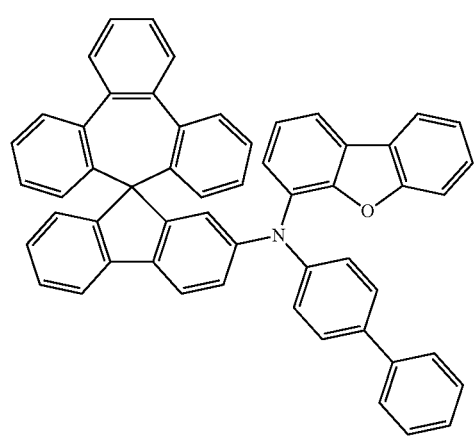
(48)
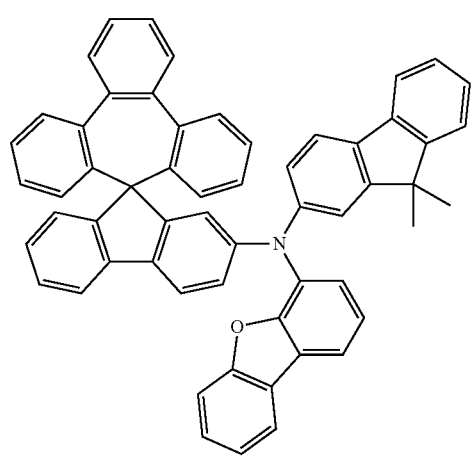
(51)
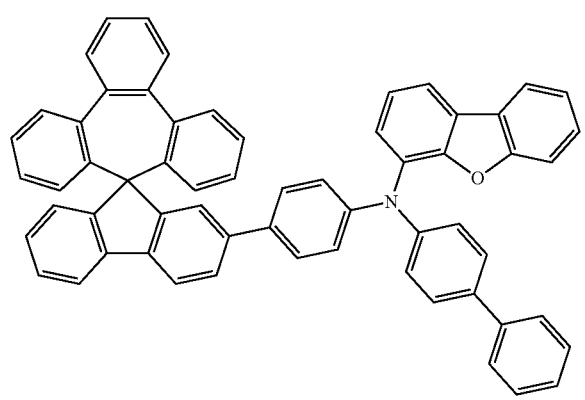
(49)
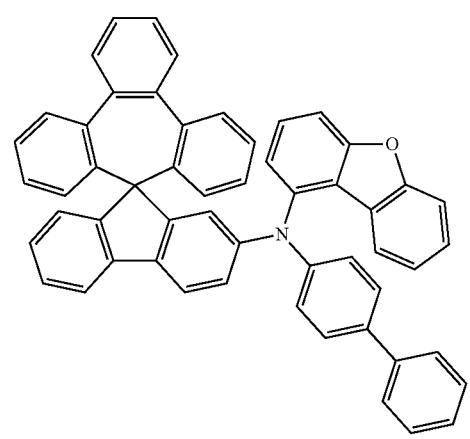
(52)

(53)
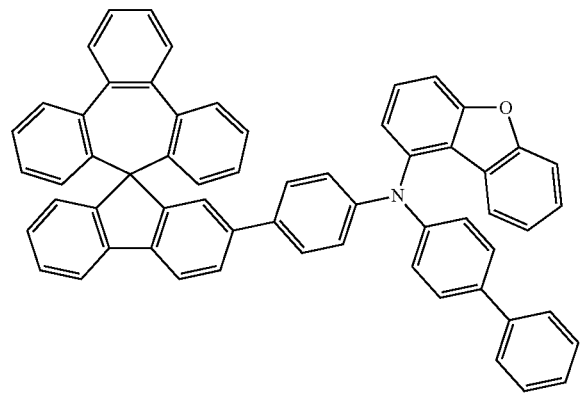
(54)
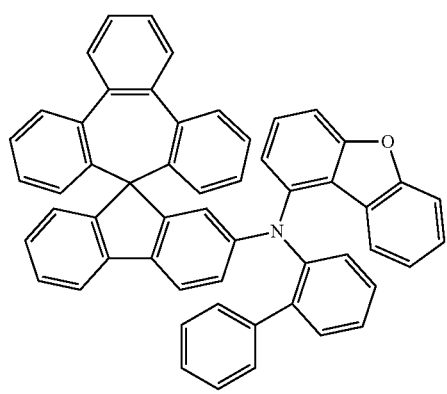
(55)
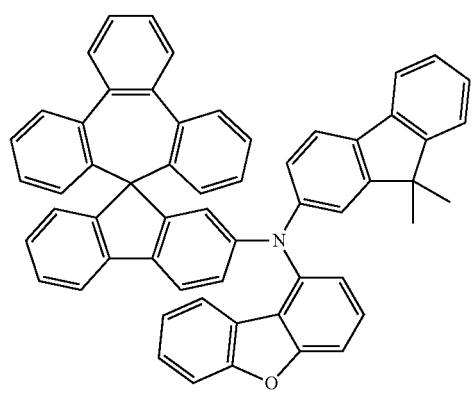
(56)
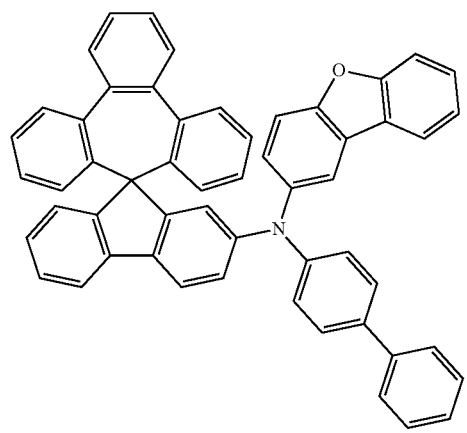
(57)
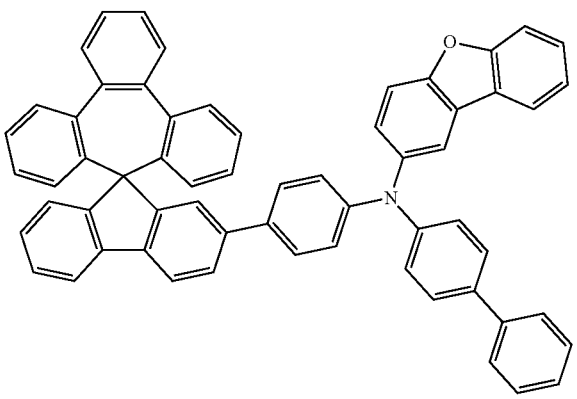
(58)
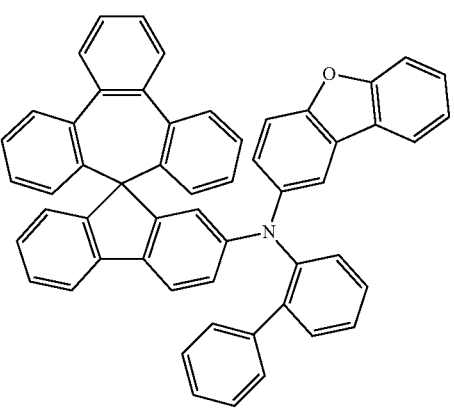
(59)
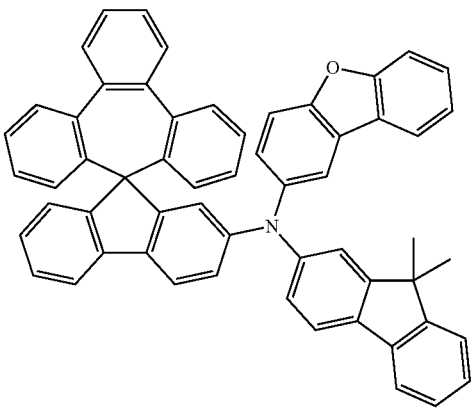
(60)
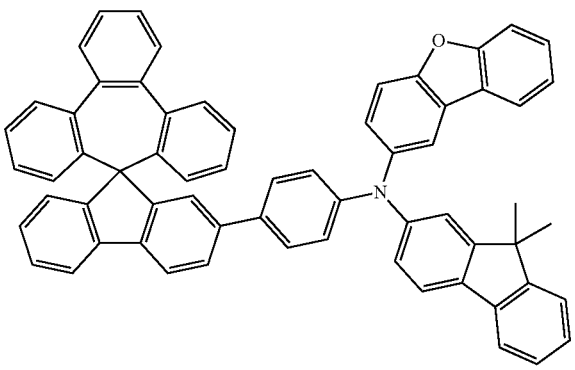

(61)
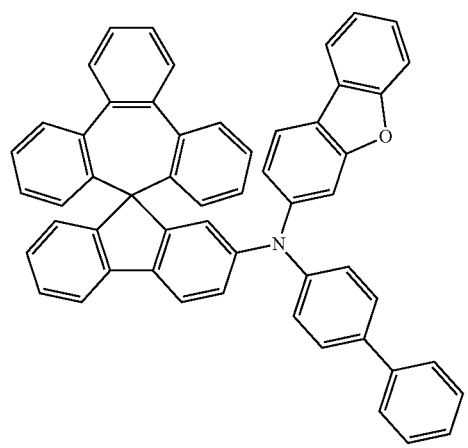
(62)
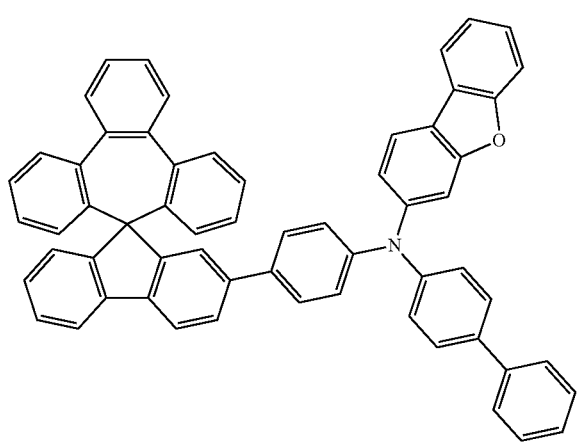
(63)
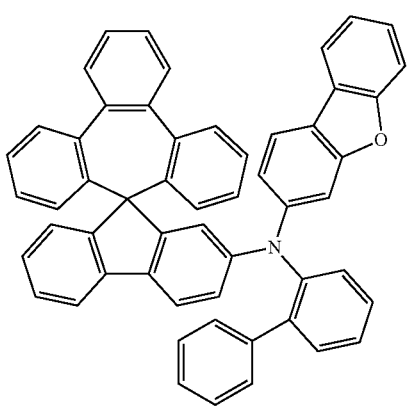
(64)
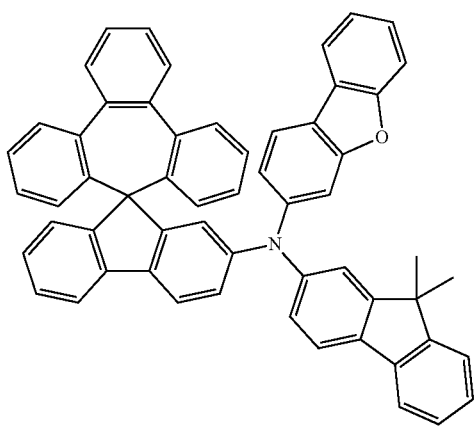
(65)
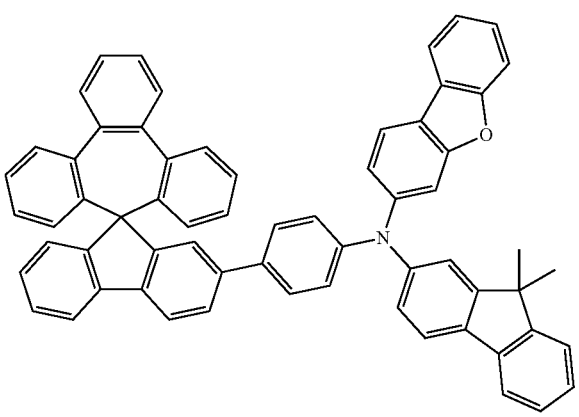
(66)
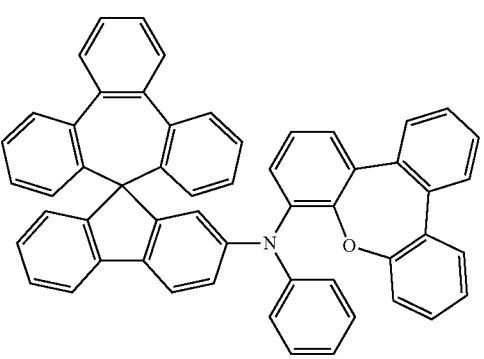

(67)
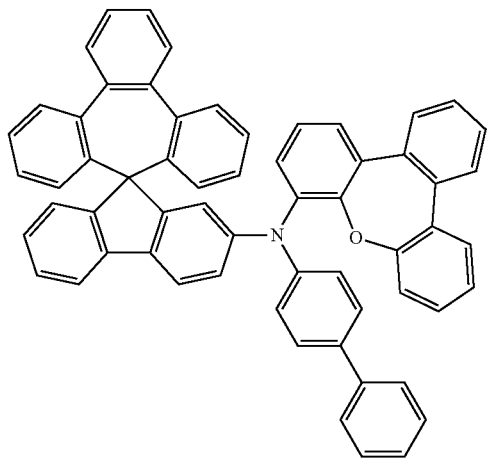
(68)
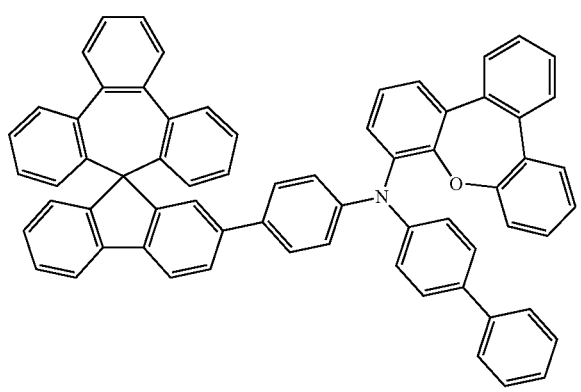
(69)
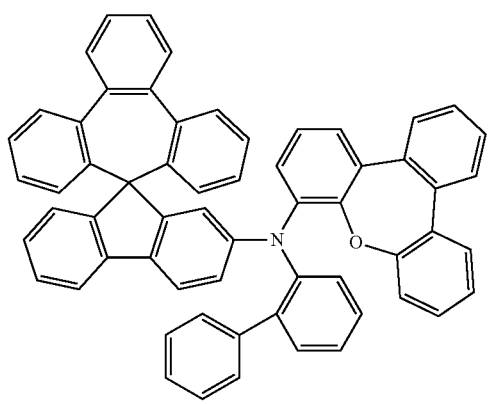
(70)
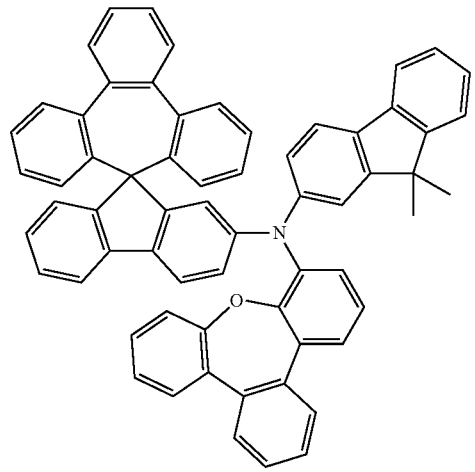
(71)
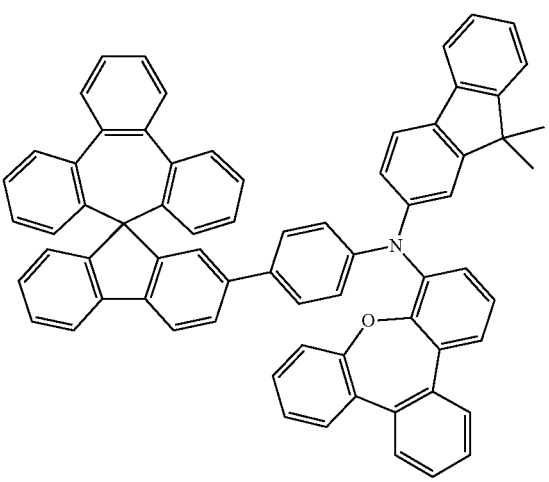
(72)
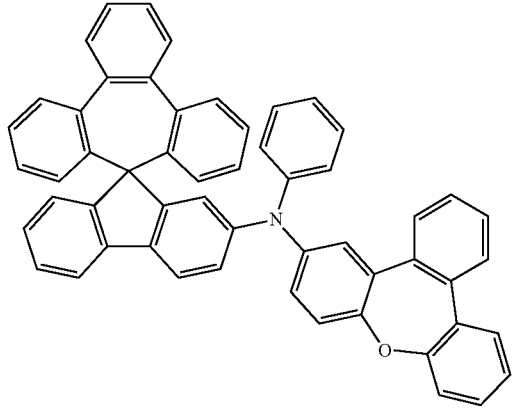

(73)
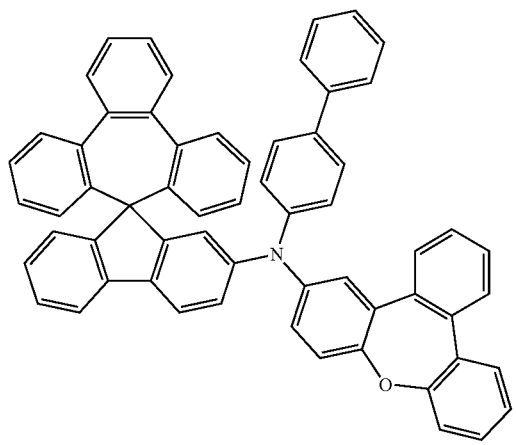
(74)
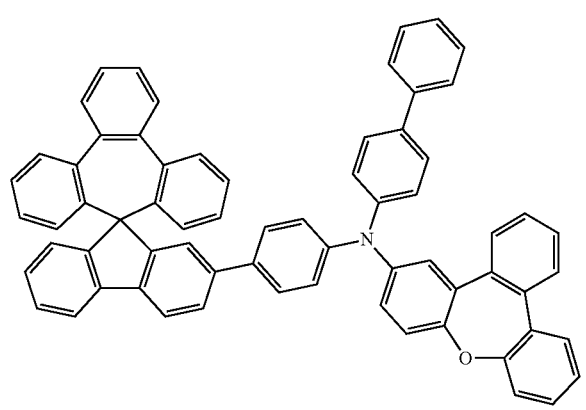
(75)
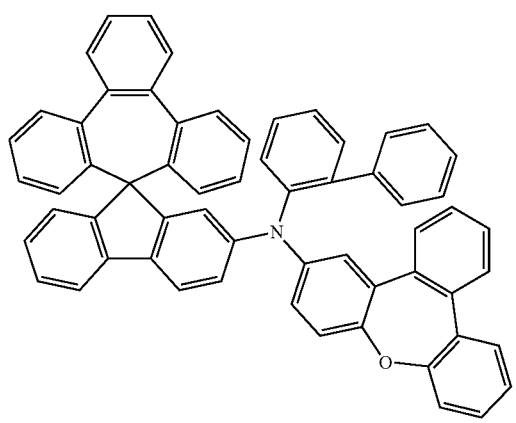
(76)
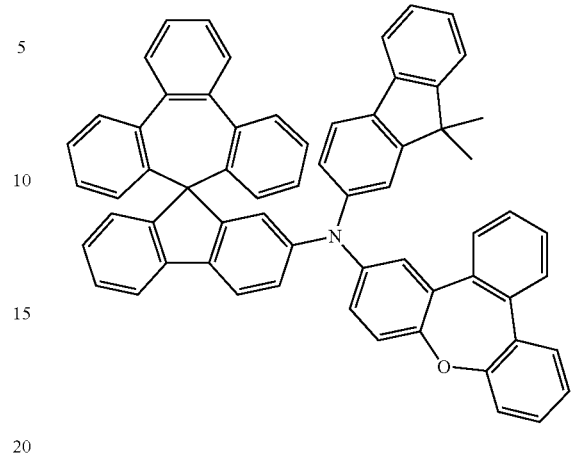
(77)
(78)
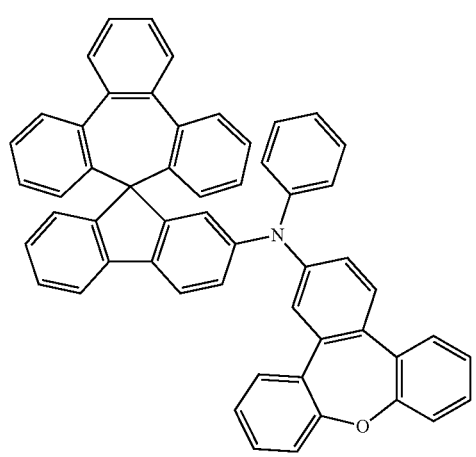

(79)
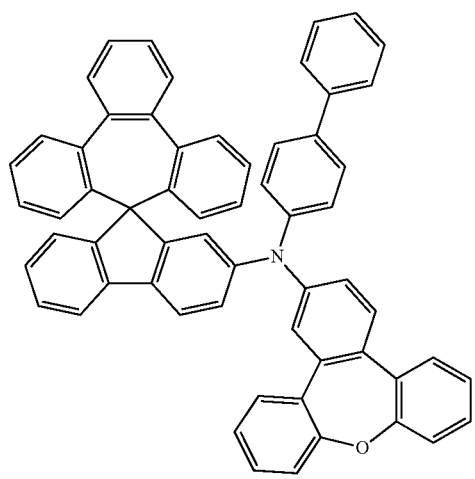
(80)
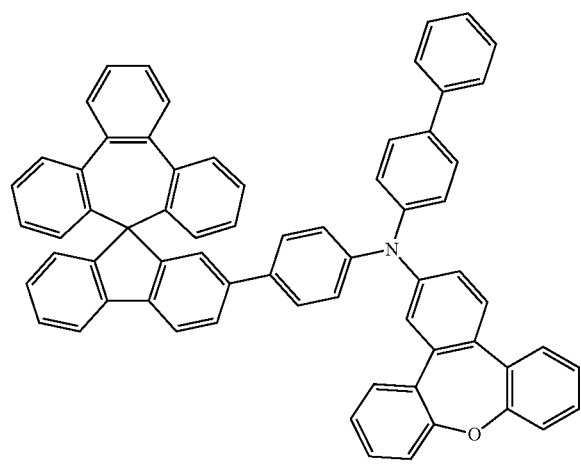
(81)
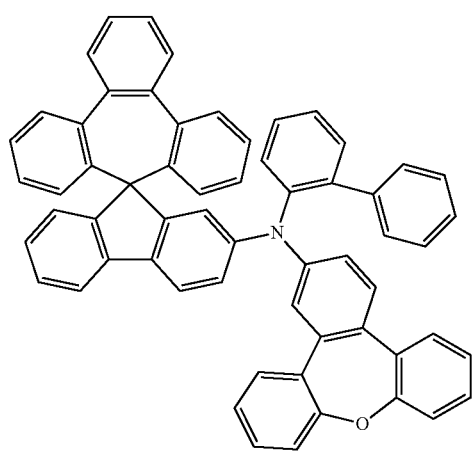
(82)
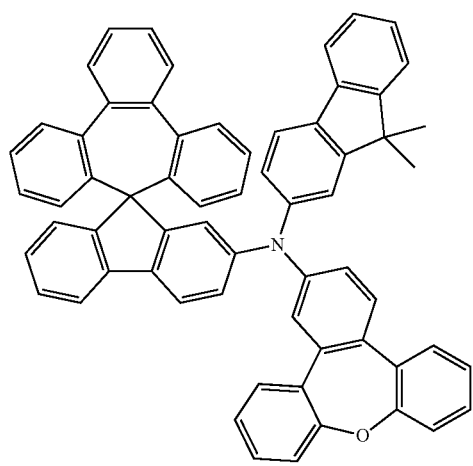
(83)
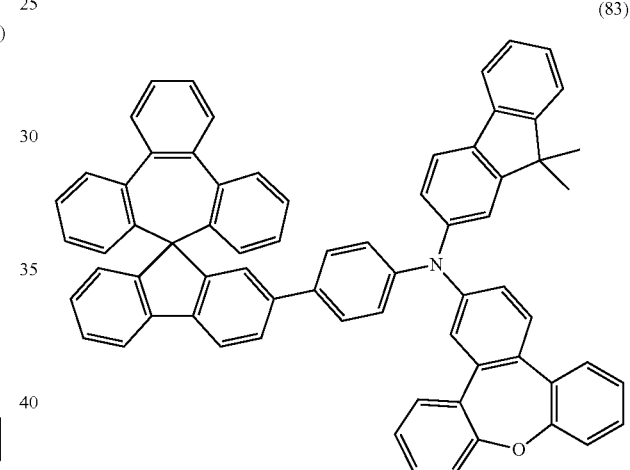
(84)
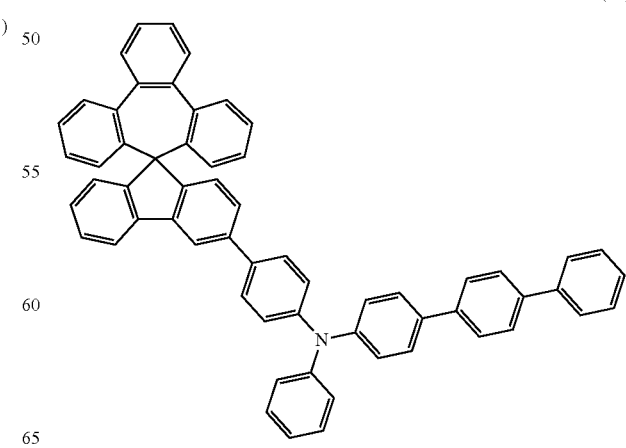

(85)
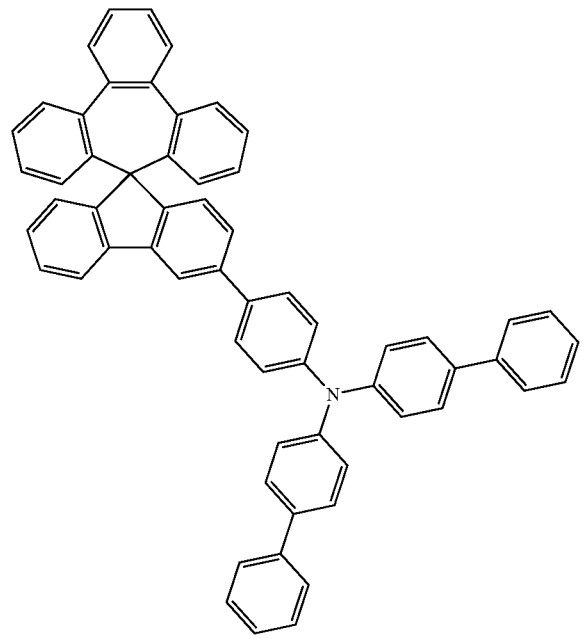
(86)
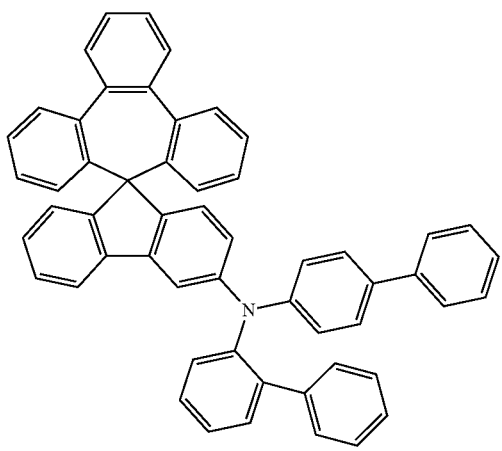
(87)
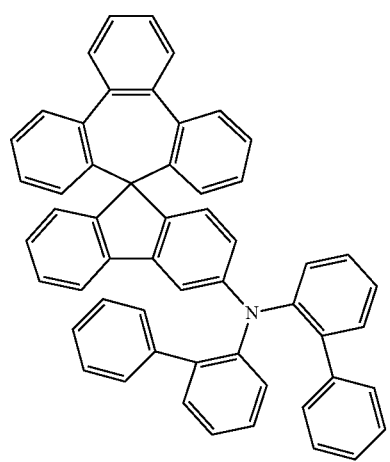
(88)
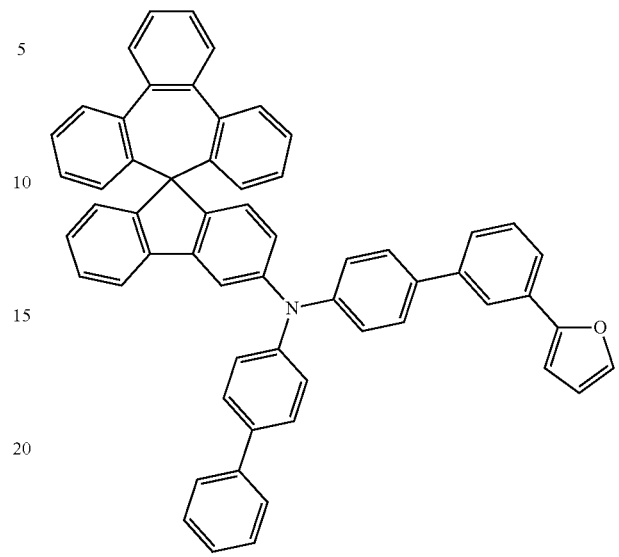
(89)
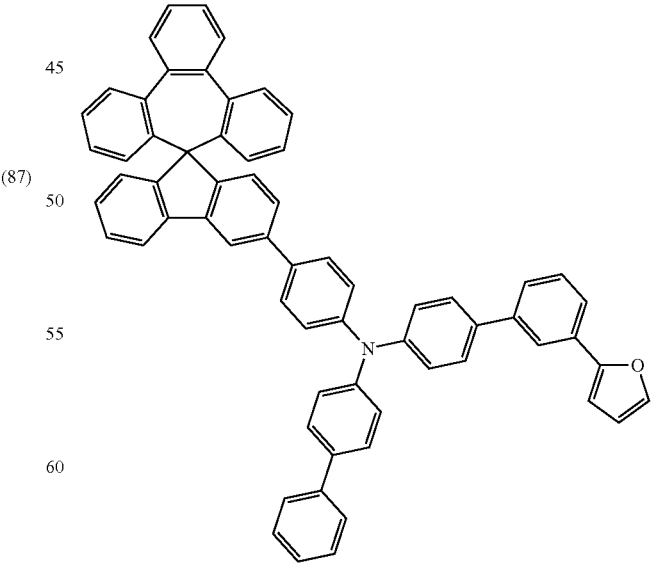

(90)
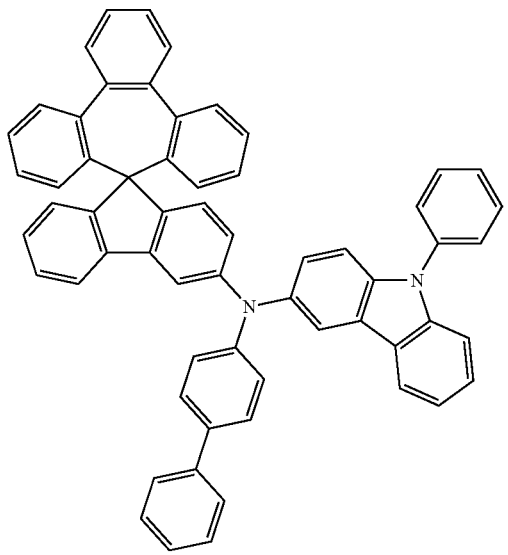
(91)
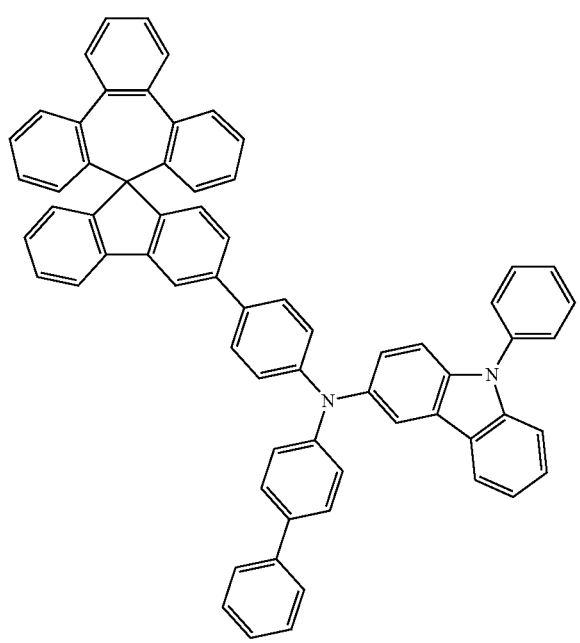
(92)
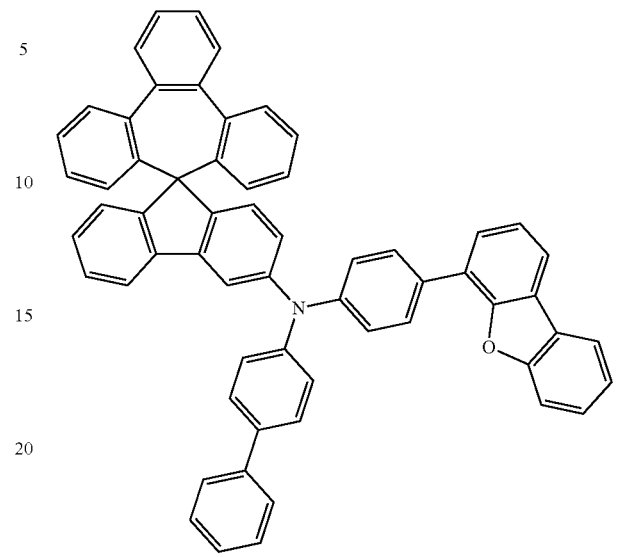
(93)
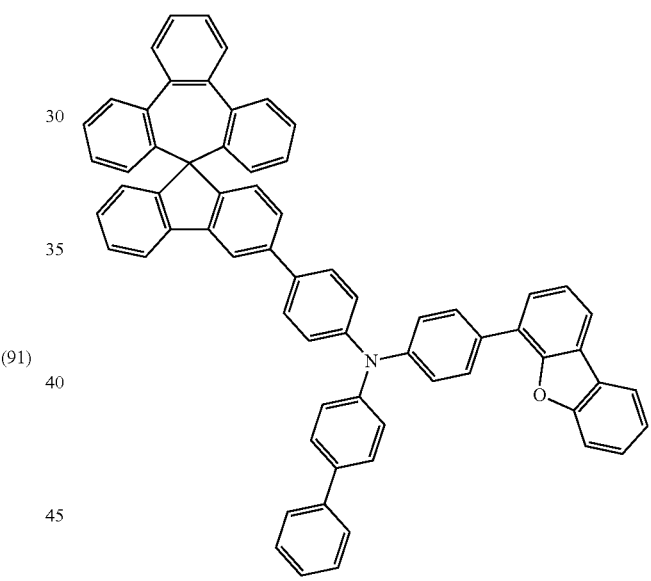
(94)
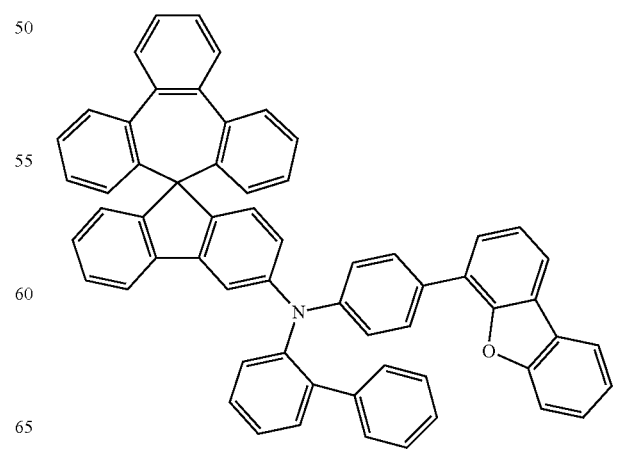

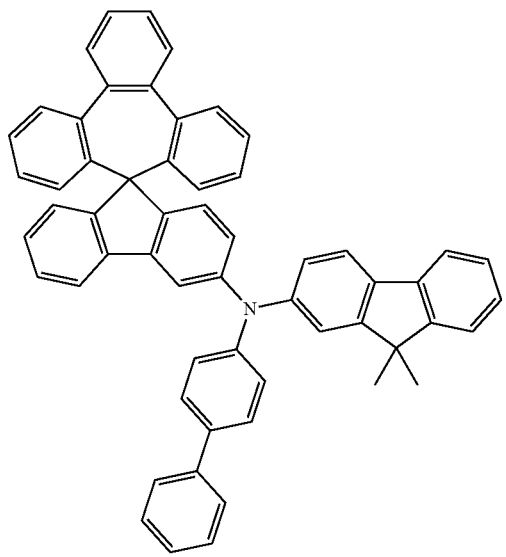
(95)
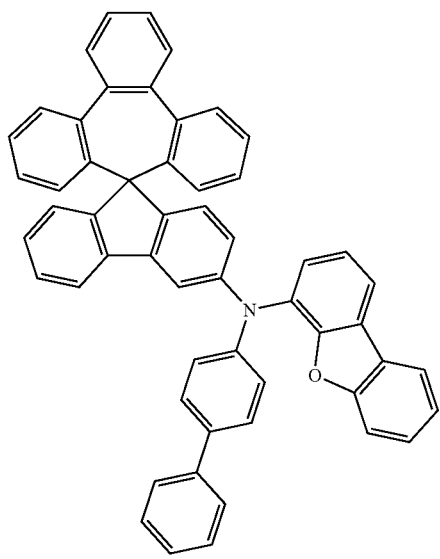
(97)
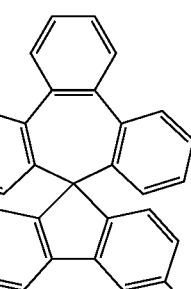
(98)
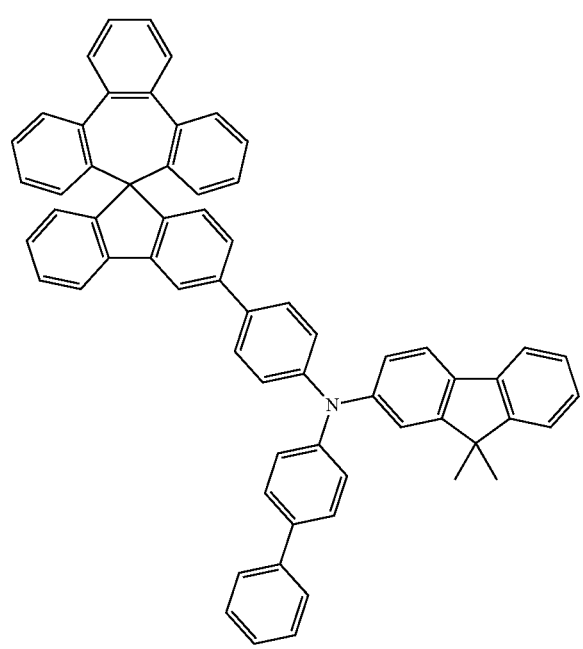
(96)
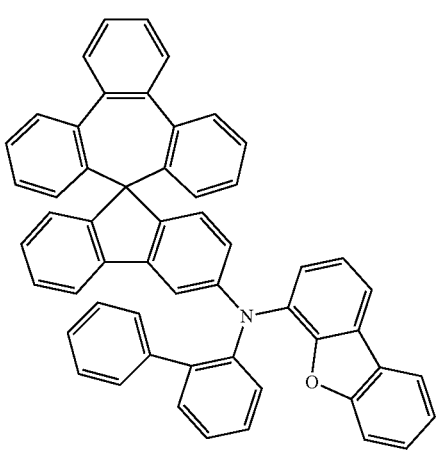
(99)

(100) 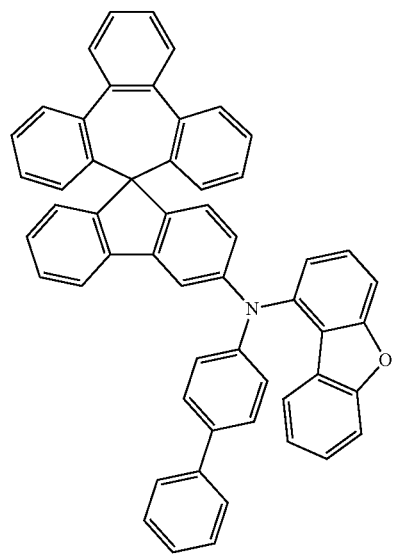
(102) 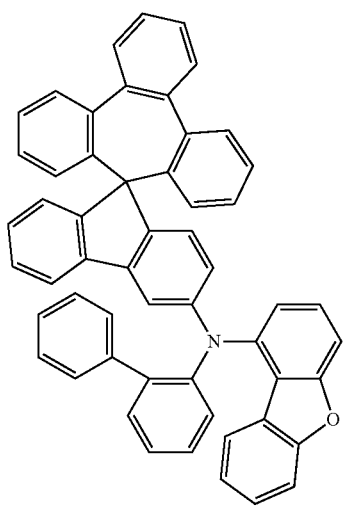
(101) 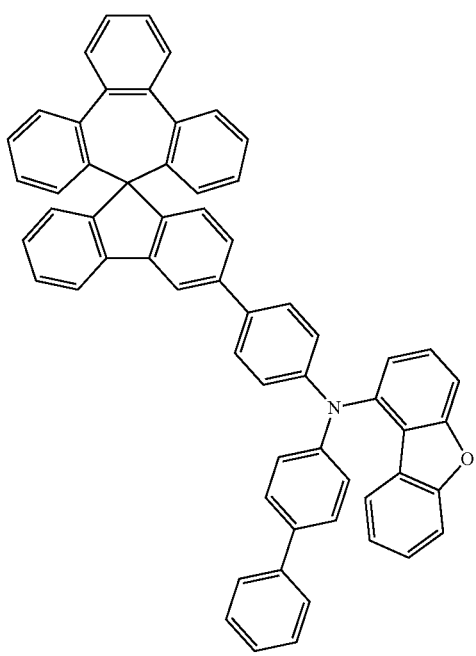
(103) 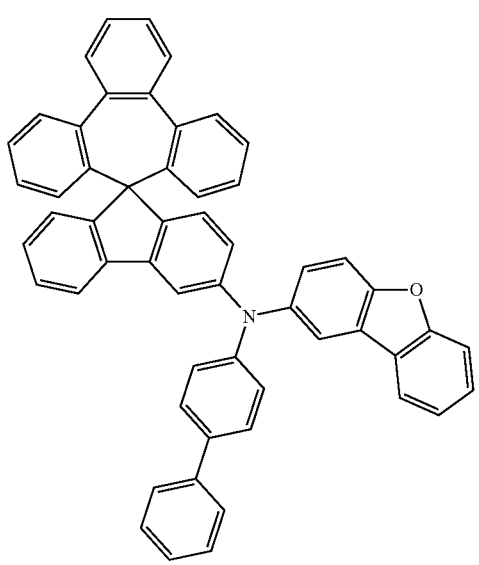

(104)
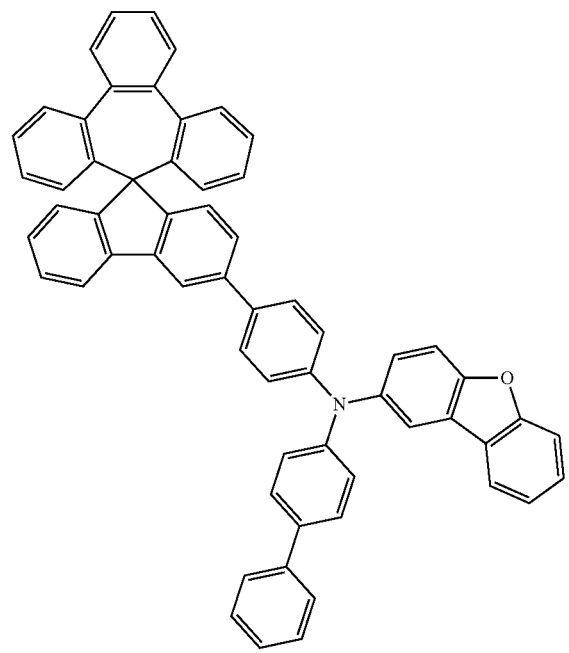
(106)
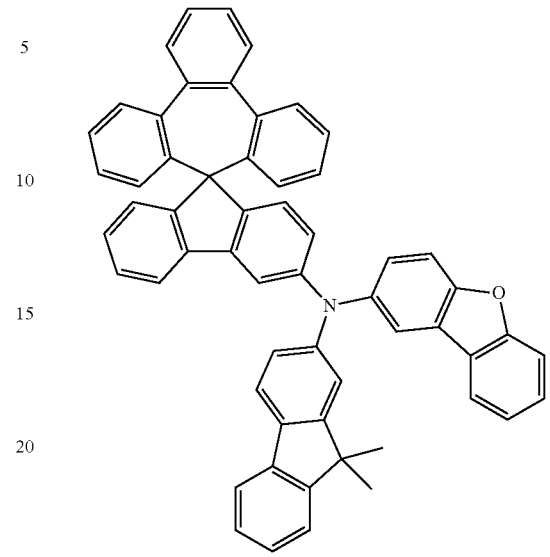
(105)
(107)
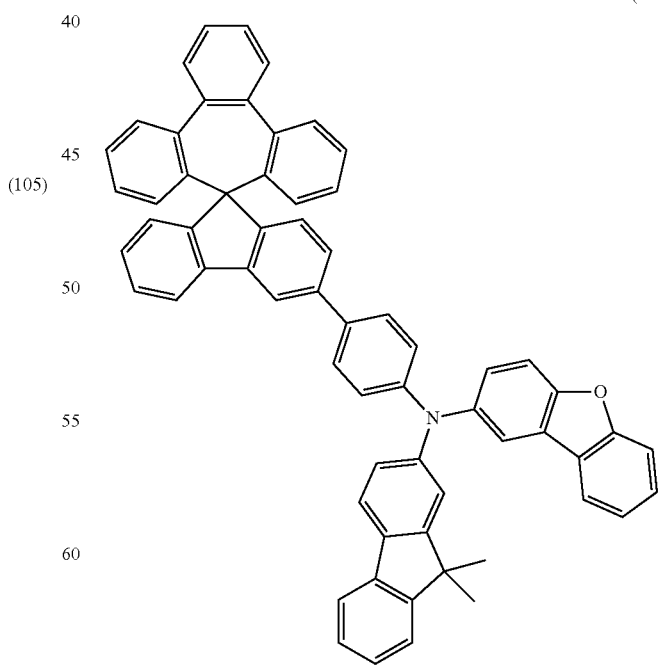

(108)
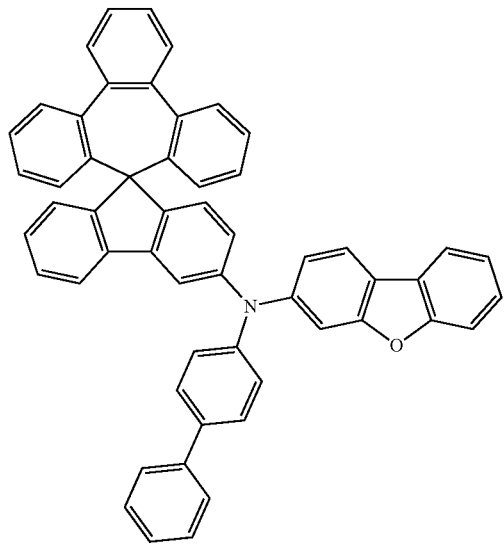
(109)
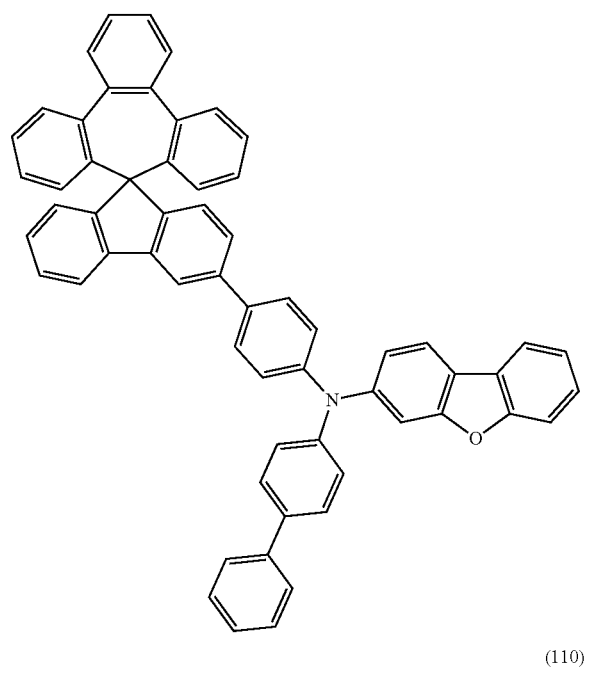
(110)
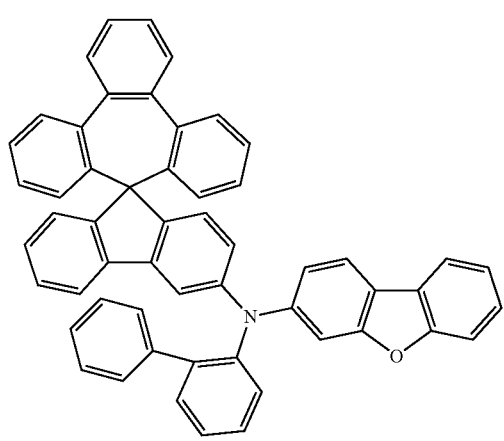
(111)
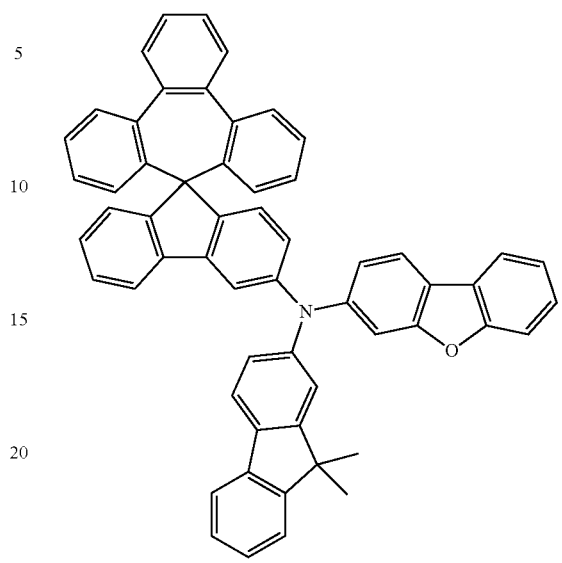
(112)
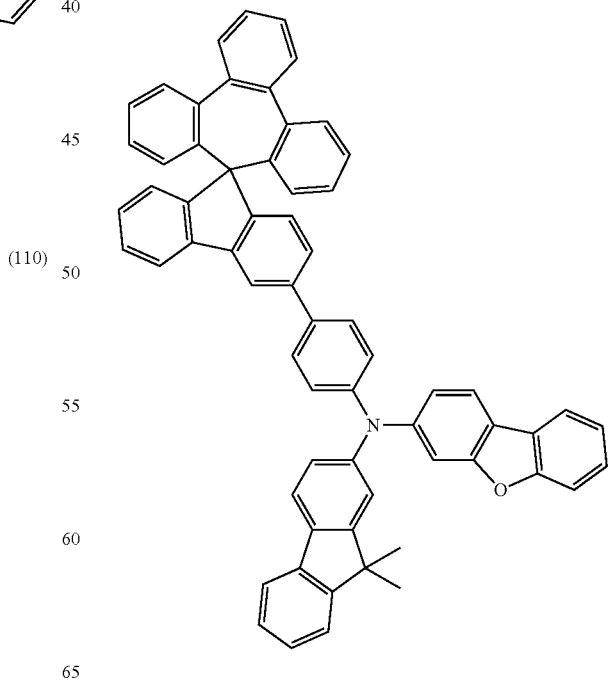

(113)
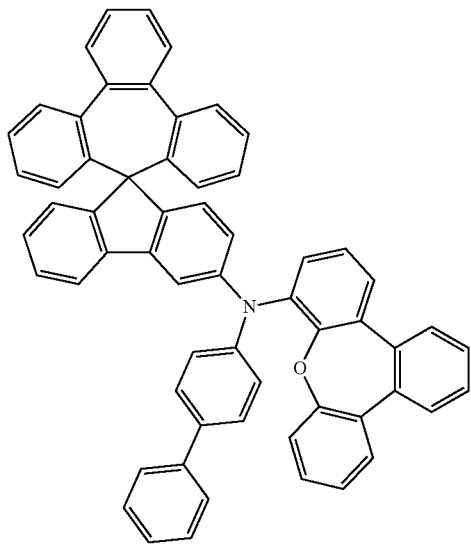
(114)
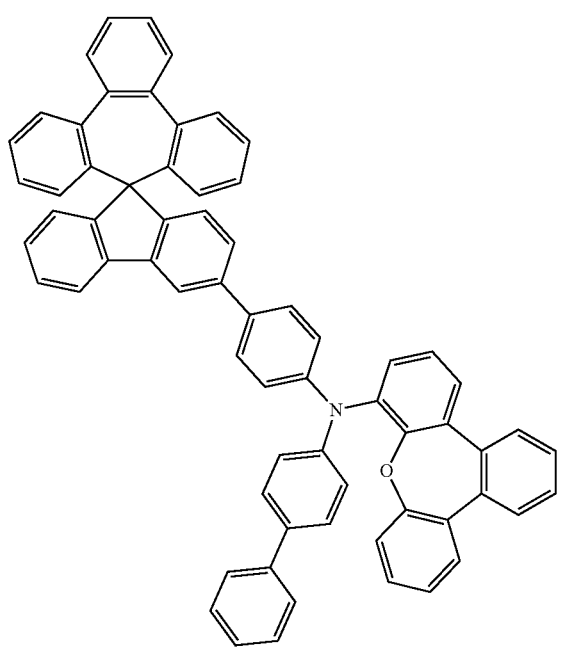
(115)
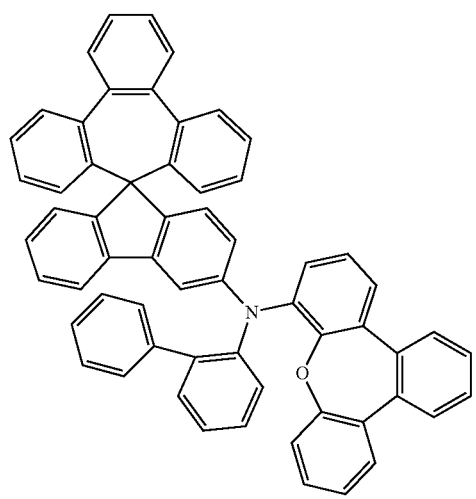
(116)
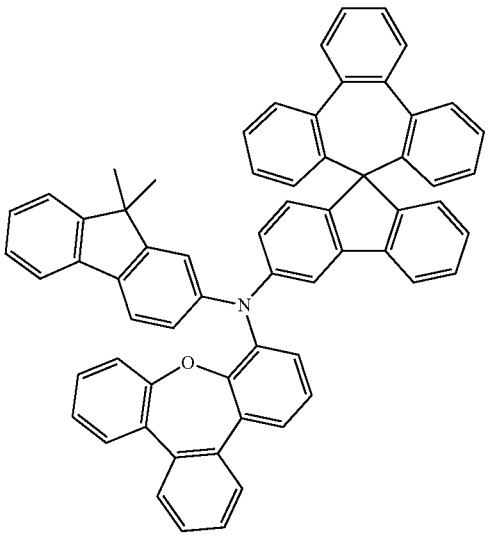
(117)
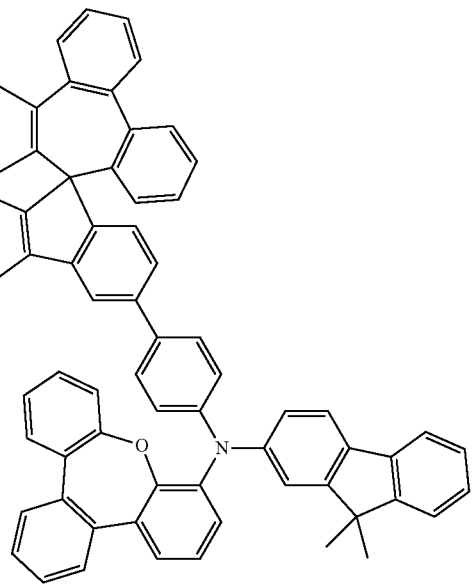

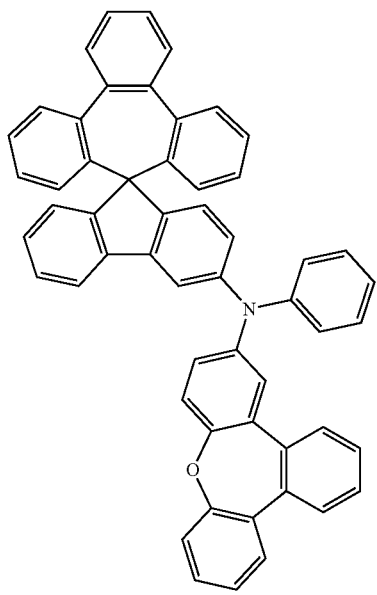
(118)
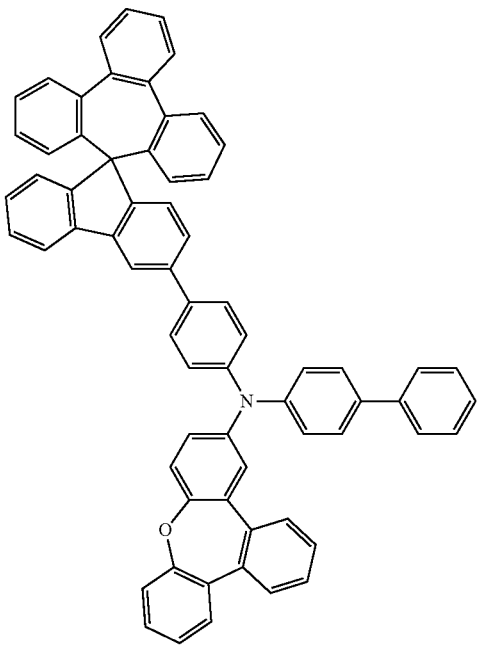
(120)
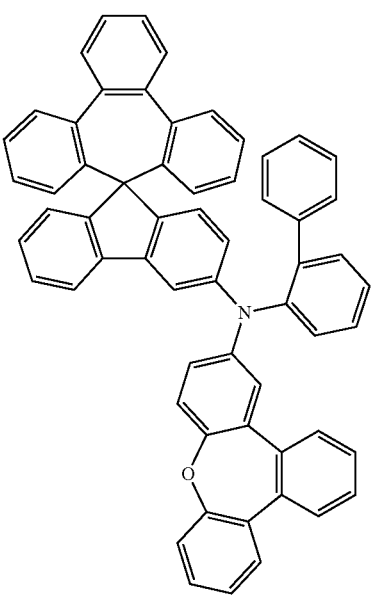
(121)

(122) 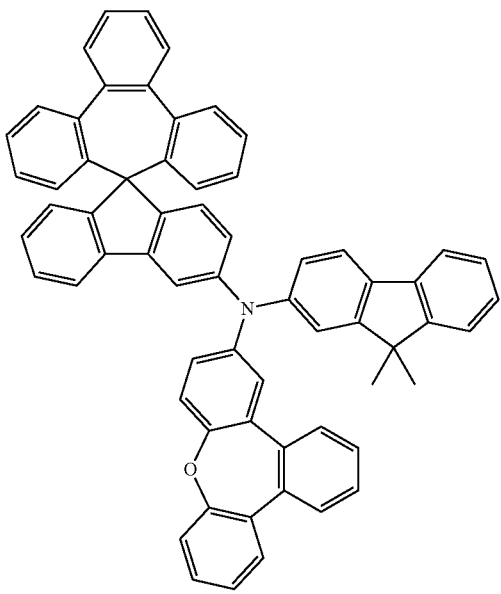
(124) 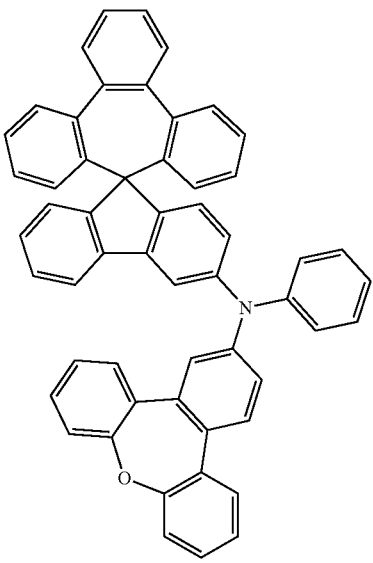
(123) 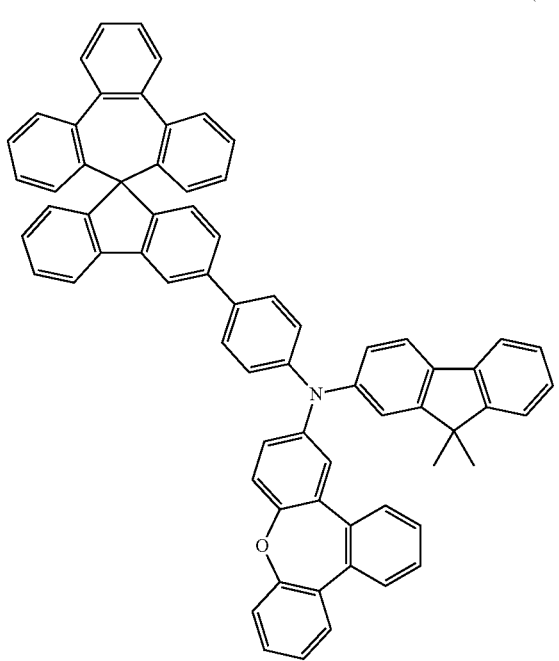
(125) 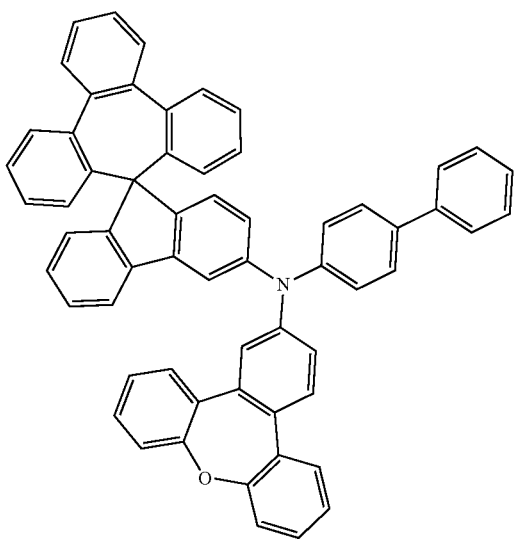

(126)
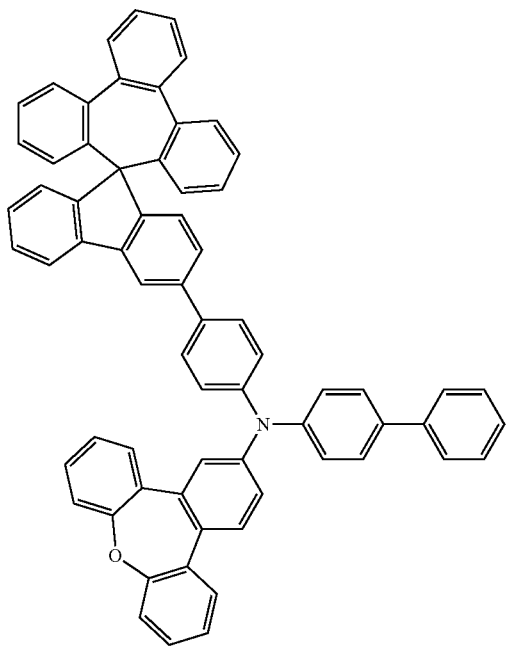
(127)
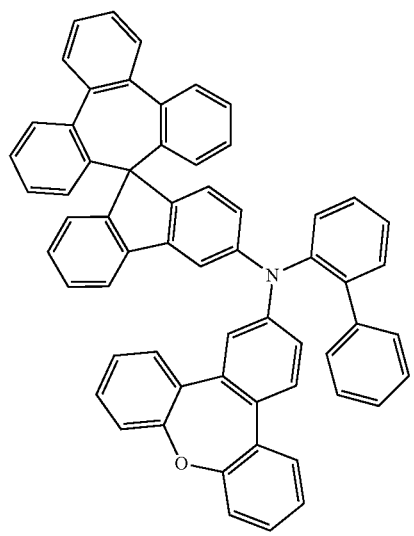
(128)
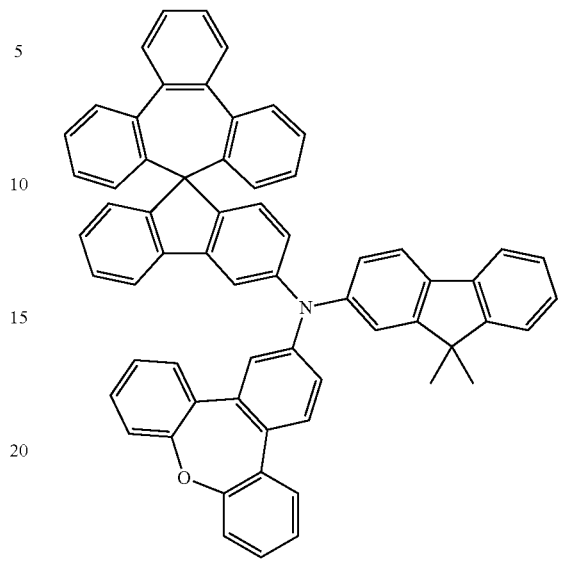
(129)
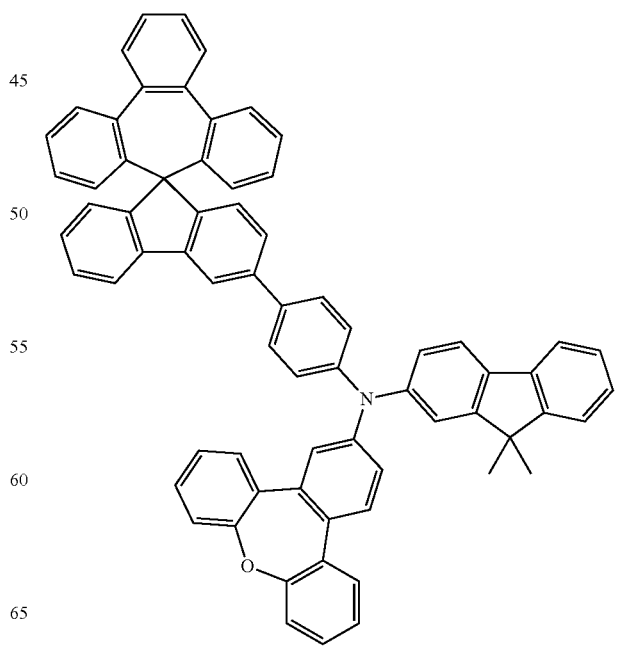

(130)
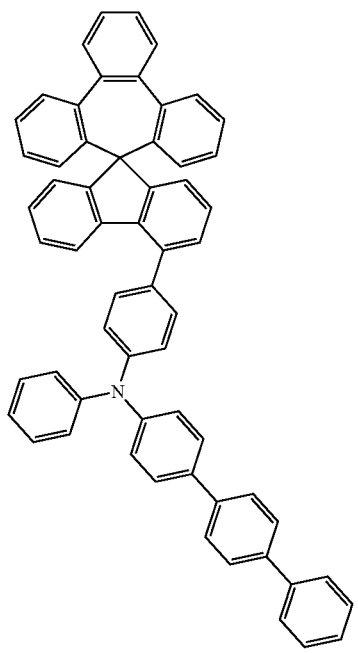
(132)
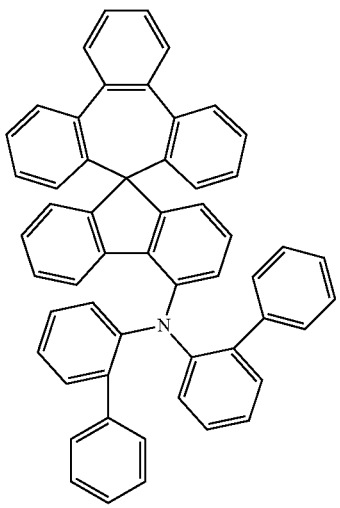
(131)
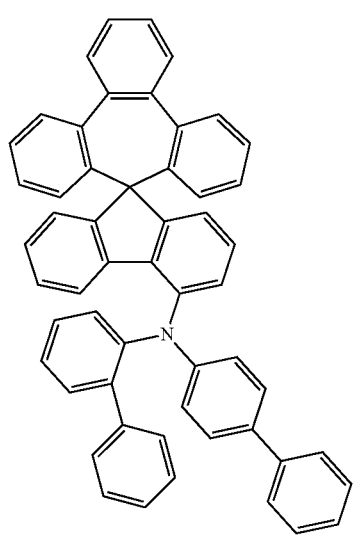
(133)
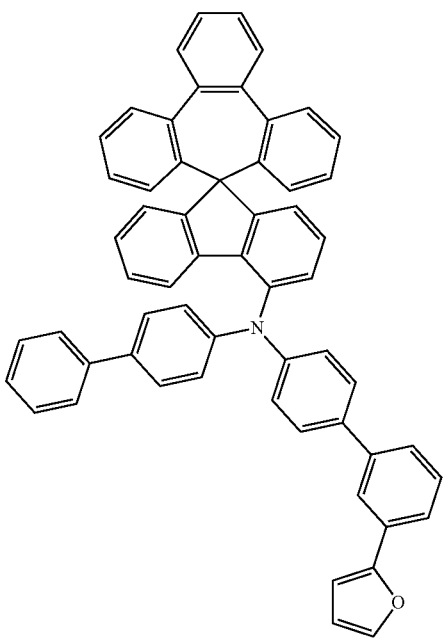

(134)
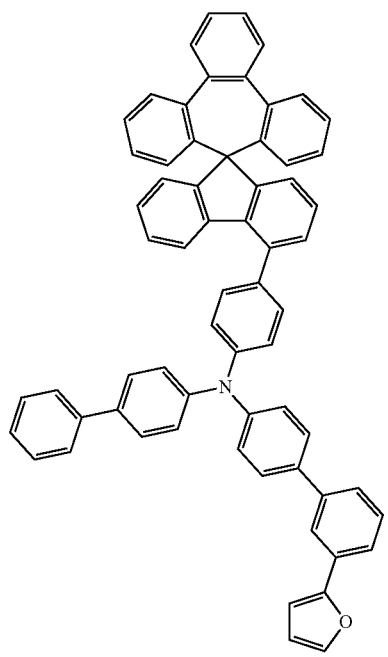
(136)
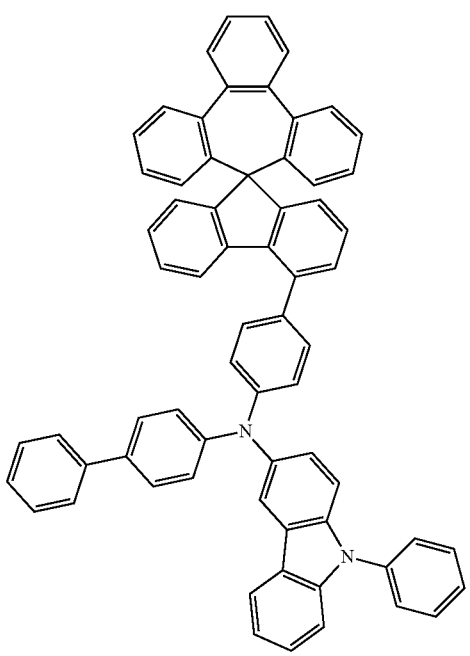
(135)
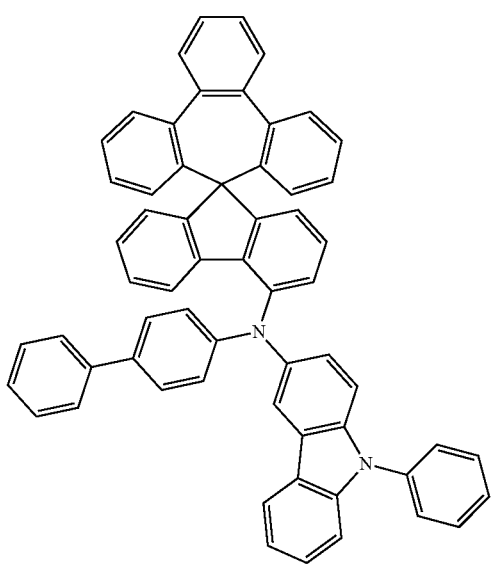
(137)
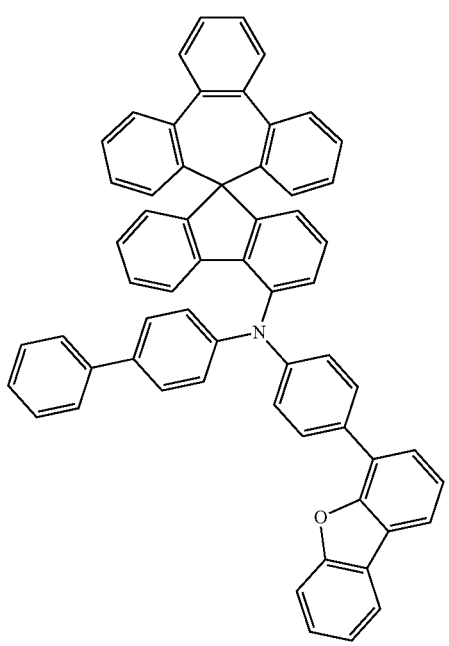

(138)
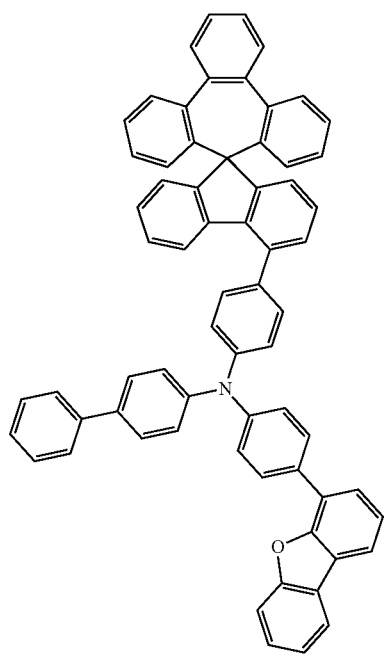
(139)
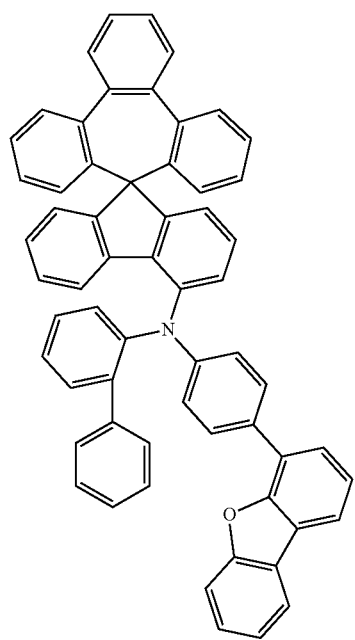
(140)
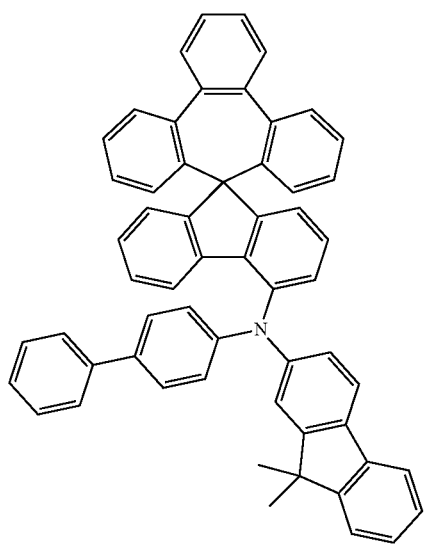
(141)
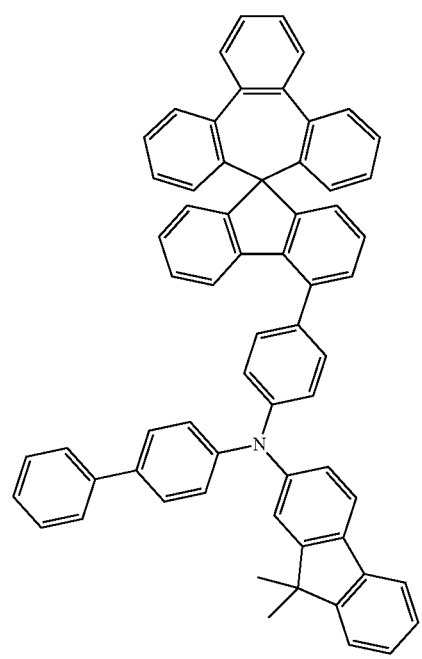

-continued
(142)
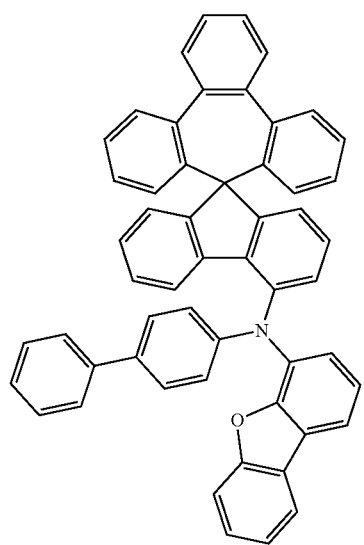
(143)
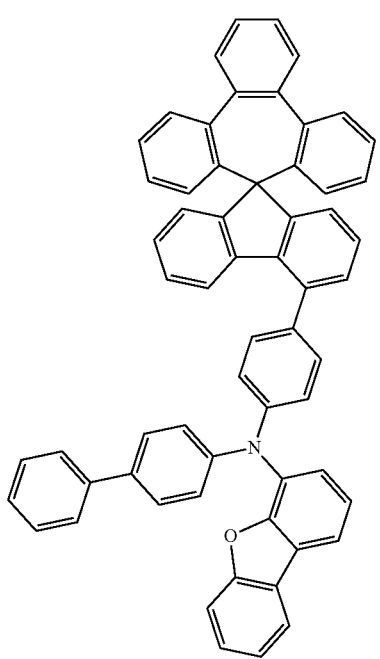
(144)
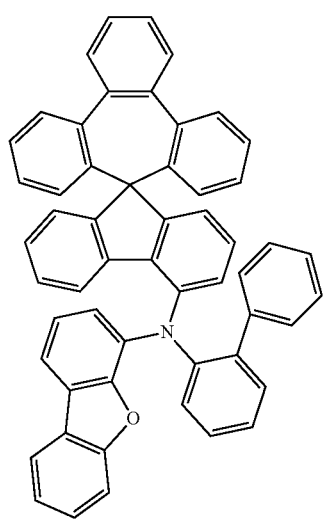
(145)
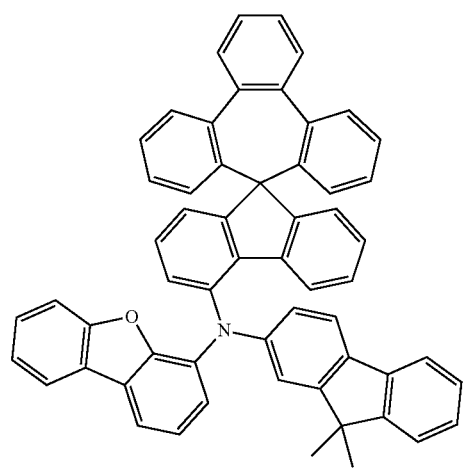
(146)
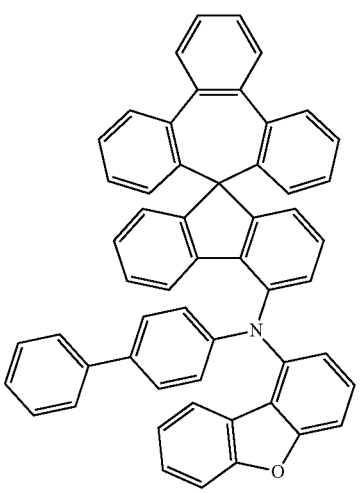

(147)
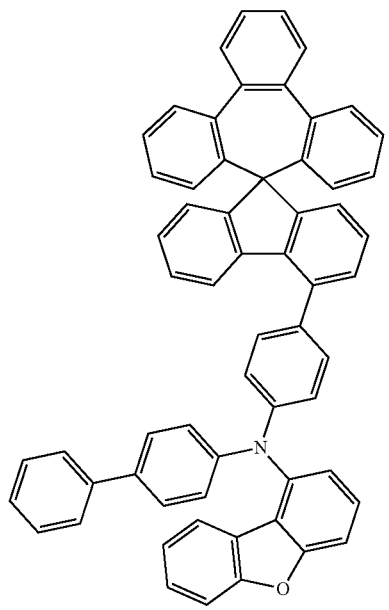
(148)
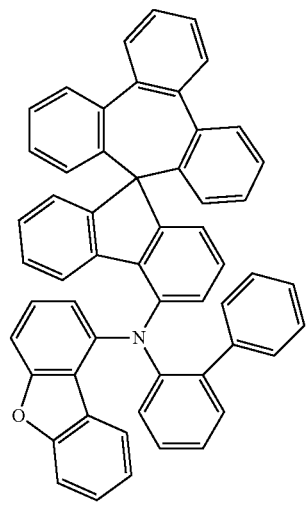
(149)
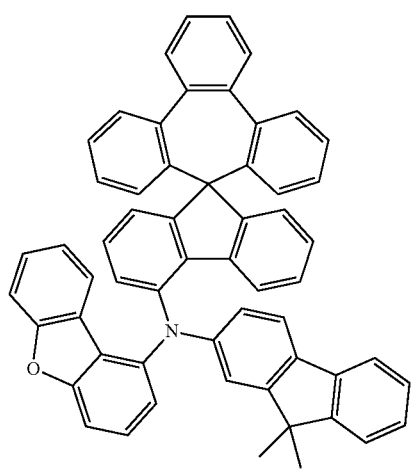
(150)
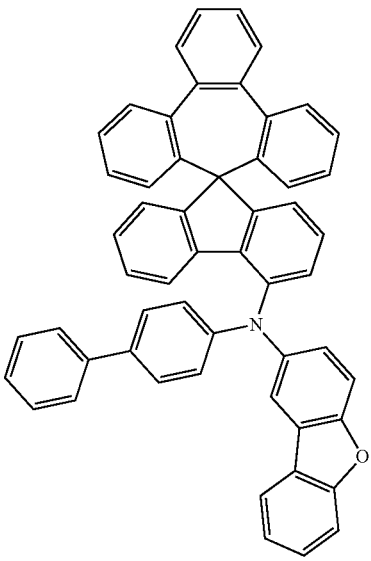
(151)
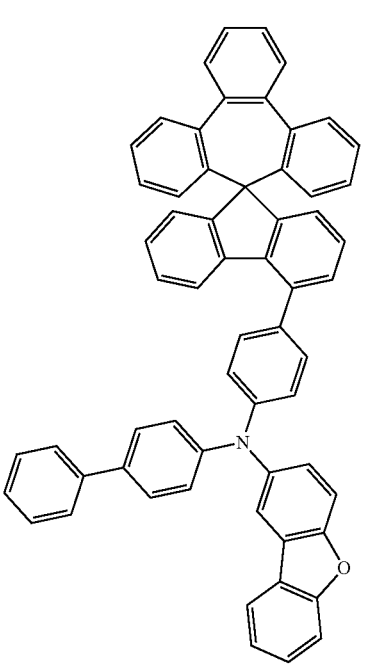

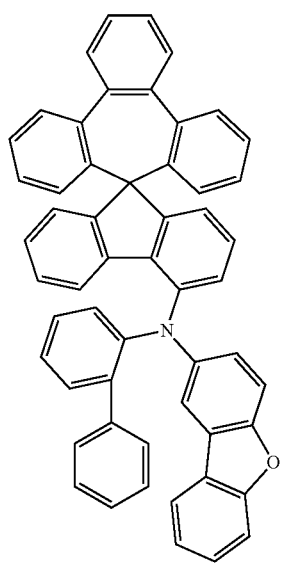 (152)
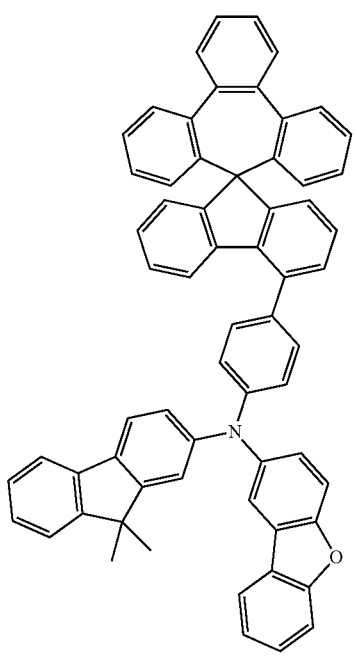 (154)
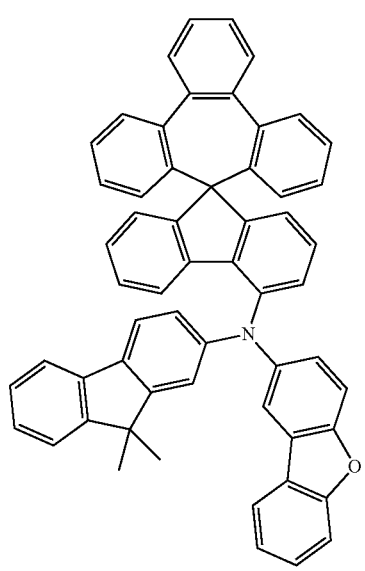 (153)
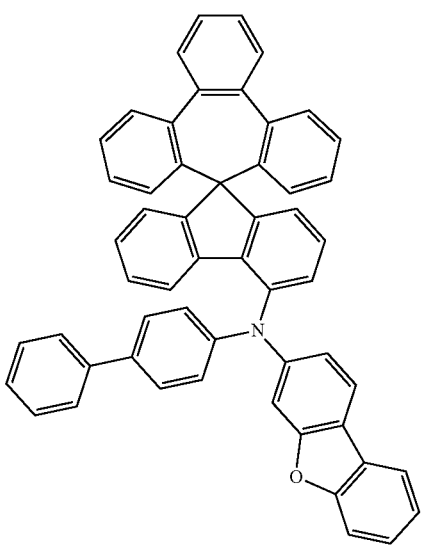 (155)

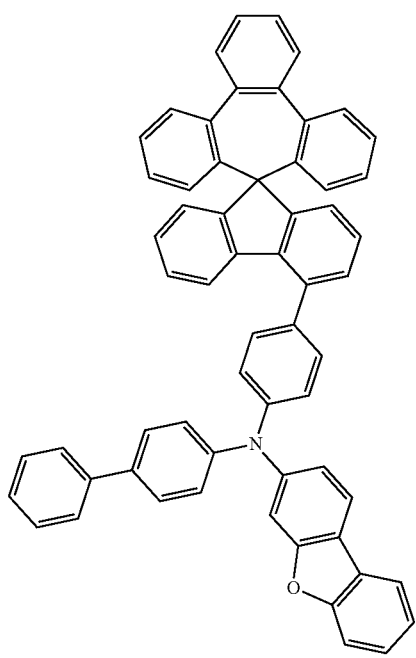
(156)
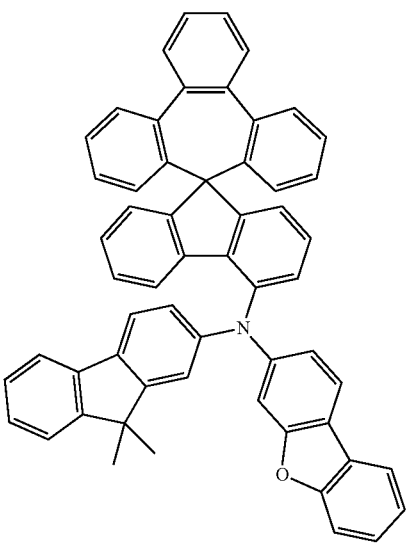
(158)
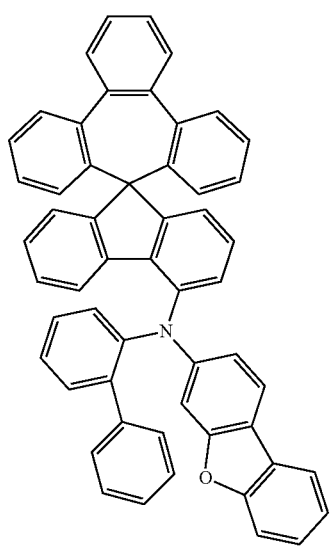
(157)
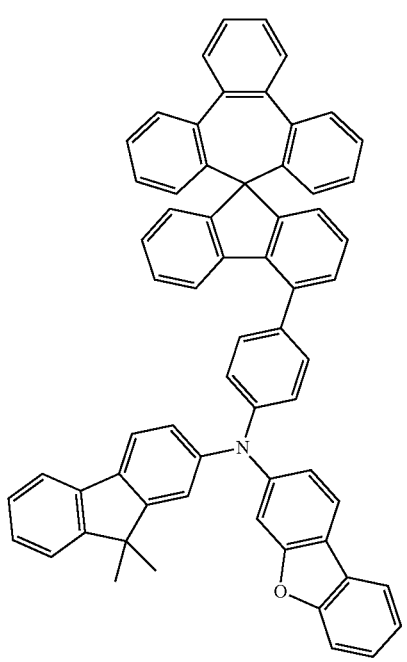
(159)

(160)
(161)
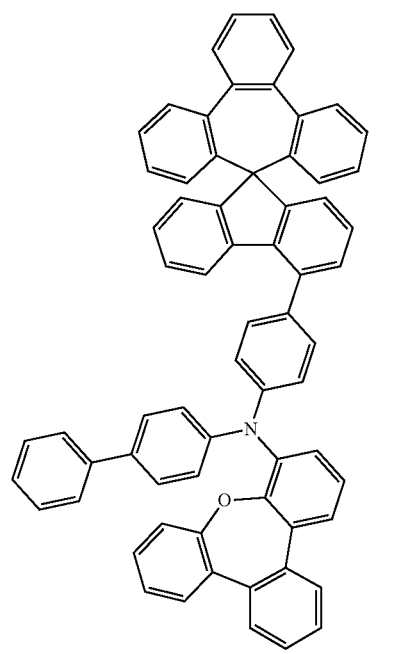
(162)
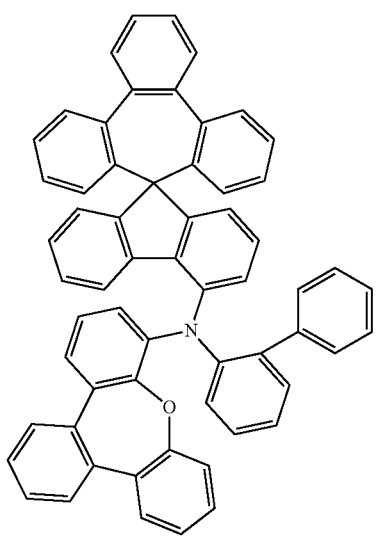
(163)
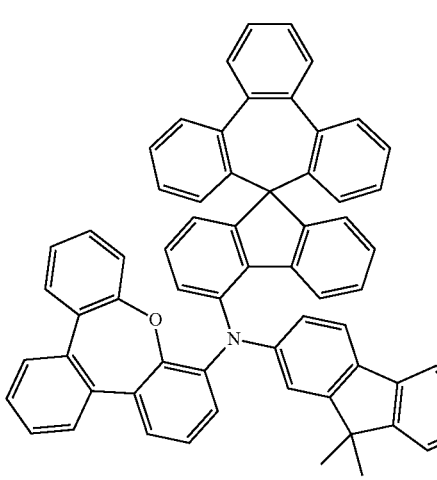
(164)

(165)
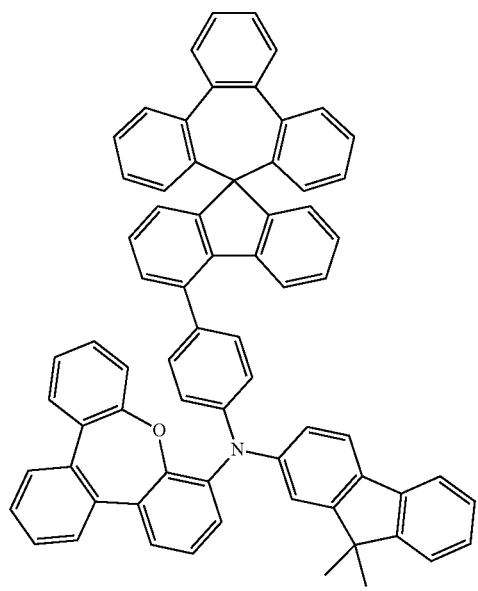
(166)
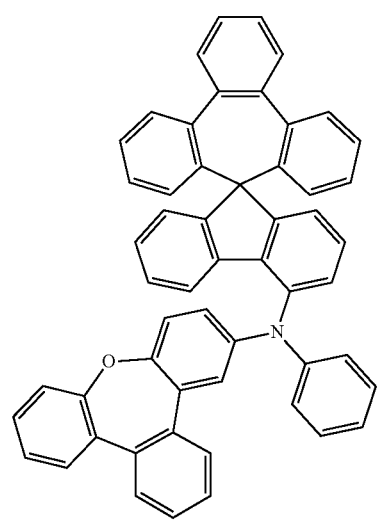
(167)
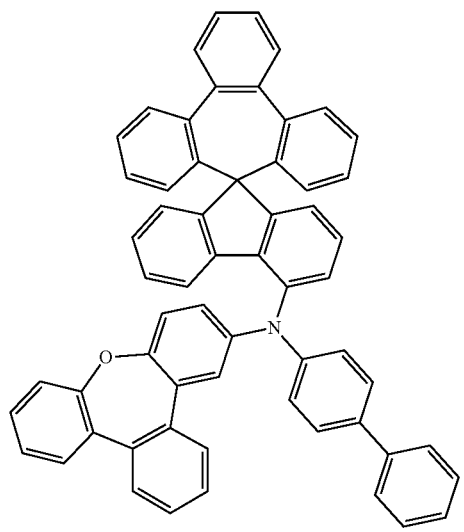
(168)
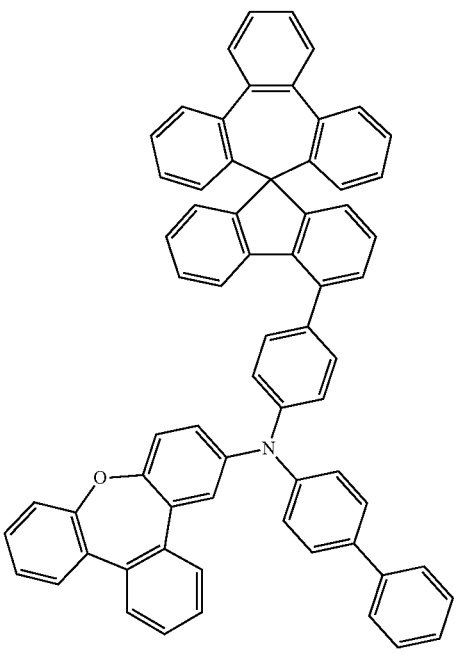
(169)
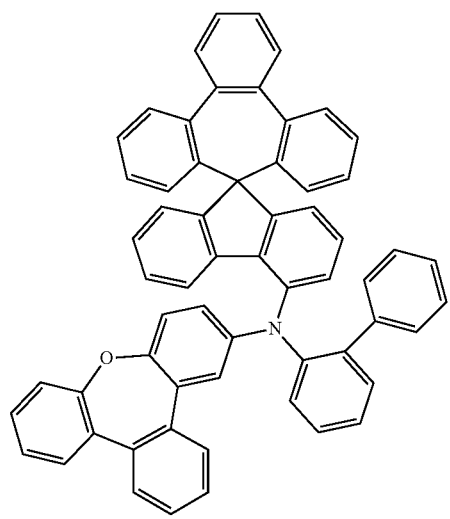

(170) 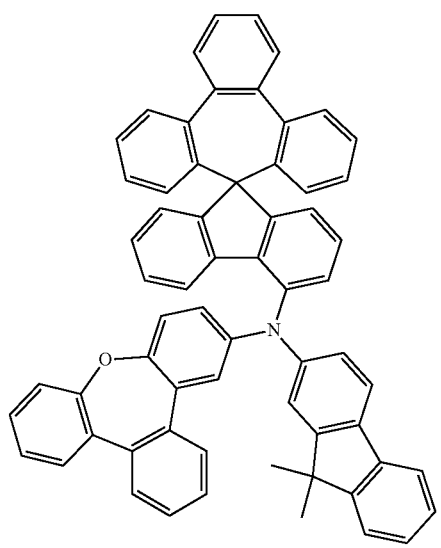
(172) 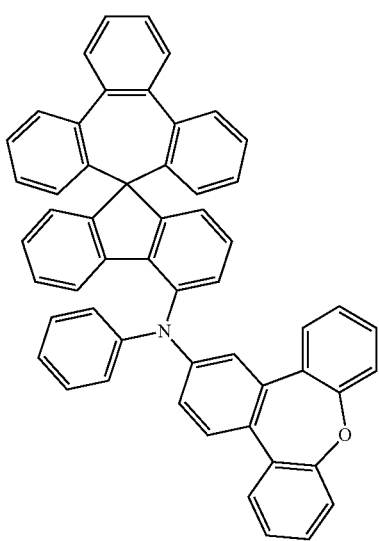
(171) 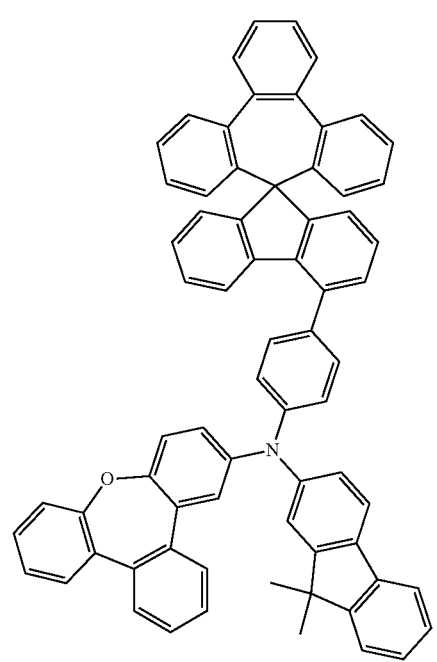
(173) 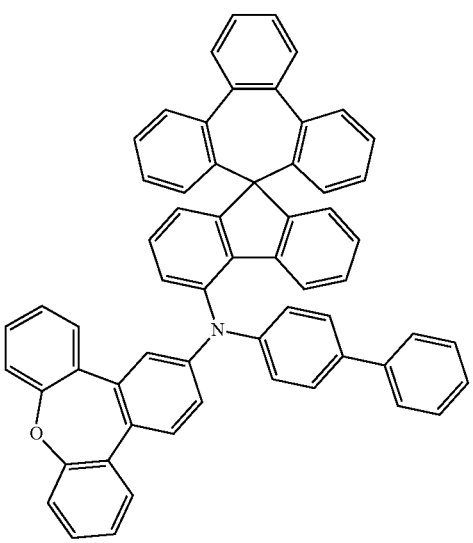

(174)
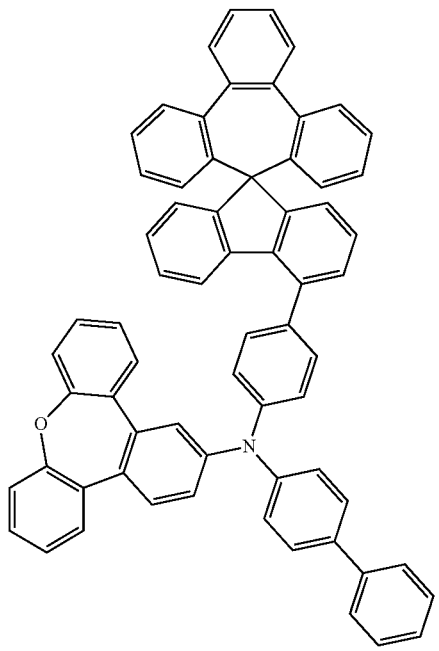
(176)
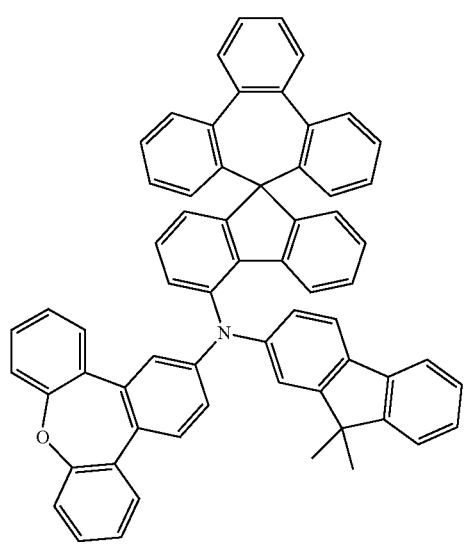
(177)
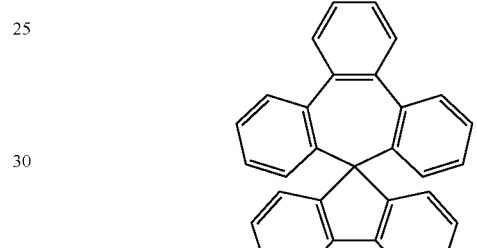
(175)
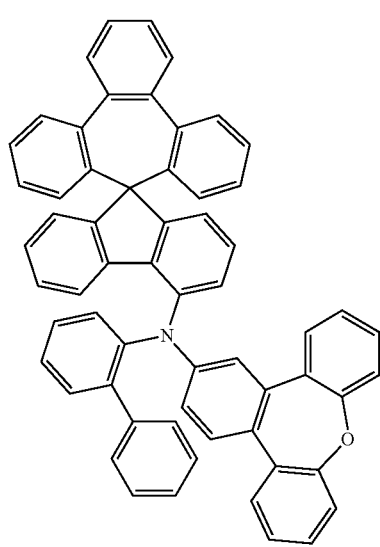
(178)
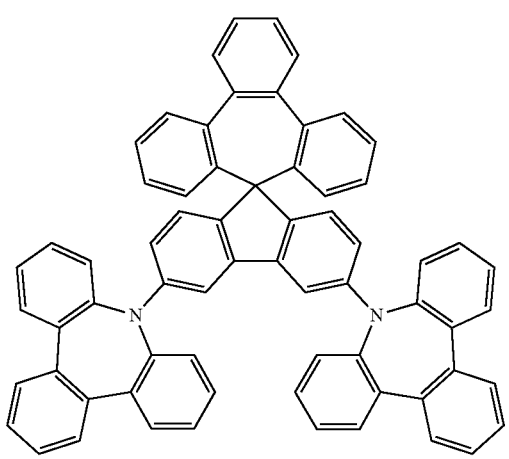

-continued
(179)
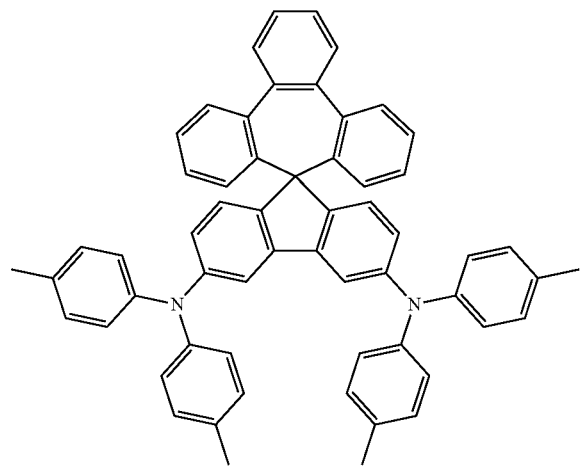
(180)
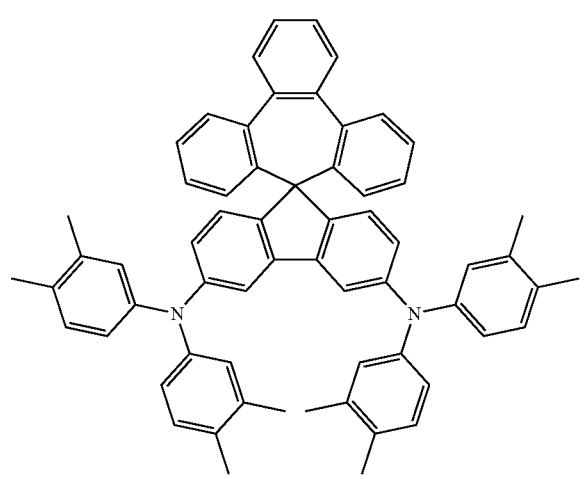
(181)
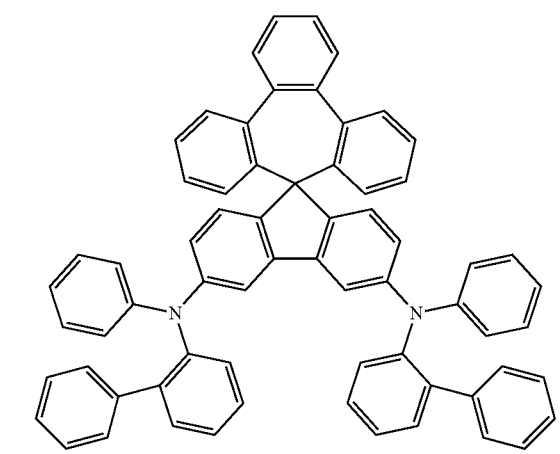
-continued
(182)
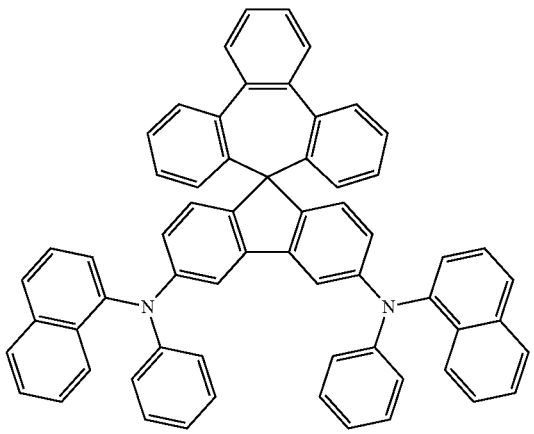
(183)
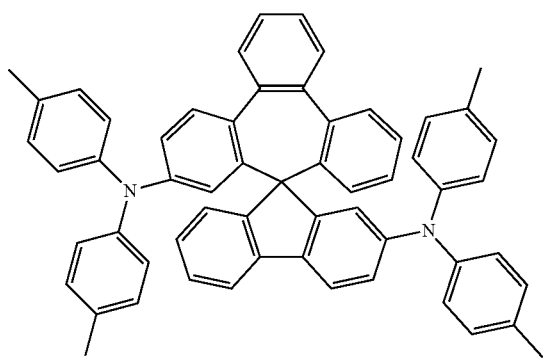
(184)
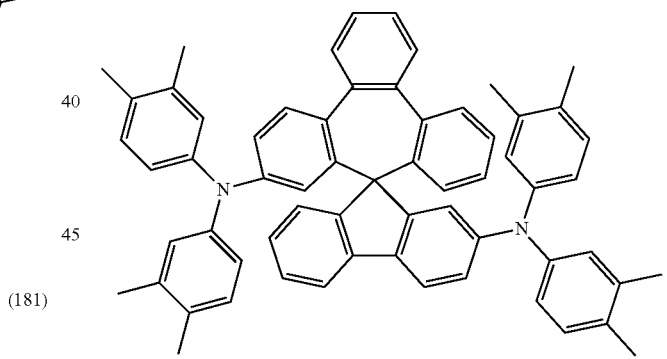
(185)
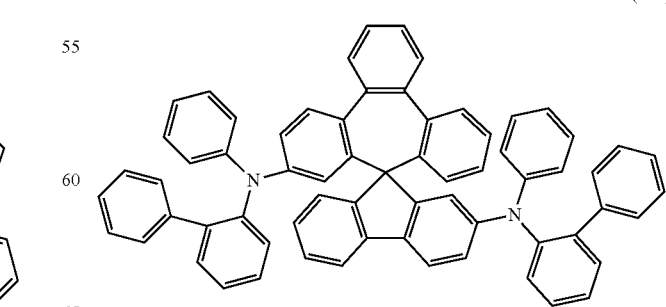

(186)
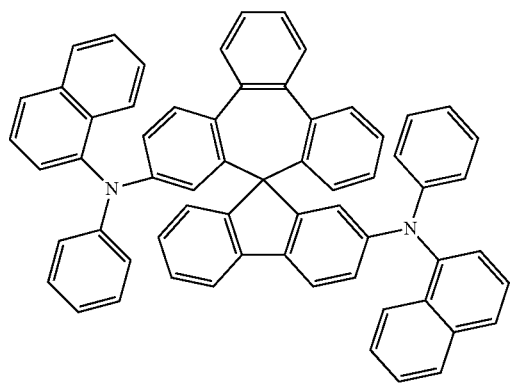
(187)
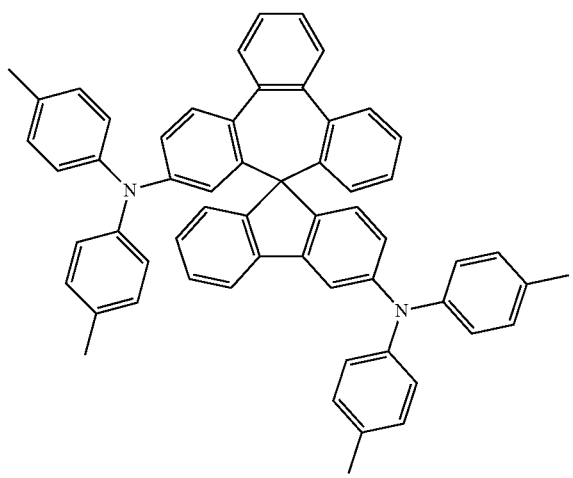
(188)
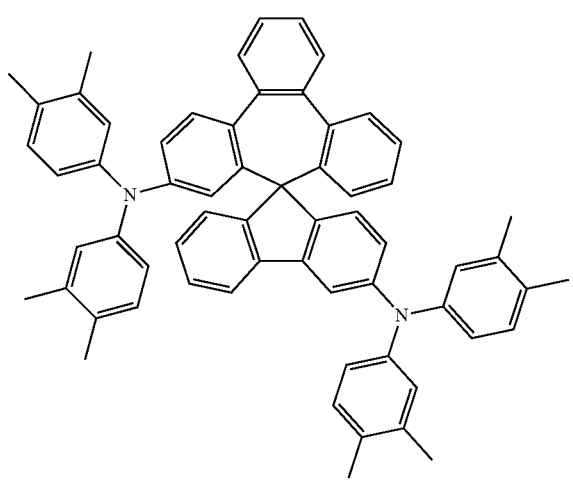
(189)
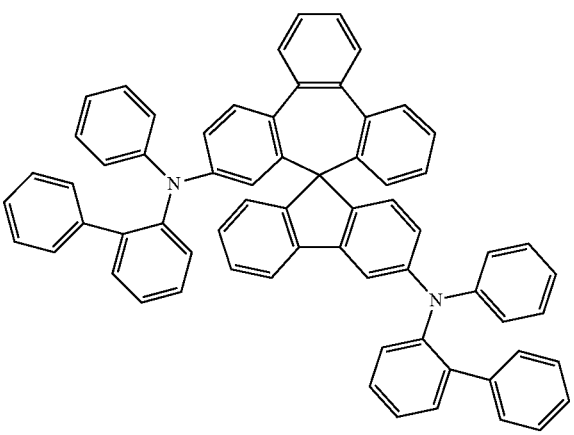
(190)
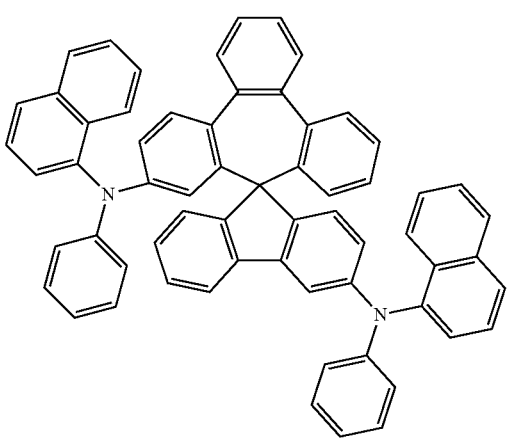
(191)
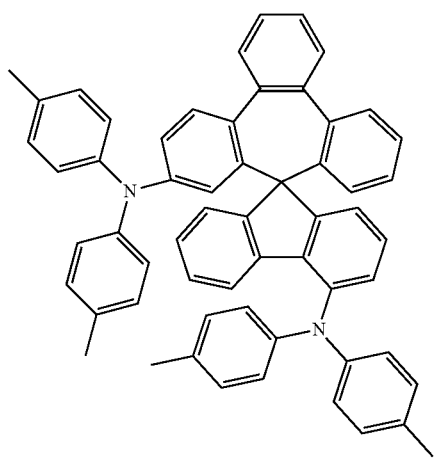

(192)
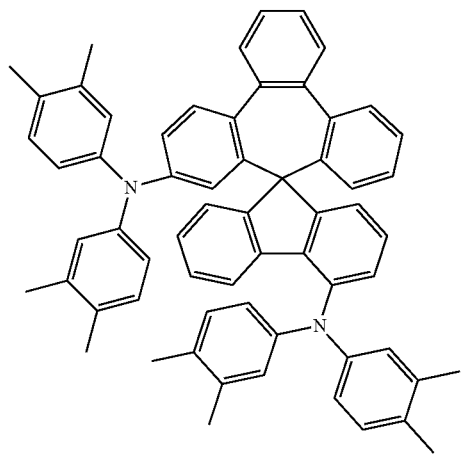
(195)
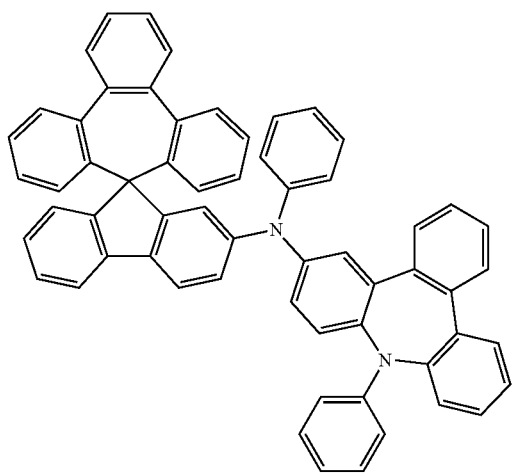
(193)
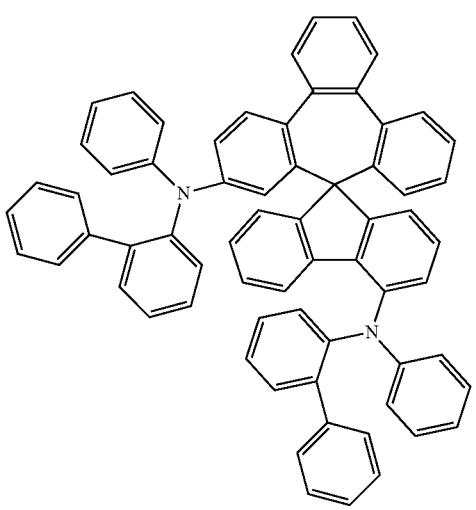
(196)
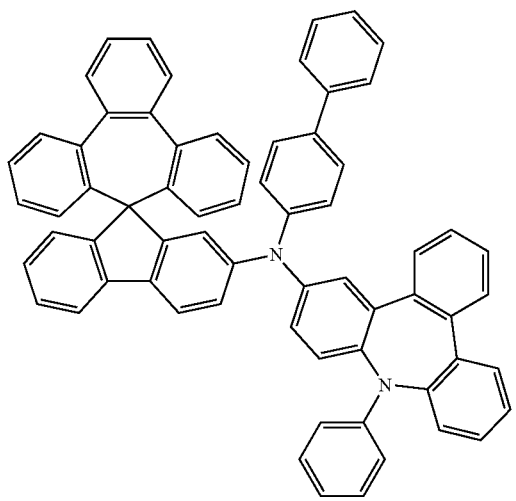
(194)
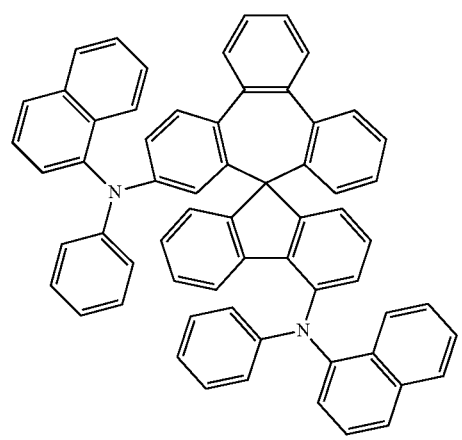
(197)
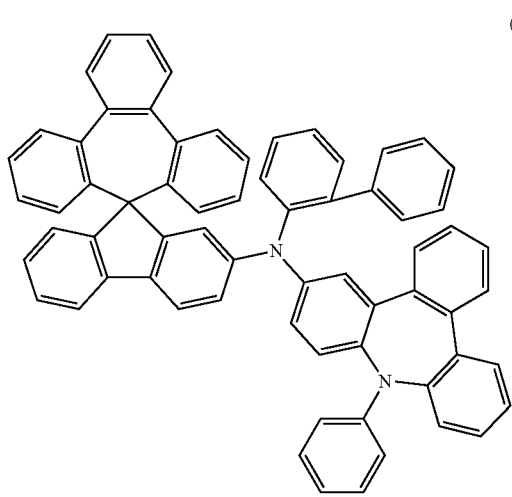

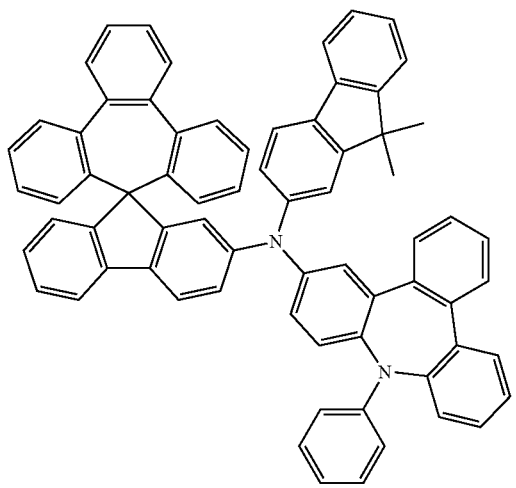
(198)
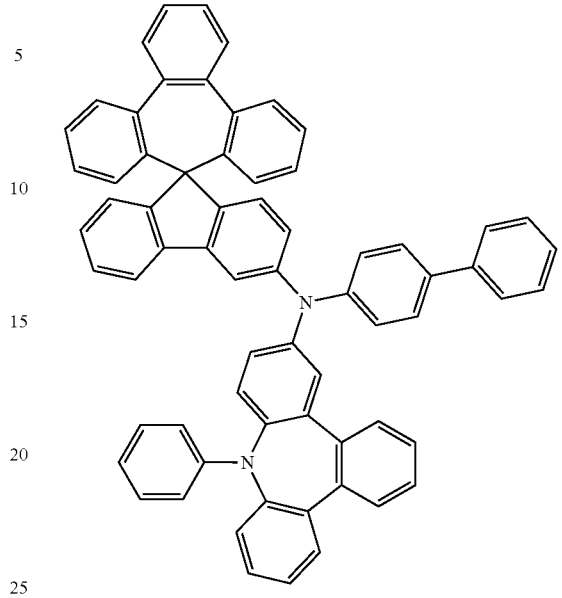
(200)
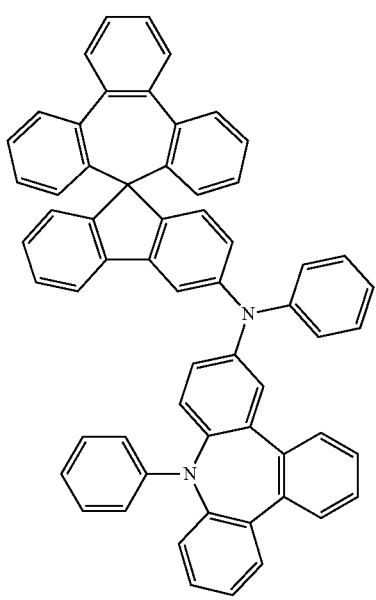
(199)
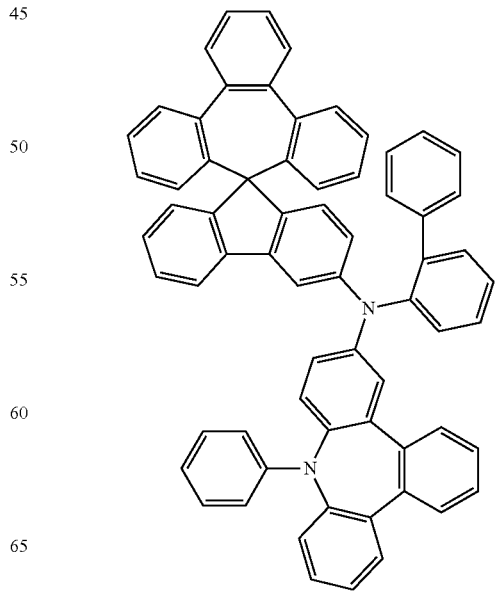
(201)

(202)
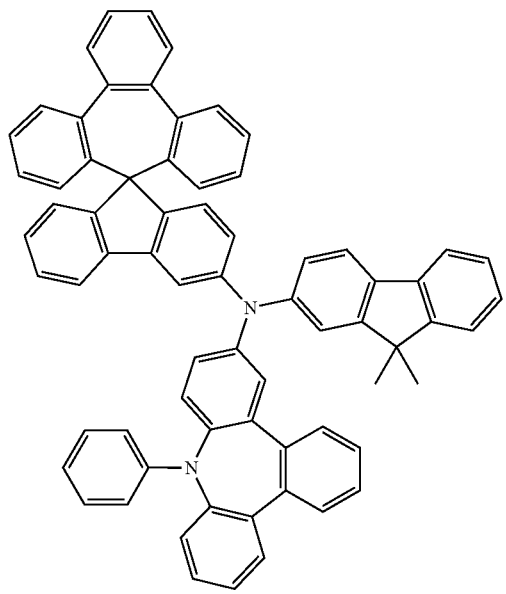
(203)
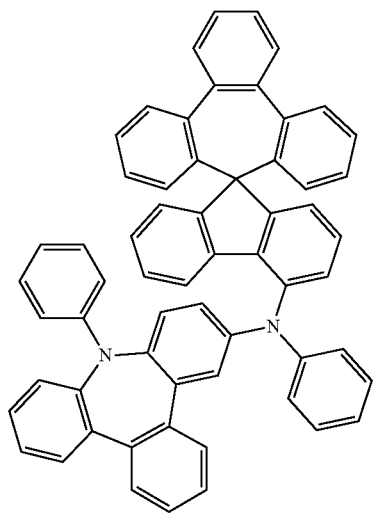
(204)
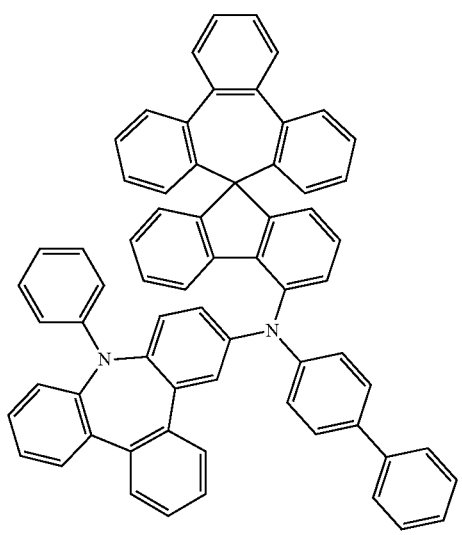
(205)
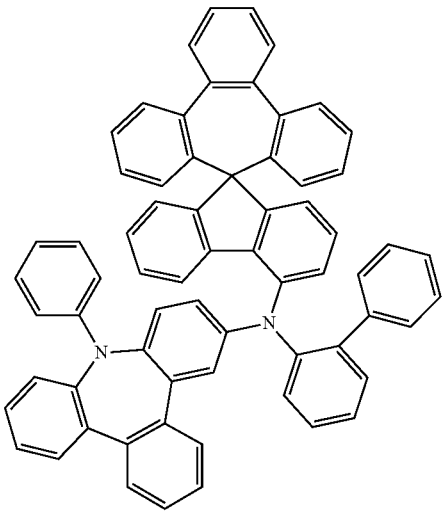
(206)
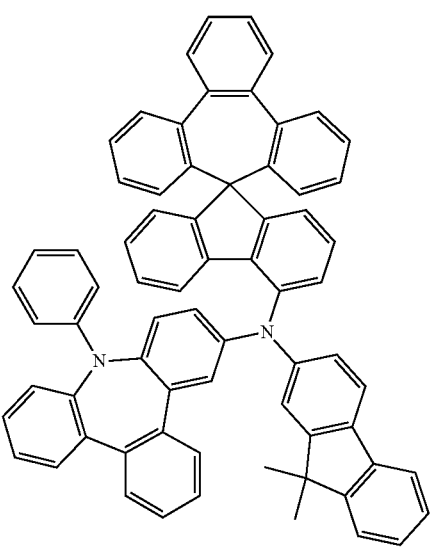
(207)
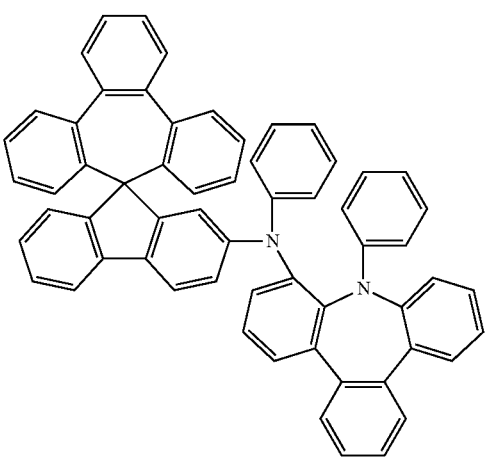

(208)
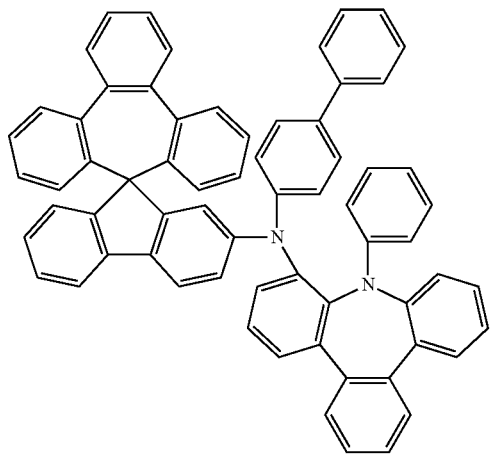
(209)
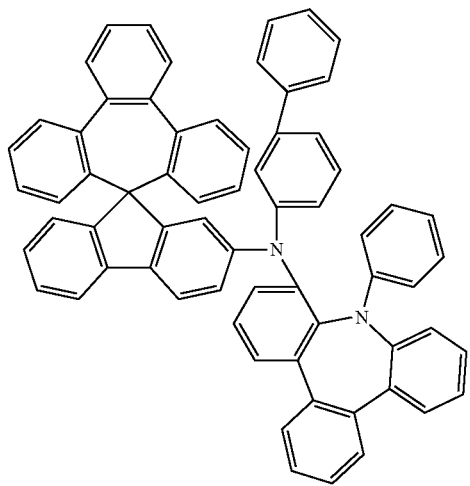
(210)
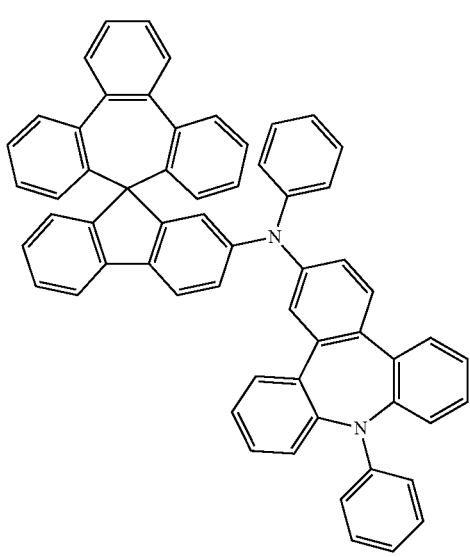
(211)
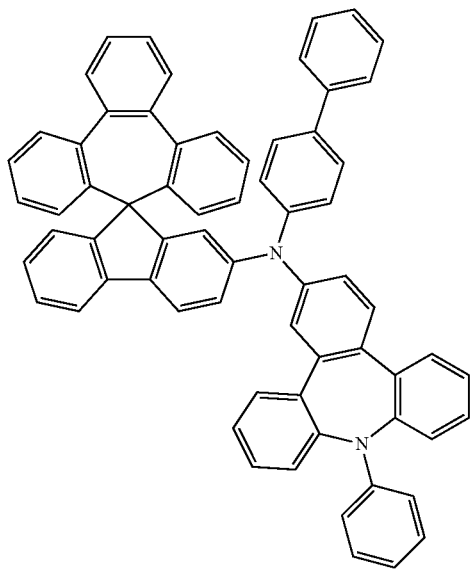
(212)
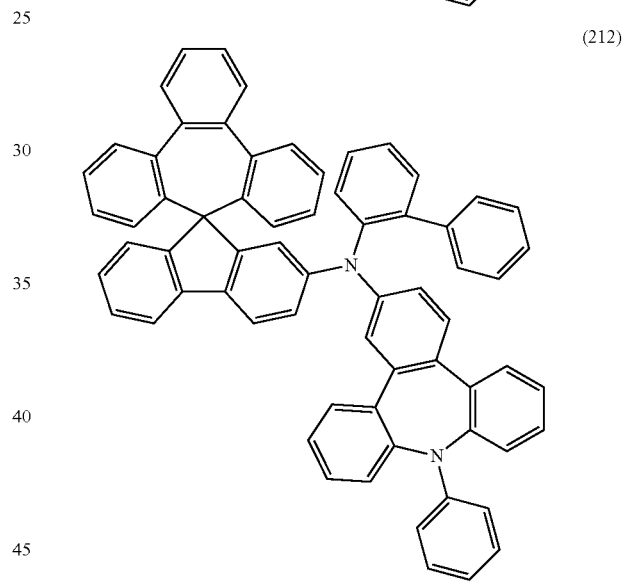
(213)
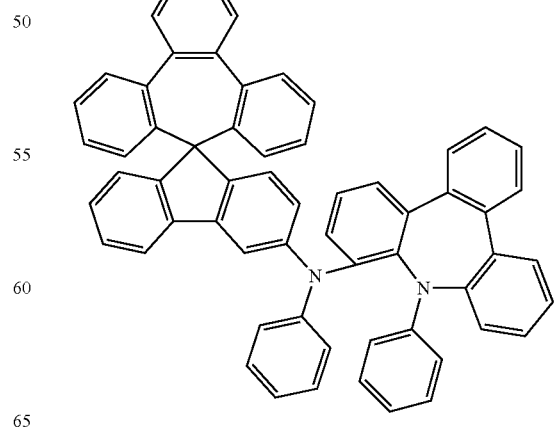

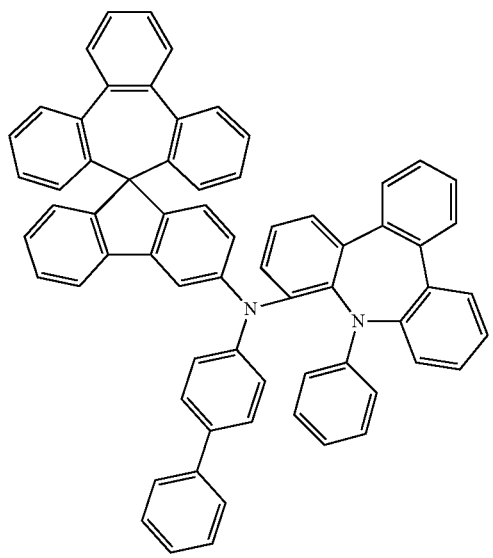
(214)
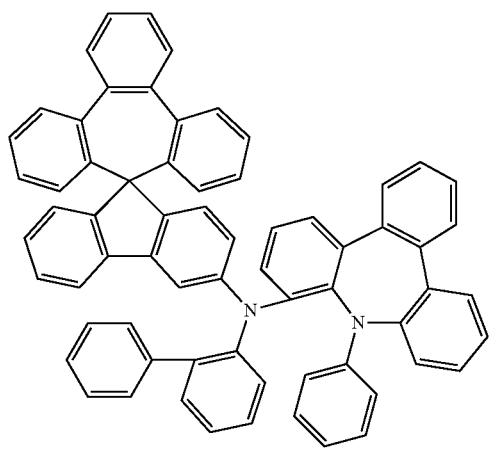
(215)
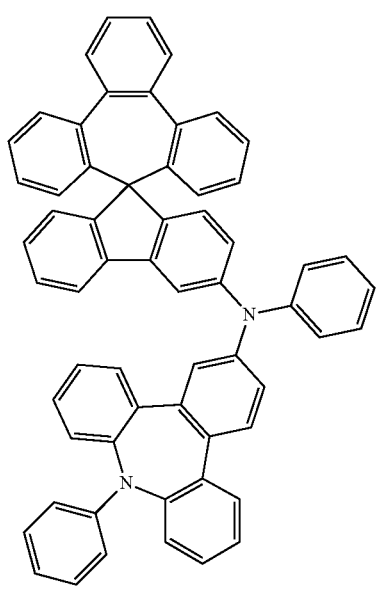
(216)
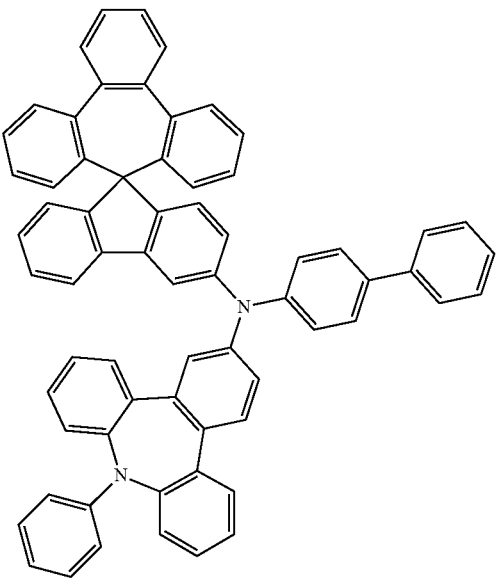
(217)
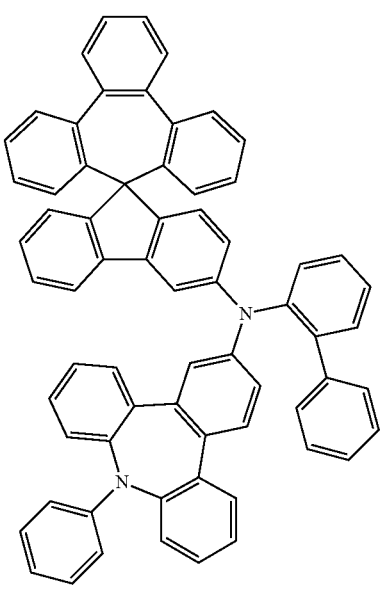
(218)

(219)
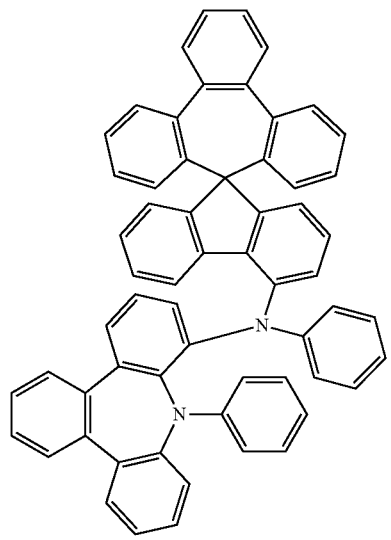
(220)
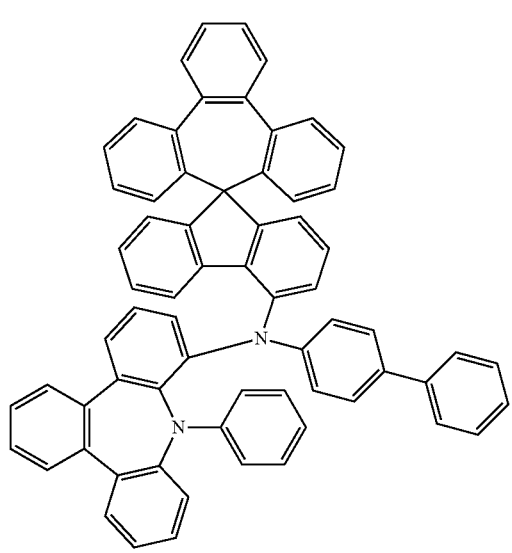
(221)
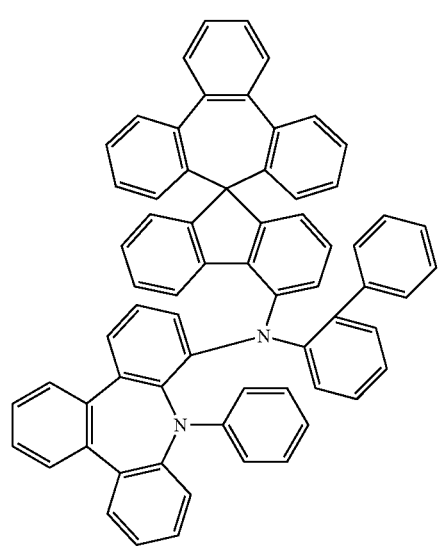
(222)
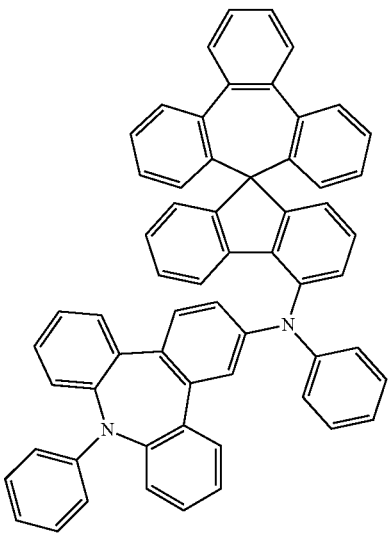
(223)
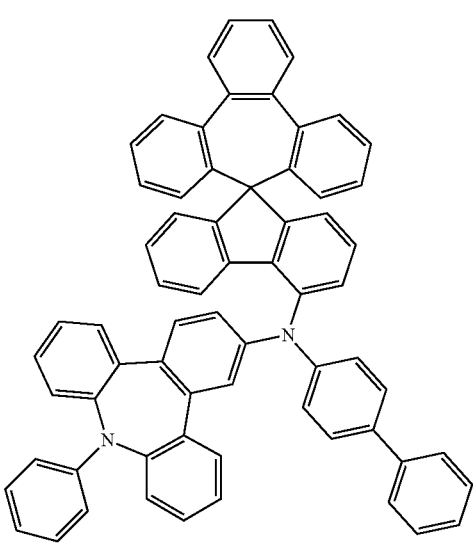
(224)
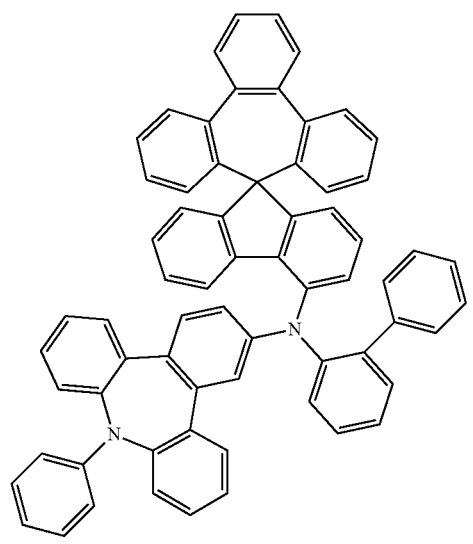

Herein, at least one hydrogen atom of the compounds (1) to (224) can further be optionally substituted with the aforementioned substituents.

Organic Electronic Device

An organic electronic device comprising the aforementioned compounds is also provided in the present disclosure.

In one embodiment, the organic electronic device comprises: a first electrode; a second electrode; and an organic layer disposed between the first electrode and the second electrode, wherein the organic layer comprises any one of the aforementioned compounds.

Herein, the term "organic layer" refers to single layer or multilayers disposed between the first electrode and the second electrode of the organic electronic device.

The application of the organic electronic device of the present disclosure comprises, but is not limited to, an organic light emitting device, an organic solar cell device, an organic thin film transistor, an organic photodetector, a flat panel display, a computer monitor, a television, a billboard, a light for interior or exterior illumination, a light for interior or exterior signaling, a heads up display, a fully transparent display, a flexible display, a laser printer, a telephone, a cell phone, a tablet computer, a laptop computer, a digital camera, a camcorder, a viewfinder, a micro-display, a vehicle, a large area wall, a theater or stadium screen, or a sign. Preferably, the organic electronic device of the present disclosure is applied to an organic light emitting device, or an organic solar cell device.

Figure 2:
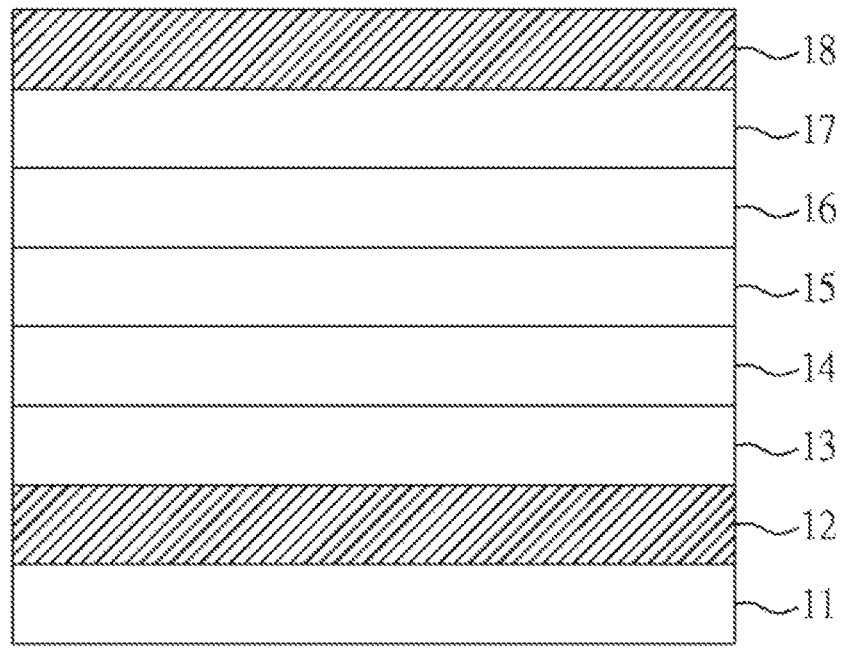
FIG. 2 is a perspective view showing an OLED device of the present invention.

In one embodiment, the organic electronic device can be an organic light emitting device. FIG. 2 is a perspective view showing an exemplary structure of an organic light emitting device capable of using in one embodiment of the present disclosure. As shown in FIG. 2, the organic light emitting device comprises: a substrate 11; an anode 12; a cathode 18; and an organic layer comprising a hole injection layer 13, a hole transporting layer 14, a light emitting layer 15, an electron transporting layer 16 and an electron injection layer 17. However, the present disclosure is not limited thereto. Other layers capable of improving the luminous efficiency of the organic light emitting device, for example an electron blocking layer or a hole blocking layer, can also be formed in the organic light emitting device of the present disclosure. When the organic light emitting device of the present disclosure further comprises the electron blocking layer, the electron blocking layer can be disposed between the hole transporting layer 14 and the light emitting layer 15. When the organic light emitting device of the present disclosure further comprises the hole blocking layer, the hole blocking layer can be disposed between the electron transporting layer 16 and the light emitting layer 15.

In one embodiment, the organic light emitting device of the present disclosure may include a hole transporting layer, which comprises the aforesaid compounds. In another embodiment, the organic light emitting device of the present disclosure may include a hole injection layer, which comprises the aforesaid compounds. In further another embodiment, the organic light emitting device of the present disclosure may include an electron blocking layer, which comprises the aforesaid compounds. However, the present disclosure is not limited thereto.

In one embodiment, the light emitting layer may contain a phosphorescent light emitting material which may comprise iridium or platinum. In another embodiment, the light emitting layer may contain a quantum dots or semiconductor nanocrystal materials. However, the present disclosure is not limited thereto.

Figure 3:
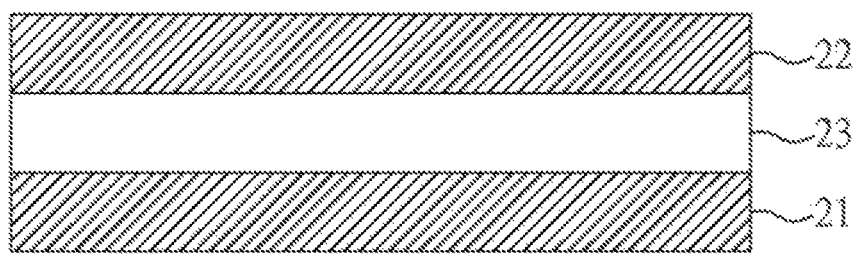
FIG. 3 is a perspective view showing an organic solar cell device of the present invention.
Figure 4:
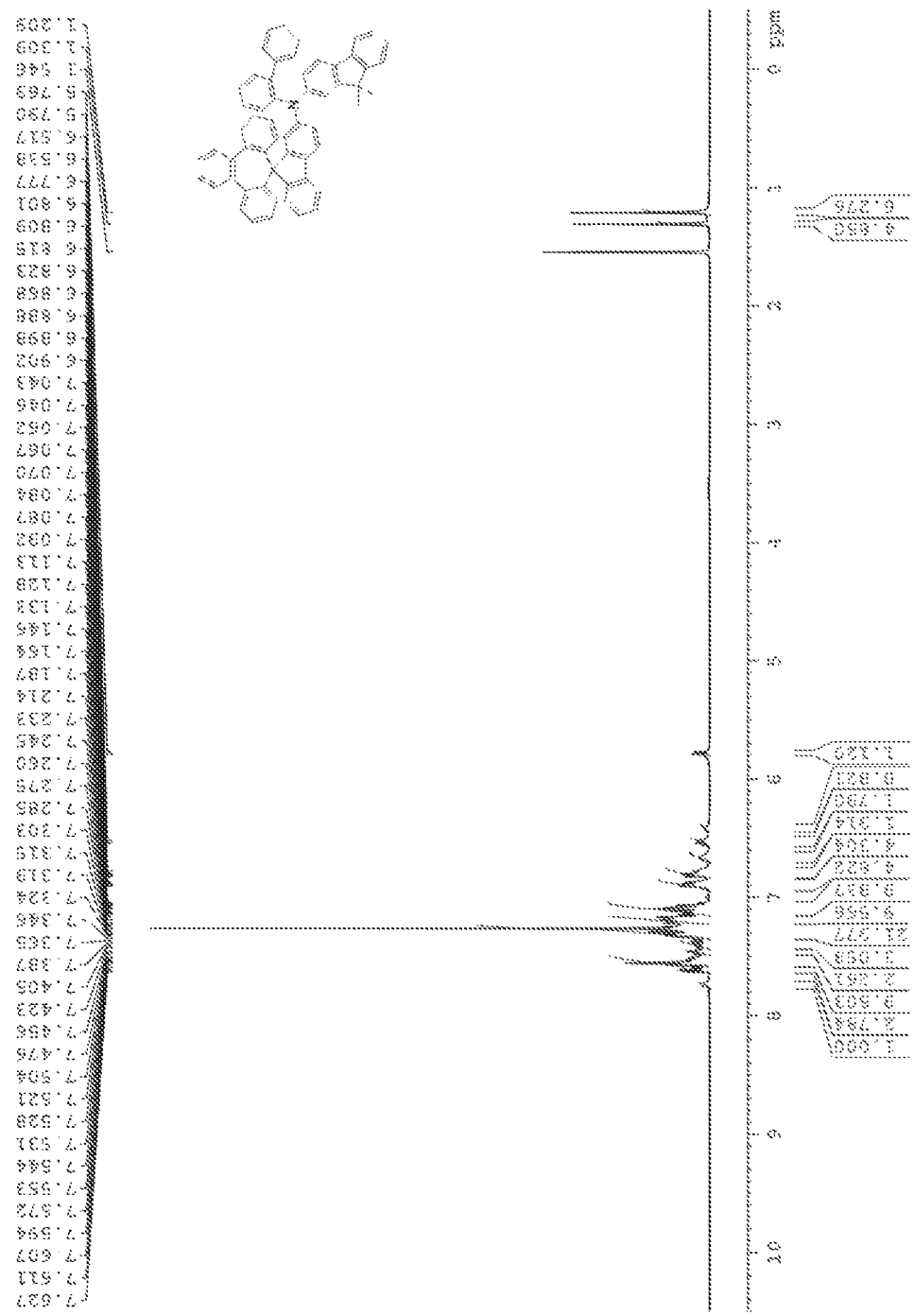
FIG. 4 is 1H NMR data of Compound (1) (SGM134) of the present disclosure.
Figure 5:
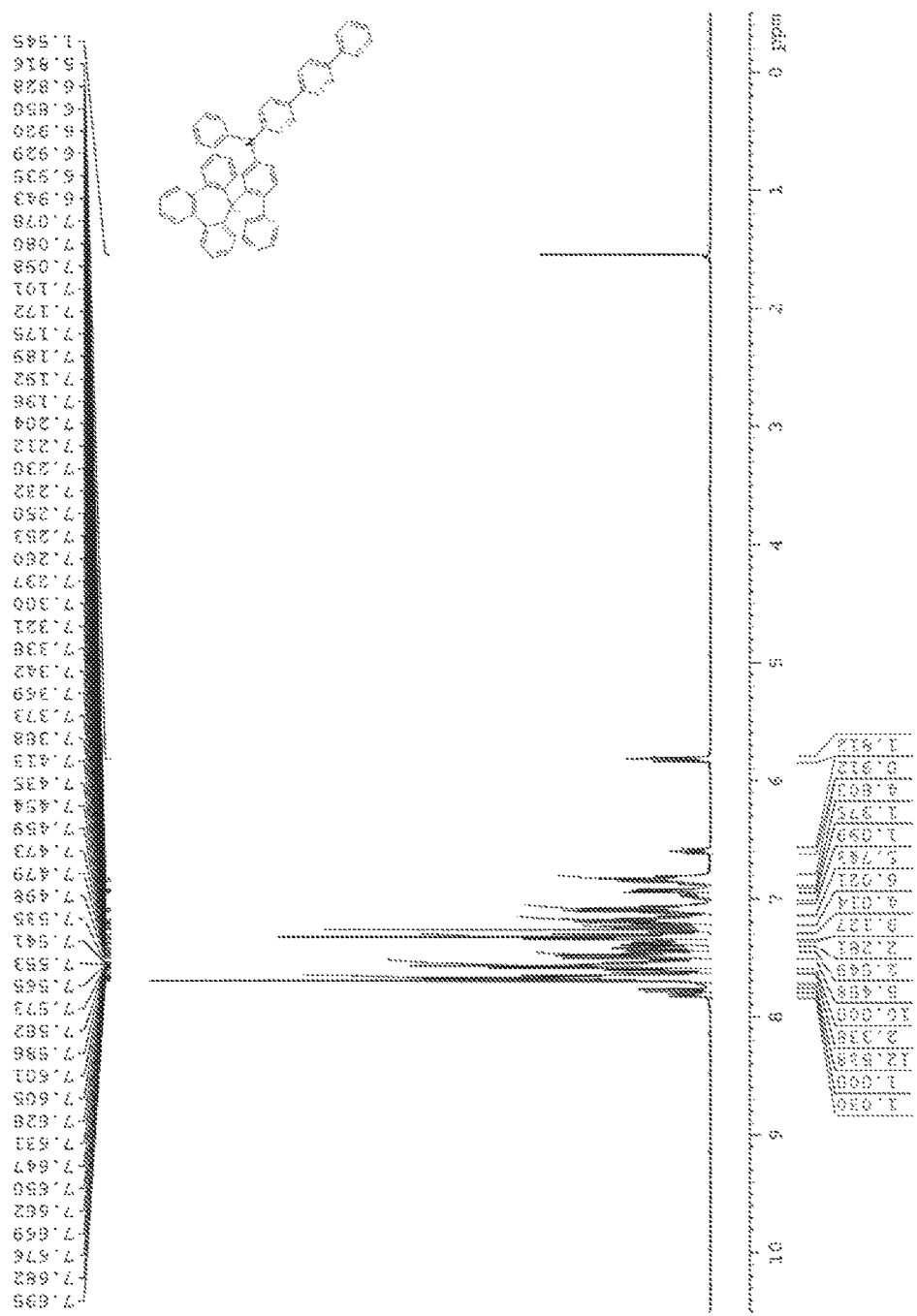
FIG. 5 is 1H NMR data of Compound (2) (SGM137) of the present disclosure.
Figure 6:
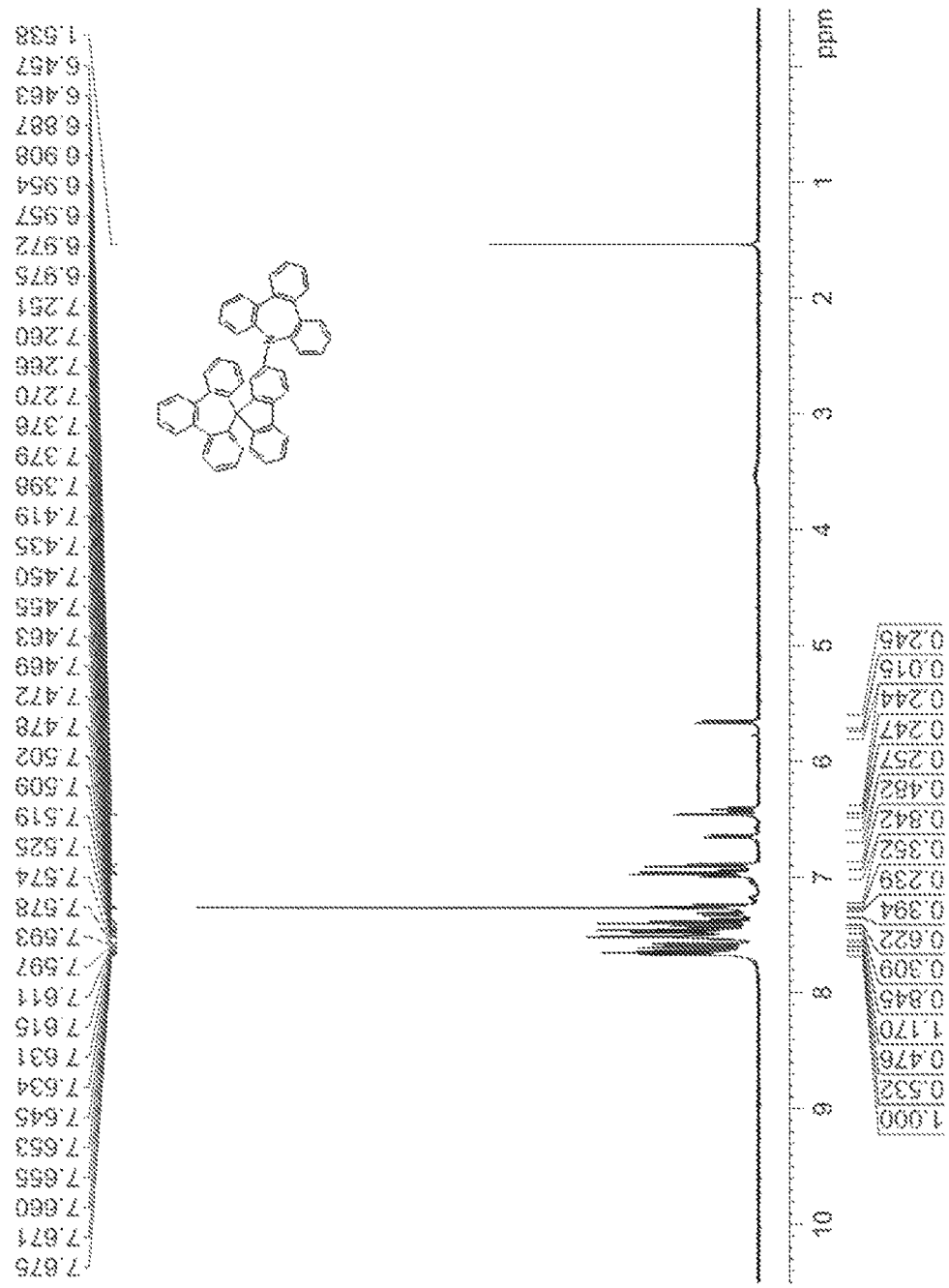
FIG. 6 is 1H NMR data of Compound (4) (SGM423) of the present disclosure.
Figure 7:
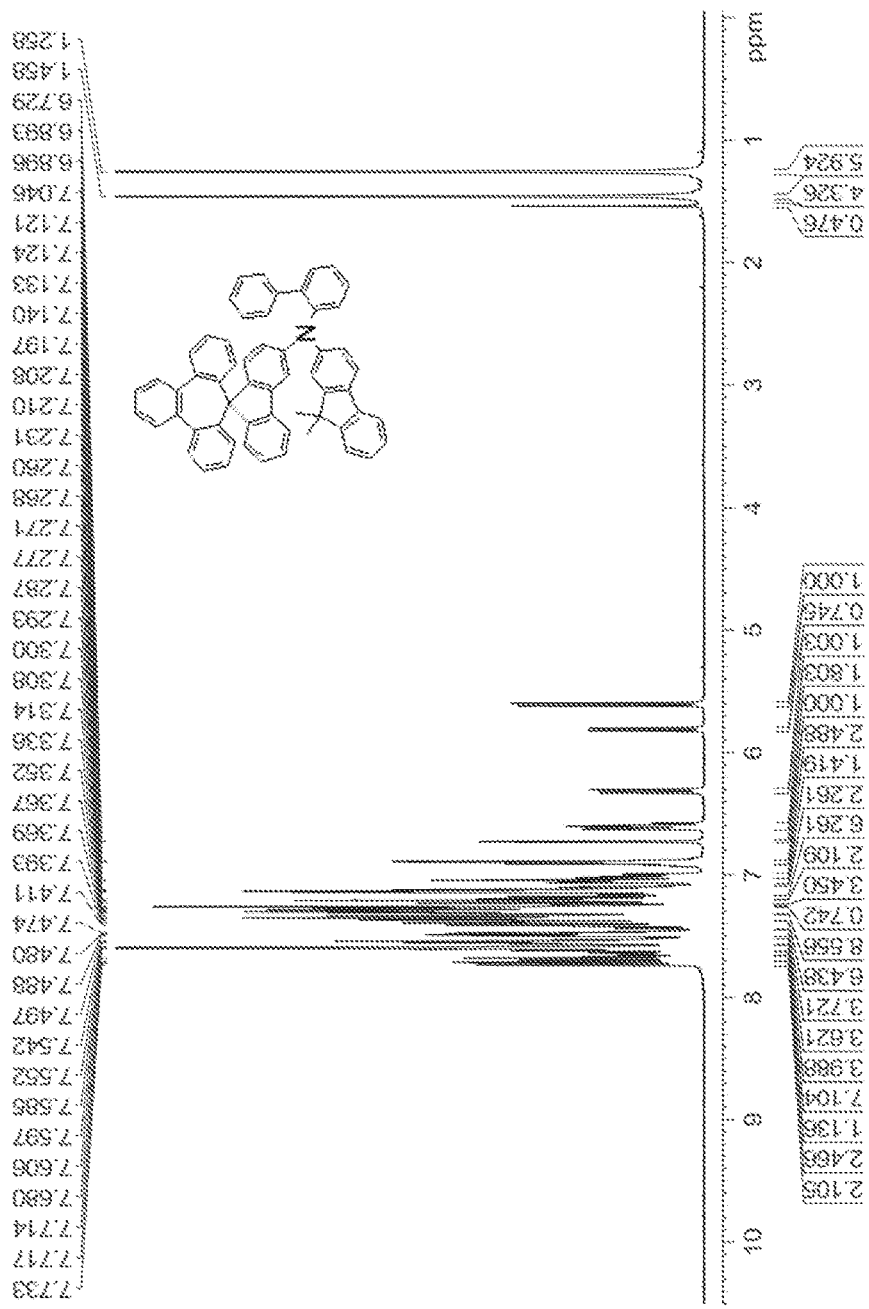
FIG. 7 is 1H NMR data of Compound (7) (SGM135) of the present disclosure.
Figure 8:
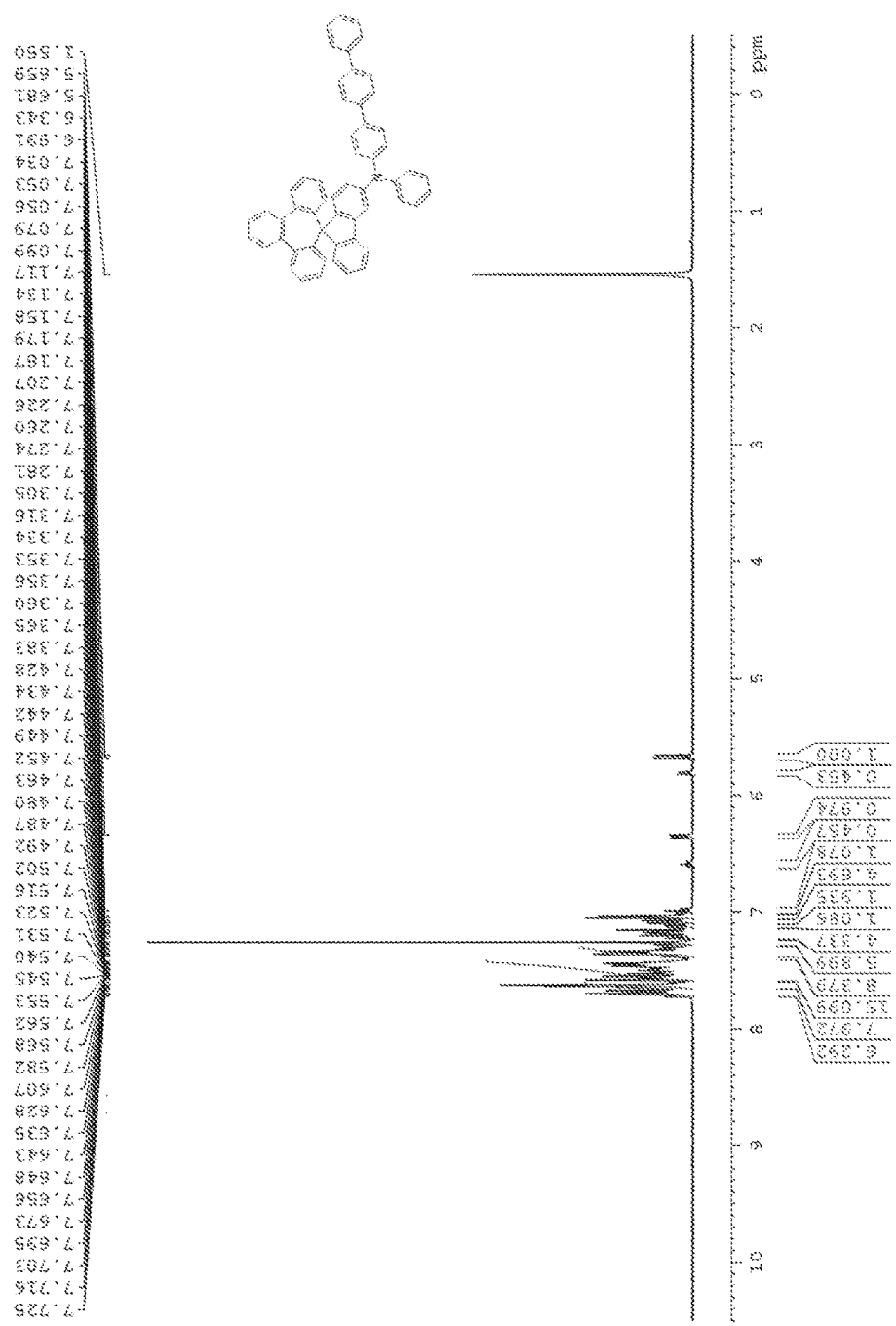
FIG. 8 is 1H NMR data of Compound (8) (SGM138) of the present disclosure.
Figure 9:
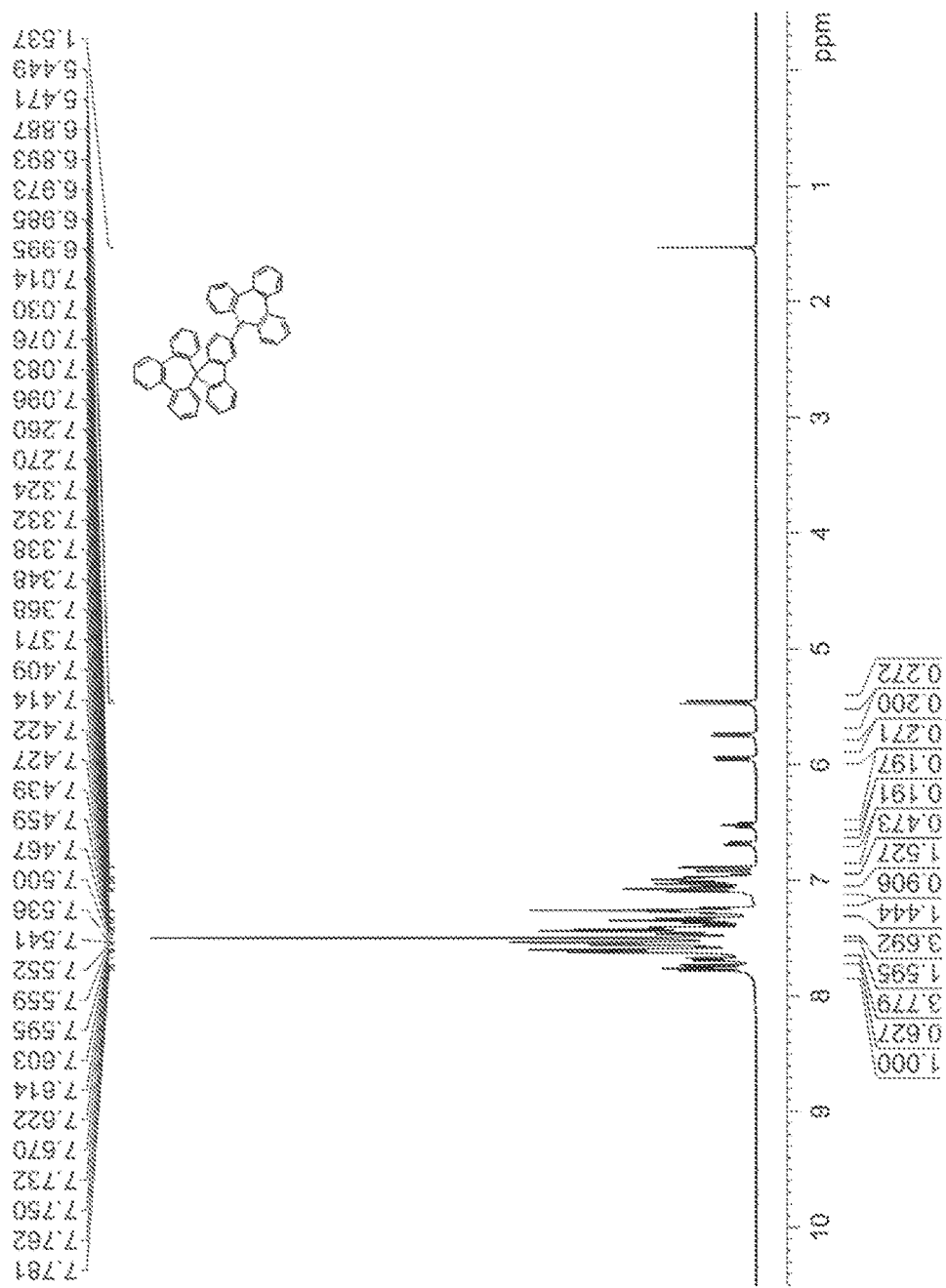
FIG. 9 is 1H NMR data of Compound (10) (SGM422) of the present disclosure.
Figure 10:
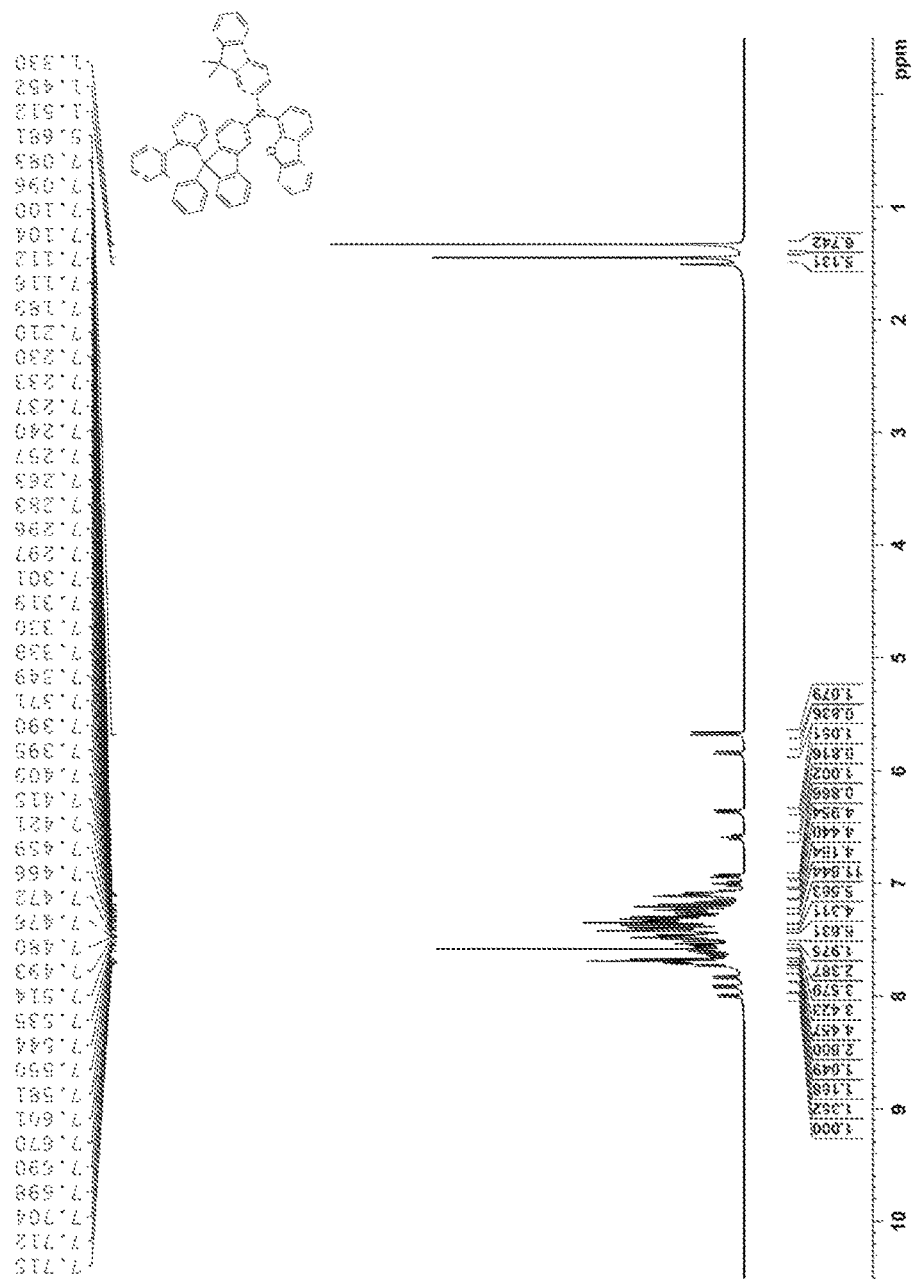
FIG. 10 is 1H NMR data of Compound (11) (SGM565) of the present disclosure.
Figure 11:
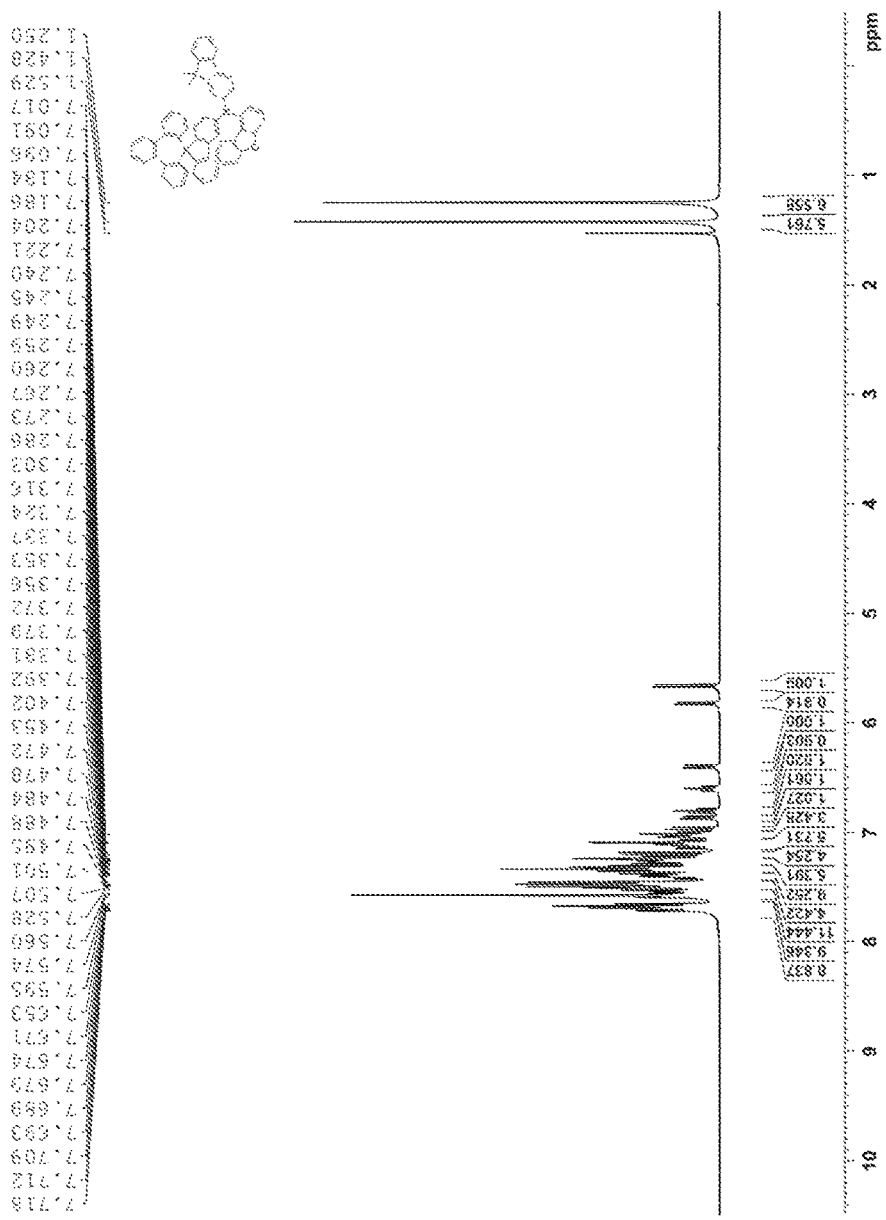
FIG. 11 is 1H NMR data of Compound (12) (SGM578) of the present disclosure.
Figure 12:
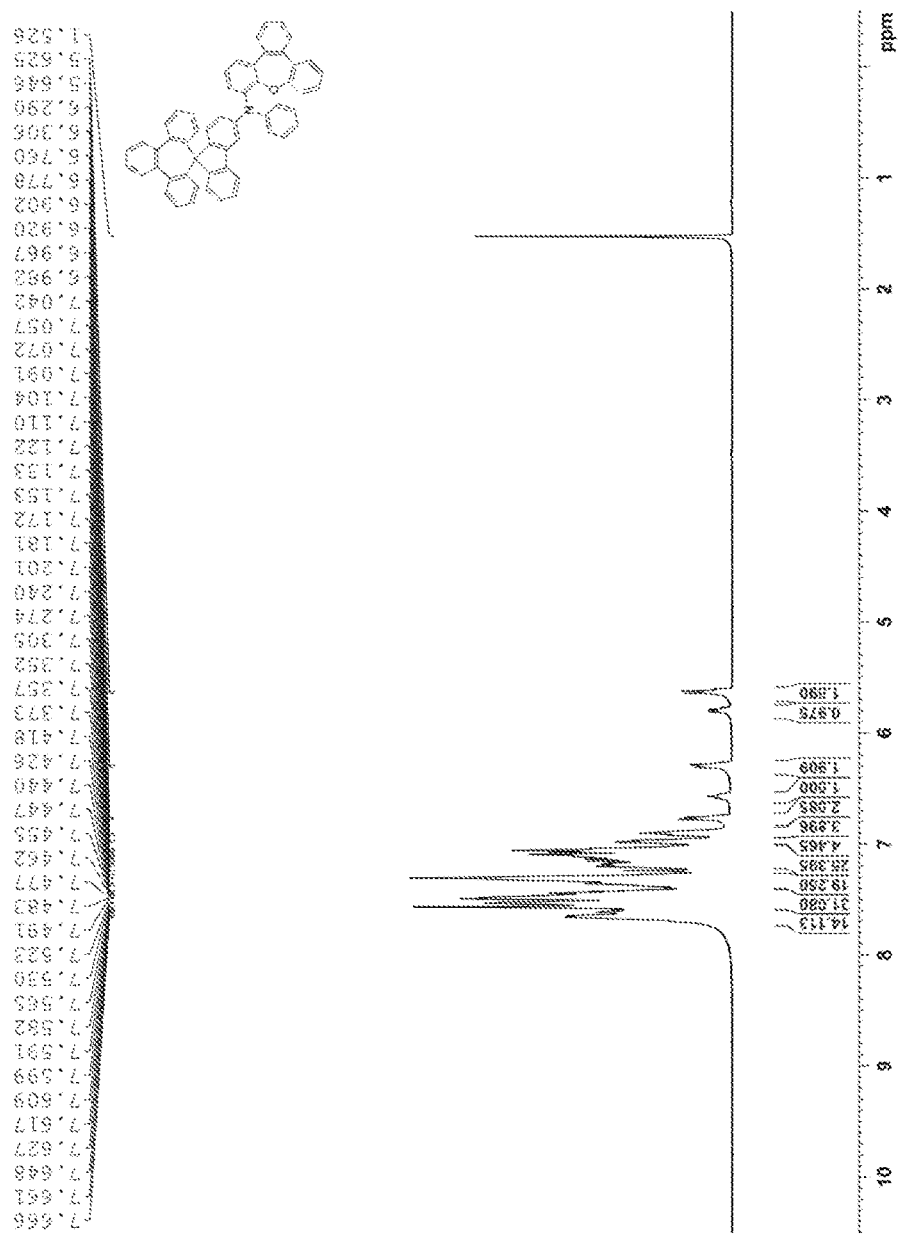
FIG. 12 is 1H NMR data of Compound (31) (SGM564) of the present disclosure.
Figure 13:
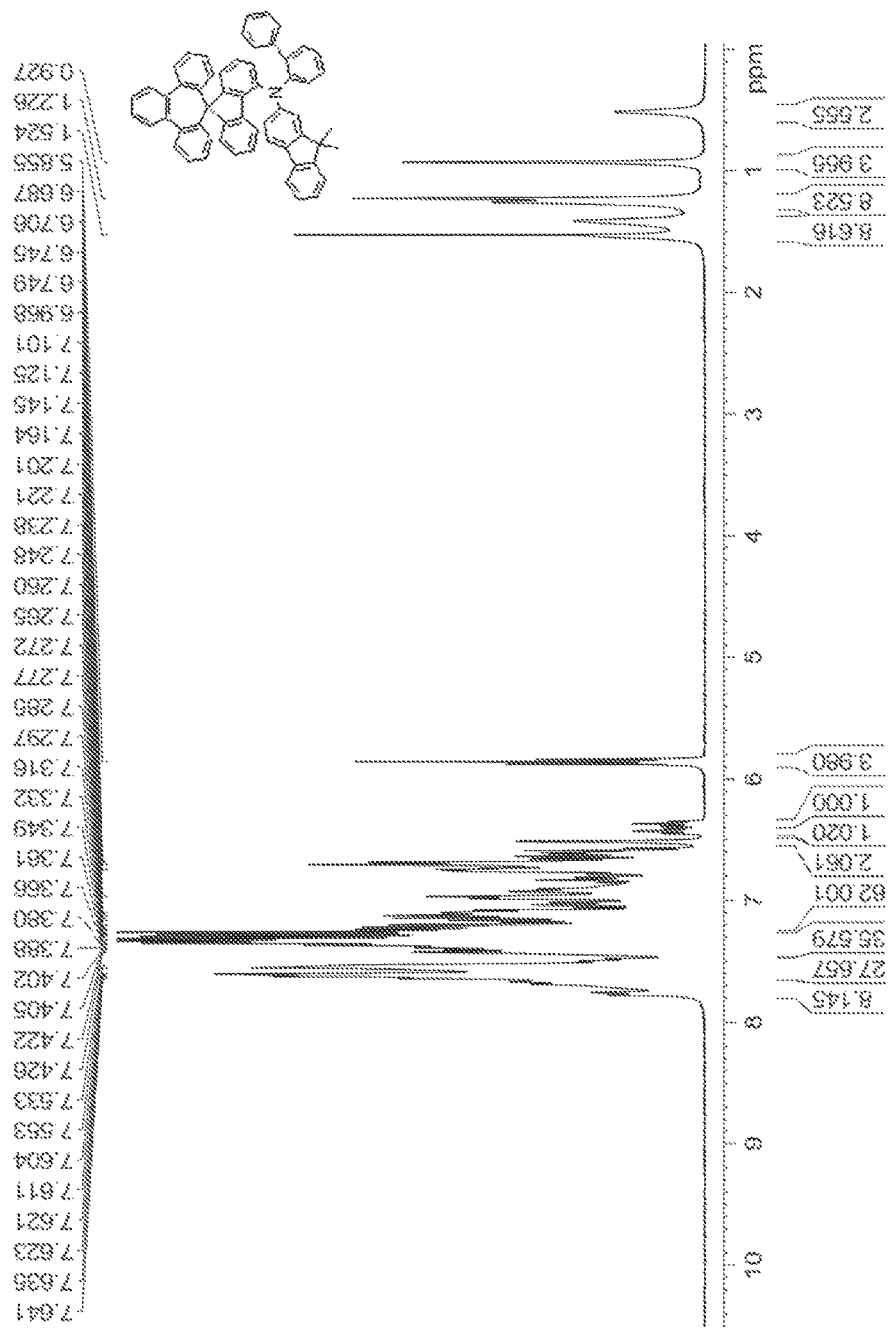
FIG. 13 is 1H NMR data of Compound (13) (SGM136) of the present disclosure.
Figure 14:
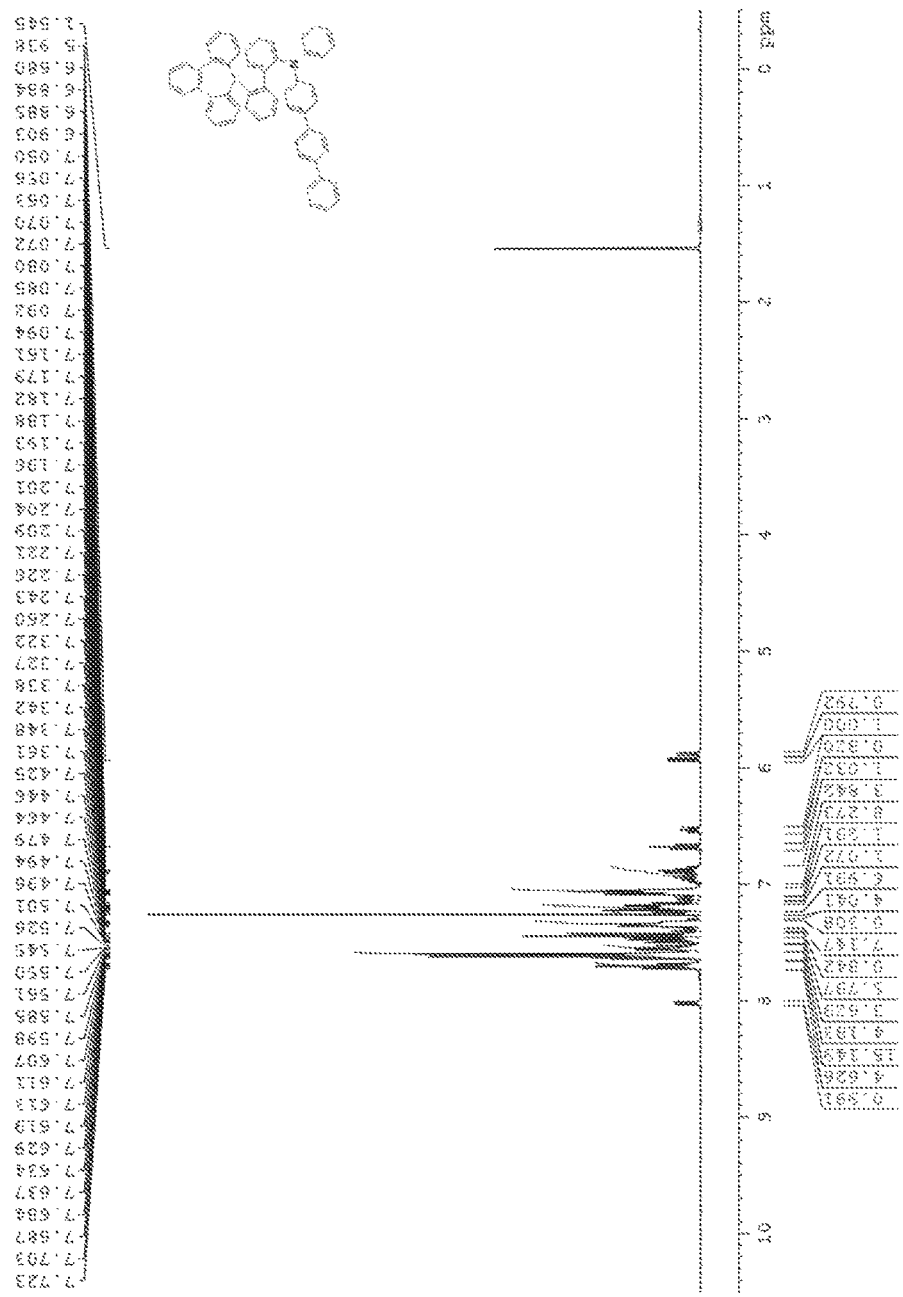
FIG. 14 is 1H NMR data of Compound (14) (SGM139) of the present disclosure.
Figure 15:
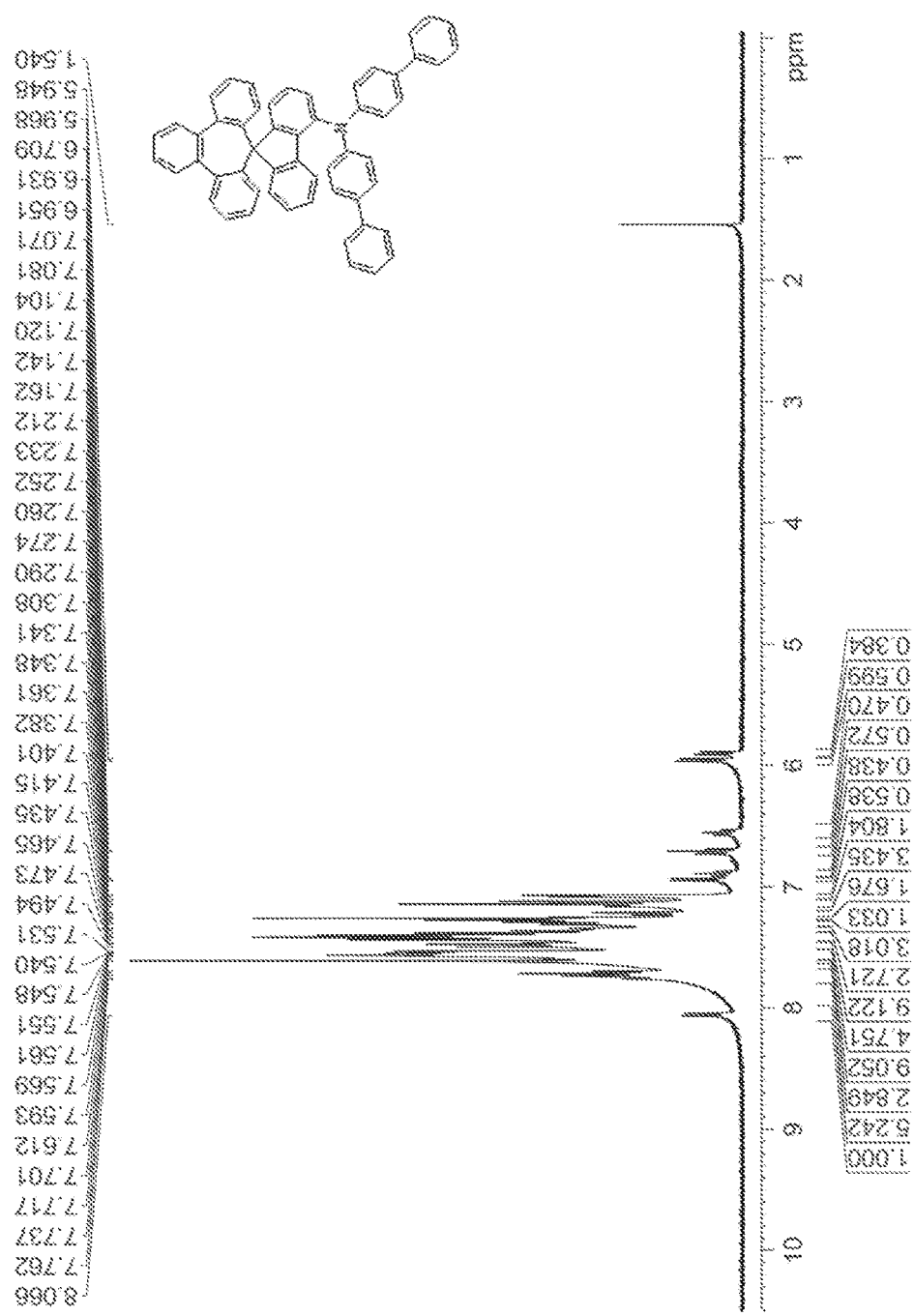
FIG. 15 is 1H NMR data of Compound (15) (SGM171) of the present disclosure.
Figure 16:
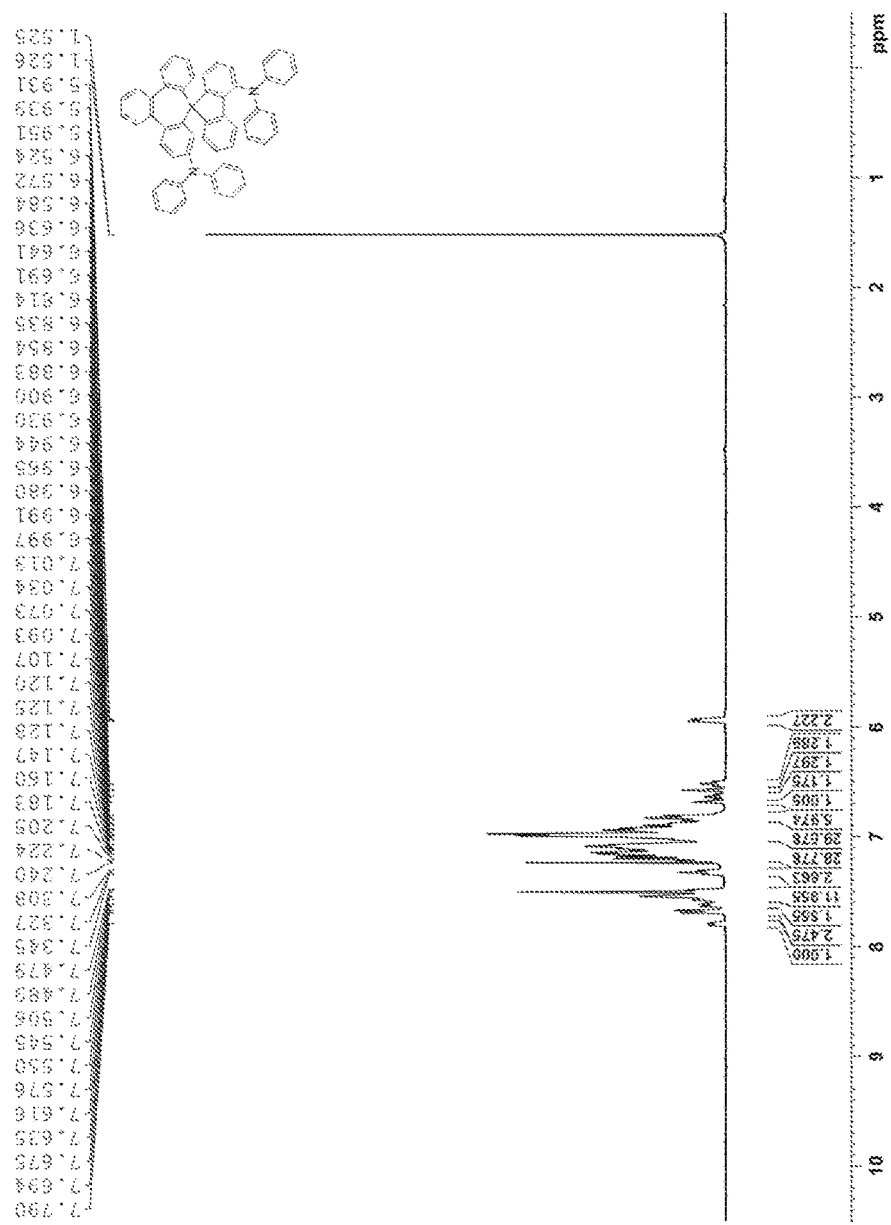
FIG. 16 is 1H NMR data of Compound (20) (SGM567) of the present disclosure.
Figure 17:
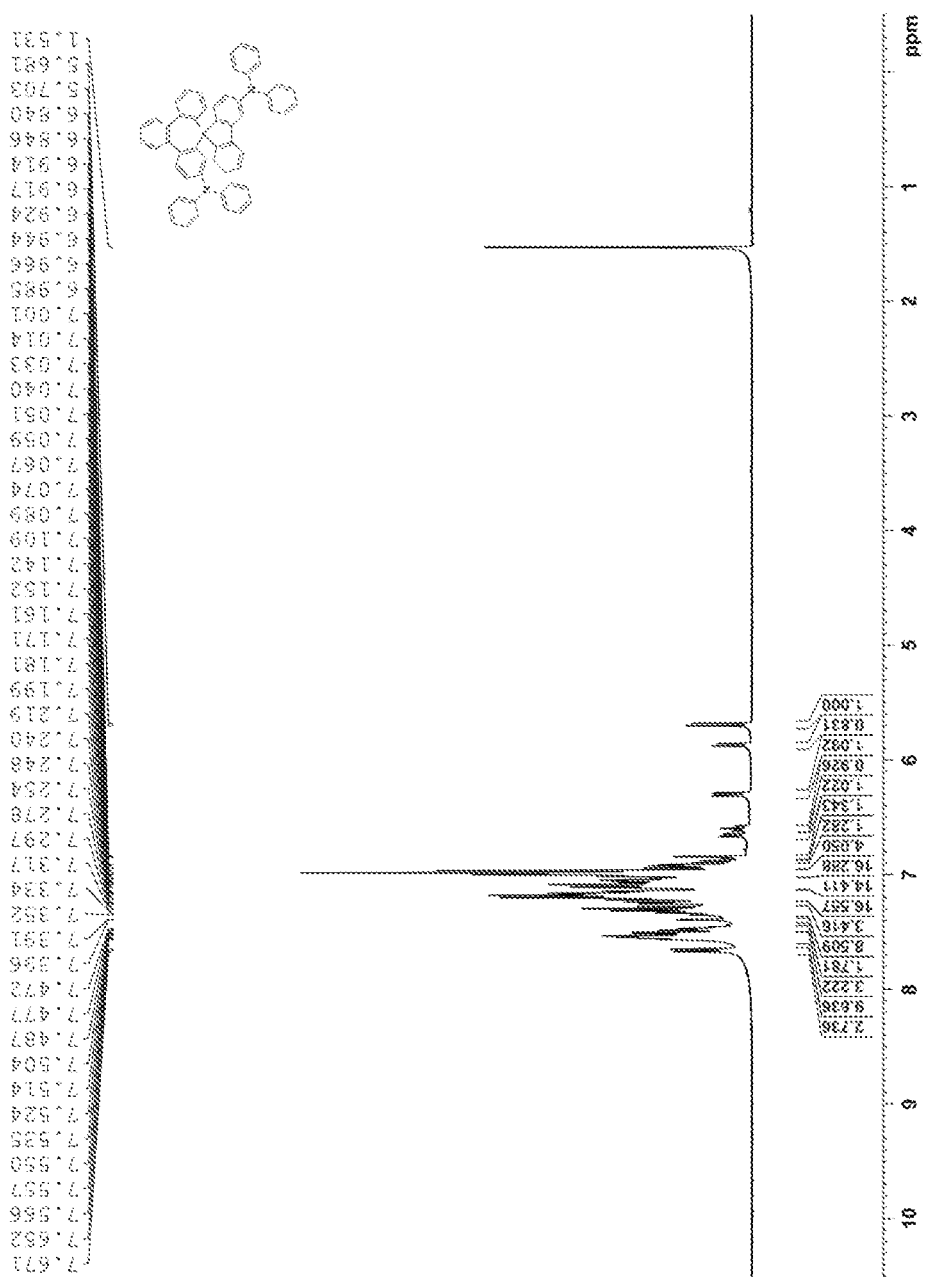
FIG. 17 is 1H NMR data of Compound (21) (SGM568) of the present disclosure.
Figure 18:
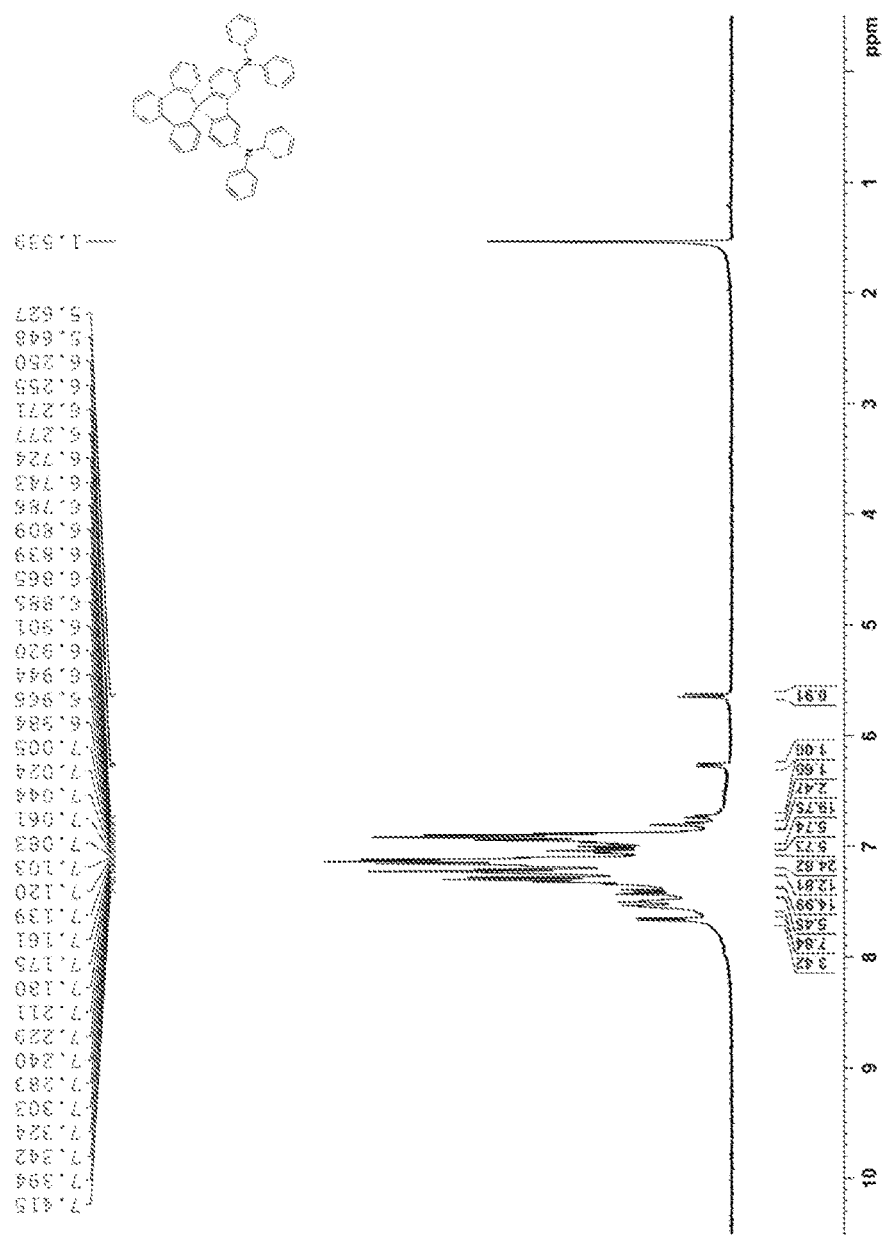
FIG. 18 is 1H NMR data of Compound (30) (SGM557) of the present disclosure.
Figure 19:
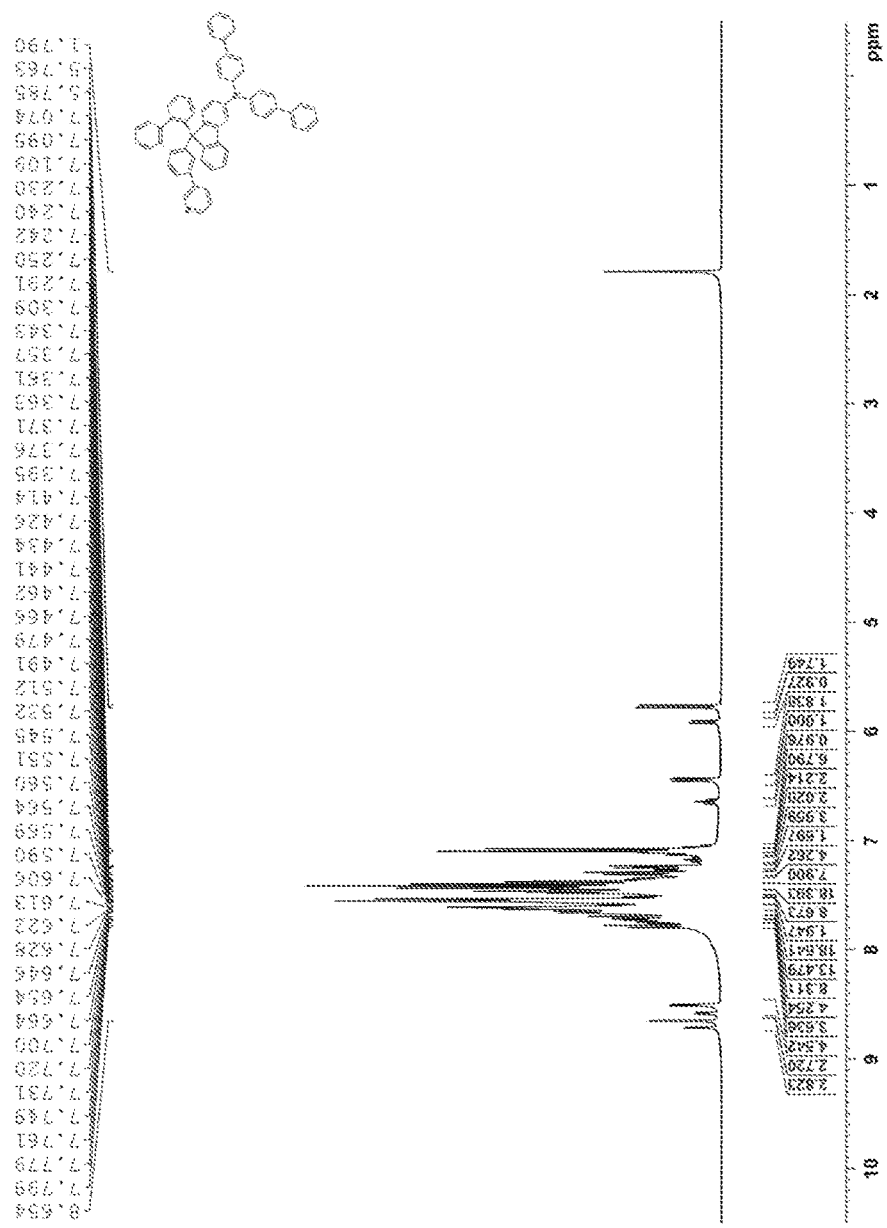
FIG. 19 is 1H NMR data of Compound (32) (SGM584) of the present disclosure.
Figure 20:
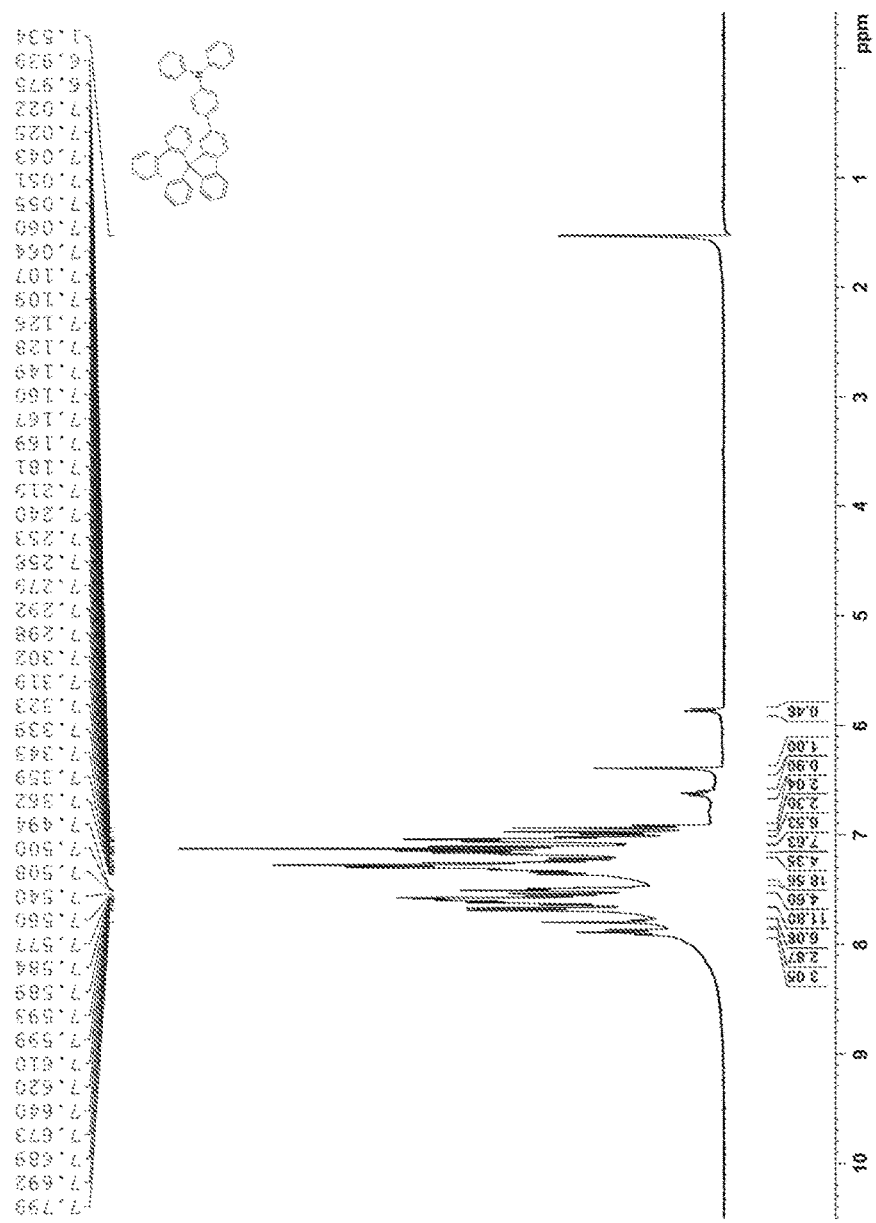
FIG. 20 is 1H NMR data of Compound (33) (SGM594) of the present disclosure.

In another embodiment, the organic electronic device can be an organic solar cell. FIG. 3 is a perspective view showing an exemplary structure of an organic solar cell used herein. As shown in FIG. 3, he organic solar cell may comprise: a first electrode 21; a second electrode 22; and an organic layer 23 disposed between the first electrode 21 and the second electrode 22 and comprising any one of the aforesaid compounds. Herein, the organic layer 23 may be served as a carrier transport layer.

Other objects, advantages, and novel features of the invention will become more apparent from the following detailed description when taken in conjunction with the accompanying drawings.

EXAMPLES

The following examples are provided in order to explain the characteristics of the present disclosure. However, the present disclosure is not limited by the following descriptions of the examples.

The following syntheses are carried out, unless indicated otherwise, under a protected-gas atmosphere. The starting materials can be purchased from Aldrich or Alfa or obtained in accordance with literature procedures.

Synthesis Example 1—Intermediates A1 to A8 and Synthesis Thereof

Intermediates A1 to A8 used for preparing the compounds of Formula (I) are listed in the following Table 1, wherein the numbers below each intermediates refers to the CAS numbers thereof.

TABLE 1

| Intermediates A1 to A8 |
| --- |
| Intermediate A1<br>102113-98-4 |
| Intermediate A2<br>897671-81-7 |
| Intermediate A3<br>1198395-24-2 |

TABLE 1-continued

Intermediates A1 to A8

Intermediate A4

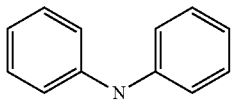

122-39-4

Intermediate A5

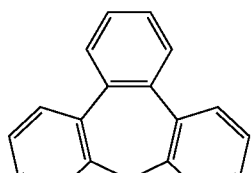

29875-73-8

Intermediate A6

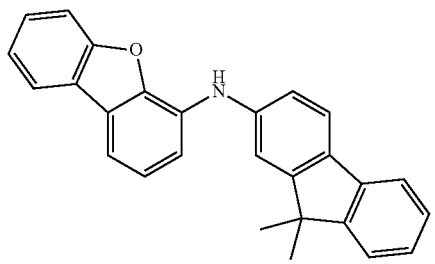 [SMILES: CC1(C)c2ccccc2-c2ccc(Nc3cccc4c3oc3ccccc34)cc21]

Intermediate A7

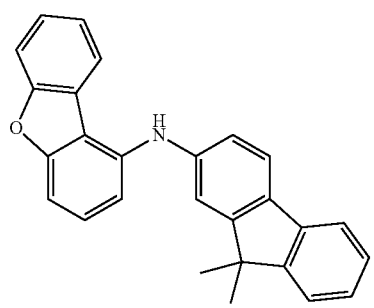 [SMILES: CC1(C)c2ccccc2-c2ccc(Nc3cccc4oc5ccccc5c34)cc21]

Intermediate A8

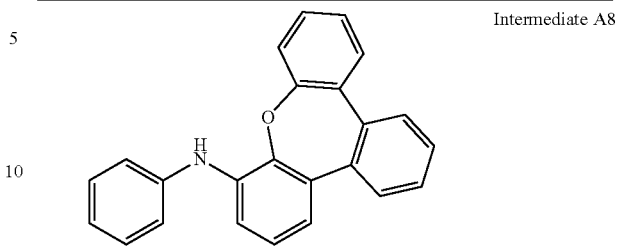

Intermediates A1 to A5

The intermediates A1 to A5 were purchased from Aldrich or Alfa, and CAS No. were listed above.

Synthesis of Intermediates A6 to A8

[Scheme I]

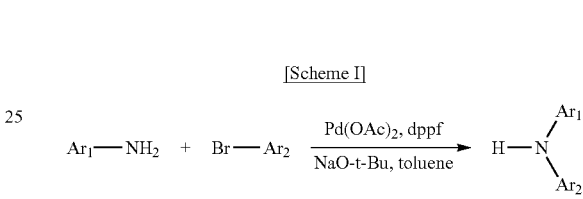

The intermediates A6 to A8 can be prepared according to the above Scheme I. The starting materials $Ar_1$—$NH_2$ (arylamine) and Br—$Ar_2$ (arylbromide) are listed in the following Table 2.

Briefly, a mixture of arylbromide (1.0 eq), arylamine (1.05 eq), $Pd(OAc)_2$ (0.01 eq), 1,1'-Bis(diphenylphosphino)ferrocene (DPPF) (0.04 eq), sodium tert-butoxide (1.5 eq), and toluene was taken in a pressure tube and heated at 80° C. for 12 h under $N_2$ atmosphere. After completion of the reaction, the volatiles were removed under vacuum, and the resulting solution extracted with dichloromethane (3×60 mL). The combined organic extract was washed with brine solution, dried over $Na_2SO_4$, and concentrated to leave a yellow solid. Further, the crude product was purified by column chromatography on silica gel by using hexane/dichloromethane mixture (2:1 v/v) as an eluent. The analysis data of the obtained products, i.e. Intermediates A11 to A14, are listed in the following Table 2.

TABLE 2

| Arylbromide | Arylamine | Intermediate | Yield(%) | EA (FD-MS) |
|---|---|---|---|---|
| 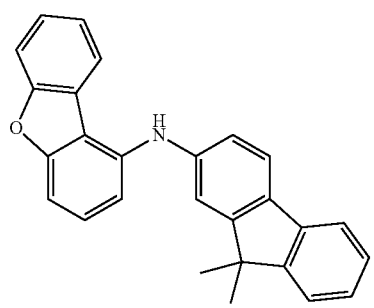 [SMILES: CC1(C)c2ccccc2-c2ccc(Nc3cccc4oc5ccccc5c34)cc21] | 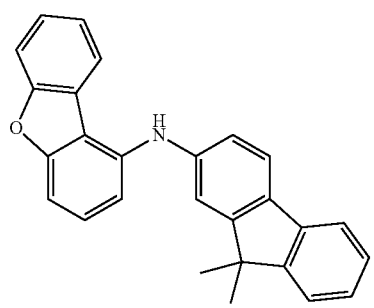 [SMILES: CC1(C)c2ccccc2-c2ccc(Nc3cccc4oc5ccccc5c34)cc21] | 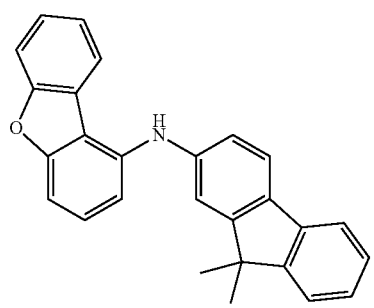 [SMILES: CC1(C)c2ccccc2-c2ccc(Nc3cccc4oc5ccccc5c34)cc21]<br>Intermediate A6 | 83.4 | $C_{27}H_{21}NO$<br>(375.46) |

TABLE 2-continued

| Arylbromide | Arylamine | Intermediate | Yield(%) | EA (FD-MS) |
|---|---|---|---|---|
| 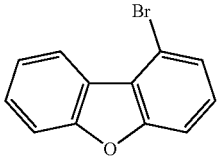 | 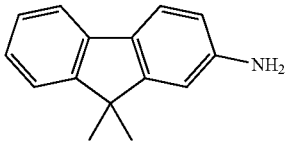 | 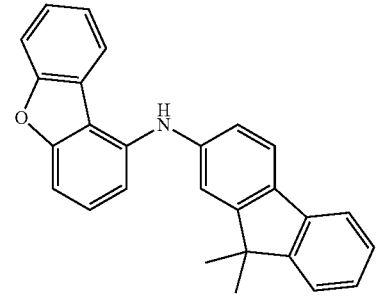 [SMILES: CC1(C)c2ccccc2-c2ccc(Nc3cccc4oc5ccccc5c34)cc21]  Intermediate A7 | 80.2 | $C_{27}H_{21}NO$ (375.46) |
| 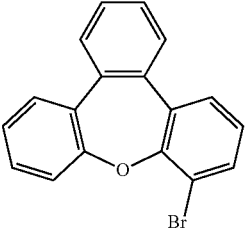 | 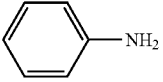 | 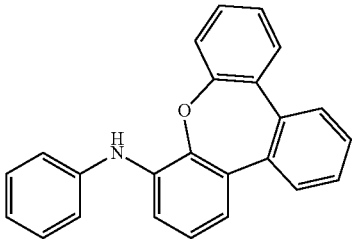 [SMILES: c1ccc(Nc2cccc3c2Oc2ccccc2-c2ccccc2-3)cc1]  Intermediate A8 | 81.7 | $C_{27}H_{21}NO$ (335.4) |

Synthesis Example 2—Intermediates B1 to B4 and Synthesis Thereof

Intermediates B1 to B4 used for preparing the compounds of Formula (I) are listed in the following Table 3.

TABLE 3

Intermediates B1 to B4

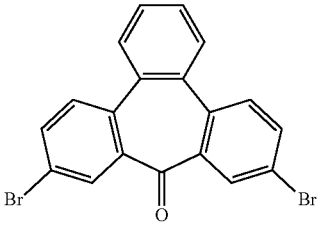 [SMILES: O=c1c2cc(Br)ccc2c2ccccc2c2ccc(Br)cc12]

Intermediate B1

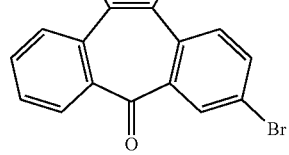

Intermediate B2

TABLE 3-continued

Intermediates B1 to B4

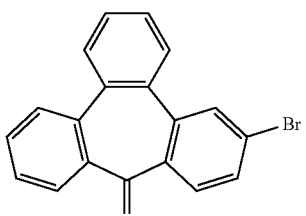

Intermediate B3

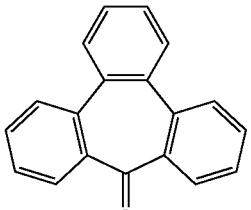

Intermediate B4

Synthesis of Intermediate B1

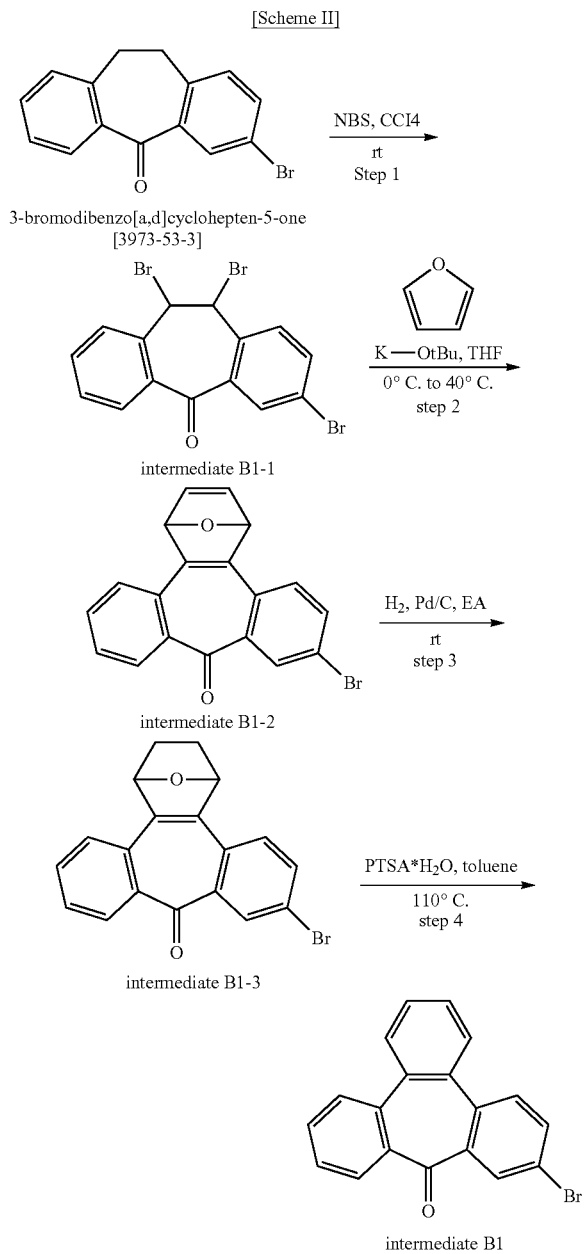

The intermediate B1 can be prepared according to the above Scheme II.

Step 1: Synthesis of Intermediate B1-1

A mixture of 3-bromodibenzo[a,d]cyclohepten-5-one (86 g, 1.0 eq), N-Bromosuccinimide (106 g, 2 eq), and benzyl peroxide (0.7 g, 0.01 eq) in carbon tetrachloride (430 ml) was heated to 85° C. The reaction was monitored by HPLC. After completion of a reaction, the precipitate was separated by filtration and washed with MeOH, then purified by recrystalization. The purified product was concentrated to dryness, whereby a white solid product was obtained in an amount of 123 g in 92.3% yield. FD-MS analysis $C_{15}H_9Br_3O$: theoretical value 444.94, observed value 444.94.

Step 2: Synthesis of Intermediate B1-2

The obtained intermediate B1-1 (116.0 g, 1.0 eq) was dissolved in 960 ml of furan/THF (v/v=2/1), the reaction was cooled to 0° C. and then treated with KO-t-Bu (87.8 g, 3.0 eq). The reaction was allowed to stir for 1 h at 0° C. prior to rate up to room temperature and stirred for additional 12 h. After completion of the reaction, it was quenched by DI water and the organic layer was recovered by solvent extraction operation and dried over sodium sulfate. The solvent was removed from the organic layer by distillation under reduced pressure, and the resulting residue was purified by silica gel column chromatography. The purified product was concentrated to dryness, whereby a light yellow solid product was obtained in an amount of 46.8 g in 51.1 percent yield. FD-MS analysis $C_{19}H_{11}BrO_2$: theoretical value 351.19, observed value 351.19.

Step 3: Synthesis of Intermediate B1-3

A suspension of the obtained intermediate B1-2 (53.5 g, 1.0 eq) and 5% Pd/C (8.1 g, 0.025 eq) in 535 ml ethyl acetate was stirred for 3-6 h under a hydrogen atmosphere provided by a balloon of hydrogen. The resulting mixture was filtered through a pad of celite and washed with ethyl acetate, and the filtrate was concentrated under reduced pressure to obtain 100 g (100%) of intermediate B1-3 as a yellow solid. The obtained compound, intermediate B1-3, was directly used in following reaction without further purified.

Step 4: Synthesis of Intermediate B1

The obtained intermediate B1-3 (53 g, 1.0 eq) and p-toluenesulfonic acid (57 g, 2.0 eq) in 530 ml of toluene was heated to reflux for 12 hours. The reaction mixture was cooled to room temperature and then quenched with a saturated aqueous solution of $NaHCO_3$ and extracted with $CH_2Cl_2$. The organic layer was washed with water, brine and dried with anhydrous $Na_2SO_4$ subsequently. Then the resulting solution was concentrated under reduced pressure and purified by column chromatography on silica gel with $CH_2Cl_2$/hexane 1/1 (v/v) as eluent. 46.0 g of intermediate B1 was obtained as light yellow solids in 91.5% yield. FD-MS analysis $C_{19}H_{11}BrO$: theoretical value 335.19, observed value 335.19.

Synthesis of Intermediates B2 and B4

The synthesis procedure of intermediate B2 and B4 were used the same manner as those for preparing the intermediate B1, except that 3-bromodibenzo[a,d]cyclohepten-5-one used for preparing the intermediate B1 was replaced by 2-bromodibenzo[a,d]cyclohepten-5-one for preparing the intermediate B2, replaced by 3,7-dibromodibenzo[a,d]cyclohepten-5-one for preparing the intermediate B3, or replaced by dibenzo[a,d]cyclohepten-5-one for preparing the intermediate B4. The intermediates in all the steps, yields and MS analysis data are listed in the following Table 4.

TABLE 4

| Step | Starting | 1st | 2nd |
|---|---|---|---|
| Structure | (structure) | (structure) | (structure) |
| Yield(%) | NA | 92.3 | 60.3 |
| Formula (FD-MS) | NA | C₁₅H₉Br₃O (444.94) | C₁₉H₁₁BrO₂ (351.19) |
| Structure | (structure) | (structure) | (structure) |
| Yield(%) | NA | 91.5 | 58.2 |
| Formula (FD-MS) | NA | C₁₅H₉Br₃O (444.94) | C₁₉H₁₁BrO₂ (351.19) |
| Structure | (structure) | (structure) | (structure) |
| Yield(%) | NA | 93.7 | 75.8 |
| Formula (FD-MS) | NA | C₁₅H₈Br₄O (523.84) | C₁₉H₁₀Br₂O₂ (430.09) |
| structure | (structure) | (structure) | (structure) |
| Yield(%) FD-MS (theoretical) | NA (208.26) | 97.5 (366.05) | 63.7 (272.3) |

| Step | 3rd-1 | 3rd-2 |
|---|---|---|
| Structure | (structure) | (structure) |
| | | Intermediate B1 |
| Yield(%) | NA | 91.5 |
| Formula (FD-MS) | C₁₉H₁₃BrO₂ (353.21) | C₁₉H₁₁BrO (335.19) |

TABLE 4-continued

| Structure | | |
|---|---|---|
| | (structure with O bridge, Br) | Intermediate B2 (structure with Br) |
| Yield(%) | NA | 93.5 |
| Formula (FD-MS) | C$_{19}$H$_{13}$BrO$_2$ (353.21) | C$_{19}$H$_{11}$BrO (335.19) |
| Structure | | |
| | (structure with O bridge, 2 Br) | Intermediate B3 (structure with 2 Br) |
| Yield(%) | NA | 93.0 |
| Formula (FD-MS) | C$_{19}$H$_{12}$Br$_2$O$_2$ (432.11) | C$_{19}$H$_{10}$Br$_2$O (414.09) |
| structure | | |
| | (structure with O bridge) | Intermediate B4 |
| Yield(%) FD-MS (theoretical) | NA (274.31) | 93.2 (256.3) |

Synthesis Example 3—Intermediate C1 to C4 and Synthesis Thereof

Intermediates C1 to C used for preparing the compounds of Formula (I) are listed in the following Table 5, wherein the numbers below each intermediates refers to the CAS numbers thereof.

TABLE 5

| Intermediates C1 to C4 | |
|---|---|
| (structure: 2-bromo-4'-chlorobiphenyl) 179526-95-5 | Intermediate C1 |
| (structure: 2-bromo-3'-chlorobiphenyl) 154407-17-7 | Intermediate C2 |

TABLE 5-continued

| Intermediates C1 to C4 | |
|---|---|
| (structure: 2,2'-dibromobiphenyl) 13029-09-9 | Intermediate C3 |
| (structure with Br, 2 Cl) | Intermediate C4 |

Synthesis of Intermediate C4

A solution of 1-bromo-2-chloro-4-iodobenzene (1.0 eq), 4-Chlorophenylboronic acid (1.1 eq), Pd(OAc)$_2$ (0.95 g, 0.01 eq), PPh$_3$ (4.45 g, 0.04 eq), and 3.0 M K$_2$CO$_3$ aqueous solution (58.6 g, 2.0 eq in 144 mL H$_2$O) in toluene (730 mL) was heated under nitrogen at 65° C. for 12 h. After cooling to room temperature, the solvent was then removed using a rotary evaporator, and the remaining substance was purified with column chromatography to obtain intermediate C4 (65%) MS: [M]$^+$=301.99.

Synthesis Example 4—Intermediates D1 to D13 and Synthesis Thereof

Intermediates D1 to D13 used for preparing the compounds of Formula (I) are listed in the following Table 6.

TABLE 6

Intermediates D1 to D13

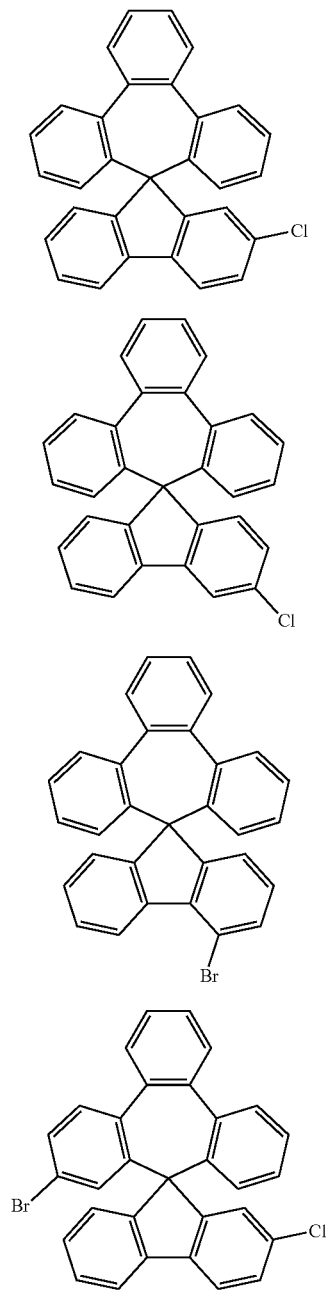

Intermediate D1

Intermediate D2

Intermediate D3

Intermediate D4

TABLE 6-continued

Intermediates D1 to D13

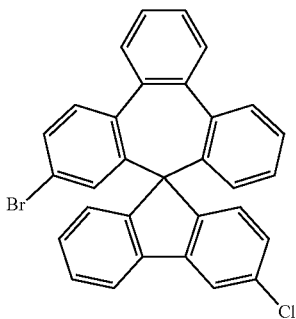

Intermediate D5

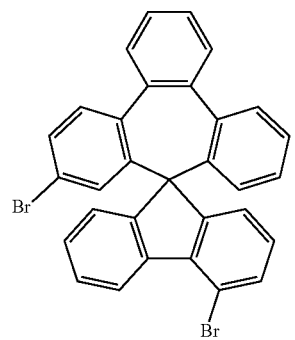 [SMILES: Brc1ccc2c(c1)C1(c3ccccc3-c3ccccc3-2)c2ccccc2-c2c(Br)cccc21]

Intermediate D6

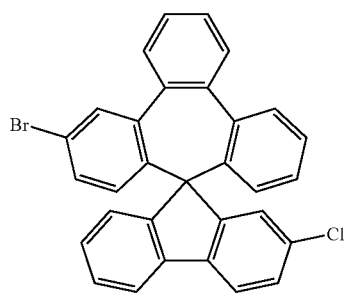 [SMILES: Clc1ccc2c(c1)C1(c3ccccc3-c3ccccc3-c3cc(Br)ccc31)c1ccccc1-2]

Intermediate D7

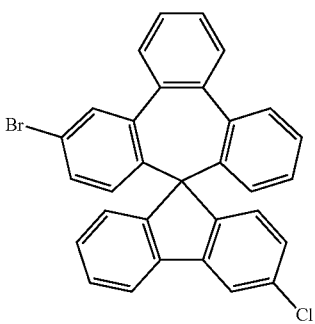 [SMILES: Clc1ccc2c(c1)-c1ccccc1C21c2ccccc2-c2ccccc2-c2cc(Br)ccc21]

Intermediate D8

TABLE 6-continued
Intermediates D1 to D13
Intermediate D9
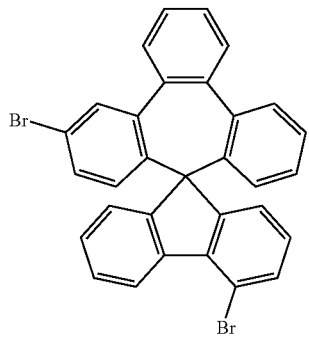 [SMILES: Brc1ccc2c(c1)-c1ccccc1-c1ccccc1C21c2ccccc2-c2c(Br)cccc21]
Intermediate D10
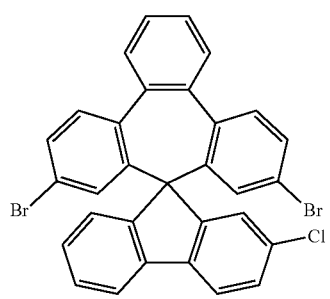 [SMILES: Clc1ccc2c(c1)C1(c3cc(Br)ccc3-c3ccccc3-c3ccc(Br)cc31)c1ccccc1-2]
Intermediate D11
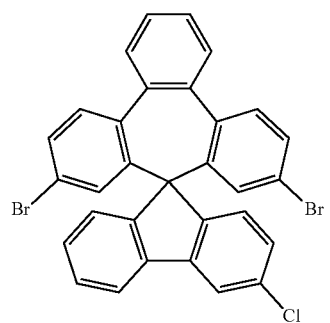 [SMILES: Clc1ccc2c(c1)-c1ccccc1C21c2cc(Br)ccc2-c2ccccc2-c2ccc(Br)cc21]
Intermediate D12
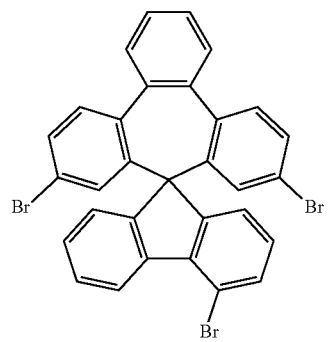 [SMILES: Brc1ccc2c(c1)C1(c3cc(Br)ccc3-c3ccccc3-2)c2ccccc2-c2c(Br)cccc21]
TABLE 6-continued
Intermediates D1 to D13
Intermediate D13
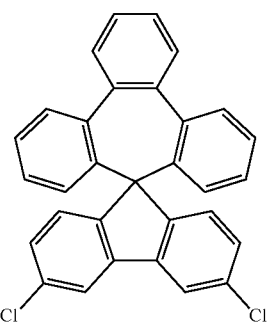 [SMILES: Clc1ccc2c(c1)-c1cc(Cl)ccc1C21c2ccccc2-c2ccccc2-c2ccccc21]
Intermediate D14
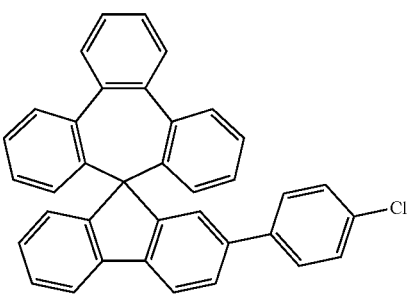 [SMILES: Clc1ccc(-c2ccc3c(c2)C2(c4ccccc4-c4ccccc4-c4ccccc42)c2ccccc2-3)cc1]
Intermediate D15
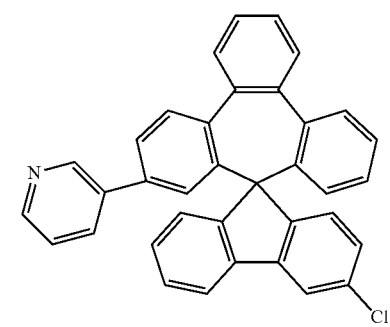 [SMILES: Clc1ccc2c(c1)-c1ccccc1C21c2ccccc2-c2ccccc2-c2ccc(-c3cccnc3)cc21]
Synthesis of Intermediate D1
[Scheme III]
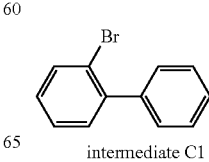 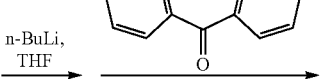
intermediate C1    step 1    intermediate B4

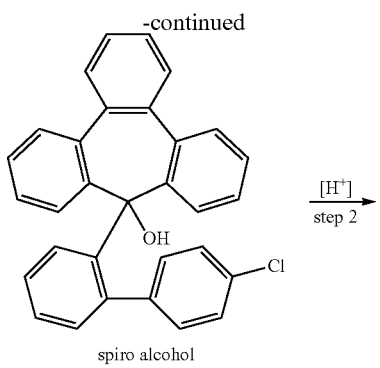

spiro alcohol

[H⁺] step 2 intermediate D1

The intermediate D1 can be prepared according to the above Scheme III.

Step 1: Synthesis of Spiro Alcohol

To the intermediate C1 (1.0 eq) in anhydrous THF (0.4 M), n-BuLi (1 eq) was added dropwise and stirred at −78° C. After stirring for 20 min, intermediate B4 (0.7 eq) was added to the mixture and the reaction mixture was allowed to warm to room temperature. The reaction was monitored by HPLC. After completion of a reaction, the reaction solution was quenched with water, and a water layer was extracted with ethyl acetate. The extracted solution and an organic layer were combined and washed with saturated saline, and then dried with magnesium sulfate. After drying, this mixture was subjected to suction filtration, and then the filtrate was concentrated. 65 g of spiro alcohol was obtained as a light yellow, powdery solid and was directly used in step 2 without further purified.

Step 2: Synthesis of Intermediate D1

To the obtained spiro alcohol (1 eq), acetic acid (w/v=1/3 to the reactant) and $H_2SO_4$ (5 drops) were added, and the mixture was stirred at 110° C. for 6 hr. The reaction was monitored by HPLC. After completion of a reaction, the precipitate was separated by filtration. The remaining substance was purified with column chromatography to obtain 58 g of intermediate D1 as white solid in a yield of 93.0%. FD-MS analysis $C_{31}H_{19}Br$: theoretical value 471.39, observed value 471.39.

Synthesis of Intermediates D2 to D13

The procedures for preparing the intermediates D2 to D13 were similar to that for preparing the intermediate D1, except that the intermediate B4 and the intermediate C1 used for preparing the intermediate D1 were substituted with the compounds listed in the following Table 7. The obtained intermediates D1 to D13 are present in white solids. In addition, the yields and MS analysis data of the intermediates D1 to D12 are also listed in the following Table 7.

TABLE 7

| Intermediate C | Intermediate B | Spiro-alcohol | Intermediate D | Yield (%) | Formula (FD-MS) |
|---|---|---|---|---|---|
| Intermediate C1 | Intermediate B4 | | intermediate D1 | 93.0 | $C_{31}H_{19}Cl$ (426.94) |
| Intermediate C2 | Intermediate B4 | | intermediate D2 | 89.1 | $C_{31}H_{19}Cl$ (426.94) |

TABLE 7-continued

| Intermediate C | Intermediate B | Spiro-alcohol | Intermediate D | Yield (%) | Formula (FD-MS) |
|---|---|---|---|---|---|
| Intermediate C3 | Intermediate B4 | | intermediate D3 | 83.2 | $C_{31}H_{19}Br$ (471.39) |
| Intermediate C1 | Intermediate B1 | | intermediate D4 | 88.7 | $C_{31}H_{18}BrCl$ (505.83) |
| Intermediate C2 | Intermediate B1 | | intermediate D5 | 88.7 | $C_{31}H_{18}BrCl$ (505.813) |
| Intermediate C3 | Intermediate B1 | | intermediate D6 | 86.9 | $C_{31}H_{18}Br_2$ (550.28) |
| Intermediate C1 | Intermediate B2 | | intermediate D7 | 87.5 | $C_{31}H_{18}BrCl$ (505.83) |

TABLE 7-continued

| Intermediate C | Intermediate B | Spiro-alcohol | Intermediate D | Yield (%) | Formula (FD-MS) |
|---|---|---|---|---|---|
| Intermediate C2 | Intermediate B2 | | intermediate D8 | 83.2 | $C_{31}H_{18}BrCl$ (505.83) |
| Intermediate C3 | Intermediate B2 | | intermediate D9 | 85.8 | $C_{31}H_{18}Br_2$ (550.28) |
| Intermediate C1 | Intermediate B3 | | intermediate D10 | 79.8 | $C_{31}H_{17}Br_2Cl$ (584.73) |
| Intermediate C2 | Intermediate B3 | | intermediate D11 | 80.1 | $C_{31}H_{17}Br_2Cl$ (584.73) |

TABLE 7-continued

| Intermediate C | Intermediate B | Spiro-alcohol | Intermediate D | Yield (%) | Formula (FD-MS) |
|---|---|---|---|---|---|
| Intermediate C3 | Intermediate B3 | | intermediate D12 | 89.5 | $C_{31}H_{17}Br_3$ (629.18) |
| Intermediate C4 | Intermediate B4 | | Intermediate D13 | 75.4 | $C_{31}H_{18}Cl_2$ (461.38) |

Synthesis of Intermediate D14 and D15

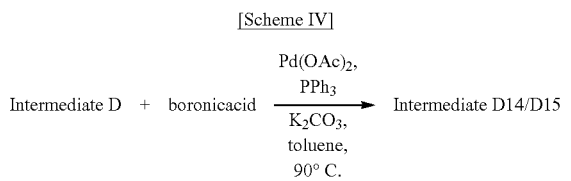

[Scheme IV]

Intermediate D + boronicacid $\xrightarrow[\text{K}_2\text{CO}_3, \text{ toluene, } 90° \text{C.}]{\text{Pd(OAc)}_2, \text{PPh}_3}$ Intermediate D14/D15

The intermediate D14 and D15 can be prepared according to the above Scheme IV.

Intermediates D1 or D5 (1.0 eq), Boronic acid (1.1 eq), Pd(OAc)$_2$ (0.01 eq), PPh$_3$ (0.04 eq), K$_2$CO$_3$ (1.5 eq, 3M) in toluene was heated at 100° C. for 12 h. After completion of the reaction, the volatiles were removed under vacuum, and the resulting solution extracted with dichloromethane (3×60 mL). The combined organic extract was washed with brine solution, dried over Na$_2$SO$_4$, and concentrated to leave a yellow solid. Further, the crude product was purified by column chromatography on silica gel. In addition, the yields and MS analysis data of the intermediates D14 and D15 are listed in the following Table 8.

TABLE 8

| Intermediate D | Boronic acid | Intermediate D | Yield (%) | Formula (FD-MS) |
|---|---|---|---|---|
| Intermediate D1 | (HO)$_2$B—⌬—Cl  1679-18-1 | Intermediate D14 | 94.3 | $C_{37}H_{23}Cl$ (503.03) |

TABLE 8-continued

| Intermediate D | Boronic acid | Intermediate D | Yield (%) | Formula (FD-MS) |
|---|---|---|---|---|
| Intermediate D5 | 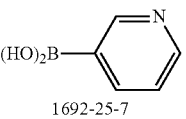<br>1692-25-7 | 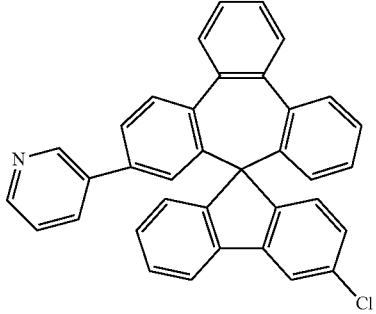 [SMILES: Clc1ccc2c(c1)-c1ccccc1C21c2ccccc2-c2ccccc2-c2ccc(-c3cccnc3)cc21]<br>Intermediate D15 | 92.5 | $C_{36}H_{22}ClN$<br>(504.02) |

Synthesis Example 5—Compounds (1) to (30)

Synthesis of Compounds (1) to (26)

The compounds of the present disclosure can be synthesized according to the following Scheme V.

[Scheme V]

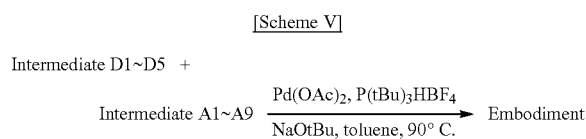

Briefly, a mixture of intermediates D1 to D15 (1.0 eq), intermediates A1 to A9 (1.05 eq), Pd(OAc)₂ (0.005 eq), P(t-Bu)₃HBF₄ (0.02 eq), and NaO'Bu (1.5 eq) in toluene (0.3 M) was heated at 90° C. for 8-24 h. After completion of the reaction, the volatiles were removed under vacuum, and the resulting solution extracted with dichloromethane (3×60 mL). The combined organic extract was washed with brine solution, dried over Na₂SO₄, and concentrated to leave a yellow solid. Further, the crude product was purified by column chromatography on silica gel to give final compound with white solid.

Synthesis of Compound (27)

Intermediate A9 (1.0 eq), intermediate D3 (2.1 eq), Pd(OAc)₂ (0.01 eq), P(t-Bu)₃HBF₄ (0.04 eq), and NaO'Bu (3.0 eq) in toluene (0.3M) was heated at 90° C. for 24 h. After completion of the reaction, the volatiles were removed under vacuum, and the resulting solution extracted with dichloromethane (3×60 mL). The combined organic extract was washed with brine solution, dried over Na₂SO₄, and concentrated to leave a yellow solid. Further, the crude product was purified by column chromatography on silica gel to give final compound with white solid.

The products (1) to (30), the used intermediates, the yields, and the MS analysis data are listed in the following Table 9.

TABLE 9

| SGM | Intermediate A | Intermediate D | Embodiment | Yield (%) | EA/ (FD-MS) |
|---|---|---|---|---|---|
| 134 (1) | Intermediate A3 | Intermediate D1 | 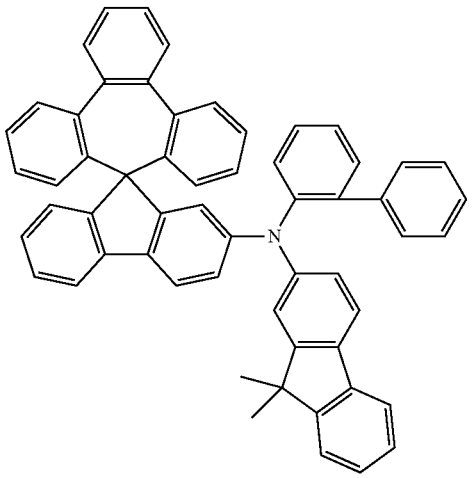 [SMILES: CC1(C)c2ccccc2-c2ccc(N(c3ccc4c(c3)C3(c5ccccc5-c5ccccc5-c5ccccc53)c3ccccc3-4)c3ccccc3-c3ccccc3)cc21] | 64.9 | $C_{58}H_{41}N$ (751.95) |

TABLE 9-continued

| SGM | Intermediate A | IntermediateD | Embodiment | Yield (%) | EA/ (FD-MS) |
|---|---|---|---|---|---|
| 137 (2) | Intermediate A2 | Intermediate D1 | | 93.4 | $C_{55}H_{37}N$ (711.89) |
| 423 (4) | Intermediate A5 | Intermediate D1 | | 67.4 | $C_{49}H_{31}N$ (633.78) |
| 135 (7) | Intermediate A3 | Intermediate D2 | | 94.6 | $C_{58}H_{41}N$ (751.95) |

TABLE 9-continued
| SGM | Intermediate A | IntermediateD | Embodiment | Yield (%) | EA/ (FD-MS) |
|---|---|---|---|---|---|
| 138 (8) | Intermediate A2 | Intermediate D2 | 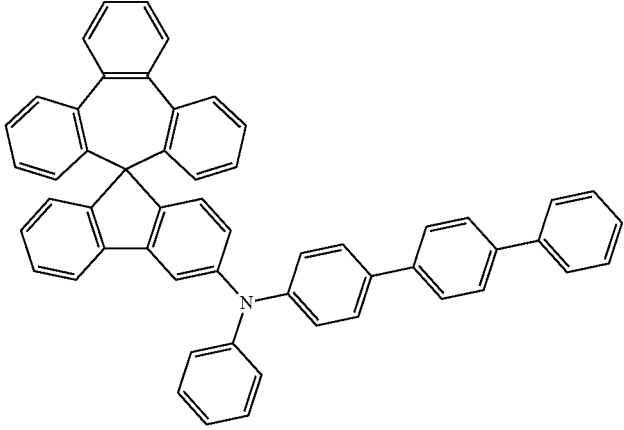 [SMILES: c1ccc(-c2ccc(-c3ccc(N(c4ccccc4)c4ccc5c(c4)-c4ccccc4C54c5ccccc5-c5ccccc5-c5ccccc54)cc3)cc2)cc1] | 60.5 | $C_{55}H_{37}N$ (711.89) |
| 422 (10) | Intermediate A5 | Intermediate D2 | 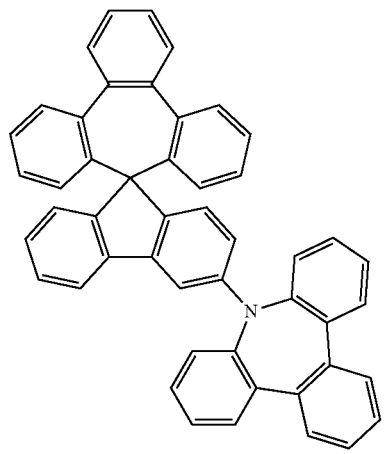 [SMILES: c1ccc2c(c1)-c1ccccc1N(c1ccc3c(c1)-c1ccccc1C31c3ccccc3-c3ccccc3-c3ccccc31)c1ccccc1-2] | 67.7 | $C_{49}H_{31}N$ (633.78) |
| 565 (11) | Intermediate A6 | Intermediate D2 | 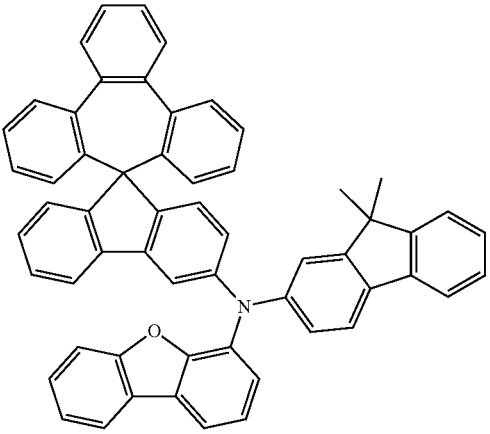 [SMILES: CC1(C)c2ccccc2-c2ccc(N(c3ccc4c(c3)-c3ccccc3C43c4ccccc4-c4ccccc4-c4ccccc43)c3cccc4c3oc3ccccc34)cc21] | 74.7 | $C_{58}H_{39}NO$ (765.94) |

TABLE 9-continued

| SGM | Intermediate A | IntermediateD | Embodiment | Yield (%) | EA/ (FD-MS) |
|---|---|---|---|---|---|
| 578 (12) | Intermediate A7 | Intermediate D2 | | 83.6 | $C_{58}H_{39}NO$ (765.94) |
| 564 (31) | Intermediate A8 | Intermediate D2 | | 71.5 | $C_{55}H_{35}NO$ (725.87) |
| 136 (13) | Intermediate A3 | Intermediate D3 | | 77.8 | $C_{58}H_{41}N$ (751.95) |

TABLE 9-continued
| SGM | Intermediate A | IntermediateD | Embodiment | Yield (%) | EA/ (FD-MS) |
|---|---|---|---|---|---|
| 139 (14) | Intermediate A2 | IntermediateD3 | 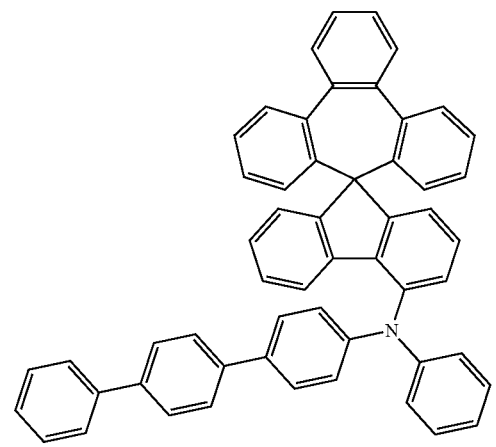 [SMILES: c1ccc(-c2ccc(-c3ccc(N(c4ccccc4)c4cccc5c4-c4ccccc4C54c5ccccc5-c5ccccc5-c5ccccc54)cc3)cc2)cc1] | 72.8 | $C_{55}H_{37}N$ (711.89) |
| 171 (15) | Intermediate A1 | Intermediate D3 | 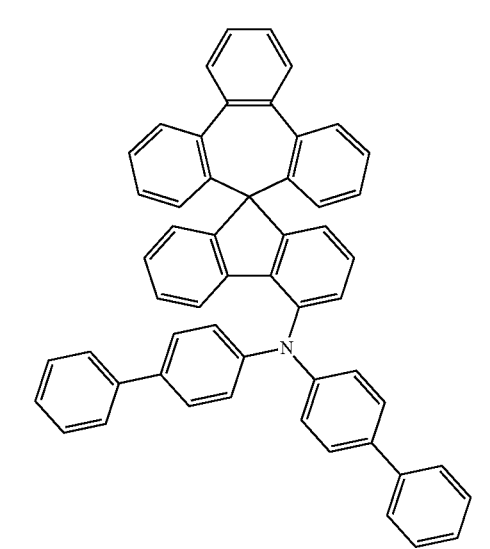 [SMILES: c1ccc(-c2ccc(N(c3ccc(-c4ccccc4)cc3)c3cccc4c3-c3ccccc3C43c4ccccc4-c4ccccc4-c4ccccc43)cc2)cc1] | 66.2 | $C_{55}H_{37}N$ (711.89) |
| 567 (20) | Intermediate A4 | IntermediateD6 | 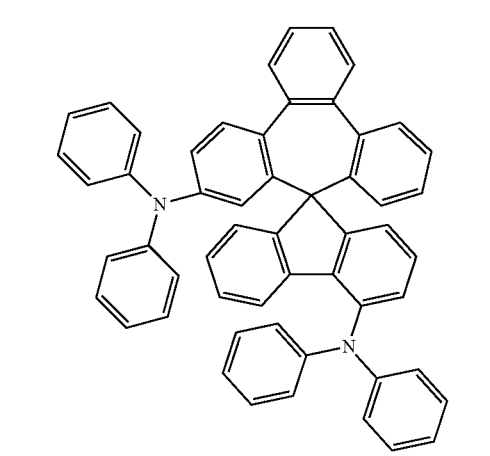 [SMILES: c1ccc(N(c2ccccc2)c2ccc3c(c2)C2(c4ccccc4-c4ccccc4-3)c3ccccc3-c3c(N(c4ccccc4)c4ccccc4)cccc32)cc1] | 86.0 | $C_{55}H_{38}N_2$ (726.9) |

TABLE 9-continued
| SGM | Intermediate A | IntermediateD | Embodiment | Yield (%) | EA/ (FD-MS) |
|---|---|---|---|---|---|
| 568 (21) | Intermediate A4 | IntermediateD5 | 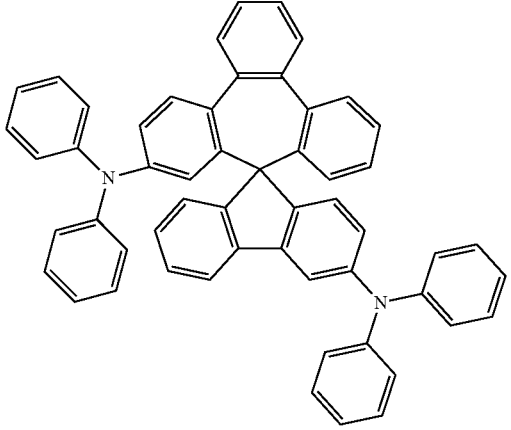 [SMILES: c1ccc(N(c2ccccc2)c2ccc3c(c2)-c2ccccc2C32c3ccccc3-c3ccccc3-c3ccc(N(c4ccccc4)c4ccccc4)cc32)cc1] | 88.9 | $C_{55}H_{38}N_2$ (726.9) |
| 584 (32) | IntermediateA1 | IntermediateD15 | 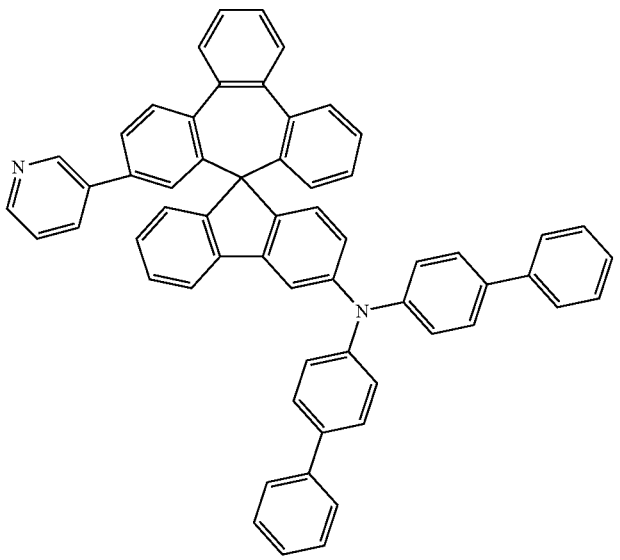 [SMILES: c1ccc(-c2ccc(N(c3ccc(-c4ccccc4)cc3)c3ccc4c(c3)-c3ccccc3C43c4ccccc4-c4ccccc4-c4ccc(-c5cccnc5)cc43)cc2)cc1] | 68.3 | $C_{60}H_{40}N_2$ (788.97) |
| 594 (33) | IntermediateA1 | IntermediateD14 | 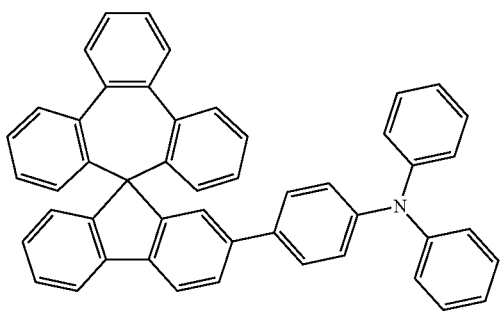 | 81.9 | $C_{61}H_{41}N$ (787.98) |

TABLE 9-continued

| SGM | Intermediate A | IntermediateD | Embodiment | Yield (%) | EA/ (FD-MS) |
|---|---|---|---|---|---|
| 557 (30) | IntermediateA4 | IntermediateD13 | 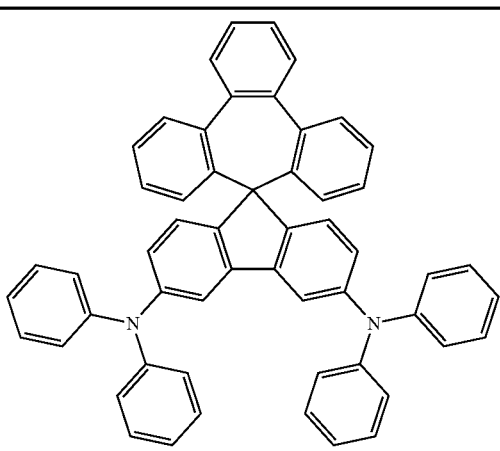 | 61.2 | $C_{55}H_{38}N_2$ (726.9) |

Example—OLED Device Fabrication

A glass substrate having ITO (indium tin oxide) coated thereon to a thickness 1500 Å was placed in distilled water containing a detergent dissolved therein, and was ultrasonically washed. Herein, the detergent was a product manufactured by Fischer Co., and the distilled water was filtered twice through a filter (Millipore Co.). After the ITO had been washed with detergent for 30 minutes, it was ultrasonically washed twice with distilled water for 10 minutes followed by isopropyl alcohol, acetone, and methanol, which was then dried, after which it was transported to a plasma cleaner. Then, the substrate was clean with oxygen plasma for 5 minutes, and then transferred to a vacuum evaporator.

Various organic materials and metal materials were sequentially deposited on the ITO substrate to obtain the OLED device of the present examples. The vacuum degree during the deposition was maintained at $1 \times 10^{-6}$ to $3 \times 10^{-7}$ torr. In addition, the formulas and the code names of the materials used in the following OLED devices were listed in the following Table 10.

Preparation of Blue OLED Device

To fabricate the blue OLED device of the present examples, HAT was firstly deposited on the ITO substrate to form a first hole injection layer with a thickness of 100 Å. HI-2 was deposited on the first hole injection layer with a dopant HAT (5.0 wt %) to form a second hole injection layer having a thickness of 750 Å.

Next, HT-1 or compounds of the present disclosure was deposited to form a first hole transporting layer (HT1) with a thickness of 100 Å; and/or HT-2 or compounds of the present disclosure was deposited to form a second hole transporting layer (HT2) with a thickness of 100 Å. Then, BH with a dopant BD (3.5 wt %) was deposited on the first or second hole transporting layer to form a light emitting layer having a thickness of 250 Å. ET with a dopant Liq (35.0 wt %) was deposited on the light emitting layer to form an electron transporting layer with a thickness of 250 Å. Liq was deposited on the electron transporting layer to form an electron injection layer with a thickness of 15 Å. Al was deposited on the electron injection layer to form a cathode with a thickness of 1500 Å.

After the aforementioned process, the blue OLED device used in the following test was obtained.

Preparation of Green OLED Device

The preparation of the green OLED device was similar to that of the blue OLED device, except that the second hole injection layer, the light emitting layer and the electron transporting layer.

Herein, the thickness of the second hole injection layer was 1300 Å. GH with a dopant GD (10 wt %) was deposited on the first or second hole transporting layer to form a light emitting layer having a thickness of 400 Å. The thickness of the electron transporting layer was 350 Å.

Preparation of Red OLED Device

The preparation of the red OLED device was similar to that of the blue OLED device, except that the second hole injection layer, the light emitting layer and the electron transporting layer.

Herein, the thickness of the second hole injection layer was 2100 Å. RH with a dopant RD (3.5 wt %) was deposited on the first or second hole transporting layer to form a light emitting layer having a thickness of 300 Å. The thickness of the electron transporting layer was 350 Å.

TABLE 10
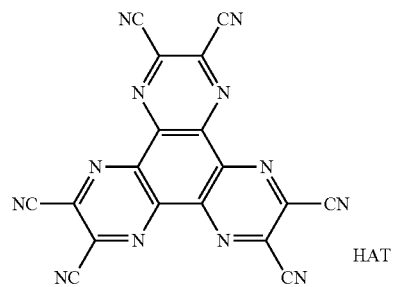
HI-1
HAT
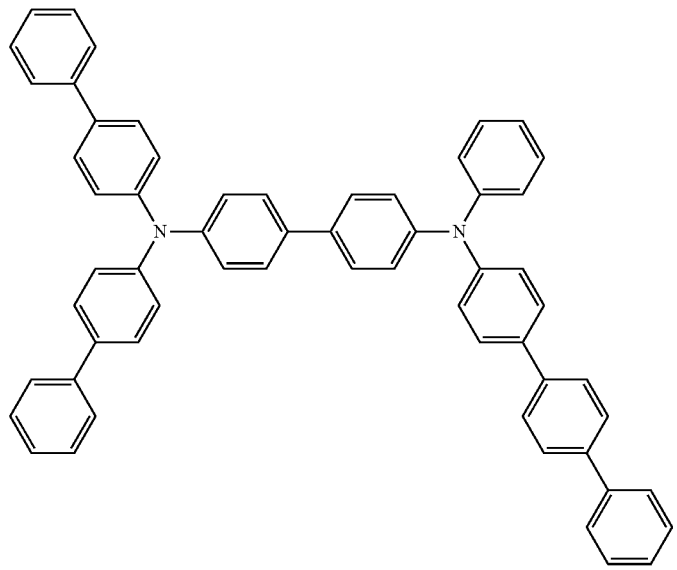 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]
HI-2
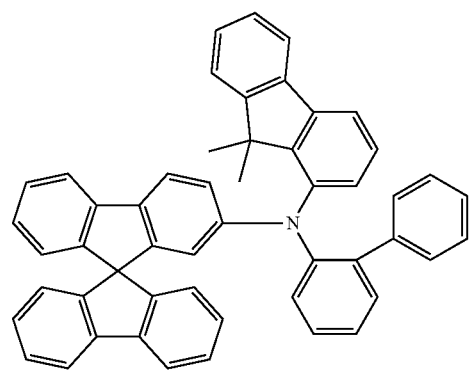 [SMILES: CC1(C)c2ccccc2-c2cccc(N(c3ccc4c(c3)C3(c5ccccc5-c5ccccc53)c3ccccc3-4)c3ccccc3-c3ccccc3)c21]
HT-1
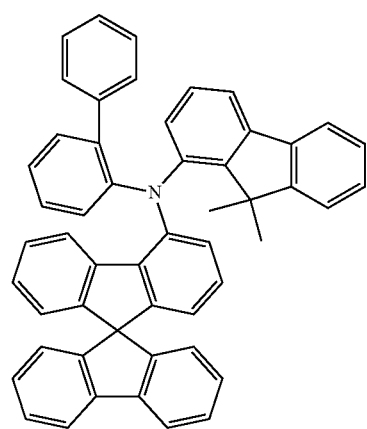 [SMILES: CC1(C)c2ccccc2-c2cccc(N(c3ccccc3-c3ccccc3)c3cccc4c3-c3ccccc3C43c4ccccc4-c4ccccc43)c21]
HT-2

TABLE 10-continued
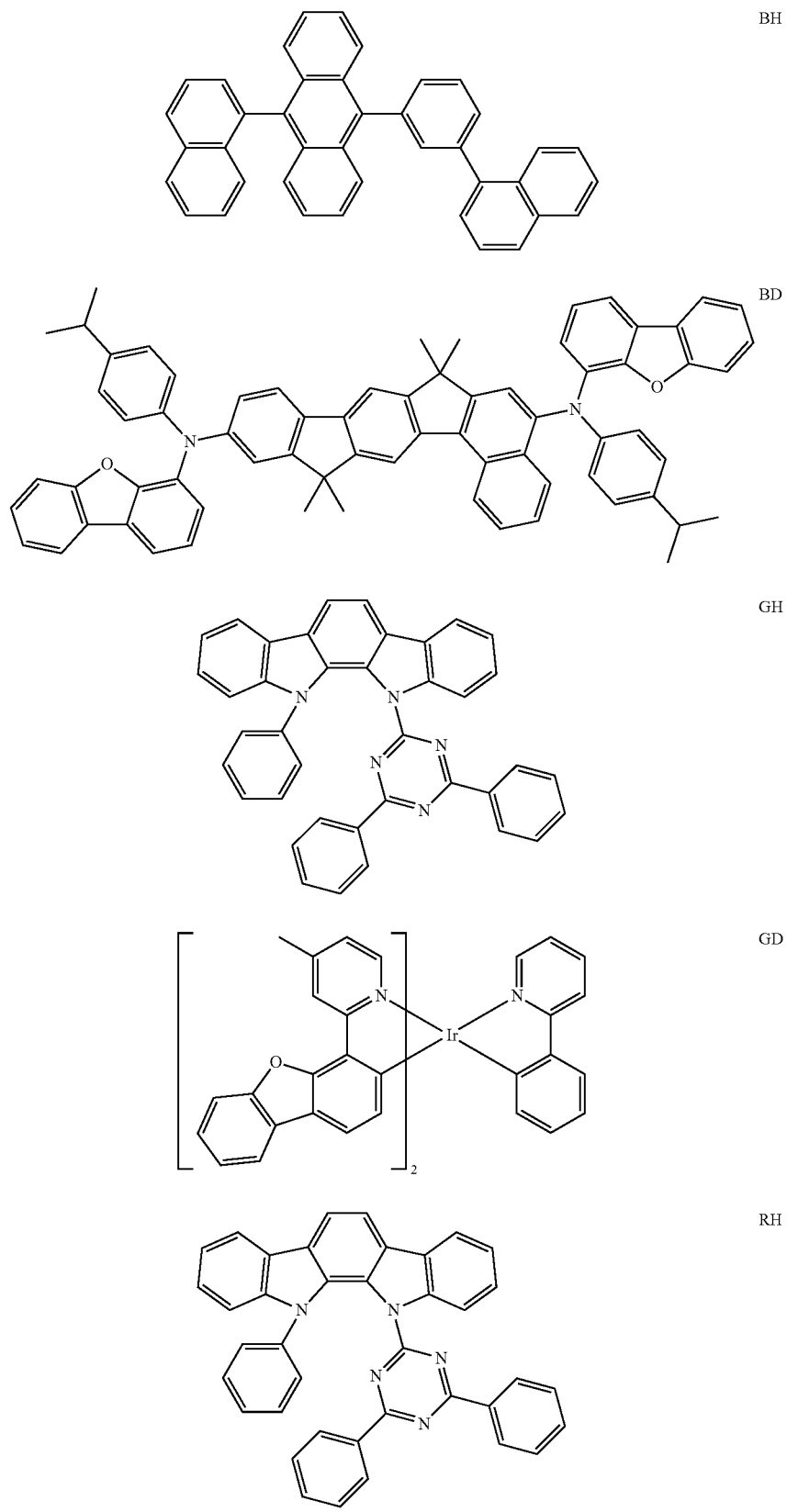

TABLE 10-continued

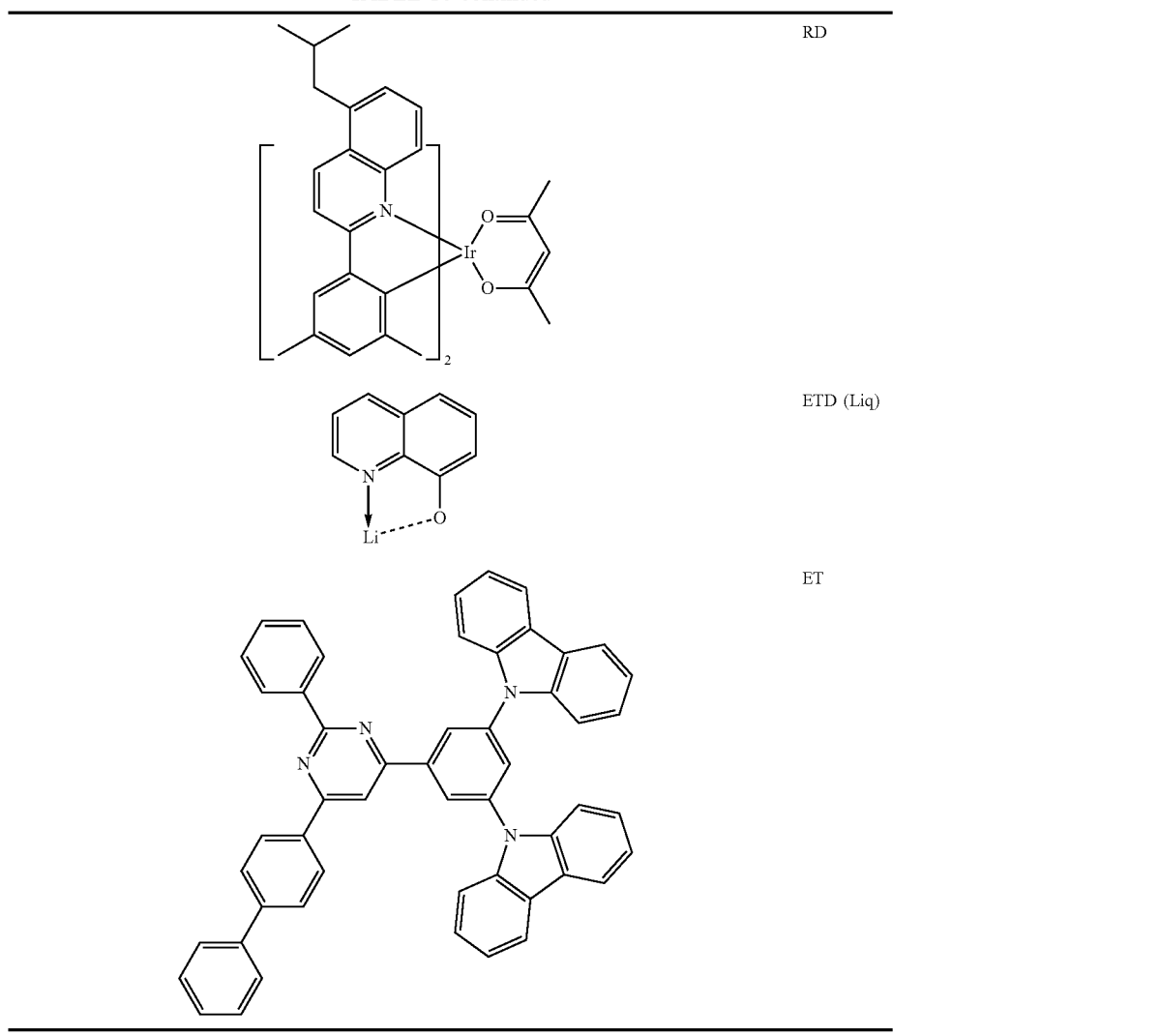

OLED Device Measurement

Device performances of the obtained blue, green and red OLED devices were measured by PR-650. For the blue and red OLED devices, the data were collected at 1000 nits. For the green OLED devices, the data were collected at 3000 nits. Data such as CIE, luminous efficiency (Eff.) and driving voltage (Voltage) are listed in the following Tables 11 to 13.

TABLE 11

| Example | HT1 | HT2 | Color CIE(x, y) | Voltage (V) | Efficiency (cd/A) |
|---|---|---|---|---|---|
| Example 1 | — | SGM136 | B (0.136, 0.175) | 4.30 | 13.5 |
| Example 2 | — | SGM137 | B (0.135, 0.182) | 4.38 | 13.1 |
| Example 3 | — | SGM138 | B (0.135, 0.184) | 4.34 | 13.4 |
| Example 4 | — | SGM139 | B (0.135, 0.173) | 4.33 | 13.4 |
| Example 5 | — | SGM171 | B (0.135, 0.186) | 4.19 | 14.1 |
| Comp Exp (1) | HT-1 | HT-2 | B (0.135, 0.185) | 4.39 | 12.1 |

TABLE 12

| Example | HT1 | HT2 | Color CIE(x, y) | Voltage (V) | Efficiency (cd/A) |
|---|---|---|---|---|---|
| Example 6 | — | SGM135 | G (0.337, 0.625) | 2.77 | 82.3 |
| Example 7 | — | SGM138 | G (0.339, 0.623) | 3.02 | 77.9 |
| Example 8 | — | SGM423 | G (0.313, 0.638) | 3.09 | 74.4 |
| Example 9 | — | SGM557 | G (0.314, 0.638) | 3.02 | 75.1 |
| Example 10 | — | SGM564 | G (0.314, 0.638) | 3.23 | 75.5 |
| Example 11 | — | SGM568 | G (0.314, 0.639) | 2.89 | 74.4 |
| Example 12 | — | SGM584 | G (0.313, 0.637) | 3.15 | 73.7 |
| Example 13 | — | SGM594 | G (0.314, 0.638) | 2.80 | 73.6 |
| Comp Exp (2) | HT-1 | HT-2 | G (0.314, 0.637) | 2.95 | 73.5 |

TABLE 13

| Example | HT1 | HT2 | Color CIE(x, y) | Voltage (V) | Efficiency (cd/A) |
|---|---|---|---|---|---|
| Example 14 | SGM134 026 | — | R (0.665, 0.333) | 3.50 | 26.9 |
| Example 15 | — | SGM422 | R (0.657, 0.342) | 3.96 | 28.4 |
| Example 116 | — | SGM564 | R (0.660, 0.338) | 3.65 | 27.7 |
| Example 17 | — | SGM567 | R (0.661, 0.338) | 4.11 | 26.4 |
| Example 18 | — | SGM578 | R (0.660, 0.339) | 3.52 | 24.2 |
| Comp Exp (3) | HT-1 | HT-2 | R (0.661, 0.338) | 3.65 | 23.9 |

According to the results shown in Tables 11 to 13, the OLED device applied with the compound of Formula (I) shows improved luminous efficiency and low driving voltage. Therefore, the compound of Formula (I) of the present disclosure can effectively be used as a hole transporting material of an OLED device.

Although the present disclosure has been explained in relation to its preferred embodiment, it is to be understood that many other possible modifications and variations can be made without departing from the spirit and scope of the invention as hereinafter claimed.

What is claimed is:

1. A compound of Formula (I) below:

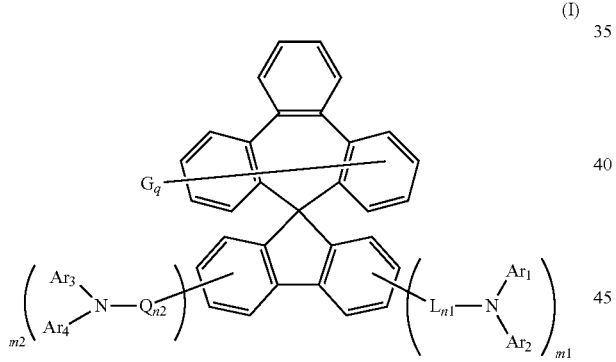

(I)

wherein, $-L_{n1}-NAr_1Ar_2$ and $-Q_{n2}-NAr_3Ar_4$ are each independently selected from the group consisting of:

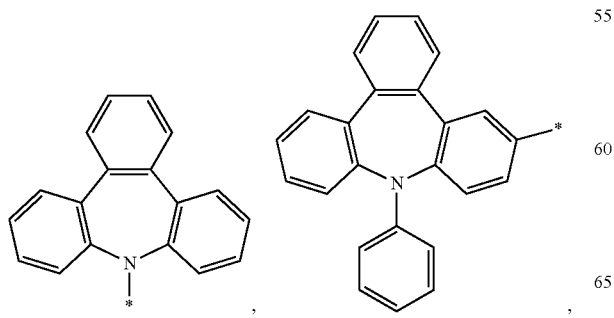

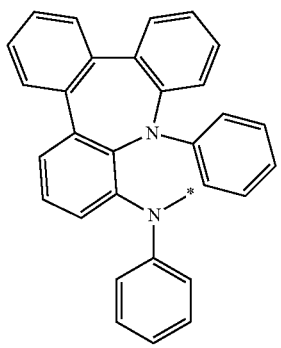

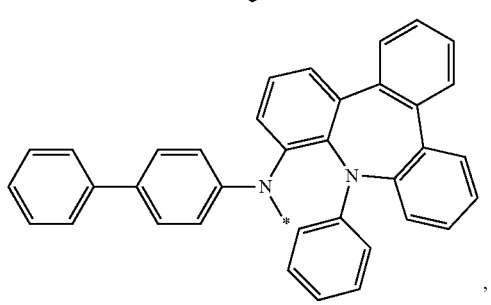

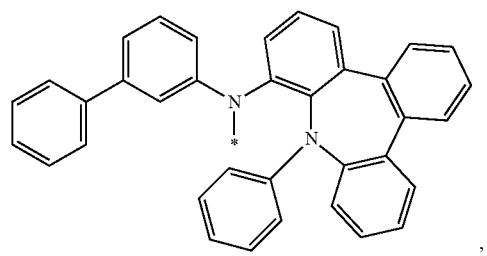

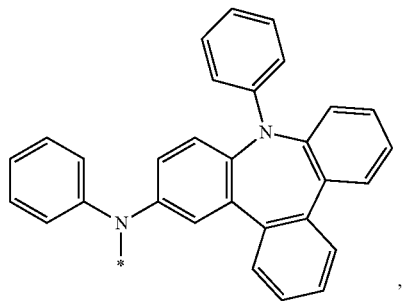

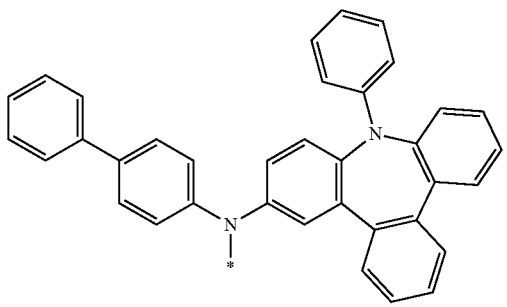

153
-continued
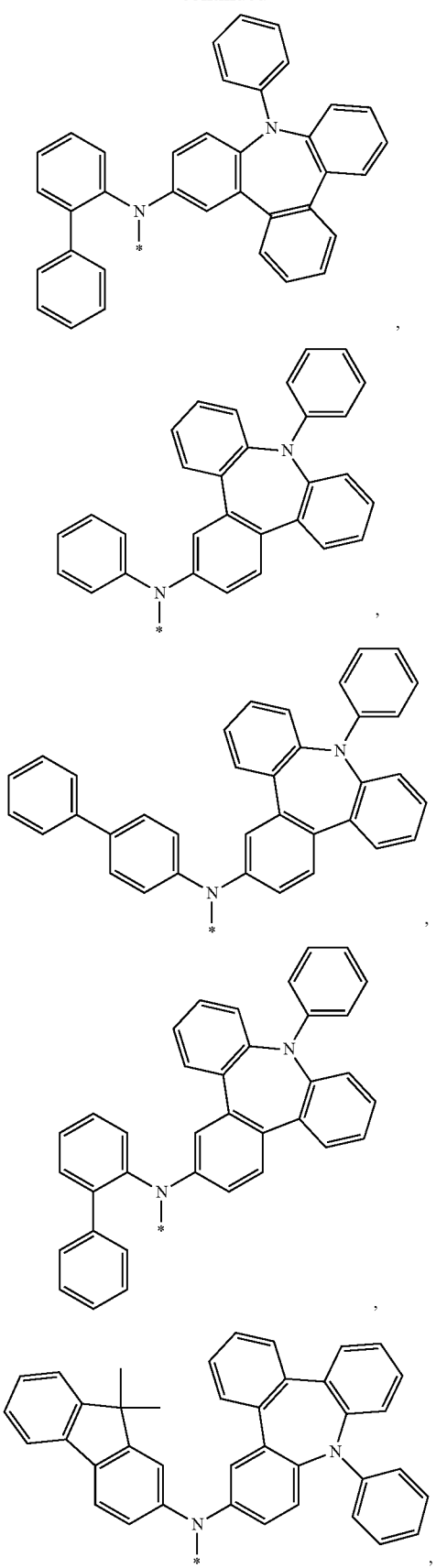
154
-continued
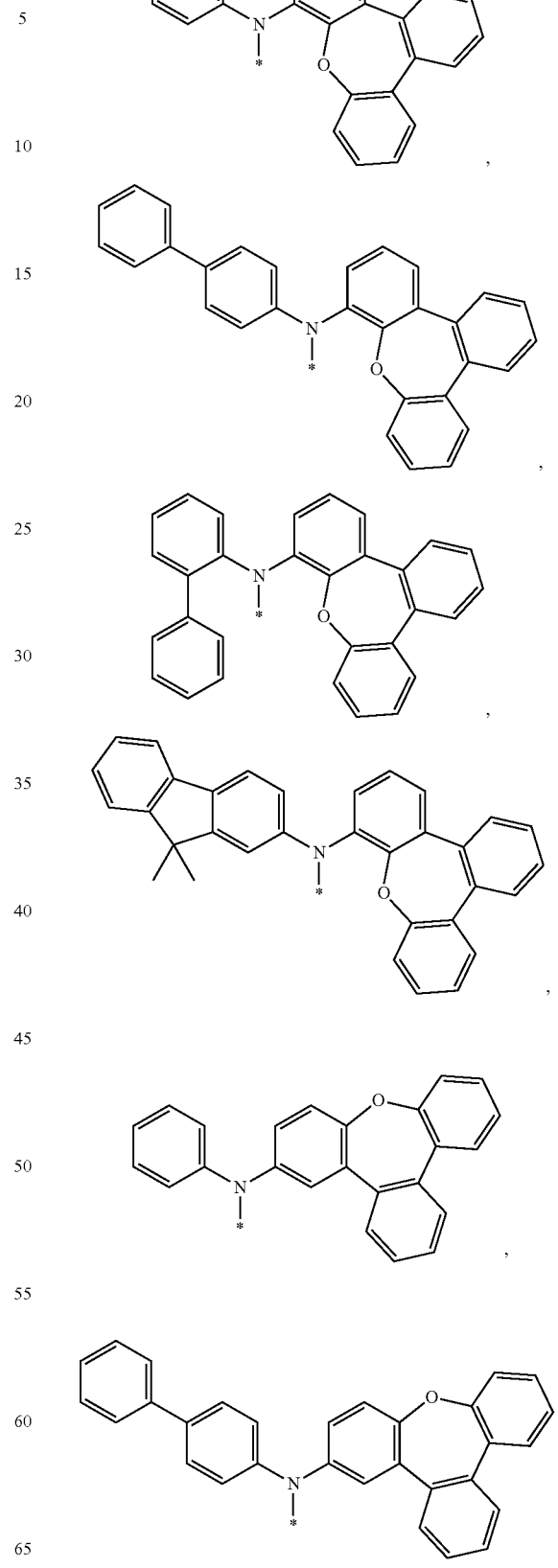

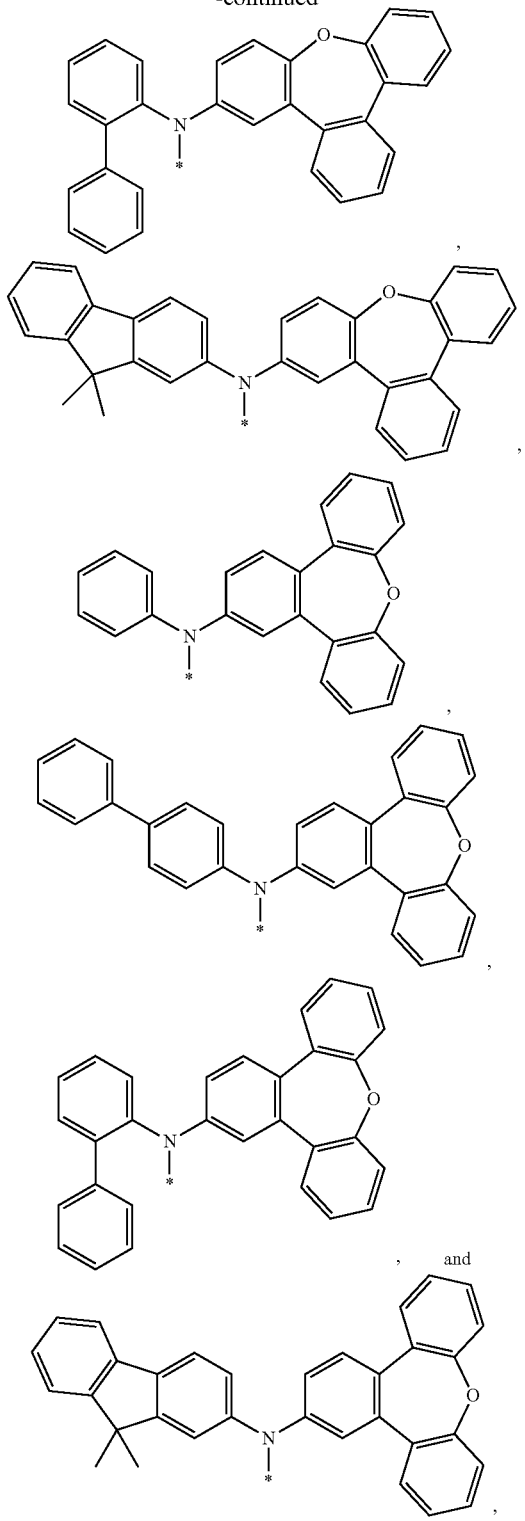

wherein * represents a bonding position;
G is deuterium, a substituted or unsubstituted $C_1$-$C_{20}$ alkyl group, a substituted or unsubstituted $C_6$-$C_{40}$ aryl group, a substituted or unsubstituted $C_1$-$C_{40}$ heterocyclic group, or —$NR_1R_2$;
$R_1$ and $R_2$ are each independently hydrogen, deuterium, a substituted or unsubstituted $C_1$-$C_{20}$ alkyl group, a substituted or unsubstituted $C_6$-$C_{40}$ aryl group, or a substituted or unsubstituted $C_1$-$C_{40}$ heterocyclic group;
n1 and n2 are each independently 0 or 1;
m1 and m2 are each independently 0, 1 or 2, and with the proviso that m1 and m2 are not 0 at the same time; and
q is 0, 1, or 2.

2. The compound of claim 1, wherein m1 is 1; and m2 is 0 or 1.

3. The compound of claim 1, wherein q is 0 or 1.

4. The compound of claim 1, wherein q is 1; and G is a substituted or unsubstituted $C_6$-$C_{40}$ aryl group, a substituted or unsubstituted $C_1$-$C_{40}$ heterocyclic group, or —$NR_1R_2$, in which $R_1$ and $R_2$ are each independently a substituted or unsubstituted $C_6$-$C_{40}$ aryl group.

5. The compound of claim 4, wherein G is a substituted or unsubstituted $C_1$-$C_{40}$ heteroaryl group containing a nitrogen atom, or —$NR_1R_2$, in which $R_1$ and $R_2$ are the same and are a substituted or unsubstituted phenyl, biphenyl or naphthylene.

6. The compound of claim 5, wherein G is unsubstituted pyridyl, or —$NR_1R_2$, in which $R_1$ and $R_2$ are unsubstituted phenyl.

7. The compound of claim 1, wherein the compound is represented by any one of Formulas (I-1) to (I-18) below:

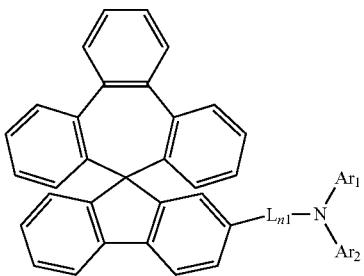

(I-1)

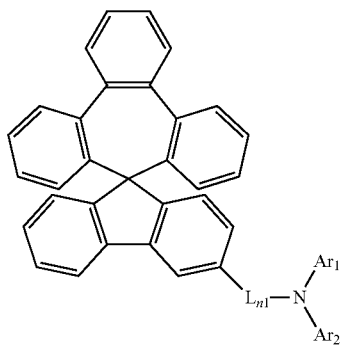

(I-2)

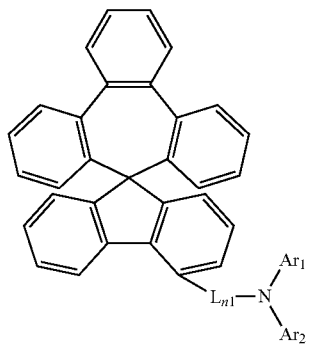

(I-3)

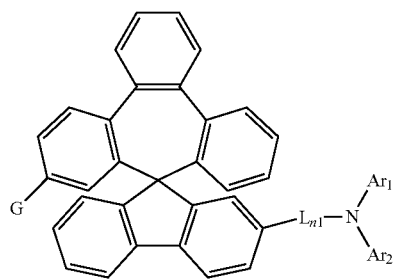
(I-4)
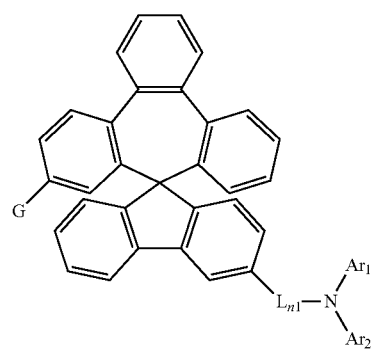
(I-5)
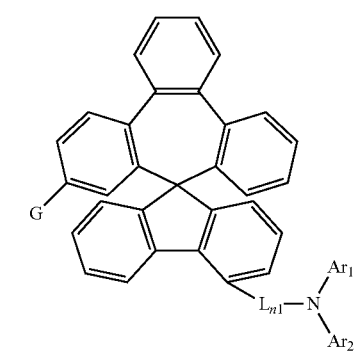
(I-6)
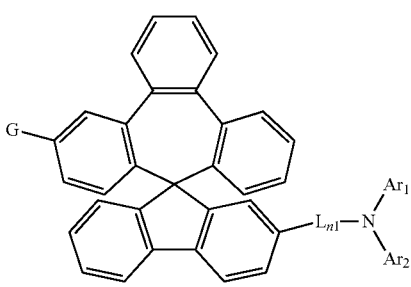
(I-7)
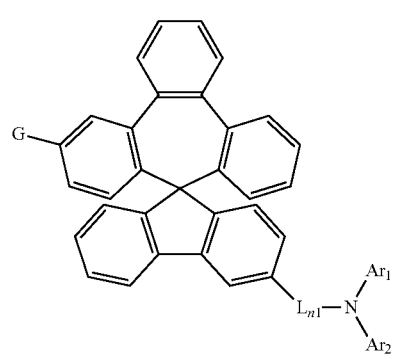
(I-8)
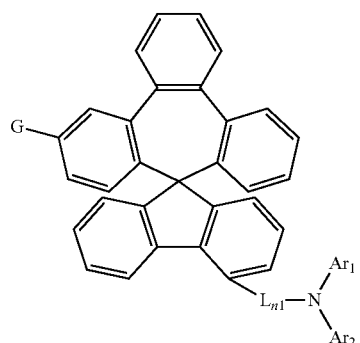
(I-9)
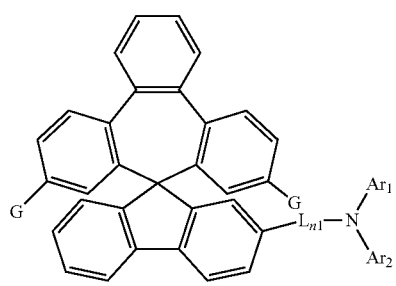
(I-10)
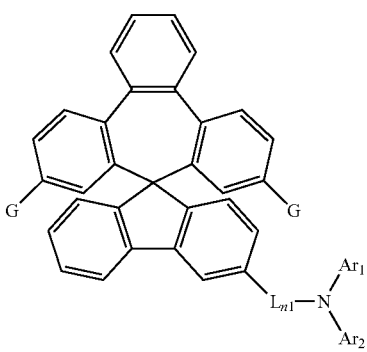
(I-11)
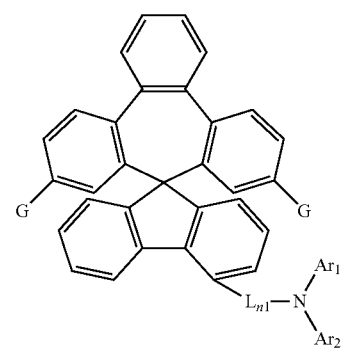
(I-12)
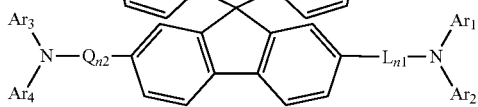
(I-13)

(I-14)
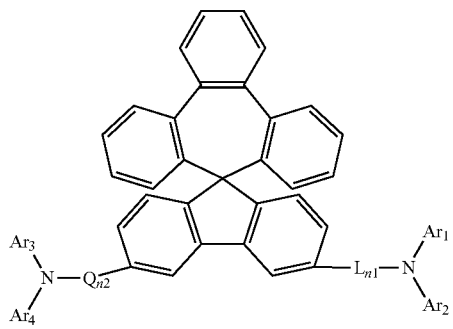
(I-15)
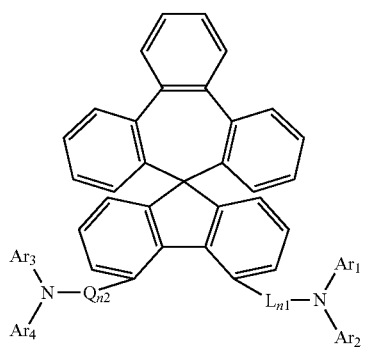
(I-16)
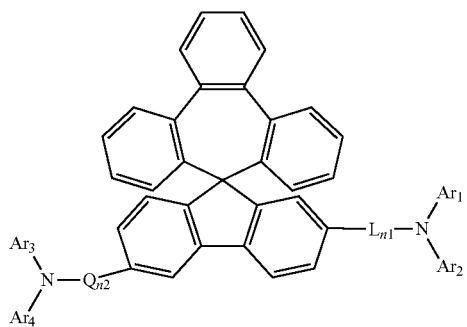
(I-17)
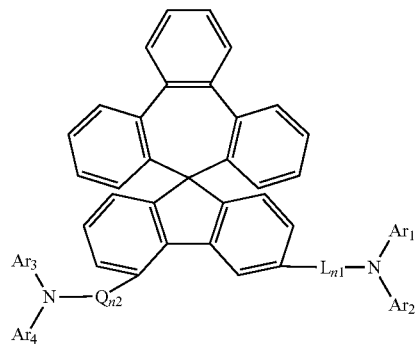
(I-18)
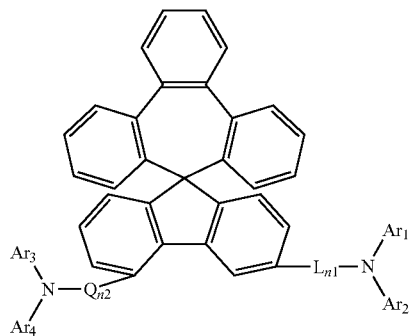
wherein Ar$_1$, Ar$_2$, Ar$_3$, Ar$_4$, L, Q, G, n1, and n2 represent the same as those in Formula (I).
8. The compound of claim 1, wherein the compound is represented by any one of the following compounds:
(4)
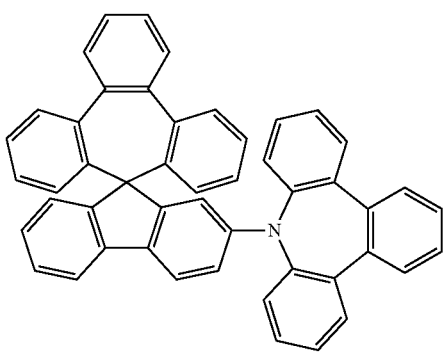
(10)
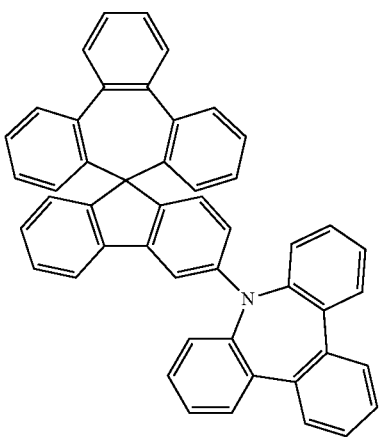

-continued
(16)
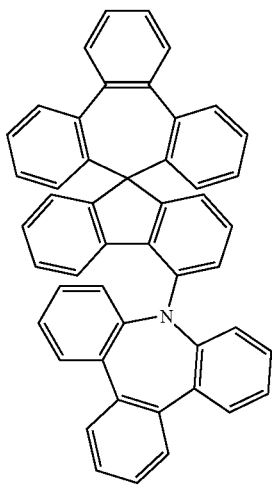
(31)
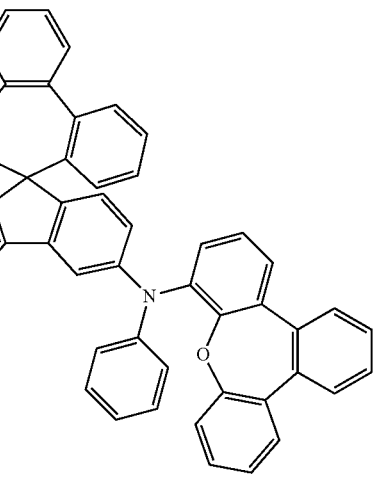
(66)
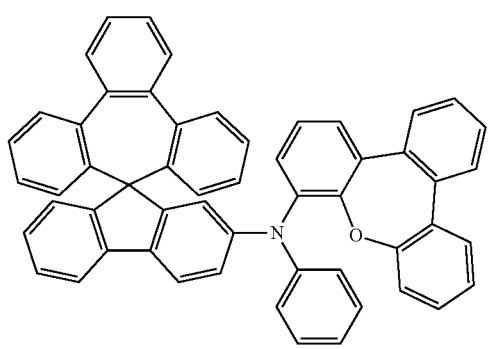
-continued
(67)
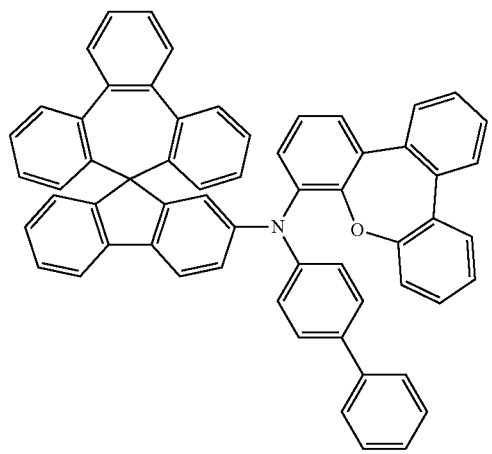
(69)
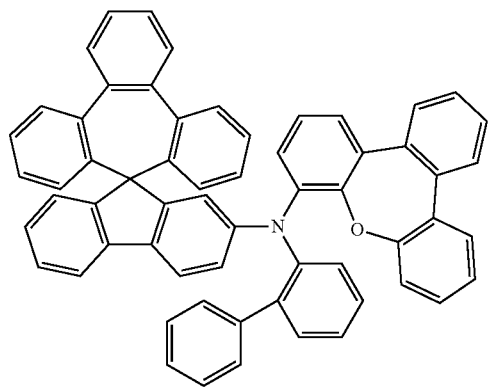
(70)
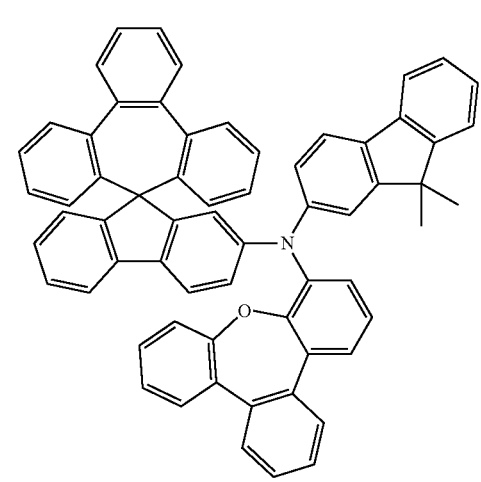

(72)
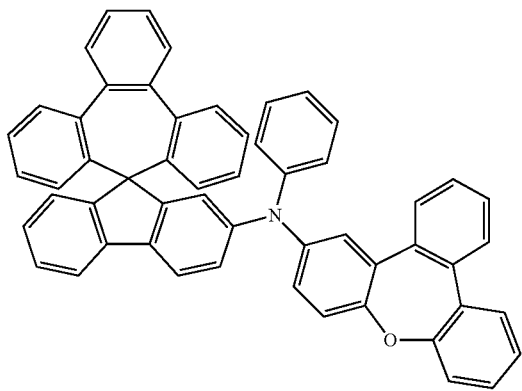
(73)
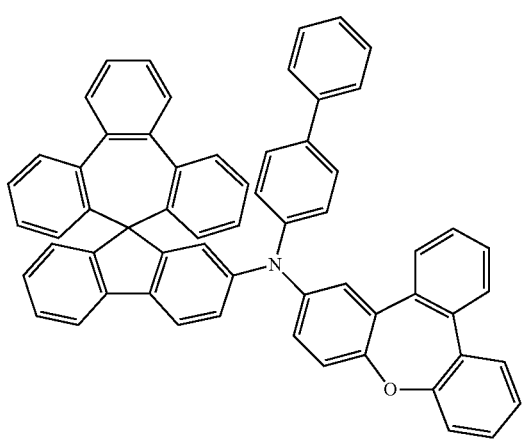
(75)
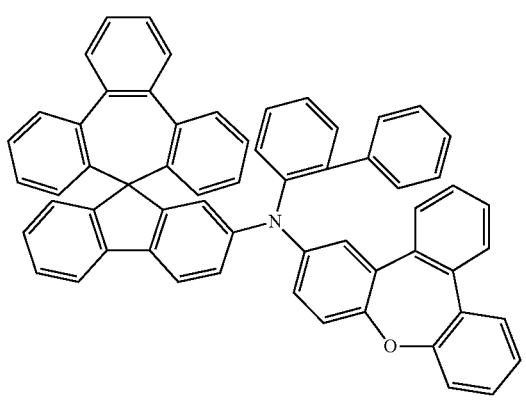
(76)
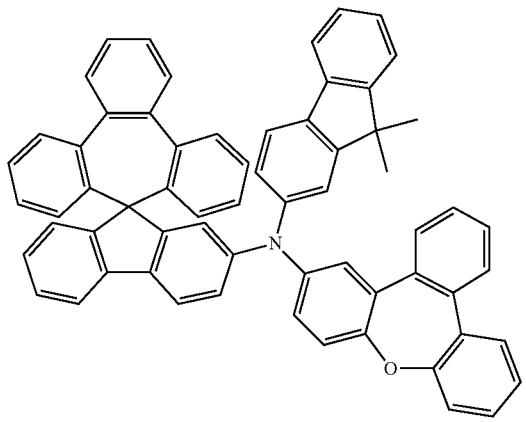
(78)
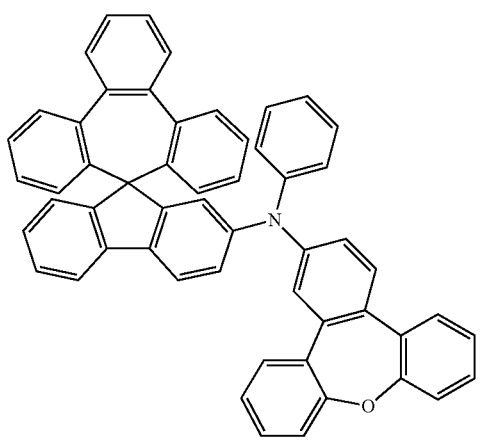
(79)
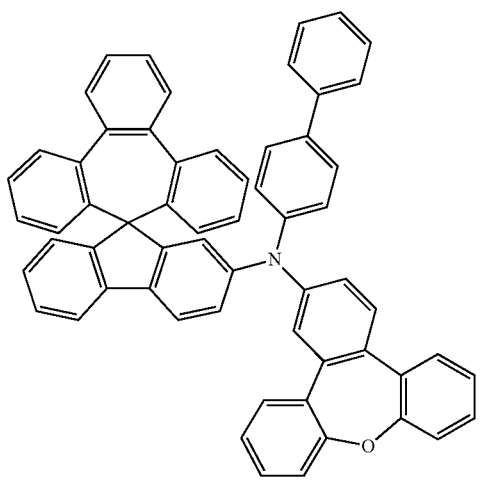

(81)
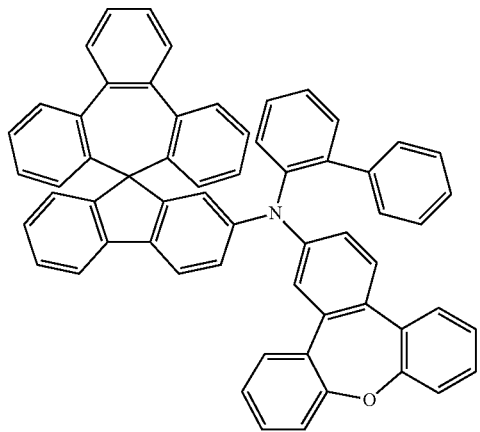
(82)
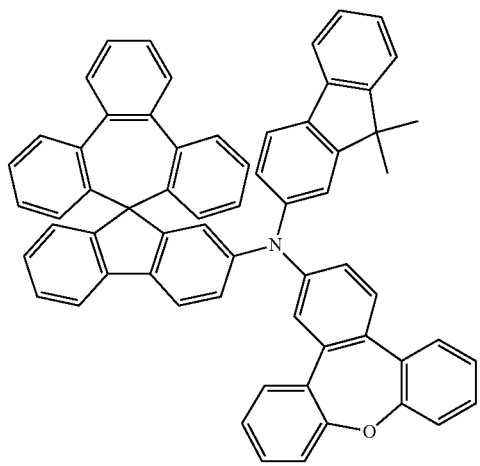
(115)
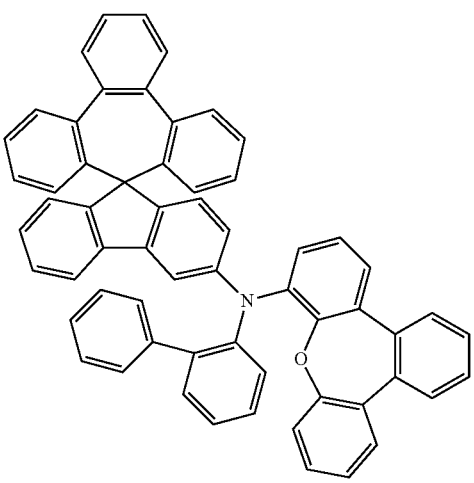
(116)
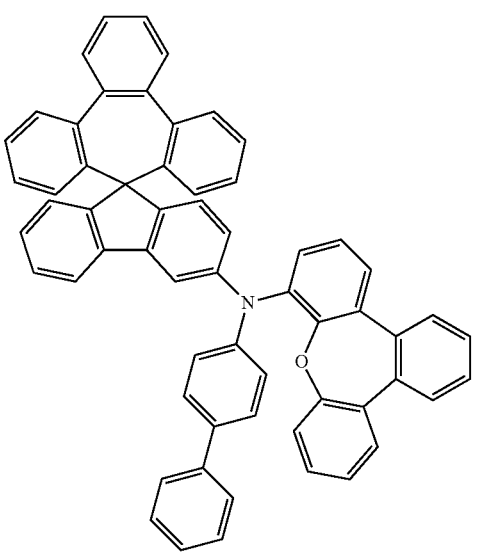
(113)
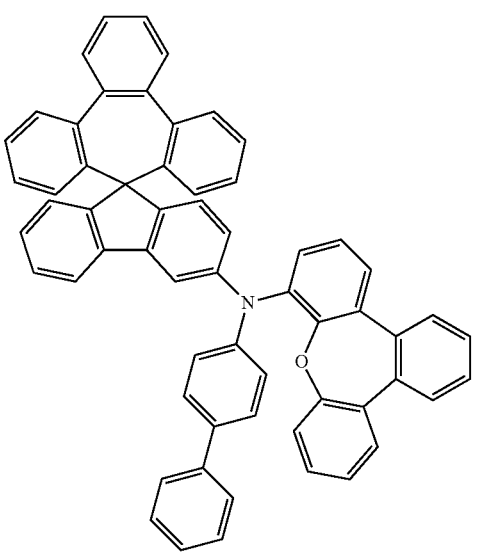
(118)
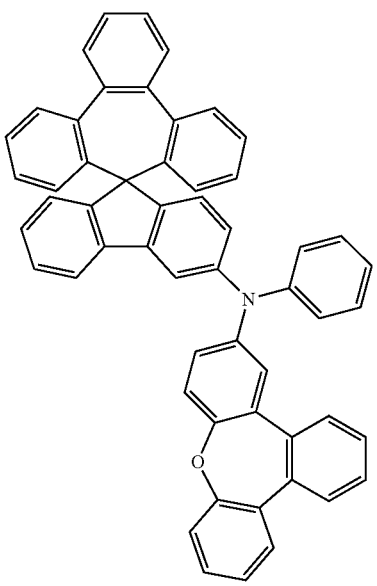

(119)
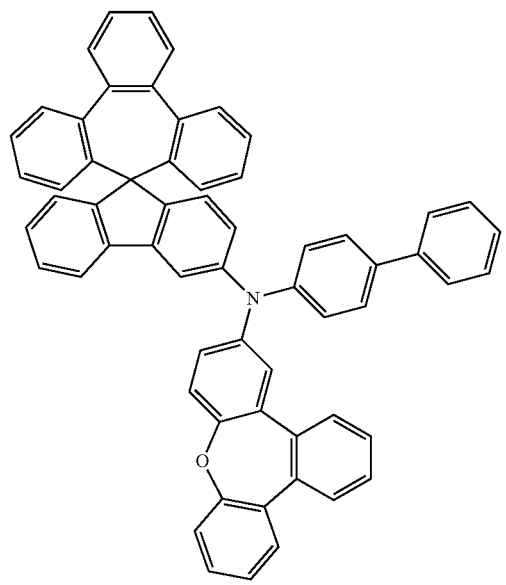
(122)
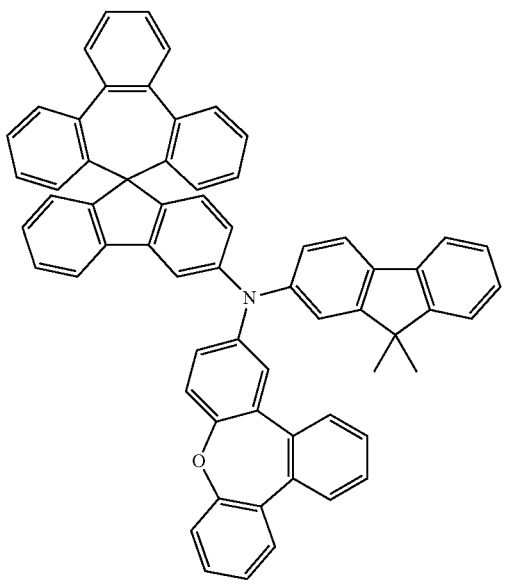
(121)
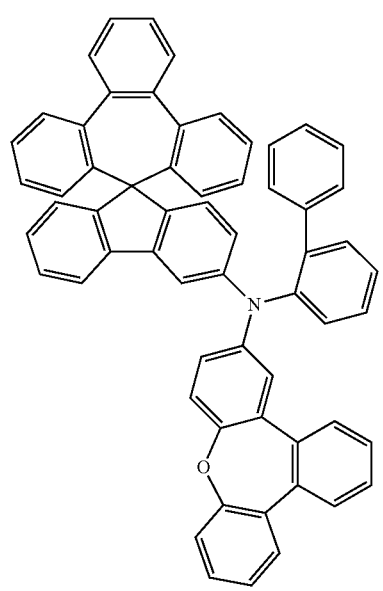
(124)
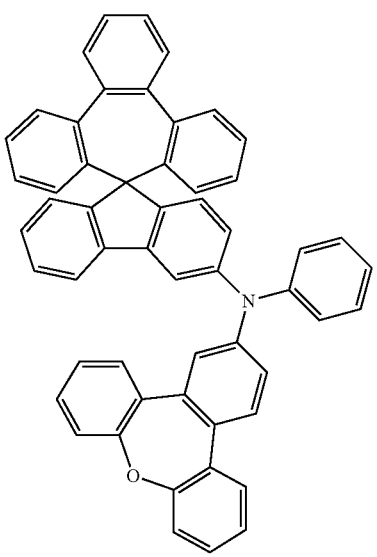

-continued
(125)
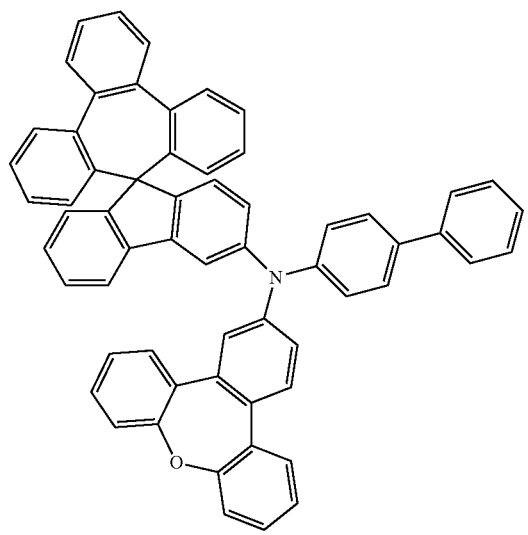
(127)
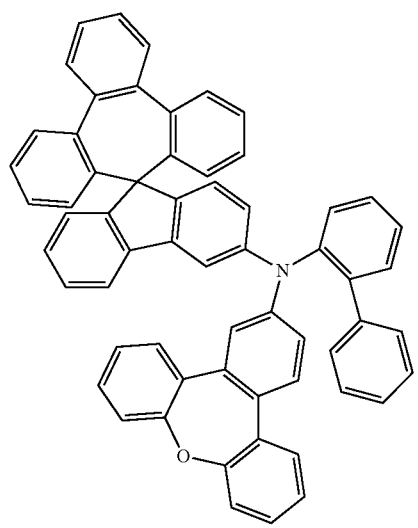
(128)
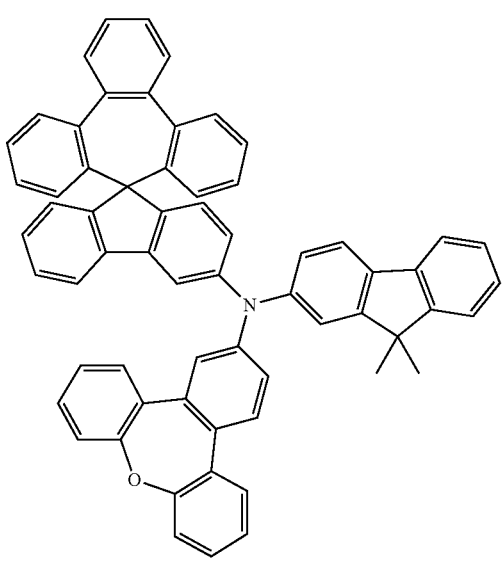
-continued
(129)
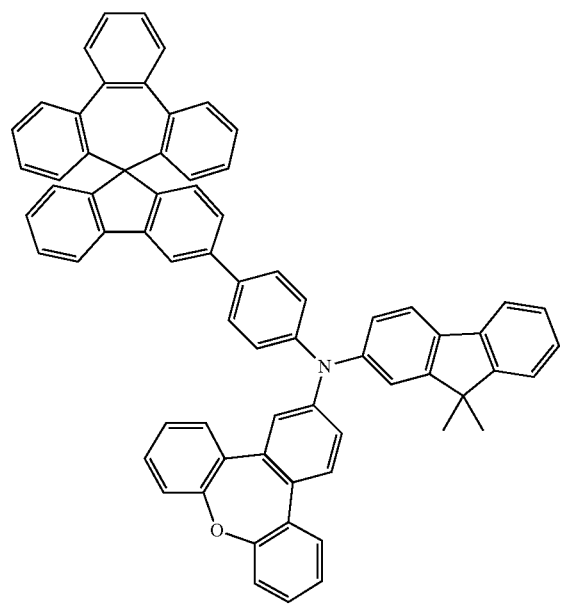
(130)
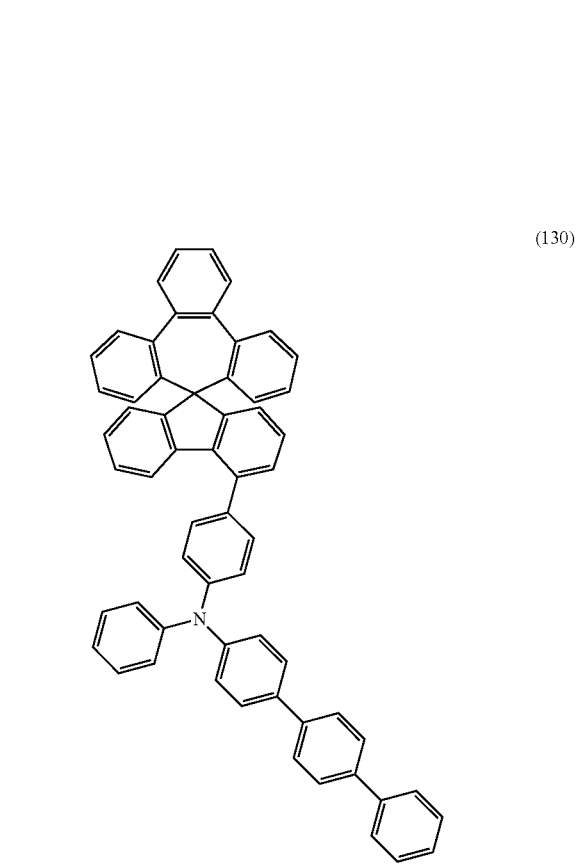

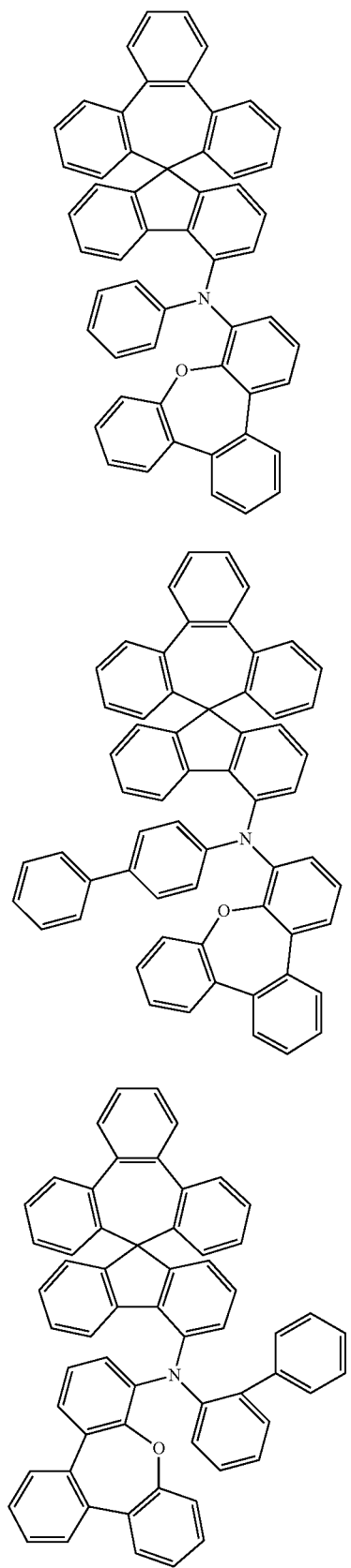
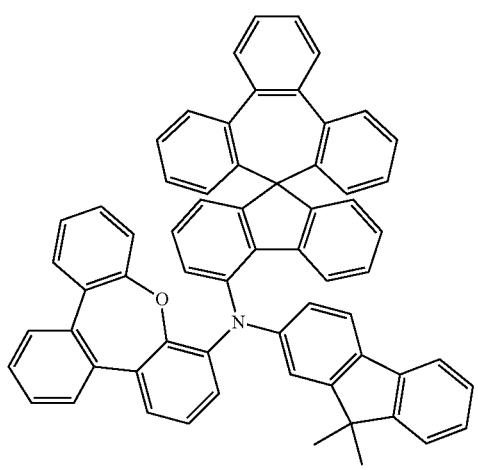
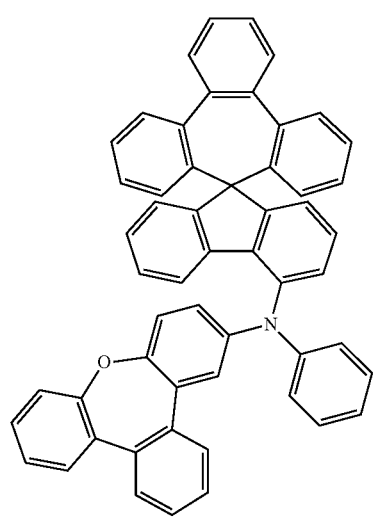
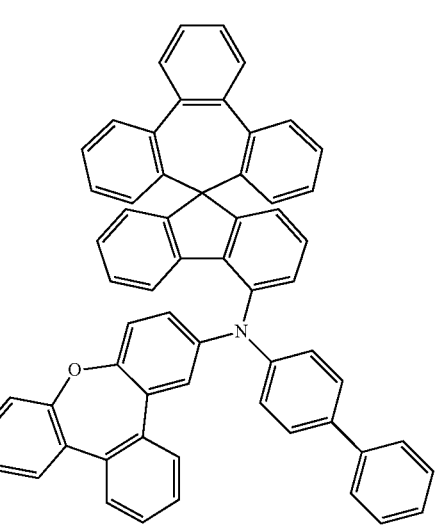

(169)
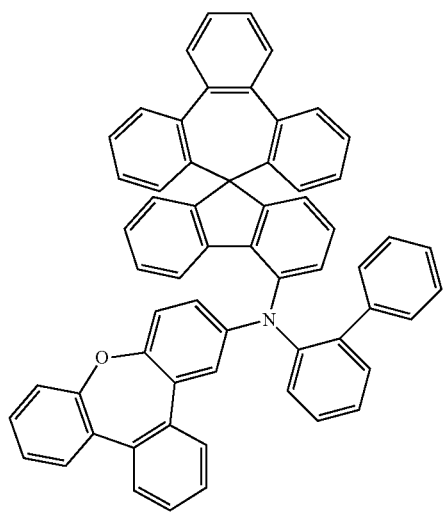
(170)
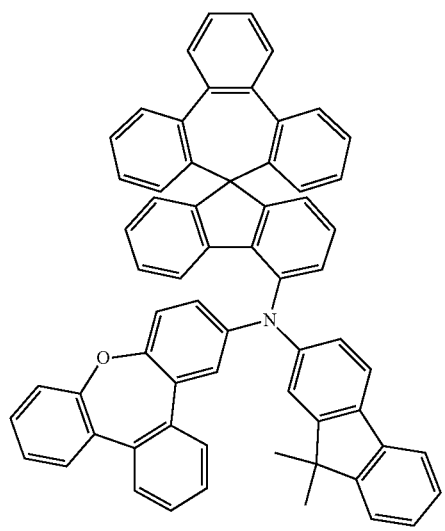
(172)
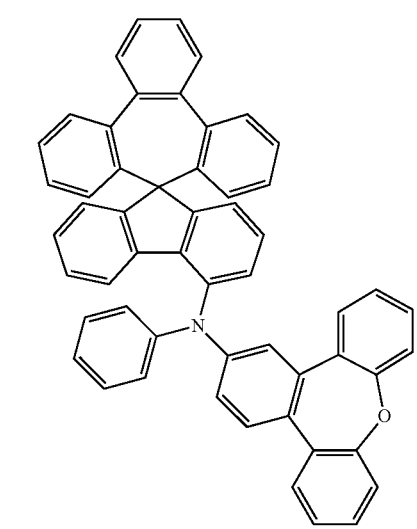
(173)
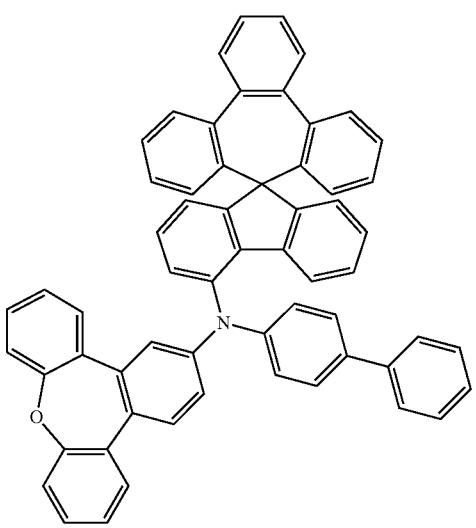
(175)
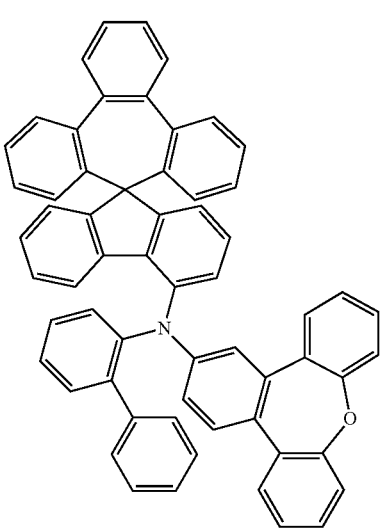
(176)
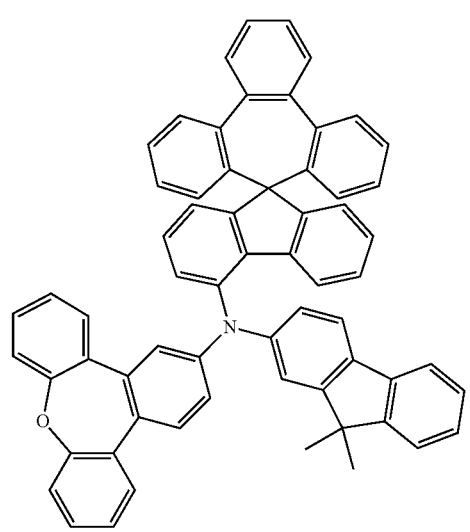

(178)
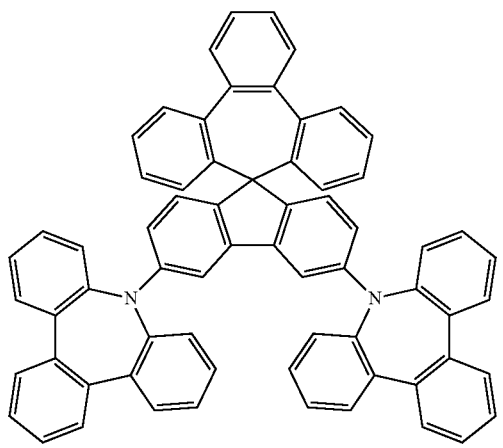
(195)
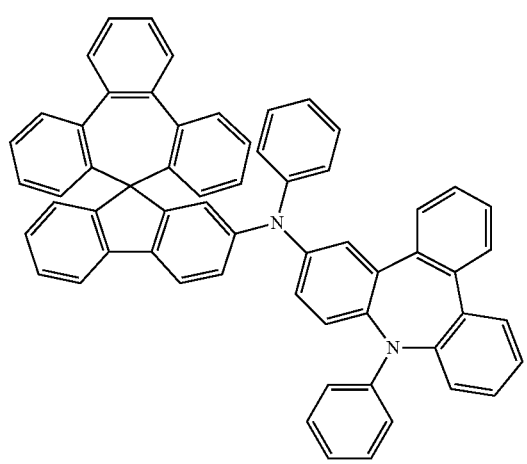
(196)
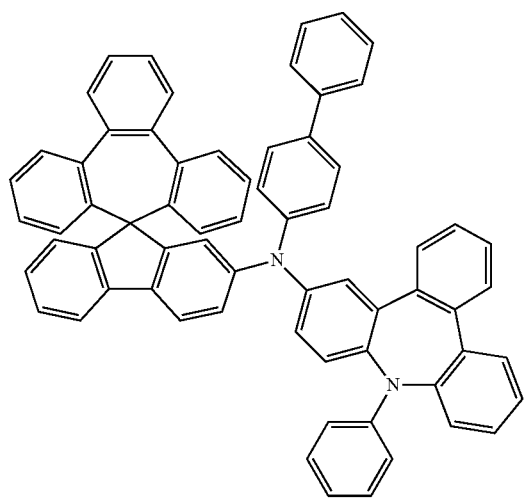
(197)
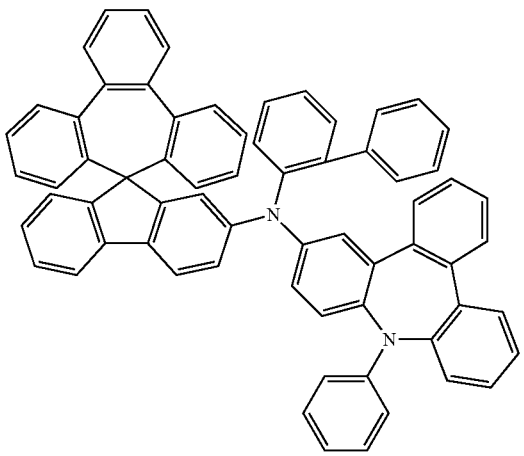
(198)
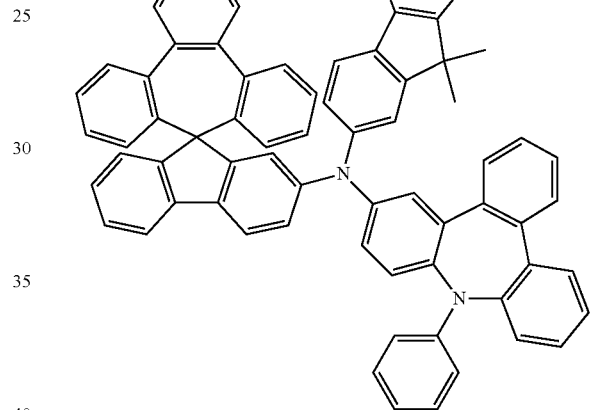
(199)
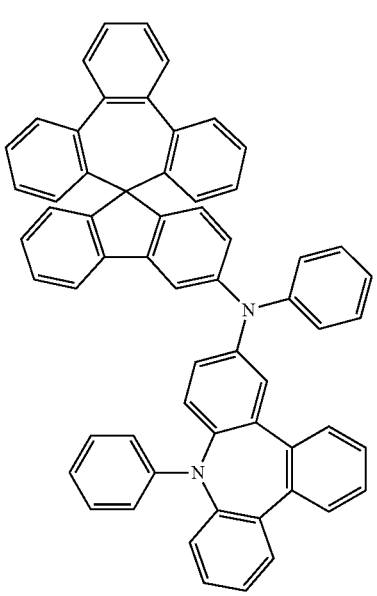

(200)
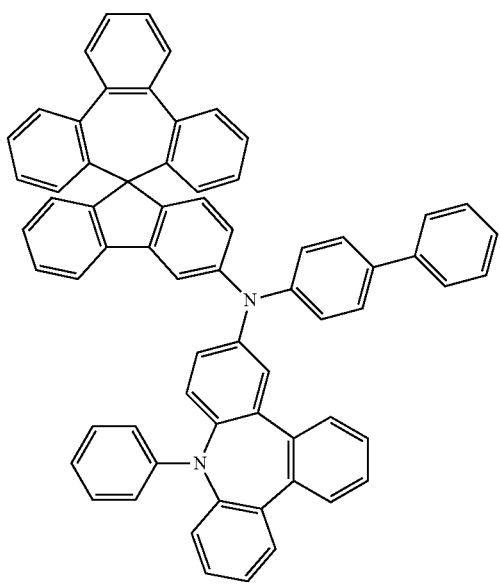
(201)
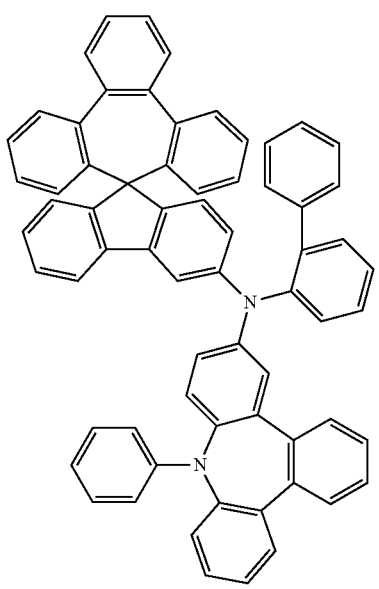
(202)
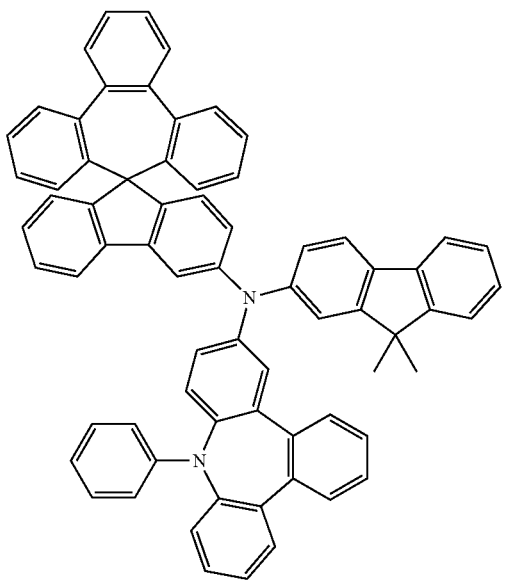
(203)
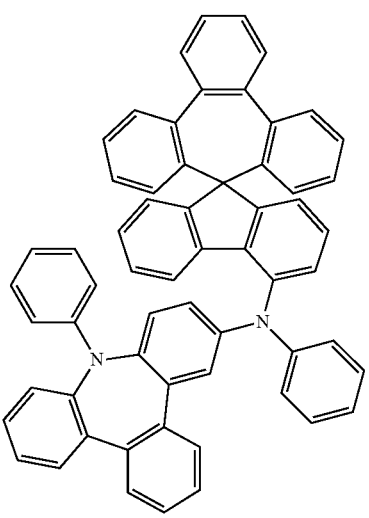
(204)
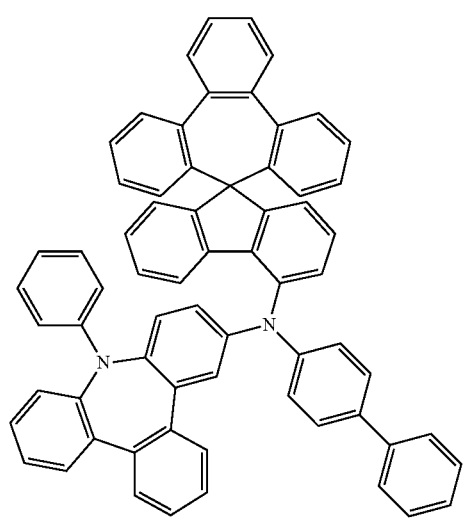

(205) 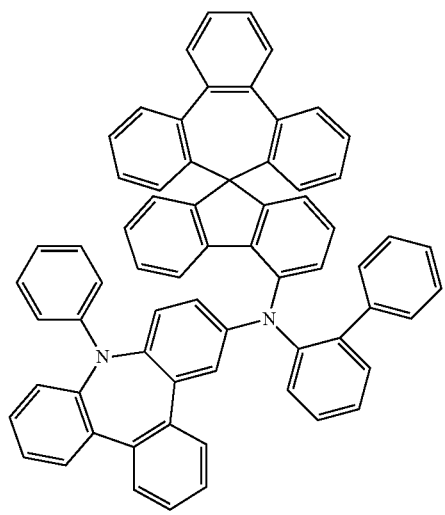
(206) 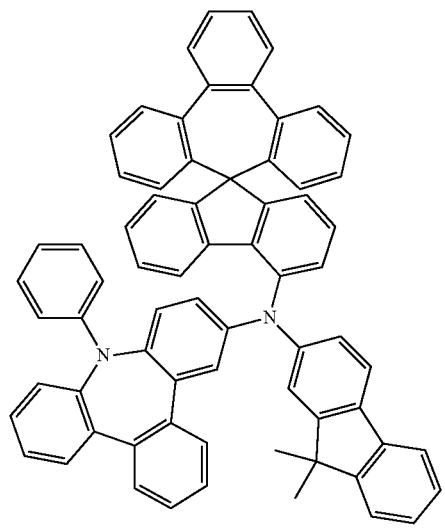
(207) 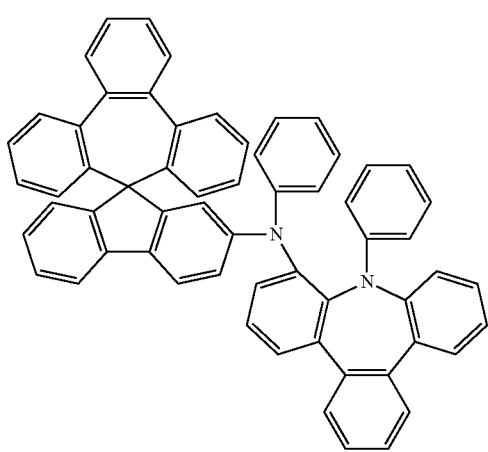
(208) 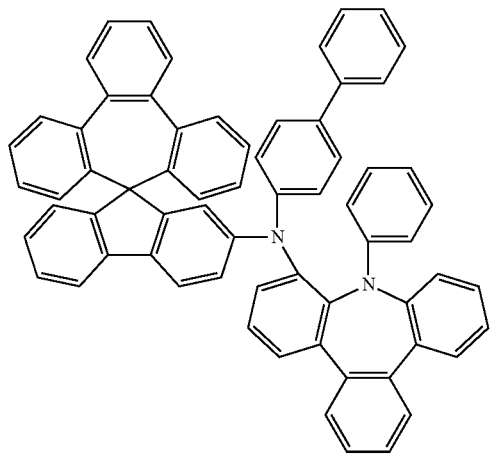
(209) 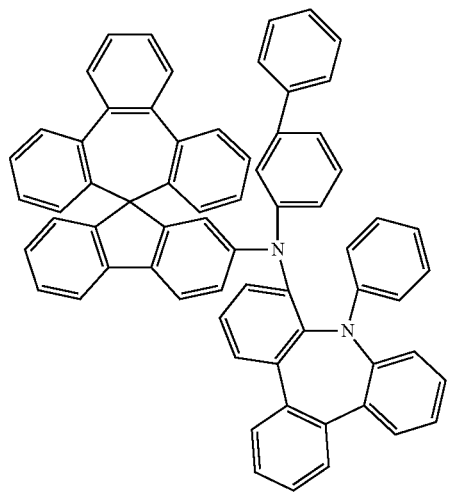
(210) 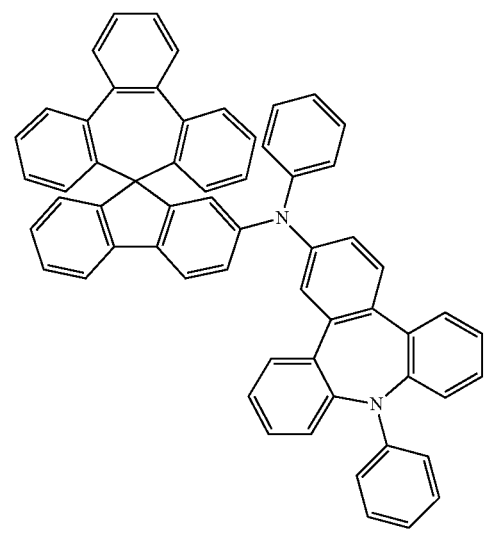

(211)
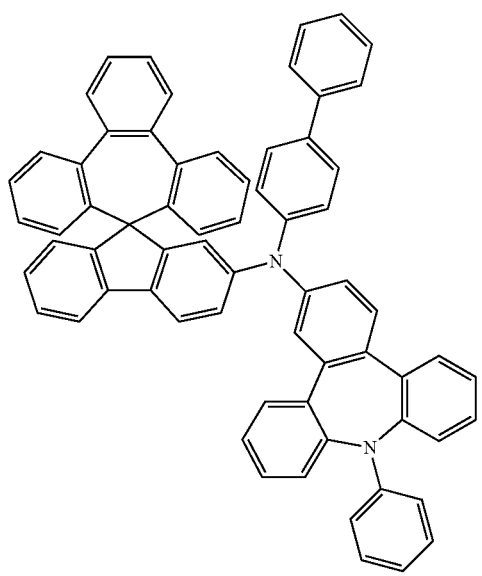
(212)
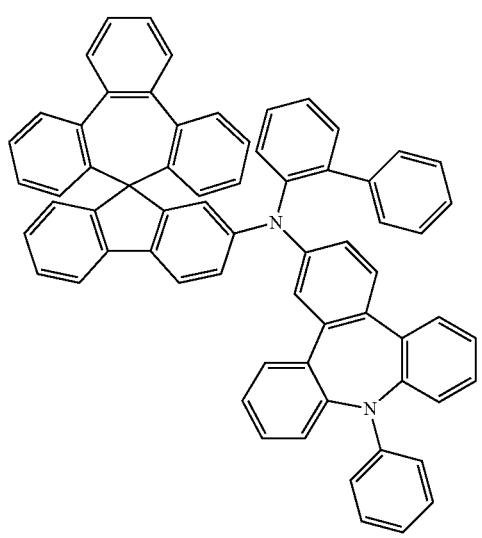
(213)
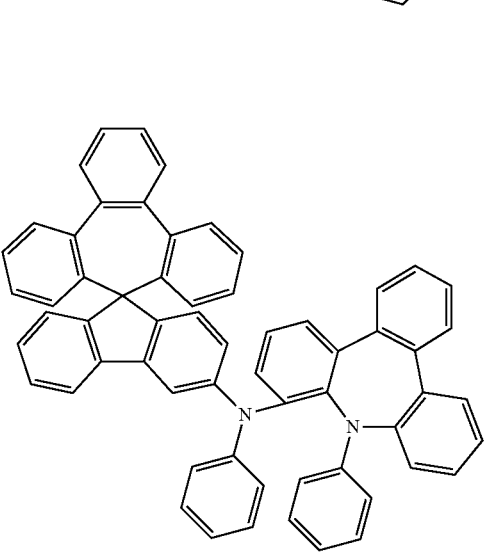
(214)
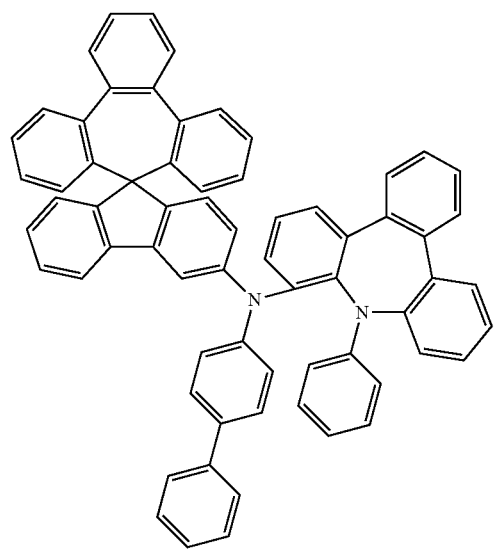
(215)
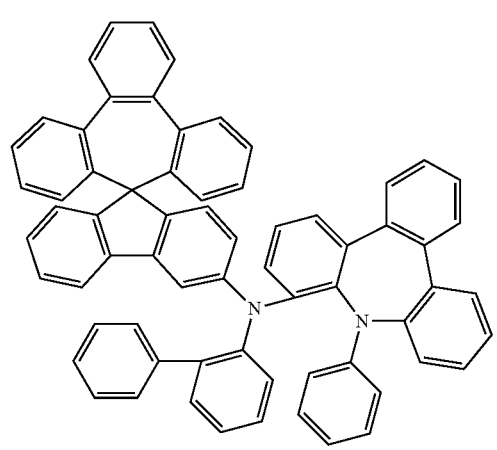
(216)
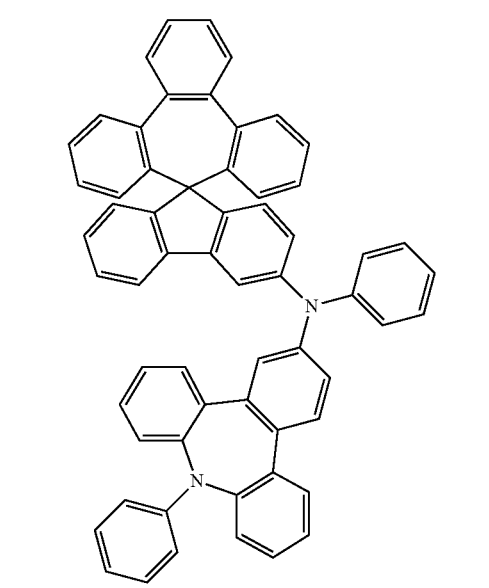

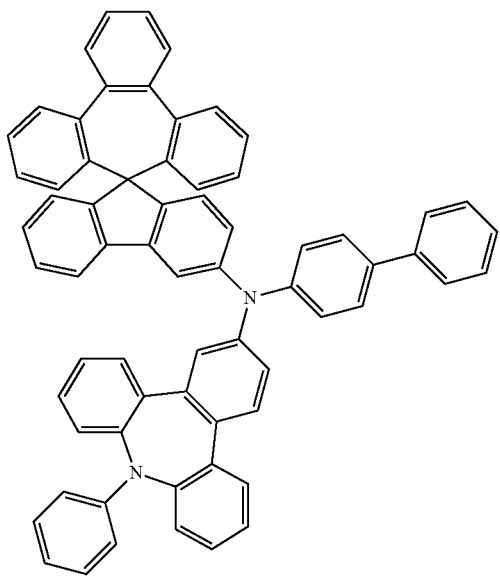
(217)
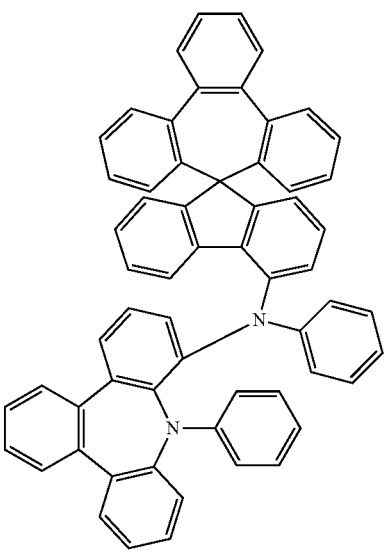
(219)
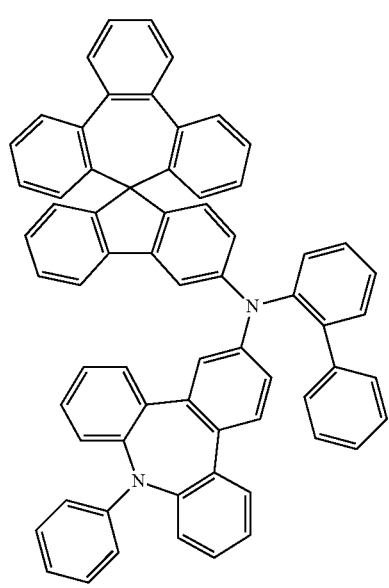
(218)
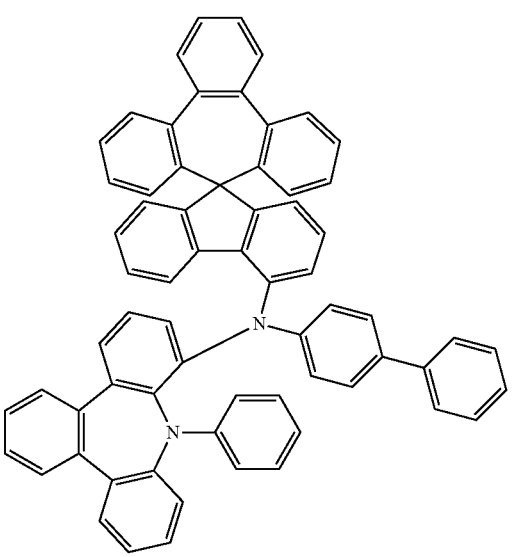
(220)
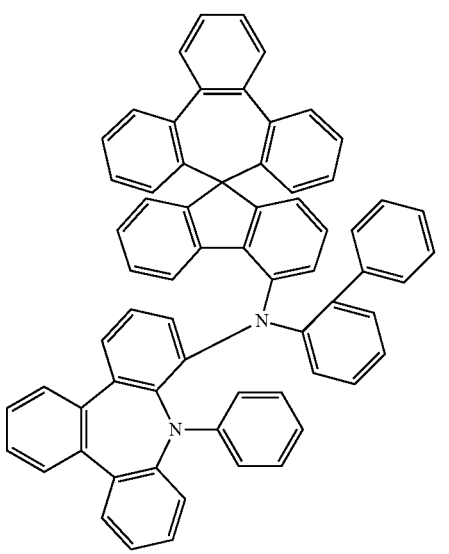
(221)

(222)

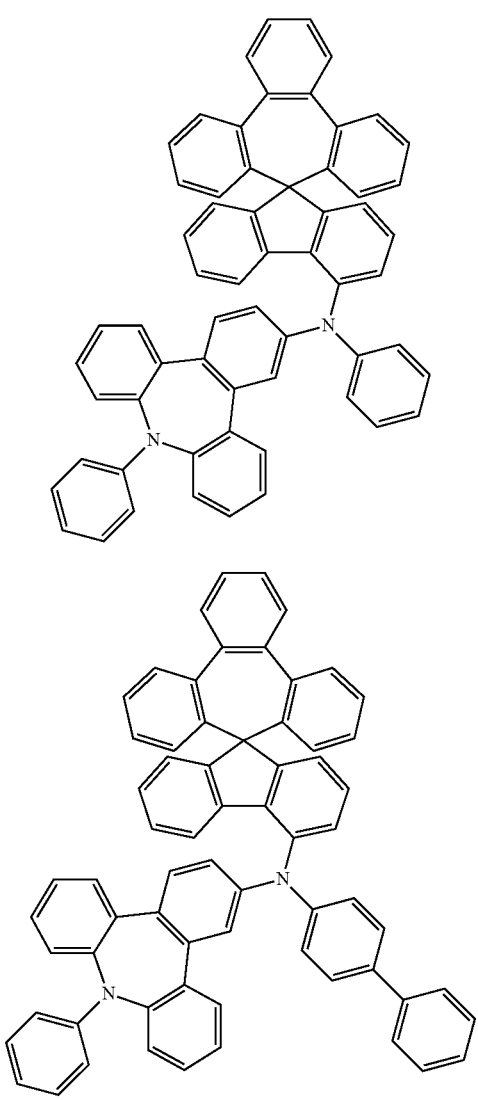

(223)

(224)

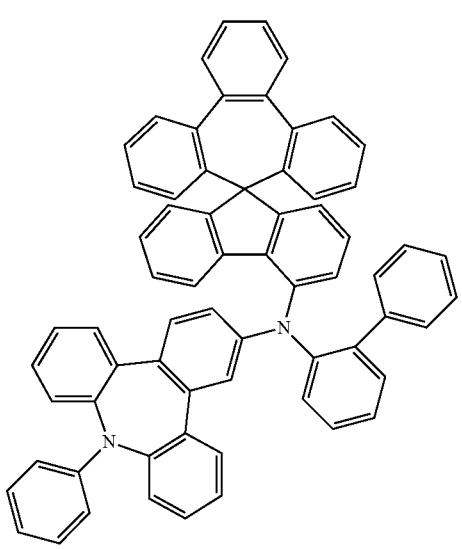

9. An organic electronic device, comprising:
   a first electrode;
   a second electrode; and
   an organic layer disposed between the first electrode and the second electrode, wherein the organic layer comprises the compound of claim 1.

10. The organic electronic device of claim 9, wherein the organic electronic device is an organic light emitting device.

11. The organic electronic device of claim 10, wherein the organic layer includes a hole transporting layer; and the hole transporting layer comprises the compound of claim 1.

12. The organic electronic device of claim 10, wherein the organic layer includes a hole injection layer; and the hole injection layer comprises the compound of claim 1.

13. The organic electronic device of claim 10, wherein the organic layer includes an electron blocking layer; and the electron blocking layer comprises the compound of claim 1.

* * * * *